United States Patent
Brown et al.

(10) Patent No.: US 10,883,129 B2
(45) Date of Patent: Jan. 5, 2021

(54) METHODS AND COMPOSITIONS FOR DEGRADING CELLULOSIC MATERIAL

(71) Applicant: Novozymes, Inc., Davis, CA (US)

(72) Inventors: Kimberly Brown, Elk Grove, CA (US); Eric Abbate, Vacaville, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 16/539,862

(22) Filed: Aug. 13, 2019

(65) Prior Publication Data

US 2019/0360012 A1   Nov. 28, 2019

Related U.S. Application Data

(62) Division of application No. 16/052,082, filed on Aug. 1, 2018, now Pat. No. 10,400,259, which is a division of application No. 15/591,935, filed on May 10, 2017, now Pat. No. 10,059,972, which is a division of application No. 14/849,204, filed on Sep. 9, 2015, now Pat. No. 9,677,102, which is a division of application No. 14/248,039, filed on Apr. 8, 2014, now Pat. No. 9,145,569, which is a division of application No. 14/010,199, filed on Aug. 26, 2013, now Pat. No. 8,703,464, which is a division of application No. 12/612,401, filed on Nov. 4, 2009, now Pat. No. 8,518,684.

(60) Provisional application No. 61/174,221, filed on Apr. 30, 2009, provisional application No. 61/115,829, filed on Nov. 18, 2008.

(51) Int. Cl.
| | | |
|---|---|---|
| C12N 9/24 | (2006.01) | |
| C12P 7/14 | (2006.01) | |
| C12P 19/14 | (2006.01) | |
| C12N 9/42 | (2006.01) | |
| C12P 19/02 | (2006.01) | |

(52) U.S. Cl.
CPC .............. *C12P 19/14* (2013.01); *C12N 9/248* (2013.01); *C12N 9/2437* (2013.01); *C12N 9/2482* (2013.01); *C12P 7/14* (2013.01); *C12P 19/02* (2013.01); *C12Y 302/01004* (2013.01); *C12Y 302/01008* (2013.01); *C12Y 302/01021* (2013.01); *C12Y 302/01091* (2013.01); *C12P 2201/00* (2013.01)

(58) Field of Classification Search
CPC ..... C12N 9/2428; C12N 9/2437; C12P 19/14; C12Y 302/01008; C12Y 302/01091
See application file for complete search history.

(56) References Cited

U.S. PATENT DOCUMENTS 7,361,495 B2   4/2008   Brown et al.

FOREIGN PATENT DOCUMENTS

| WO | 9421785 | 9/1994 |
|---|---|---|
| WO | 0118218 | 3/2001 |
| WO | 2004056981 | 7/2004 |
| WO | 2005067531 | 7/2005 |
| WO | 2007071818 | 6/2007 |
| WO | 2007089290 | 8/2007 |
| WO | 2007091231 | 8/2007 |
| WO | 2007094852 | 8/2007 |
| WO | 2008008070 | 1/2008 |
| WO | 2008095033 | 8/2008 |
| WO | 2009018537 | 2/2009 |
| WO | 2009033071 | 3/2009 |

OTHER PUBLICATIONS

Garcia-Aparicio et al, 2007, Biochem Biotechnol 137-140(1-12), 352-365.
Ustinov et al., Comparison of properties and mode of action of six secreted xylanases from Chrysosporium lucknowense, Enzyme and Microbial Technology, vol. 43, 2008, pp. 56-65.
Berlin et al., Optimization of enzyme complexes for lignocelluloses hydrolysis, Biotechnology and Bioengineering, vol. 97, 2007, pp. 287-296.
Sorensen et al., Synergistic enzyme mechanisms and effects of sequential enzyme additions on degradation of water insoluble wheat arabinoxylan, Enzymes and Microbial Technology, vol. 40, 2007, pp. 908-918.
Gusakov et al., Design of highly efficient cellulose mixtures for enzymatic hydrolysis of cellulose, Biotechnology and Bioengineering, vol. 97, 2007, pp. 1028-1038.
Selig et al., Synergistic enhancement of cellobiohydrolase performance on pretreated corn stover by addition of xylanase and esterase activities, Bioresource Technology, vol. 99, 2008, pp. 4997-5005.
Viikari et al., Thermostable enzymes in lignocelluloses hydrolysis, Advances in Biochemical Engineering, vol. 108, 2007, pp. 121-145.
Kumar et al., Bioconversion of lignocellulosic biomass: biochemical and molecular perspectives, Journal of Industrial Microbiology & Biotechnology, vol. 35, 2008, pp. 377-391.

*Primary Examiner* — Maryam Monshipouri
(74) *Attorney, Agent, or Firm* — Kelly Reynolds

(57) ABSTRACT

The present invention relates to enzyme compositions comprising a polypeptide having cellobiohydrolase II activity, a polypeptide having xylanase activity, and one or more cellulolytic proteins and their use in the degradation or conversion of cellulosic material.

21 Claims, 5 Drawing Sheets

Specification includes a Sequence Listing.

SEQUENCE LISTING

```
<160> NUMBER OF SEQ ID NOS: 119

<210> SEQ ID NO 1
<211> LENGTH: 923
<212> TYPE: DNA
<213> ORGANISM: Humicola insolens

<400> SEQUENCE: 1
atgcgttcct ccccctcct ccgctccgcc gttgtggccg ccctgccggt gttggcccct      60
gccgctgatg gcaggtccac ccgctactgg gactgctgca agccttcgtg cggctgggcc     120
aagaaggctc ccgtgaacca gcctgtcttt tcctgcaacg ccaacttcca gcgtatcacg     180
gacttcgacg ccaagtccgg ctgcgagccg ggcggtgtcg cctactcgtg cgccgaccag     240
accccatggg ctgtgaacga cgacttcgcg ctcggttttg ctgccacctc tattgccggc     300
agcaatgagg cgggctggtg ctgcgcctgc tacgagctca ccttcacatc cggtcctgtt     360
gctggcaaga agatggtcgt ccagtccacc agcactggcg gtgatcttgg cagcaaccac     420
ttcgatctca acatccccgg cggcggcgtc ggcatcttcg acggatgcac tccccagttc     480
ggcggtctgc ccggccagcg ctacggcggc atctcgtccc gcaacgagtg cgatcggttc     540
cccgacgccc tcaagcccgg ctgctactgg cgcttcgact ggttcaagaa cgccgacaat     600
ccgagcttca gcttccgtca ggtccagtgc ccagccgagc tcgtcgctcg caccggatgc     660
cgccgcaacg acgacggcaa cttccctgcc gtccagatcc cctccagcag caccagctct     720
ccggtcaacc agcctaccag caccagcacc acgtccacct ccaccacctc gagcccgcca     780
```

```
gtccagccta cgactcccag cggctgcact gctgagaggt gggctcagtg cggcggcaat    840
ggctggagcg gctgcaccac ctgcgtcgct ggcagcactt gcacgaagat taatgactgg    900
taccatcagt gcctgtagaa ttc                                            923
```

<210> SEQ ID NO 2
<211> LENGTH: 305
<212> TYPE: PRT
<213> ORGANISM: Humicola insolens

<400> SEQUENCE: 2

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Thr Ser Ser
225                 230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305
```

<210> SEQ ID NO 3
<211> LENGTH: 1188
<212> TYPE: DNA
<213> ORGANISM: Myceliophthora thermophila

<400> SEQUENCE: 3

```
cgacttgaaa cgccccaaat gaagtcctcc atcctcgcca gcgtcttcgc cacgggcgcc    60
gtggctcaaa gtggtccgtg gcagcaatgt ggtggcatcg gatggcaagg atcgaccgac   120
tgtgtgtcgg gctaccactg cgtctaccag aacgattggt acagccagtg cgtgcctggc   180
gcggcgtcga caacgctgca gacatcgacc acgtccaggc ccaccgccac cagcaccgcc   240
cctccgtcgt ccaccacctc gcctagcaag ggcaagctga agtggctcgg cagcaacgag   300
tcgggcgccg agttcgggga gggcaattac cccggcctct ggggcaagca cttcatcttc   360
ccgtcgactt cggcgattca gacgctcatc aatgatggat acaacatctt ccggatcgac   420
ttctcgatgg agcgtctggt gcccaaccag ttgacgtcgt ccttcgacca gggttacctc   480
cgcaacctga ccgaggtggt caacttcgtg acgaacgcgg gcaagtacgc cgtcctggac   540
ccgcacaact acggccggta ctacggcaac atcatcacgg acacgaacgc gttccggacc   600
ttctggacca acctgccaa gcagttcgcc tccaactcgc tcgtcatctt cgacaccaac   660
aacgagtaca acacgatgga ccagaccctg gtgctcaacc tcaaccaggc cgccatcgac   720
ggcatccggg ccgccggcgc gacctcgcag tacatcttcg tcgagggcaa cgcgtggagc   780
ggggcctgga gctggaacac gaccaacacc aacatggccg ccctgacgga cccgcagaac   840
aagatcgtgt acgagatgca ccagtacctc gactcggaca gctcgggcac ccacgccgag   900
tgcgtcagca gcaccatcgg cgcccagcgc gtcgtcggag ccacccagtg gctccgcgcc   960
aacggcaagc tcggcgtcct cggcgagttc gccggcggcg ccaacgccgt ctgccagcag  1020
gccgtcaccg gcctcctcga ccacctccag gacaacagcg acgtctggct gggtgccctc  1080
tggtgggccg ccggtccctg gtggggcgac tacatgtact cgttcgagcc tccttcgggc  1140
accggctatg tcaactacaa ctcgatcttg aagaagtact gccgtaa           1188
```

<210> SEQ ID NO 4
<211> LENGTH: 389
<212> TYPE: PRT
<213> ORGANISM: Myceliophthora thermophila

<400> SEQUENCE: 4

```
Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Gln Gly Tyr Leu Arg Asn Leu Thr Glu Val
```

```
                145                 150                 155                 160
        Val Asn Phe Val Thr Asn Ala Gly Lys Tyr Ala Val Leu Asp Pro His
                        165                 170                 175

Asn Tyr Gly Arg Tyr Tyr Gly Asn Ile Ile Thr Asp Thr Asn Ala Phe
                        180                 185                 190

Arg Thr Phe Trp Thr Asn Leu Ala Lys Gln Phe Ala Ser Asn Ser Leu
                        195                 200                 205

Val Ile Phe Asp Thr Asn Asn Glu Tyr Asn Thr Met Asp Gln Thr Leu
                        210                 215                 220

Val Leu Asn Leu Asn Gln Ala Ala Ile Asp Gly Ile Arg Ala Ala Gly
        225                 230                 235                 240

Ala Thr Ser Gln Tyr Ile Phe Val Glu Gly Asn Ala Trp Ser Gly Ala
                        245                 250                 255

Trp Ser Trp Asn Thr Thr Asn Thr Asn Met Ala Ala Leu Thr Asp Pro
                        260                 265                 270

Gln Asn Lys Ile Val Tyr Glu Met His Gln Tyr Leu Asp Ser Asp Ser
                        275                 280                 285

Ser Gly Thr His Ala Glu Cys Val Ser Ser Thr Ile Gly Ala Gln Arg
                        290                 295                 300

Val Val Gly Ala Thr Gln Trp Leu Arg Ala Asn Gly Lys Leu Gly Val
        305                 310                 315                 320

Leu Gly Glu Phe Ala Gly Gly Ala Asn Ala Val Cys Gln Gln Ala Val
                        325                 330                 335

Thr Gly Leu Leu Asp His Leu Gln Asp Asn Ser Asp Val Trp Leu Gly
                        340                 345                 350

Ala Leu Trp Trp Ala Ala Gly Pro Trp Trp Gly Asp Tyr Met Tyr Ser
                        355                 360                 365

Phe Glu Pro Pro Ser Gly Thr Gly Tyr Val Asn Tyr Asn Ser Ile Leu
                        370                 375                 380

Lys Lys Tyr Leu Pro
        385

<210> SEQ ID NO 5
<211> LENGTH: 1232
<212> TYPE: DNA
<213> ORGANISM: Basidiomycete CBS 495.95

<400> SEQUENCE: 5
ggatccactt agtaacggcc gccagtgtgc tggaaagcat gaagtctctc ttcctgtcac      60
ttgtagcgac cgtcgcgctc agctcgccag tattctctgt cgcagtctgg gggcaatgcg     120
gcggcattgg cttcagcgga agcaccgtct gtgatgcagg cgccggctgt gtgaagctca     180
acgactatta ctctcaatgc caacccggcg ctcccactgc tacatccgcg cgccaagta     240 gcaacgcacc gtccggcact cgacggcct cggccccctc ctccagcctt tgctctggca     300
gccgcacgcc gttccagttc ttcggtgtca cgaatccgg cgcggagttc ggcaacctga     360
acatccccgg tgttctgggc accgactaca cctggccgtc gccatccagc attgacttct     420
tcatgggcaa gggaatgaat accttccgta ttccgttcct catggagcgt cttgtccccc     480
ctgccactgg catcacagga cctctcgacc agacgtactt gggcggcctg cagacgattg     540
tcaactacat caccggcaaa ggcggctttg ctctcattga cccgcacaac tttatgatct     600
acaatggcca cgatctcc agtaccagcg acttccagaa gttctggcag aacctcgcag     660
gagtgtttaa atcgaacagt cacgtcatct tcgatgttat gaacgagcct cacgatattc     720
```

```
ccgcccagac cgtgttccaa ctgaaccaag ccgctgtcaa tggcatccgt gcgagcggtg    780
cgacgtcgca gctcattctg gtcgagggca aagctggac tggagcctgg acctggacga     840
cctctggcaa cagcgatgca ttcggtgcca ttaaggatcc aacaacaac gtcgcgatcc     900 agatgcatca gtacctggat agcgatggct ctggcacttc gcagacctgc gtgtctccca    960
ccatcggtgc cgagcggttg caggctgcga ctcaatggtt gaagcagaac aacctcaagg   1020
gcttcctggg cgagatcggc gccggctcta actccgcttg catcagcgct gtgcagggtg   1080
cgttgtgttc gatgcagcaa tctggtgtgt ggctcggcgc tctctggtgg gctgcgggcc   1140
cgtggtgggg cgactactac cagtccatcg agccgccctc tggcccggcg gtgtccgcga   1200
tcctcccgca ggccctgctg ccgttcgcgt aa                                 1232
```

<210> SEQ ID NO 6
<211> LENGTH: 397
<212> TYPE: PRT
<213> ORGANISM: Basidiomycete CBS 495.95

<400> SEQUENCE: 6

```
Met Lys Ser Leu Phe Leu Ser Leu Val Ala Thr Val Ala Leu Ser Ser
1               5                   10                  15

Pro Val Phe Ser Val Ala Val Trp Gly Gln Cys Gly Gly Ile Gly Phe
            20                  25                  30

Ser Gly Ser Thr Val Cys Asp Ala Gly Ala Gly Cys Val Lys Leu Asn
        35                  40                  45

Asp Tyr Tyr Ser Gln Cys Gln Pro Gly Ala Pro Thr Ala Thr Ser Ala
    50                  55                  60

Ala Pro Ser Ser Asn Ala Pro Ser Gly Thr Ser Thr Ala Ser Ala Pro
65                  70                  75                  80

Ser Ser Ser Leu Cys Ser Gly Ser Arg Thr Pro Phe Gln Phe Phe Gly
                85                  90                  95

Val Asn Glu Ser Gly Ala Glu Phe Gly Asn Leu Asn Ile Pro Gly Val
            100                 105                 110

Leu Gly Thr Asp Tyr Thr Trp Pro Ser Pro Ser Ser Ile Asp Phe Phe
        115                 120                 125

Met Gly Lys Gly Met Asn Thr Phe Arg Ile Pro Phe Leu Met Glu Arg
    130                 135                 140

Leu Val Pro Pro Ala Thr Gly Ile Thr Gly Pro Leu Asp Gln Thr Tyr
145                 150                 155                 160

Leu Gly Gly Leu Gln Thr Ile Val Asn Tyr Ile Thr Gly Lys Gly Gly
                165                 170                 175

Phe Ala Leu Ile Asp Pro His Asn Phe Met Ile Tyr Asn Gly Gln Thr
            180                 185                 190

Ile Ser Ser Thr Ser Asp Phe Gln Lys Phe Trp Gln Asn Leu Ala Gly
        195                 200                 205

Val Phe Lys Ser Asn Ser His Val Ile Phe Asp Val Met Asn Glu Pro
    210                 215                 220

His Asp Ile Pro Ala Gln Thr Val Phe Gln Leu Asn Gln Ala Ala Val
225                 230                 235                 240

Asn Gly Ile Arg Ala Ser Gly Ala Thr Ser Gln Leu Ile Leu Val Glu
                245                 250                 255

Gly Thr Ser Trp Thr Gly Ala Trp Thr Trp Thr Thr Ser Gly Asn Ser
            260                 265                 270

Asp Ala Phe Gly Ala Ile Lys Asp Pro Asn Asn Asn Val Ala Ile Gln
        275                 280                 285
```

```
Met His Gln Tyr Leu Asp Ser Asp Gly Ser Gly Thr Ser Gln Thr Cys
        290                 295                 300

Val Ser Pro Thr Ile Gly Ala Glu Arg Leu Gln Ala Ala Thr Gln Trp
305                 310                 315                 320

Leu Lys Gln Asn Asn Leu Lys Gly Phe Leu Gly Glu Ile Gly Ala Gly
                325                 330                 335

Ser Asn Ser Ala Cys Ile Ser Ala Val Gln Gly Ala Leu Cys Ser Met
                340                 345                 350

Gln Gln Ser Gly Val Trp Leu Gly Ala Leu Trp Ala Ala Gly Pro
            355                 360                 365

Trp Trp Gly Asp Tyr Tyr Gln Ser Ile Glu Pro Pro Ser Gly Pro Ala
        370                 375                 380

Val Ser Ala Ile Leu Pro Gln Ala Leu Leu Pro Phe Ala
385                 390                 395
```

<210> SEQ ID NO 7
<211> LENGTH: 1303
<212> TYPE: DNA
<213> ORGANISM: Basidiomycete CBS 494.95

<400> SEQUENCE: 7

```
ggaaagcgtc agtatggtga aatttgcgct tgtggcaact gtcggcgcaa tcttgagcgc     60
ttctgcggcc aatgcggctt ctatctacca gcaatgtgga ggcattggat ggtctgggtc    120
cactgtttgc gacgccggtc tcgcttgcgt tatcctcaat gcgtactact ttcagtgctt    180
gacgcccgcc gcgggccaga caacgacggg ctcgggcgca ccggcgtcaa catcaacctc    240
tcactcaacg gtcactacgg ggagctcaca ctcaacaacc gggacgacgg cgacgaaaac    300
aactaccact ccgtcgacca ccacgaccct acccgccatc tctgtgtctg gtcgcgtctg    360
ctctggctcc aggacgaagt tcaagttctt cggtgtgaat gaaagcggcg ccgaattcgg    420
gaacactgct tggccagggc agctcgggaa agactataca tggccttcgc ctagcagcgt    480
ggactacttc atgggggctg gattcaatac attccgtatc accttcttga tggagcgtat    540
gagccctccg gctaccggac tcactggccc attcaaccag acgtacctgt cgggcctcac    600
caccattgtc gactacatca cgaacaaagg aggatacgct cttattgacc ccacaacttt    660
catgcgttac aacaacggca taatcagcag cacatctgac ttcgcgactt ggtggagcaa    720
tttggccact gtattcaaat ccacgaagaa cgccatcttc gacatccaga cgagccgta    780
cggaatcgat gcgcagaccg tatcgaact gaatcaagct gccatcaatt cgatccgcgc    840
cgctggcgct acgtcacagt tgattctggt tgaaggaacg tcatacactg gagcttggac    900
gtgggtctcg tccggaaacg gagctgcttt cgcggccgtt acggatcctt acaacaacac    960
ggcaattgaa atgcaccaat acctcgacag cgacggttct gggacaaacg aagactgtgt   1020
ctcctccacc attgggtcgc aacgtctcca agctgccact gcgtggctgc aacaaacagg   1080
actcaaggga ttcctcggag agacgggtgc tgggtcgaat cccagtgca tcgacgccgt   1140
gttcgatgaa ctttgctata tgcaacagca aggcggctcc tggatcggtg cactctggtg   1200
ggctgcgggt cctgtggg gcacgtacat ttactcgatt gaacctccga gcggtgccgc   1260
tatcccagaa gtccttcctc agggtctcgc tccattcctc tag                     1303
```

<210> SEQ ID NO 8
<211> LENGTH: 429
<212> TYPE: PRT
<213> ORGANISM: Basidiomycete CBS 494.95

<400> SEQUENCE: 8

```
Met Val Lys Phe Ala Leu Val Ala Thr Val Gly Ala Ile Leu Ser Ala
 1               5                  10                  15

Ser Ala Ala Asn Ala Ala Ser Ile Tyr Gln Gln Cys Gly Gly Ile Gly
            20                  25                  30

Trp Ser Gly Ser Thr Val Cys Asp Ala Gly Leu Ala Cys Val Ile Leu
        35                  40                  45

Asn Ala Tyr Tyr Phe Gln Cys Leu Thr Pro Ala Ala Gly Gln Thr Thr
    50                  55                  60

Thr Gly Ser Gly Ala Pro Ala Ser Thr Ser Thr Ser His Ser Thr Val
65                  70                  75                  80

Thr Thr Gly Ser Ser His Ser Thr Thr Gly Thr Thr Ala Thr Lys Thr
                85                  90                  95

Thr Thr Thr Pro Ser Thr Thr Thr Thr Leu Pro Ala Ile Ser Val Ser
            100                 105                 110

Gly Arg Val Cys Ser Gly Ser Arg Thr Lys Phe Lys Phe Phe Gly Val
        115                 120                 125

Asn Glu Ser Gly Ala Glu Phe Gly Asn Thr Ala Trp Pro Gly Gln Leu
    130                 135                 140

Gly Lys Asp Tyr Thr Trp Pro Ser Pro Ser Ser Val Asp Tyr Phe Met
145                 150                 155                 160

Gly Ala Gly Phe Asn Thr Phe Arg Ile Thr Phe Leu Met Glu Arg Met
                165                 170                 175

Ser Pro Pro Ala Thr Gly Leu Thr Gly Pro Phe Asn Gln Thr Tyr Leu
            180                 185                 190

Ser Gly Leu Thr Thr Ile Val Asp Tyr Ile Thr Asn Lys Gly Gly Tyr
        195                 200                 205

Ala Leu Ile Asp Pro His Asn Phe Met Arg Tyr Asn Asn Gly Ile Ile
    210                 215                 220

Ser Ser Thr Ser Asp Phe Ala Thr Trp Trp Ser Asn Leu Ala Thr Val
225                 230                 235                 240

Phe Lys Ser Thr Lys Asn Ala Ile Phe Asp Ile Gln Asn Glu Pro Tyr
                245                 250                 255

Gly Ile Asp Ala Gln Thr Val Tyr Glu Leu Asn Gln Ala Ala Ile Asn
            260                 265                 270

Ser Ile Arg Ala Ala Gly Ala Thr Ser Gln Leu Ile Leu Val Glu Gly
        275                 280                 285

Thr Ser Tyr Thr Gly Ala Trp Thr Trp Val Ser Ser Gly Asn Gly Ala
    290                 295                 300

Ala Phe Ala Ala Val Thr Asp Pro Tyr Asn Asn Thr Ala Ile Glu Met
305                 310                 315                 320

His Gln Tyr Leu Asp Ser Asp Gly Ser Gly Thr Asn Glu Asp Cys Val
                325                 330                 335

Ser Ser Thr Ile Gly Ser Gln Arg Leu Gln Ala Ala Thr Ala Trp Leu
            340                 345                 350

Gln Gln Thr Gly Leu Lys Gly Phe Leu Gly Glu Thr Gly Ala Gly Ser
        355                 360                 365

Asn Ser Gln Cys Ile Asp Ala Val Phe Asp Glu Leu Cys Tyr Met Gln
    370                 375                 380

Gln Gln Gly Gly Ser Trp Ile Gly Ala Leu Trp Trp Ala Ala Gly Pro
385                 390                 395                 400

Trp Trp Gly Thr Tyr Ile Tyr Ser Ile Glu Pro Pro Ser Gly Ala Ala
```

```
                405               410              415
Ile Pro Glu Val Leu Pro Gln Gly Leu Ala Pro Phe Leu
              420              425
```

<210> SEQ ID NO 9
<211> LENGTH: 1580
<212> TYPE: DNA
<213> ORGANISM: Thielavia terrestris

<400> SEQUENCE: 9

```
agcccccgt tcaggcacac ttggcatcag atcagcttag cagcgcctgc acagcatgaa      60
gctctcgcag tcggccgcgc tggcggcact caccgcgacg gcgctcgccg ccccctcgcc    120
cacgacgccg caggcgccga ggcaggcttc agccggctgc tcgtctgcgg tcacgctcga    180
cgccagcacc aacgtttgga gaagtacacg gctgcacccc aacagctact accgcaagga    240
ggttgaggcc gcggtggcgc agatctcgga cccggacctc gccgccaagg ccaagaaggt    300
ggccgacgtc ggcaccttcc tgtggctcga ctcgatcgag aacatcggca agctggagcc    360
ggcgatccag gacgtgccct gcgagaacat cctgggcctg gtcatctacg acctgccggg    420
ccgcgactgc gcggccaagg cgtccaacgg cgagctcaag gtcggcgaga tcgaccgcta    480
caagaccgag tacatcgaca gtgagtgctg ccccccgggt tcgagaagag cgtggggaa    540
agggaaaggg ttgactgact gacacggcgc actgcagaga tcgtgtcgat cctcaaggca    600
cacccccaaca cggcgttcgc gctggtcatc gagccggact cgctgcccaa cctggtgacc    660
aacagcaact ggacacgtg ctcgagcagc gcgtcgggct accgcgaagg cgtggcttac    720
gccctcaaga acctcaacct gcccaacgtg atcatgtacc tcgacgccgg ccacggcggc    780
tggctcggct gggacgccaa cctgcagccc ggcgcgcagg agctagccaa ggcgtacaag    840
aacgccggct cgcccaagca gctccgcggc ttctcgacca acgtggccgg ctggaactcc    900
tggtgagctt ttttccattc catttcttct cctcttctc tcttcgctcc cactctgcag    960
ccccccctcc cccaagcacc cactggcgtt ccggcttgct gactcggcct cccttttccc   1020
gggcaccagg gatcaatcgc ccggcgaatt ctcccaggcg tccgacgcca agtacaacaa   1080
gtgccagaac gagaagatct acgtcagcac cttcggctcc gcgctccagt cggccggcat   1140
gcccaaccac gccatcgtcg acacgggccg caacggcgtc accggcctgc gcaaggagtg   1200
gggtgactgg tgcaacgtca acggtgcagg ttcgttgtct tcttttctc ctctttgtt   1260
tgcacgtcgt ggtccttttc aagcagccgt gtttggttgg gggagatgga ctccggctga   1320
tgttctgctt cctctctagg cttcggcgtg cgcccgacga gcaacacggg cctcgagctg   1380
gccgacgcgt tcgtgtgggt caagcccggc ggcgagtcgg acggcaccag cgacagctcg   1440
tcgccgcgct acgacagctt ctgcggcaag gacgacgcct tcaagccctc gcccgaggcc   1500
ggcacctgga acgaggccta cttcgagatg ctgctcaaga acgccgtgcc gtcgttctaa   1560
gacggtccag catcatccgg                                                1580
```

<210> SEQ ID NO 10
<211> LENGTH: 396
<212> TYPE: PRT
<213> ORGANISM: Thielavia terrestris

<400> SEQUENCE: 10

```
Met Lys Leu Ser Gln Ser Ala Ala Leu Ala Ala Leu Thr Ala Thr Ala
1               5                   10                  15

Leu Ala Ala Pro Ser Pro Thr Thr Pro Gln Ala Pro Arg Gln Ala Ser
```

```
                20                  25                  30
Ala Gly Cys Ser Ser Ala Val Thr Leu Asp Ala Ser Thr Asn Val Trp
                35                  40                  45
Lys Lys Tyr Thr Leu His Pro Asn Ser Tyr Tyr Arg Lys Glu Val Glu
 50                  55                  60
Ala Ala Val Ala Gln Ile Ser Asp Pro Asp Leu Ala Ala Lys Ala Lys
 65                  70                  75                  80
Lys Val Ala Asp Val Gly Thr Phe Leu Trp Leu Asp Ser Ile Glu Asn
                85                  90                  95
Ile Gly Lys Leu Glu Pro Ala Ile Gln Asp Val Pro Cys Glu Asn Ile
                100                 105                 110
Leu Gly Leu Val Ile Tyr Asp Leu Pro Gly Arg Asp Cys Ala Ala Lys
                115                 120                 125
Ala Ser Asn Gly Glu Leu Lys Val Gly Glu Ile Asp Arg Tyr Lys Thr
                130                 135                 140
Glu Tyr Ile Asp Lys Ile Val Ser Ile Leu Lys Ala His Pro Asn Thr
145                 150                 155                 160
Ala Phe Ala Leu Val Ile Glu Pro Asp Ser Leu Pro Asn Leu Val Thr
                165                 170                 175
Asn Ser Asn Leu Asp Thr Cys Ser Ser Ala Ser Gly Tyr Arg Glu
                180                 185                 190
Gly Val Ala Tyr Ala Leu Lys Asn Leu Asn Leu Pro Asn Val Ile Met
                195                 200                 205
Tyr Leu Asp Ala Gly His Gly Gly Trp Leu Gly Trp Asp Ala Asn Leu
                210                 215                 220
Gln Pro Gly Ala Gln Glu Leu Ala Lys Ala Tyr Lys Asn Ala Gly Ser
225                 230                 235                 240
Pro Lys Gln Leu Arg Gly Phe Ser Thr Asn Val Ala Gly Trp Asn Ser
                245                 250                 255
Trp Asp Gln Ser Pro Gly Glu Phe Ser Gln Ala Ser Ala Lys Tyr
                260                 265                 270
Asn Lys Cys Gln Asn Glu Lys Ile Tyr Val Ser Thr Phe Gly Ser Ala
                275                 280                 285
Leu Gln Ser Ala Gly Met Pro Asn His Ala Ile Val Asp Thr Gly Arg
                290                 295                 300
Asn Gly Val Thr Gly Leu Arg Lys Glu Trp Gly Asp Trp Cys Asn Val
305                 310                 315                 320
Asn Gly Ala Gly Phe Gly Val Arg Pro Thr Ser Asn Thr Gly Leu Glu
                325                 330                 335
Leu Ala Asp Ala Phe Val Trp Val Lys Pro Gly Gly Glu Ser Asp Gly
                340                 345                 350
Thr Ser Asp Ser Ser Ser Pro Arg Tyr Asp Ser Phe Cys Gly Lys Asp
                355                 360                 365
Asp Ala Phe Lys Pro Ser Pro Glu Ala Gly Thr Trp Asn Glu Ala Tyr
                370                 375                 380
Phe Glu Met Leu Leu Lys Asn Ala Val Pro Ser Phe
385                 390                 395

<210> SEQ ID NO 11
<211> LENGTH: 1203
<212> TYPE: DNA
<213> ORGANISM: Thielavia terrestris

<400> SEQUENCE: 11
```

-continued

```
atgaagtacc tcaacctcct cgcagctctc ctcgccgtcg ctcctctctc cctcgctgca    60
cccagcatcg aggccagaca gtcgaacgtc aacccataca tcggcaagag cccgctcgtt   120
attaggtcgt acgcccaaaa gcttgaggag accgtcagga ccttccagca acgtggcgac   180
cagctcaacg ctgcgaggac acggacggtg cagaacgttg cgactttcgc ctggatctcg   240
gataccaatg gtattggagc cattcgacct ctcatccaag atgctctcgc ccagcaggct   300
cgcactggac agaaggtcat cgtccaaatc gtcgtctaca acctcccaga tcgcgactgc   360
tctgccaacg cctcgactgg agagttcacc gtaggaaacg acggtctcaa ccgatacaag   420
aactttgtca acaccatcgc ccgcgagctc tcgactgctg acgctgacaa gctccacttt   480
gccctcctcc tcgaacccga cgcacttgcc aacctcgtca ccaacgcgaa tgccccagg   540 tgccgaatcg ccgctcccgc ttacaaggag ggtatcgcct acccctcgc caccttgtcc   600 aagcccaacg tcgacgtcta catcgacgcc gccaacggtg gctggctcgg ctggaacgac   660
aacctccgcc ccttcgccga actcttcaag gaagtctacg acctcgcccg ccgcatcaac   720
cccaacgcca aggtccgcgg cgtccccgtc aacgtctcca actacaacca gtaccgcgct   780
gaagtccgcg agcccttcac cgagtggaag gacgcctggg acgagagccg ctacgtcaac   840
gtcctcaccc gcacctcaa cgccgtcggc ttctccgcgc acttcatcgt tgaccaggga   900
cgcggtggca agggcggtat caggacggag tggggccagt ggtgcaacgt taggaacgct   960
gggttcggta tcaggcctac tgcggatcag ggcgtgctcc agaacccgaa tgtggatgcg  1020
attgtgtggg ttaagccggg tggagagtcg gatggcacga gtgatttgaa ctcgaacagg  1080
tatgatccta cgtgcaggag tccggtggcg catgttcccg ctcctgaggc tggccagtgg  1140
ttcaacgagt atgttgttaa cctcgttttg aacgctaacc ccctcttga gcctacctgg  1200 taa                                                                1203
```

<210> SEQ ID NO 12
<211> LENGTH: 400
<212> TYPE: PRT
<213> ORGANISM: Thielavia terrestris

<400> SEQUENCE: 12

```
Met Lys Tyr Leu Asn Leu Leu Ala Ala Leu Ala Val Ala Pro Leu
1               5                   10                  15

Ser Leu Ala Ala Pro Ser Ile Glu Ala Arg Gln Ser Asn Val Asn Pro
            20                  25                  30

Tyr Ile Gly Lys Ser Pro Leu Val Ile Arg Ser Tyr Ala Gln Lys Leu
        35                  40                  45

Glu Glu Thr Val Arg Thr Phe Gln Gln Arg Gly Asp Gln Leu Asn Ala
    50                  55                  60

Ala Arg Thr Arg Thr Val Gln Asn Val Ala Thr Phe Ala Trp Ile Ser
65                  70                  75                  80

Asp Thr Asn Gly Ile Gly Ala Ile Arg Pro Leu Ile Gln Asp Ala Leu
                85                  90                  95

Ala Gln Gln Ala Arg Thr Gly Gln Lys Val Ile Val Gln Ile Val Val
            100                 105                 110

Tyr Asn Leu Pro Asp Arg Asp Cys Ser Ala Asn Ala Ser Thr Gly Glu
        115                 120                 125

Phe Thr Val Gly Asn Asp Gly Leu Asn Arg Tyr Lys Asn Phe Val Asn
    130                 135                 140

Thr Ile Ala Arg Glu Leu Ser Thr Ala Asp Ala Asp Lys Leu His Phe
145                 150                 155                 160
```

Ala Leu Leu Leu Glu Pro Asp Ala Leu Ala Asn Leu Val Thr Asn Ala
            165                 170                 175

Asn Ala Pro Arg Cys Arg Ile Ala Ala Pro Ala Tyr Lys Glu Gly Ile
        180                 185                 190

Ala Tyr Thr Leu Ala Thr Leu Ser Lys Pro Asn Val Asp Val Tyr Ile
    195                 200                 205

Asp Ala Ala Asn Gly Gly Trp Leu Gly Trp Asn Asp Asn Leu Arg Pro
210                 215                 220

Phe Ala Glu Leu Phe Lys Glu Val Tyr Asp Leu Ala Arg Arg Ile Asn
225                 230                 235                 240

Pro Asn Ala Lys Val Arg Gly Val Pro Val Asn Val Ser Asn Tyr Asn
                245                 250                 255

Gln Tyr Arg Ala Glu Val Arg Glu Pro Phe Thr Glu Trp Lys Asp Ala
            260                 265                 270

Trp Asp Glu Ser Arg Tyr Val Asn Val Leu Thr Pro His Leu Asn Ala
        275                 280                 285

Val Gly Phe Ser Ala His Phe Ile Val Asp Gln Gly Arg Gly Gly Lys
    290                 295                 300

Gly Gly Ile Arg Thr Glu Trp Gly Gln Trp Cys Asn Val Arg Asn Ala
305                 310                 315                 320

Gly Phe Gly Ile Arg Pro Thr Ala Asp Gln Gly Val Leu Gln Asn Pro
                325                 330                 335

Asn Val Asp Ala Ile Val Trp Val Lys Pro Gly Gly Glu Ser Asp Gly
            340                 345                 350

Thr Ser Asp Leu Asn Ser Asn Arg Tyr Asp Pro Thr Cys Arg Ser Pro
        355                 360                 365

Val Ala His Val Pro Ala Pro Glu Ala Gly Gln Trp Phe Asn Glu Tyr
    370                 375                 380

Val Val Asn Leu Val Leu Asn Ala Asn Pro Pro Leu Glu Pro Thr Trp
385                 390                 395                 400

<210> SEQ ID NO 13
<211> LENGTH: 1501
<212> TYPE: DNA
<213> ORGANISM: Thielavia terrestris

<400> SEQUENCE: 13
gccgttgtca agatgggcca agaagacgctg cacggattcg ccgccacggc tttggccgtt      60
ctcccctttg tgaaggctca gcagcccggc aacttcacgc cggaggtgca cccgcaactg     120
ccaacgtgga agtgcacgac cgccggcggc tgcgttcagc aggacacttc ggtggtgctc     180
gactggaact accgttggat ccacaatgcc gacggcaccg cctcgtgcac gacgtccagc     240
ggggtcgacc acacgctgtg tccagatgag gcgacctgcg cgaagaactg cttcgtggaa     300
ggcgtcaact acacgagcag cggtgtcacc acatccggca gttcgctgac gatgaggcag     360
tatttcaagg ggagcaacgg gcagaccaac agcgtttcgc ctcgtctcta cctgctcggc     420
tcggatggaa actacgtaat gctcaagctg ctcggccagg agctgagctt cgatgtcgat     480
ctctccacgc tccctgcgg cgagaacggc gcgctgtacc tgtccagat ggacgcgacc     540 ggtggcagga accagtacaa caccggcggt gccaactacg gctcgggcta ctgtgacgcc     600
cagtgtcccg tgcagacgtg gatgaacggc acgctgaaca ccaacgggca gggctactgc     660
tgcaacgaga tggacatcct cgaggccaac tcccgcgcca acgcgatgac acctcacccc     720
tgcgccaacg gcagctgcga caagagcggg tgcggactca acccctacgc cgagggctac     780

```
aagagctact acggaccggg cctcacggtt gacacgtcga agcccttcac catcattacc    840
cgcttcatca ccgacgacgg cacgaccagc ggcaccctca accagatcca gcggatctat    900
gtgcagaatg caagacggt cgcgtcggct gcgtccggag gcgacatcat cacggcatcc     960
ggctgcacct cggcccaggc gttcggcggg ctggccaaca tgggcgcggc gcttggacgg   1020
ggcatggtgc tgaccttcag catctggaac gacgctgggg gctacatgaa ctggctcgac   1080
agcggcaaca acgcccgtg cagcagcacc gagggcaacc cgtccaacat cctgccaac    1140
tacccggaca cccacgtggt cttctccaac atccgctggg gagacatcgg ctcgacggtc   1200
caggtctcgg gaggcggcaa cggcggctcg accaccacca cgtcgaccac cacgctgagg   1260
acctcgacca cgaccaccac caccgccccg acggccactg ccacgcactg gggacaatgc   1320
ggcggaatcg gggtacgtca accgcctcct gcattctgtt gaggaagtta actaacgtgg   1380
cctacgcagt ggactggacc gaccgtctgc gaatcgccgt acgcatgcaa ggagctgaac   1440
ccctggtact accagtgcct ctaaagtatt gcagtgaagc catactccgt gctcggcatg   1500
g                                                                    1501
```

<210> SEQ ID NO 14
<211> LENGTH: 464
<212> TYPE: PRT
<213> ORGANISM: Thielavia terrestris

<400> SEQUENCE: 14

```
Met Gly Gln Lys Thr Leu His Gly Phe Ala Ala Thr Ala Leu Ala Val
1               5                   10                  15

Leu Pro Phe Val Lys Ala Gln Gln Pro Gly Asn Phe Thr Pro Glu Val
            20                  25                  30

His Pro Gln Leu Pro Thr Trp Lys Cys Thr Thr Ala Gly Gly Cys Val
        35                  40                  45

Gln Gln Asp Thr Ser Val Val Leu Asp Trp Asn Tyr Arg Trp Ile His
    50                  55                  60

Asn Ala Asp Gly Thr Ala Ser Cys Thr Thr Ser Ser Gly Val Asp His
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Thr Thr Ser Gly Ser Ser Leu
            100                 105                 110

Thr Met Arg Gln Tyr Phe Lys Gly Ser Asn Gly Gln Thr Asn Ser Val
        115                 120                 125

Ser Pro Arg Leu Tyr Leu Leu Gly Ser Asp Gly Asn Tyr Val Met Leu
    130                 135                 140

Lys Leu Leu Gly Gln Glu Leu Ser Phe Asp Val Asp Leu Ser Thr Leu
145                 150                 155                 160

Pro Cys Gly Glu Asn Gly Ala Leu Tyr Leu Ser Glu Met Asp Ala Thr
                165                 170                 175

Gly Gly Arg Asn Gln Tyr Asn Thr Gly Gly Ala Asn Tyr Gly Ser Gly
            180                 185                 190

Tyr Cys Asp Ala Gln Cys Pro Val Gln Thr Trp Met Asn Gly Thr Leu
        195                 200                 205

Asn Thr Asn Gly Gln Gly Tyr Cys Cys Asn Glu Met Asp Ile Leu Glu
    210                 215                 220

Ala Asn Ser Arg Ala Asn Ala Met Thr Pro His Pro Cys Ala Asn Gly
225                 230                 235                 240
```

```
Ser Cys Asp Lys Ser Gly Cys Gly Leu Asn Pro Tyr Ala Glu Gly Tyr
            245                 250                 255
Lys Ser Tyr Tyr Gly Pro Gly Leu Thr Val Asp Ser Lys Pro Phe
            260                 265                 270
Thr Ile Ile Thr Arg Phe Ile Thr Asp Asp Gly Thr Thr Ser Gly Thr
            275                 280                 285
Leu Asn Gln Ile Gln Arg Ile Tyr Val Gln Asn Gly Lys Thr Val Ala
            290                 295                 300
Ser Ala Ala Ser Gly Gly Asp Ile Ile Thr Ala Ser Gly Cys Thr Ser
305                 310                 315                 320
Ala Gln Ala Phe Gly Gly Leu Ala Asn Met Gly Ala Ala Leu Gly Arg
            325                 330                 335
Gly Met Val Leu Thr Phe Ser Ile Trp Asn Asp Ala Gly Gly Tyr Met
            340                 345                 350
Asn Trp Leu Asp Ser Gly Asn Asn Gly Pro Cys Ser Ser Thr Glu Gly
            355                 360                 365
Asn Pro Ser Asn Ile Leu Ala Asn Tyr Pro Asp Thr His Val Val Phe
            370                 375                 380
Ser Asn Ile Arg Trp Gly Asp Ile Gly Ser Thr Val Gln Val Ser Gly
385                 390                 395                 400
Gly Gly Asn Gly Gly Ser Thr Thr Thr Ser Thr Thr Thr Leu Arg
            405                 410                 415
Thr Ser Thr Thr Thr Thr Thr Thr Ala Pro Thr Ala Thr Ala Thr His
            420                 425                 430
Trp Gly Gln Cys Gly Gly Ile Gly Trp Thr Gly Pro Thr Val Cys Glu
            435                 440                 445
Ser Pro Tyr Ala Cys Lys Glu Leu Asn Pro Trp Tyr Tyr Gln Cys Leu
450                 455                 460
```

<210> SEQ ID NO 15
<211> LENGTH: 1368
<212> TYPE: DNA
<213> ORGANISM: Thielavia terrestris

<400> SEQUENCE: 15

```
accgatccgc tcgaagatgg cgcccaagtc tacagttctg gccgcctggc tgctctcctc      60
gctggccgcg gcccagcaga tcggcaaagc cgtgcccgag gtccacccca aactgacaac     120
gcagaagtgc actctccgcg gcgggtgcaa gcctgtccgc acctcggtcg tgctcgactc     180
gtccgcgcgc tcgctgcaca aggtcgggga ccccaacacc agctgcagcg tcggcggcga     240
cctgtgctcg gacgcgaagt cgtgcggcaa gaactgcgcg ctcgagggcg tcgactacgc     300
ggcccacggc gtggcgacca agggcgacgc cctcacgctg caccagtggc tcaaggggggc     360
cgacggcacc tacaggaccg tctcgccgcg cgtatacctc ctgggcgagg acgggaagaa     420
ctacgaggac ttcaagctgc tcaacgccga gctcagcttc gacgtcgacg tgtcccagct     480
cgtctgcggc atgaacggcg ccctgtactt ctccgagatg gagatggacg gcggccgcag     540
cccgctgaac ccggcggggcg ccacgtacgg cacgggctac tgcgacgcgc agtgccccaa     600
gttggacttt atcaacggcg aggtatttct tctctcttct gttttttcttt tccatcgctt     660
tttctgaccg gaatccgccc tcttagctca acaccaacca cacgtacggg gcgtgctgca     720
acgagatgga catctgggag gccaacgcgc tggcgcaggc gctcacgccg cacccgtgca     780
acgcgacgcg ggtgtacaag tgcgacacgg cggacgagtg cgggcagccg gtgggcgtgt     840
```

-continued

```
gcgacgaatg ggggtgctcg tacaacccgt ccaacttcgg ggtcaaggac tactacgggc    900
gcaacctgac ggtggacacg aaccgcaagt tcacggtgac gacgcagttc gtgacgtcca    960
acgggcgggc ggacggcgag ctgaccgaga tccggcggct gtacgtgcag gacggcgtgg   1020
tgatccagaa ccacgcggtc acggcgggcg gggcgacgta cgacagcatc acggacggct   1080
tctgcaacgc gacggccacc tggacgcagc agcggggcgg gctcgcgcgc atgggcgagg   1140
ccatcggccg cggcatggtg ctcatcttca gcctgtgggt tgacaacggc ggcttcatga   1200
actggctcga cagcggcaac gccgggccct gcaacgccac cgagggcgac ccggccctga   1260
tcctgcagca gcaccggac gccagcgtca ccttctccaa catccgatgg ggcgagatcg   1320
gcagcacgta caagagcgag tgcagccact agagtagagc ttgtaatt              1368
```

<210> SEQ ID NO 16
<211> LENGTH: 423
<212> TYPE: PRT
<213> ORGANISM: Thielavia terrestris

<400> SEQUENCE: 16

```
Met Ala Pro Lys Ser Thr Val Leu Ala Ala Trp Leu Leu Ser Ser Leu
1               5                   10                  15

Ala Ala Ala Gln Gln Ile Gly Lys Ala Val Pro Glu Val His Pro Lys
                20                  25                  30

Leu Thr Thr Gln Lys Cys Thr Leu Arg Gly Gly Cys Lys Pro Val Arg
            35                  40                  45

Thr Ser Val Val Leu Asp Ser Ser Ala Arg Ser Leu His Lys Val Gly
        50                  55                  60

Asp Pro Asn Thr Ser Cys Ser Val Gly Gly Asp Leu Cys Ser Asp Ala
65                  70                  75                  80

Lys Ser Cys Gly Lys Asn Cys Ala Leu Glu Gly Val Asp Tyr Ala Ala
                85                  90                  95

His Gly Val Ala Thr Lys Gly Asp Ala Leu Thr Leu His Gln Trp Leu
            100                 105                 110

Lys Gly Ala Asp Gly Thr Tyr Arg Thr Val Ser Pro Arg Val Tyr Leu
        115                 120                 125

Leu Gly Glu Asp Gly Lys Asn Tyr Glu Asp Phe Lys Leu Leu Asn Ala
    130                 135                 140

Glu Leu Ser Phe Asp Val Asp Val Ser Gln Leu Val Cys Gly Met Asn
145                 150                 155                 160

Gly Ala Leu Tyr Phe Ser Glu Met Glu Met Asp Gly Gly Arg Ser Pro
                165                 170                 175

Leu Asn Pro Ala Gly Ala Thr Tyr Gly Thr Gly Tyr Cys Asp Ala Gln
            180                 185                 190

Cys Pro Lys Leu Asp Phe Ile Asn Gly Glu Leu Asn Thr Asn His Thr
        195                 200                 205

Tyr Gly Ala Cys Cys Asn Glu Met Asp Ile Trp Glu Ala Asn Ala Leu
    210                 215                 220

Ala Gln Ala Leu Thr Pro His Pro Cys Asn Ala Thr Arg Val Tyr Lys
225                 230                 235                 240

Cys Asp Thr Ala Asp Glu Cys Gly Gln Pro Val Gly Val Cys Asp Glu
                245                 250                 255

Trp Gly Cys Ser Tyr Asn Pro Ser Asn Phe Gly Val Lys Asp Tyr Tyr
            260                 265                 270

Gly Arg Asn Leu Thr Val Asp Thr Asn Arg Lys Phe Thr Val Thr Thr
        275                 280                 285
```

```
Gln Phe Val Thr Ser Asn Gly Arg Ala Asp Gly Glu Leu Thr Glu Ile
    290                 295                 300

Arg Arg Leu Tyr Val Gln Asp Gly Val Val Ile Gln Asn His Ala Val
305                 310                 315                 320

Thr Ala Gly Gly Ala Thr Tyr Asp Ser Ile Thr Asp Gly Phe Cys Asn
                325                 330                 335

Ala Thr Ala Thr Trp Thr Gln Gln Arg Gly Gly Leu Ala Arg Met Gly
            340                 345                 350

Glu Ala Ile Gly Arg Gly Met Val Leu Ile Phe Ser Leu Trp Val Asp
        355                 360                 365

Asn Gly Gly Phe Met Asn Trp Leu Asp Ser Gly Asn Ala Gly Pro Cys
    370                 375                 380

Asn Ala Thr Glu Gly Asp Pro Ala Leu Ile Leu Gln Gln His Pro Asp
385                 390                 395                 400

Ala Ser Val Thr Phe Ser Asn Ile Arg Trp Gly Glu Ile Gly Ser Thr
                405                 410                 415

Tyr Lys Ser Glu Cys Ser His
            420
```

```
<210> SEQ ID NO 17
<211> LENGTH: 1000
<212> TYPE: DNA
<213> ORGANISM: Thielavia terrestris

<400> SEQUENCE: 17
atgaccctac ggctccctgt catcagcctg ctggcctcgc tggcagcagg cgccgtcgtc    60
gtcccacggg cggagtttca ccccctctc ccgacttgga aatgcacgac ctccggggggc   120
tgcgtgcagc agaacaccag cgtcgtcctg accgtgact cgaagtacgc cgcacacagc    180
gccggctcgc ggacggaatc ggattacgcg gcaatgggag tgtccacttc gggcaatgcc    240
gtgacgctgt accactacgt caagaccaac ggcaccctcg tccccgcttc gccgcgcatc    300
tacctcctgg gcgcggacgg caagtacgtg cttatggacc tcctcaacca ggagctgtcg    360
gtggacgtcg acttctcggc gctgccgtgc ggcgagaacg gggccttcta cctgtccgag    420
atggcggcgg acgggcgggg cgacgcgggg gcgggcgacg ggtactgcga cgcgcagtgc    480
cagggctact gctgcaacga gatggacatc ctcgaggcca actcgatggc gacgccatg     540
acgccgcacc cgtgcaaggg caacaactgc gaccgcagcg gctgcggcta caacccgtac    600
gccagcggcc agcgcggctt ctacgggccc ggcaagacgg tcgacacgag caagcccttc    660
accgtcgtca cgcagttcgc cgccagcggc ggcaagctga cccagatcac ccgcaagtac    720
atccagaacg gccgggagat cggcggcggc ggcaccatct ccagctgcgg ctccgagtct    780
tcgacgggcg gcctgaccgg catgggcgag gcgctggggc gcggaatggt gctggccatg    840
agcatctgga cgacgcggc ccaggagatg gcatggctcg atgccggcaa caacggccct    900
tgcgccagtg gccagggcag cccgtccgtc attcagtcgc agcatcccga cacccacgtc    960
gtcttctcca acatcaggtg gggcgacatc gggtctacca                        1000
```

```
<210> SEQ ID NO 18
<211> LENGTH: 336
<212> TYPE: PRT
<213> ORGANISM: Thielavia terrestris

<400> SEQUENCE: 18

Met Thr Leu Arg Leu Pro Val Ile Ser Leu Leu Ala Ser Leu Ala Ala
```

```
1               5                   10                  15

Gly Ala Val Val Val Pro Arg Ala Glu Phe His Pro Pro Leu Pro Thr
            20                  25                  30

Trp Lys Cys Thr Thr Ser Gly Gly Cys Val Gln Gln Asn Thr Ser Val
        35                  40                  45

Val Leu Asp Arg Asp Ser Lys Tyr Ala Ala His Ser Ala Gly Ser Arg
    50                  55                  60

Thr Glu Ser Asp Tyr Ala Ala Met Gly Val Ser Thr Ser Gly Asn Ala
65                  70                  75                  80

Val Thr Leu Tyr His Tyr Val Lys Thr Asn Gly Thr Leu Val Pro Ala
                85                  90                  95

Ser Pro Arg Ile Tyr Leu Leu Gly Ala Asp Gly Lys Tyr Val Leu Met
            100                 105                 110

Asp Leu Leu Asn Gln Glu Leu Ser Val Asp Val Asp Phe Ser Ala Leu
        115                 120                 125

Pro Cys Gly Glu Asn Gly Ala Phe Tyr Leu Ser Glu Met Ala Ala Asp
    130                 135                 140

Gly Arg Gly Asp Ala Gly Ala Gly Asp Gly Tyr Cys Asp Ala Gln Cys
145                 150                 155                 160

Gln Gly Tyr Cys Cys Asn Glu Met Asp Ile Leu Glu Ala Asn Ser Met
                165                 170                 175

Ala Thr Ala Met Thr Pro His Pro Cys Lys Gly Asn Asn Cys Asp Arg
            180                 185                 190

Ser Gly Cys Gly Tyr Asn Pro Tyr Ala Ser Gly Gln Arg Gly Phe Tyr
        195                 200                 205

Gly Pro Gly Lys Thr Val Asp Thr Ser Lys Pro Phe Thr Val Val Thr
    210                 215                 220

Gln Phe Ala Ala Ser Gly Gly Lys Leu Thr Gln Ile Thr Arg Lys Tyr
225                 230                 235                 240

Ile Gln Asn Gly Arg Glu Ile Gly Gly Gly Gly Thr Ile Ser Ser Cys
                245                 250                 255

Gly Ser Glu Ser Ser Thr Gly Gly Leu Thr Gly Met Gly Glu Ala Leu
            260                 265                 270

Gly Arg Gly Met Val Leu Ala Met Ser Ile Trp Asn Asp Ala Ala Gln
        275                 280                 285

Glu Met Ala Trp Leu Asp Ala Gly Asn Asn Gly Pro Cys Ala Ser Gly
    290                 295                 300

Gln Gly Ser Pro Ser Val Ile Gln Ser Gln His Pro Asp Thr His Val
305                 310                 315                 320

Val Phe Ser Asn Ile Arg Trp Gly Asp Ile Gly Ser Thr Thr Lys Asn
                325                 330                 335
```

<210> SEQ ID NO 19
<211> LENGTH: 1480
<212> TYPE: DNA
<213> ORGANISM: Cladorrhinum foecundissimum

<400> SEQUENCE: 19

```
gatccgaatt cctcctctcg ttctttagtc acagaccaga catctgccca cgatggttca      60
caagttcgcc ctcctcaccg gcctcgccgc ctccctcgca tctgcccagc agatcggcac     120
cgtcgtcccc gagtctcacc ccaagcttcc caccaagcgc tgcactctcg ccggtggctg     180
ccagaccgtc gacacctcca tcgtcatcga cgccttccag cgtcccctcc acaagatcgg     240
cgacccttcc actccttgcg tcgtcggcgg ccctctctgc cccgacgcca agtcctgcgc     300
```

-continued

```
tgagaactgc gcgctcgagg gtgtcgacta tgcctcctgg ggcatcaaga ccgagggcga      360
cgccctaact ctcaaccagt ggatgcccga cccggcgaac cctggccagt acaagacgac      420
tactccccgt acttaccttg ttgctgagga cggcaagaac tacgaggatg tgaagctcct      480
ggctaaggag atctcgtttg atgccgatgt cagcaacctt ccctgcggca tgaacggtgc      540
tttctacttg tctgagatgt tgatggatgg tggacgtggc gaccctcaacc ctgctggtgc      600
cgagtatggt accggttact gtgatgcgca gtgcttcaag ttggatttca tcaacggcga      660
ggccaacatc gaccaaaagc acggcgcctg ctgcaacgaa atggacattt cgaatccaa      720
ctcgcgcgcc aagaccttcg tcccccaccc ctgcaacatc acgcaggtct acaagtgcga      780
aggcgaagac gagtgcggcc agcccgtcgg cgtgtgcgac aagtgggggt gcggcttcaa      840
cgagtacaaa tggggcgtcg agtccttcta cggccgggc tcgcagttcg ccatcgactc      900
ctccaagaag ttcaccgtca ccacgcagtt cctgaccgac aacggcaagg aggacggcgt      960
cctcgtcgag atccgcgct tgtggcacca ggatggcaag ctgatcaaga acaccgctat     1020
ccaggttgag gagaactaca gcacggactc ggtgagcacc gagttctgcg agaagactgc     1080
ttctttcacc atgcagcgcg gtggtctcaa ggcgatgggc gaggctatcg gtcgtggtat     1140
ggtgctggtt ttcagcatct gggcggatga ttcgggtttt atgaactggt tggatgcgga     1200
gggtaatggc ccttgcagcg cgactgaggg cgatccgaag gagattgtca gaataagcc     1260
ggatgctagg gttacgttct caaacattag gattggtgag gttggtagca cgtatgctcc     1320
gggtgggaag tgcggtgtta agagcagggt tgctaggggg cttactgctt cttaaggggg     1380
gtgtgaagag aggaggaggt gttgttgggg gttggagatg ataattgggc gagatggtgt     1440
agagcgggtt ggttggatat gaatacgttg aattggatgt                           1480
```

<210> SEQ ID NO 20
<211> LENGTH: 440
<212> TYPE: PRT
<213> ORGANISM: Cladorrhinum foecundissimum

<400> SEQUENCE: 20

```
Met Val His Lys Phe Ala Leu Leu Thr Gly Leu Ala Ala Ser Leu Ala
1               5                   10                  15

Ser Ala Gln Gln Ile Gly Thr Val Val Pro Glu Ser His Pro Lys Leu
            20                  25                  30

Pro Thr Lys Arg Cys Thr Leu Ala Gly Gly Cys Gln Thr Val Asp Thr
        35                  40                  45

Ser Ile Val Ile Asp Ala Phe Gln Arg Pro Leu His Lys Ile Gly Asp
    50                  55                  60

Pro Ser Thr Pro Cys Val Val Gly Gly Pro Leu Cys Pro Asp Ala Lys
65                  70                  75                  80

Ser Cys Ala Glu Asn Cys Ala Leu Glu Gly Val Asp Tyr Ala Ser Trp
                85                  90                  95

Gly Ile Lys Thr Glu Gly Asp Ala Leu Thr Leu Asn Gln Trp Met Pro
            100                 105                 110

Asp Pro Ala Asn Pro Gly Gln Tyr Lys Thr Thr Pro Arg Thr Tyr
        115                 120                 125

Leu Val Ala Glu Asp Gly Lys Asn Tyr Glu Asp Val Lys Leu Leu Ala
    130                 135                 140

Lys Glu Ile Ser Phe Asp Ala Asp Val Ser Asn Leu Pro Cys Gly Met
145                 150                 155                 160
```

```
Asn Gly Ala Phe Tyr Leu Ser Glu Met Leu Met Asp Gly Gly Arg Gly
            165                 170                 175

Asp Leu Asn Pro Ala Gly Ala Gly Tyr Gly Thr Gly Tyr Cys Asp Ala
        180                 185                 190

Gln Cys Phe Lys Leu Asp Phe Ile Asn Gly Glu Ala Asn Ile Asp Gln
    195                 200                 205

Lys His Gly Ala Cys Cys Asn Glu Met Asp Ile Phe Glu Ser Asn Ser
210                 215                 220

Arg Ala Lys Thr Phe Val Pro His Pro Cys Asn Ile Thr Gln Val Tyr
225                 230                 235                 240

Lys Cys Glu Gly Glu Asp Glu Cys Gly Gln Pro Val Gly Val Cys Asp
            245                 250                 255

Lys Trp Gly Cys Gly Phe Asn Glu Tyr Lys Trp Gly Val Glu Ser Phe
        260                 265                 270

Tyr Gly Arg Gly Ser Gln Phe Ala Ile Asp Ser Ser Lys Lys Phe Thr
    275                 280                 285

Val Thr Thr Gln Phe Leu Thr Asp Asn Gly Lys Glu Asp Gly Val Leu
290                 295                 300

Val Glu Ile Arg Arg Leu Trp His Gln Asp Gly Lys Leu Ile Lys Asn
305                 310                 315                 320

Thr Ala Ile Gln Val Glu Glu Asn Tyr Ser Thr Asp Ser Val Ser Thr
            325                 330                 335

Glu Phe Cys Glu Lys Thr Ala Ser Phe Thr Met Gln Arg Gly Gly Leu
        340                 345                 350

Lys Ala Met Gly Glu Ala Ile Gly Arg Gly Met Val Leu Val Phe Ser
    355                 360                 365

Ile Trp Ala Asp Asp Ser Gly Phe Met Asn Trp Leu Asp Ala Glu Gly
370                 375                 380

Asn Gly Pro Cys Ser Ala Thr Glu Gly Asp Pro Lys Glu Ile Val Lys
385                 390                 395                 400

Asn Lys Pro Asp Ala Arg Val Thr Phe Ser Asn Ile Arg Ile Gly Glu
            405                 410                 415

Val Gly Ser Thr Tyr Ala Pro Gly Gly Lys Cys Gly Val Lys Ser Arg
        420                 425                 430

Val Ala Arg Gly Leu Thr Ala Ser
    435                 440

<210> SEQ ID NO 21
<211> LENGTH: 1380
<212> TYPE: DNA
<213> ORGANISM: Trichoderma reesei

<400> SEQUENCE: 21
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccgggggggtg cgtggcccag gacacctcgg tggtccttga ctggaactac     180
cgctggatgc acgacgcaaa ctacaactcg tgcaccgtca acggcggcgt caacaccacg     240
ctctgccctg acgaggcgac ctgtggcaag aactgcttca tcgagggcgt cgactacgcc     300
gcctcgggcg tcacgacctc gggcagcagc ctcaccatga accagtacat gcccagcagc     360
tctggcggct acagcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
```

-continued

```
tataacacgg ccggtgccaa ctacgggagc ggctactgcg atgctcagtg ccccgtccag    600
acatggagga acggcaccct caacactagc caccagggct tctgctgcaa cgagatggat    660
atcctggagg gcaactcgag ggcgaatgcc ttgaccccctc actcttgcac ggccacggcc    720
tgcgactctg ccggttgcgg cttcaacccc tatggcagcg gctacaaaag ctactacggc    780
cccggagata ccgttgacac ctccaagacc ttcaccatca tcacccagtt caacacggac    840
aacggctcgc cctcgggcaa ccttgtgagc atcacccgca agtaccagca aaacggcgtc    900
gacatcccca gcgcccagcc cggcggcgac accatctcgt cctgcccgtc cgcctcagcc    960
tacgcgggcc tcgccaccat gggcaaggcc ctgagcagcg gcatggtgct cgtgttcagc    1020
atttggaacg acaacagcca gtacatgaac tggctcgaca gcggcaacgc cggcccctgc    1080
agcagcaccg agggcaaccc atccaacatc ctggccaaca ccccaacac gcacgtcgtc    1140
ttctccaaca tccgctgggg agacattggg tctactacga actcgactgc gccccgccc    1200
ccgcctgcgt ccagcacgac gttttcgact acacggagga gctcgacgac ttcgagcagc    1260
ccgagctgca cgcagactca ctgggggcag tgcggtggca ttgggtacag cgggtgcaag    1320
acgtgcacgt cgggcactac gtgccagtat agcaacgact actactcgca atgcctttag    1380
```

<210> SEQ ID NO 22
<211> LENGTH: 459
<212> TYPE: PRT
<213> ORGANISM: Trichoderma reesei

<400> SEQUENCE: 22

```
Met Ala Pro Ser Val Thr Leu Pro Leu Thr Thr Ala Ile Leu Ala Ile
1               5                   10                  15
Ala Arg Leu Val Ala Ala Gln Gln Pro Gly Thr Ser Thr Pro Glu Val
                20                  25                  30
His Pro Lys Leu Thr Thr Tyr Lys Cys Thr Lys Ser Gly Gly Cys Val
            35                  40                  45
Ala Gln Asp Thr Ser Val Val Leu Asp Trp Asn Tyr Arg Trp Met His
        50                  55                  60
Asp Ala Asn Tyr Asn Ser Cys Thr Val Asn Gly Gly Val Asn Thr Thr
65                  70                  75                  80
Leu Cys Pro Asp Glu Ala Thr Cys Gly Lys Asn Cys Phe Ile Glu Gly
                85                  90                  95
Val Asp Tyr Ala Ala Ser Gly Val Thr Thr Ser Gly Ser Ser Leu Thr
            100                 105                 110
Met Asn Gln Tyr Met Pro Ser Ser Gly Gly Tyr Ser Ser Val Ser
        115                 120                 125
Pro Arg Leu Tyr Leu Leu Asp Ser Asp Gly Glu Tyr Val Met Leu Lys
    130                 135                 140
Leu Asn Gly Gln Glu Leu Ser Phe Asp Val Asp Leu Ser Ala Leu Pro
145                 150                 155                 160
Cys Gly Glu Asn Gly Ser Leu Tyr Leu Ser Gln Met Asp Glu Asn Gly
                165                 170                 175
Gly Ala Asn Gln Tyr Asn Thr Ala Gly Ala Asn Tyr Gly Ser Gly Tyr
            180                 185                 190
Cys Asp Ala Gln Cys Pro Val Gln Thr Trp Arg Asn Gly Thr Leu Asn
        195                 200                 205
Thr Ser His Gln Gly Phe Cys Cys Asn Glu Met Asp Ile Leu Glu Gly
    210                 215                 220
```

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
            245                 250                 255

Ser Tyr Tyr Gly Pro Gly Asp Thr Val Asp Thr Ser Lys Thr Phe Thr
        260                 265                 270

Ile Ile Thr Gln Phe Asn Thr Asp Asn Gly Ser Pro Ser Gly Asn Leu
    275                 280                 285

Val Ser Ile Thr Arg Lys Tyr Gln Gln Asn Gly Val Asp Ile Pro Ser
290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
            325                 330                 335

Leu Val Phe Ser Ile Trp Asn Asp Asn Ser Gln Tyr Met Asn Trp Leu
        340                 345                 350

Asp Ser Gly Asn Ala Gly Pro Cys Ser Ser Thr Glu Gly Asn Pro Ser
    355                 360                 365

Asn Ile Leu Ala Asn Asn Pro Asn Thr His Val Val Phe Ser Asn Ile
370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
            405                 410                 415

Thr Ser Ser Ser Pro Ser Cys Thr Gln Thr His Trp Gly Gln Cys Gly
        420                 425                 430

Gly Ile Gly Tyr Ser Gly Cys Lys Thr Cys Thr Ser Gly Thr Thr Cys
    435                 440                 445

Gln Tyr Ser Asn Asp Tyr Tyr Ser Gln Cys Leu
450                 455

<210> SEQ ID NO 23
<211> LENGTH: 1545
<212> TYPE: DNA
<213> ORGANISM: Trichoderma reesei

<400> SEQUENCE: 23
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct cgcgcaagaa ctgctgtctg acggtgccg cctacgcgtc cacgtacgga     300
gttaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtgcggctt gaacggagct     480
ctctacttcg tgtccatgga cgcggatggt ggcgtgagca agtatcccac caacaccgct     540
ggcgccaagt acggcacggg gtactgtgac agccagtgtc ccgcgatct gaagttcatc     600 aatggccagg ccaacgttga gggctgggag ccgtcatcca caacgcgaa cacgggcatt     660 ggaggacacg gaagctgctg ctctgagatg gatatctggg aggccaactc catctccgag     720
gctcttaccc cccaccttg cacgactgtc ggccaggaga tctgcgaggg tgatgggtgc     780

```
ggcggaactt actccgataa cagatatggc ggcacttgcg atcccgatgg ctgcgactgg    840
aacccatacc gcctgggcaa caccagcttc tacggccctg gctcaagctt taccctcgat    900
accaccaaga aattgaccgt tgtcacccag ttcgagacgt cgggtgccat caaccgatac    960
tatgtccaga atggcgtcac tttccagcag cccaacgccg agcttggtag ttactctggc   1020
aacgagctca cgatgatta ctgcacagct gaggaggcag aattcggcgg atcctctttc   1080
tcagacaagg gcggcctgac tcagttcaag aaggctacct ctggcggcat ggttctggtc   1140
atgagtctgt gggatgatta ctacgccaac atgctgtggc tggactccac ctacccgaca   1200
aacgagacct cctccacacc cggtgccgtg cgcggaagct gctccaccag ctccggtgtc   1260
cctgctcagg tcgaatctca gtctcccaac gccaaggtca ccttctccaa catcaagttc   1320
ggacccattg gcagcaccgg caaccctagc ggcggcaacc ctcccggcgg aaacccgcct   1380
ggcaccacca ccacccgccg cccagccact accactggaa gctctcccgg acctacccag   1440
tctcactacg gccagtgcgg cggtattggc tacagcggcc ccacggtctg cgccagcggc   1500
acaacttgcc aggtcctgaa cccttactac tctcagtgcc tgtaa                   1545
```

<210> SEQ ID NO 24
<211> LENGTH: 514
<212> TYPE: PRT
<213> ORGANISM: Trichoderma reesei

<400> SEQUENCE: 24

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240
```

```
Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 25
<211> LENGTH: 1611
<212> TYPE: DNA
<213> ORGANISM: Trichoderma reesei

<400> SEQUENCE: 25
atgattgtcg gcattctcac cacgctggct acgctggcca cactcgcagc tagtgtgcct    60
ctagaggagc ggcaagcttg ctcaagcgtc tggtaattat gtgaaccctc tcaagagacc   120
caaatactga gatatgtcaa ggggccaatg tggtggccag aattggtcgg gtccgacttg   180
ctgtgcttcc ggaagcacat gcgtctactc aacgactat tactcccagt gtcttcccgg   240
cgctgcaagc tcaagctcgt ccacgcgcgc cgcgtcgacg acttctcgag tatccccac    300 aacatcccgg tcgagctccg cgacgcctcc acctggttct actactacca gagtacctcc   360
agtcggatcg ggaaccgcta cgtattcagg caaccctttt gttggggtca ctccttgggc   420
caatgcatat tacgcctctg aagttagcag cctcgctatt cctagcttga ctggagccat   480
ggccactgct gcagcagctg tcgcaaaggt tccctctttt atgtggctgt aggtcctccc   540
```

-continued

```
ggaaccaagg caatctgtta ctgaaggctc atcattcact gcagagatac tcttgacaag    600
accoctctca tggagcaaac cttggccgac atccgcaccg ccaacaagaa tggcggtaac    660
tatgccggac agtttgtggt gtatgacttg ccggatcgcg attgcgctgc ccttgcctcg    720
aatggcgaat actctattgc cgatggtggc gtcgccaaat ataagaacta tatcgacacc    780
attcgtcaaa ttgtcgtgga atattccgat atccggaccc tcctggttat tggtatgagt    840
ttaaacacct gcctccccc cccttccct tcctttcccg ccggcatctt gtcgttgtgc       900
taactattgt tccctcttcc agagcctgac tctcttgcca acctggtgac caacctcggt    960
actccaaagt gtgccaatgc tcagtcagcc taccttgagt gcatcaacta cgccgtcaca   1020
cagctgaacc ttccaaatgt tgcgatgtat ttggacgctg gccatgcagg atggcttggc   1080
tggccggcaa accaagaccc ggccgctcag ctatttgcaa atgtttacaa gaatgcatcg   1140
tctccgagag ctcttcgcgg attggcaacc aatgtcgcca actacaacgg gtggaacatt   1200
accagccccc catcgtacac gcaaggcaac gctgtctaca cgagaagct gtacatccac    1260
gctattggac gtcttcttgc caatcacggc tggtccaacg ccttcttcat cactgatcaa   1320
ggtcgatcgg gaaagcagcc taccggacag caacagtggg gagactggtg caatgtgatc   1380
ggcaccggat ttggtattcg cccatccgca aacactgggg actcgttgct ggattcgttt   1440
gtctgggtca agccaggcgg cgagtgtgac ggcaccagcg acagcagtgc gccacgattt   1500
gactcccact gtgcgctccc agatgccttg caaccggcgc ctcaagctgg tgcttggttc   1560
caagcctact ttgtgcagct tctcacaaac gcaaacccat cgttcctgta a            1611
```

<210> SEQ ID NO 26
<211> LENGTH: 471
<212> TYPE: PRT
<213> ORGANISM: Trichoderma reesei

<400> SEQUENCE: 26

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
        50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190
```

```
Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
        210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
                260                 265                 270

Ala Val Thr Gln Leu Asn Leu Pro Asn Val Ala Met Tyr Leu Asp Ala
                275                 280                 285

Gly His Ala Gly Trp Leu Gly Trp Pro Ala Asn Gln Asp Pro Ala Ala
                290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
                340                 345                 350

Tyr Ile His Ala Ile Gly Arg Leu Leu Ala Asn His Gly Trp Ser Asn
                355                 360                 365

Ala Phe Phe Ile Thr Asp Gln Gly Arg Ser Gly Lys Gln Pro Thr Gly
                370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
                420                 425                 430

Pro Arg Phe Asp Ser His Cys Ala Leu Pro Asp Ala Leu Gln Pro Ala
                435                 440                 445

Pro Gln Ala Gly Ala Trp Phe Gln Ala Tyr Phe Val Gln Leu Leu Thr
                450                 455                 460

Asn Ala Asn Pro Ser Phe Leu
465                 470

<210> SEQ ID NO 27
<211> LENGTH: 2046
<212> TYPE: DNA
<213> ORGANISM: Humicola insolens

<400> SEQUENCE: 27
gccgtgacct tgcgcgcttt gggtggcggt ggcgagtcgt ggacggtgct tgctggtcgc      60
cggccttccc ggcgatccgc gtgatgagag ggccaccaac ggcgggatga tgctccatgg     120
ggaacttccc catggagaag agagagaaac ttgcggagcc gtgatctggg gaaagatgct     180
ccgtgtctcg tctatataac tcgagtctcc ccgagccctc aacaccacca gctctgatct     240 caccatccccc atcgacaatc acgcaaacac agcagttgtc gggccattcc ttcagacaca    300
tcagtcaccc tccttcaaaa tgcgtaccgc caagttcgcc accctcgccg cccttgtggc     360
ctcggccgcc gccagcagg cgtgcagtct caccaccgag aggcaccctt ccctctcttg      420
gaacaagtgc accgccggcg gccagtgcca gaccgtccag gcttccatca ctctcgactc     480
```

```
caactggcgc tggactcacc aggtgtctgg ctccaccaac tgctacacgg caacaagtg      540
ggatactagc atctgcactg atgccaagtc gtgcgctcag aactgctgcg tcgatggtgc      600
cgactacacc agcacctatg gcatcaccac caacggtgat ccctgagcc tcaagttcgt       660
caccaagggc cagcactcga ccaacgtcgg ctcgcgtacc tacctgatgg acggcgagga      720
caagtatcag agtacgttct atcttcagcc ttctcgcgcc ttgaatcctg ctaacgttt      780
acacttcaca gccttcgagc tcctcggcaa cgagttcacc ttcgatgtcg atgtctccaa     840
catcggctgc ggtctcaacg cgccctgta cttcgtctcc atggacgccg atggtggtct      900
cagccgctat cctggcaaca aggctggtgc aagtacggt accggctact gcgatgctca     960
gtgcccccgt gacatcaagt tcatcaacgg cgaggccaac attgagggct ggaccggctc    1020
caccaacgac cccaacgccg cgcgggccg ctatggtacc tgctgctctg agatggatat     1080
ctgggaagcc aacaacatgg ctactgcctt cactcctcac ccttgcacca tcattggcca    1140
gagccgctgc gagggcgact cgtgcggtgg cacctacagc aacgagcgct acgccggcgt    1200
ctgcgacccc gatggctgcg acttcaactc gtaccgccag ggcaacaaga ccttctacgg    1260
caagggcatg accgtcgaca ccaccaagaa gatcactgtc gtcacccagt tcctcaagga    1320
tgccaacggc gatctcggcg agatcaagcg cttctacgtc caggatggca agatcatccc    1380
caactccgag tccaccatcc ccggcgtcga gggcaattcc atcacccagg actggtgcga    1440
ccgccagaag gttgcctttg cgacattga cgacttcaac cgcaagggcg gcatgaagca    1500
gatgggcaag gccctcgccg cccccatggt cctggtcatg tccatctggg atgaccacgc    1560
ctccaacatg ctctggctcg actcgacctt ccctgtcgat gccgctggca agcccggcgc    1620
cgagcgcggt gcctgcccga ccacctcggg tgtccctgct gaggttgagg ccgaggcccc   1680
caacagcaac gtcgtcttct ccaacatccg cttcggcccc atcggctcga ccgttgctgg    1740
tctccccggc gcgggcaacg gcggcaacaa cggcggcaac ccccgcccc ccaccaccac    1800
cacctcctcg gctccggcca ccaccaccac cgccagcgct ggcccaagg ctggccgctg    1860
gcagcagtgc ggcggcatcg gcttcactgg cccgacccag tgcgaggagc cctacatttg    1920
caccaagctc aacgactggt actctcagtg cctgtaaatt ctgagtcgct gactcgacga    1980
tcacggccgg tttttgcatg aaaggaaaca aacgaccgcg ataaaaatgg agggtaatga    2040
gatgtc                                                                2046
```

<210> SEQ ID NO 28
<211> LENGTH: 525
<212> TYPE: PRT
<213> ORGANISM: Humicola insolens

<400> SEQUENCE: 28

```
Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95
```

```
Thr Ser Thr Tyr Gly Ile Thr Thr Asn Gly Asp Ser Leu Ser Leu Lys
                100                 105                 110
Phe Val Thr Lys Gly Gln His Ser Thr Asn Val Gly Ser Arg Thr Tyr
                115                 120                 125
Leu Met Asp Gly Glu Asp Lys Tyr Gln Thr Phe Glu Leu Leu Gly Asn
                130                 135             140
Glu Phe Thr Phe Asp Val Asp Val Ser Asn Ile Gly Cys Gly Leu Asn
145                 150                 155                 160
Gly Ala Leu Tyr Phe Val Ser Met Asp Ala Asp Gly Gly Leu Ser Arg
                165                 170                 175
Tyr Pro Gly Asn Lys Ala Gly Ala Lys Tyr Gly Thr Gly Tyr Cys Asp
                180                 185                 190
Ala Gln Cys Pro Arg Asp Ile Lys Phe Ile Asn Gly Glu Ala Asn Ile
                195                 200                 205
Glu Gly Trp Thr Gly Ser Thr Asn Asp Pro Asn Ala Gly Ala Gly Arg
                210                 215                 220
Tyr Gly Thr Cys Cys Ser Glu Met Asp Ile Trp Glu Ala Asn Asn Met
225                 230                 235                 240
Ala Thr Ala Phe Thr Pro His Pro Cys Thr Ile Ile Gly Gln Ser Arg
                245                 250                 255
Cys Glu Gly Asp Ser Cys Gly Gly Thr Tyr Ser Asn Glu Arg Tyr Ala
                260                 265                 270
Gly Val Cys Asp Pro Asp Gly Cys Asp Phe Asn Ser Tyr Arg Gln Gly
                275                 280                 285
Asn Lys Thr Phe Tyr Gly Lys Gly Met Thr Val Asp Thr Thr Lys Lys
                290                 295                 300
Ile Thr Val Val Thr Gln Phe Leu Lys Asp Ala Asn Gly Asp Leu Gly
305                 310                 315                 320
Glu Ile Lys Arg Phe Tyr Val Gln Asp Gly Lys Ile Ile Pro Asn Ser
                325                 330                 335
Glu Ser Thr Ile Pro Gly Val Glu Gly Asn Ser Ile Thr Gln Asp Trp
                340                 345                 350
Cys Asp Arg Gln Lys Val Ala Phe Gly Asp Ile Asp Asp Phe Asn Arg
                355                 360                 365
Lys Gly Gly Met Lys Gln Met Gly Lys Ala Leu Ala Gly Pro Met Val
                370                 375                 380
Leu Val Met Ser Ile Trp Asp Asp His Ala Ser Asn Met Leu Trp Leu
385                 390                 395                 400
Asp Ser Thr Phe Pro Val Asp Ala Ala Gly Lys Pro Gly Ala Glu Arg
                405                 410                 415
Gly Ala Cys Pro Thr Thr Ser Gly Val Pro Ala Glu Val Glu Ala Glu
                420                 425                 430
Ala Pro Asn Ser Asn Val Val Phe Ser Asn Ile Arg Phe Gly Pro Ile
                435                 440                 445
Gly Ser Thr Val Ala Gly Leu Pro Gly Ala Gly Asn Gly Gly Asn Asn
                450                 455                 460
Gly Gly Asn Pro Pro Pro Thr Thr Thr Ser Ser Ala Pro Ala
465                 470                 475                 480
Thr Thr Thr Thr Ala Ser Ala Gly Pro Lys Ala Gly Arg Trp Gln Gln
                485                 490                 495
Cys Gly Gly Ile Gly Phe Thr Gly Pro Thr Gln Cys Glu Glu Pro Tyr
                500                 505                 510
```

Ile Cys Thr Lys Leu Asn Asp Trp Tyr Ser Gln Cys Leu
    515                 520                 525

<210> SEQ ID NO 29
<211> LENGTH: 1812
<212> TYPE: DNA
<213> ORGANISM: Myceliophthora thermophila

<400> SEQUENCE: 29

| | | |
|---|---|---|
| atggccaaga agcttttcat caccgccgcc cttgcggctg ccgtgttggc ggccccgtc | 60 |
| attgaggagc gccagaactg cggcgctgtg tggtaagaaa gcccggtctg agtttcccat | 120 |
| gactttctca tcgagtaatg gcataaggcc caccccttcg actgactgtg agaatcgatc | 180 |
| aaatccagga ctcaatgcgg cggcaacggg tggcagggtc ccacatgctg cgcctcgggc | 240 |
| tcgacctgcg ttgcgcagaa cgagtggtac tctcagtgcc tgcccaacaa tcaggtgacg | 300 |
| agttccaaca ctccgtcgtc gacttccacc tcgcagcgca gcagcagcac tccagcagc | 360 |
| agcaccagga gcggcagctc ctcctcctcc accaccacgc ccctcccgt ctccagcccc | 420 |
| gtgactagca ttcccggcgg tgcgaccacc acggcgagct actctggcaa ccccttctcg | 480 |
| ggcgtccggc tcttcgccaa cgactactac aggtccgagg tccacaatct cgccattcct | 540 |
| agcatgaccg gtactctggc ggccaaggct tccgccgtcg ccgaagtccc tagcttccag | 600 |
| tggctcgacc ggaacgtcac catcgacacc ctgatggtcc agactctgtc ccagatccgg | 660 |
| gctgccaata atgccggtgc caatcctccc tatgctggtg agttacatgg cggcgacttg | 720 |
| ccttctcgtc ccccacctt cttgacggga tcggttacct gacctggagg caaaacaaaa | 780 |
| ccagcccaac ttgtcgtcta cgacctcccc gaccgtgact gcgccgccgc tgcgtccaac | 840 |
| ggcgagtttt cgattgcaaa cggcggcgcc gccaactaca ggagctacat cgacgctatc | 900 |
| cgcaagcaca tcattgagta ctcggacatc cggatcatcc tggttatcga gcccgactcg | 960 |
| atggccaaca tggtgaccaa catgaacgtg ccaagtgca gcaacgccgc gtcgacgtac | 1020 |
| cacgagttga ccgtgtacgc gctcaagcag ctgaacctgc caacgtcgc catgtatctc | 1080 |
| gacgccggcc acgccggctg gctcggctgg cccgccaaca tccagcccgc cgccgacctg | 1140 |
| tttgccggca tctacaatga cgccggcaag ccggctgccg tccgcggcct ggccactaac | 1200 |
| gtcgccaact acaacgcctg gagtatcgct tcggccccgt cgtacacgtc ccctaaccct | 1260 |
| aactacgacg agaagcacta catcgaggcc ttcagcccgc tcctgaacgc ggccggcttc | 1320 |
| cccgcacgct tcattgtcga cactggccgc aacggcaaac aacctaccgg tatggtttt | 1380 |
| ttcttttttt ttctctgttc ccctcccct tcccttcag ttggcgtcca aaggtctct | 1440 |
| tagtcttgct tcttctcgga ccaaccttcc cccaccccca aaacgcaccg cccacaaccg | 1500 |
| ttcgactcta tactcttggg aatgggcgcc gaaactgacc gttcgacagg caacaacag | 1560 |
| tggggtgact ggtgcaatgt caagggcact ggctttggcg tgcgcccgac ggccaacacg | 1620 |
| ggccacgacc tggtcgatgc cttttgtctgg gtcaagcccg gcggcgagtc cgacggcaca | 1680 |
| agcgacacca gcgccgcccg ctacgactac cactgcggcc tgtccgatgc cctgcagcct | 1740 |
| gctccggagg ctggacagtg gttccaggcc tacttcgagc agctgctcac caacgccaac | 1800 |
| ccgcccttct aa | 1812 |

<210> SEQ ID NO 30
<211> LENGTH: 482
<212> TYPE: PRT
<213> ORGANISM: Myceliophthora thermophila

<400> SEQUENCE: 30

```
Met Ala Lys Lys Leu Phe Ile Thr Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Asn Gln Val Thr Ser Ser Asn Thr Pro Ser Ser Thr Ser Thr Ser Gln
65                  70                  75                  80

Arg Ser Ser Ser Thr Ser Ser Ser Thr Arg Ser Gly Ser Ser Ser
                85                  90                  95

Ser Ser Thr Thr Thr Pro Pro Val Ser Ser Pro Val Thr Ser Ile
                100                 105                 110

Pro Gly Gly Ala Thr Thr Thr Ala Ser Tyr Ser Gly Asn Pro Phe Ser
            115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Ile Arg Ala Ala Asn Asn
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Asp Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ala Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415
```

```
Ala Asn Thr Gly His Asp Leu Val Asp Ala Phe Val Trp Val Lys Pro
            420                 425                 430
Gly Gly Glu Ser Asp Gly Thr Ser Asp Thr Ser Ala Ala Arg Tyr Asp
        435                 440                 445
Tyr His Cys Gly Leu Ser Asp Ala Leu Gln Pro Ala Pro Glu Ala Gly
450                 455                 460
Gln Trp Phe Gln Ala Tyr Phe Glu Gln Leu Leu Thr Asn Ala Asn Pro
465                 470                 475                 480
Pro Phe
```

<210> SEQ ID NO 31
<211> LENGTH: 1725
<212> TYPE: DNA
<213> ORGANISM: Myceliophthora thermophila

<400> SEQUENCE: 31

| | | | | | |
|---|---|---|---|---|---|
| gagggcagct | cacctgaaga | ggcttgtaag | atcaccctct | gtgtattgca | ccatgattgt | 60 |
| cggcattctc | accacgctgg | ctacgctggc | cacactcgca | gctagtgtgc | ctctagagga | 120 |
| gcggcaagct | tgctcaagcg | tctggggcca | atgtggtggc | cagaattggt | cgggtccgac | 180 |
| ttgctgtgct | tccggaagca | catgcgtcta | ctccaacgac | tattactccc | agtgtcttcc | 240 |
| cggcgctgca | agctcaagct | cgtccacgcg | cgccgcgtcg | acgacttctc | gagtatcccc | 300 |
| cacaacatcc | cggtcgagct | ccgcgacgcc | tccacctggt | tctactacta | ccagagtacc | 360 |
| tccagtcgga | tcgggaaccg | ctacgtattc | aggcaaccct | tttgttgggg | tcactccttg | 420 |
| ggccaatgca | tattacgcct | ctgaagttag | cagcctcgct | attcctagct | tgactggagc | 480 |
| catggccact | gctgcagcag | ctgtcgcaaa | ggttccctct | tttatgtggc | tagatactct | 540 |
| tgacaagacc | cctctcatgg | agcaaacctt | ggccgacatc | cgcaccgcca | acaagaatgg | 600 |
| cggtaactat | gccggacagt | tgtggtgta | tgacttgccg | gatcgcgatt | gcgctgccct | 660 |
| tgcctcgaat | ggcgaatact | ctattgccga | tggtggcgtc | gccaaatata | agaactatat | 720 |
| cgacaccatt | cgtcaaattg | tcgtggaata | ttccgatatc | cggaccctcc | tggttattga | 780 |
| gcctgactct | cttgccaacc | tggtgaccaa | cctcggtact | ccaaagtgtg | ccaatgctca | 840 |
| gtcagcctac | cttgagtgca | tcaactacgc | cgtcacacag | ctgaaccttc | caaatgttgc | 900 |
| gatgtatttg | gacgctggcc | atgcaggatg | gcttggctgg | ccggcaaacc | aagacccggc | 960 |
| cgctcagcta | tttgcaaatg | tttacaagaa | tgcatcgtct | ccgagagctc | ttcgcggatt | 1020 |
| ggcaaccaat | gtcgccaact | acaacgggtg | gaacattacc | agcccccat | cgtacacgca | 1080 |
| aggcaacgct | gtctacaacg | agaagctgta | catccacgct | attggacctc | ttcttgccaa | 1140 |
| tcacggctgg | tccaacgcct | tcttcatcac | tgatcaaggt | cgatcgggaa | agcagcctac | 1200 |
| cggacagcaa | cagtggggag | actggtgcaa | tgtgatcggc | accggatttg | gtattcgccc | 1260 |
| atccgcaaac | actggggact | cgttgctgga | ttcgtttgtc | tgggtcaagc | caggcggcga | 1320 |
| gtgtgacggc | accagcgaca | gcagtgcgcc | acgatttgac | tcccactgtg | cgctcccaga | 1380 |
| tgccttgcaa | ccggcgcctc | aagctggtgc | ttggttccaa | gcctactttg | tgcagcttct | 1440 |
| cacaaacgca | aacccatcgt | tcctgtaagg | ctttcgtgac | cgggcttcaa | acaatgatgt | 1500 |
| gcgatggtgt | ggttcccggt | tggcggagtc | tttgtctact | tggttgtct | gtcgcaggtc | 1560 |
| ggtagaccgc | aaatgagcaa | ctgatggatt | gttgccagcg | atactataat | tcacatggat | 1620 |
| ggtctttgtc | gatcagtagc | tagtgagaga | gagagaacat | ctatccacaa | tgtcgagtgt | 1680 | ctattagaca tactccgaga aaaaaaaaaa aaaaaaaaaa aaaaa    1725

<210> SEQ ID NO 32
<211> LENGTH: 471
<212> TYPE: PRT
<213> ORGANISM: Myceliophthora thermophila

<400> SEQUENCE: 32

```
Met Ile Val Gly Ile Leu Thr Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Pro Gly
                85                  90                  95

Ser Thr Thr Thr Arg Val Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365
```

```
Ala Phe Phe Ile Thr Asp Gln Gly Arg Ser Gly Lys Gln Pro Thr Gly
370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
                420                 425                 430

Pro Arg Phe Asp Ser His Cys Ala Leu Pro Asp Ala Leu Gln Pro Ala
                435                 440                 445

Pro Gln Ala Gly Ala Trp Phe Gln Ala Tyr Phe Val Gln Leu Leu Thr
450                 455                 460

Asn Ala Asn Pro Ser Phe Leu
465                 470
```

<210> SEQ ID NO 33
<211> LENGTH: 1446
<212> TYPE: DNA
<213> ORGANISM: Thielavia terrestris

<400> SEQUENCE: 33

```
atggctcaga agctccttct cgccgccgcc cttgcggcca gcgccctcgc tgctcccgtc      60
gtcgaggagc gccagaactg cggttccgtc tggagccaat gcggcggcat tggctggtcc     120
ggcgcgacct gctgcgcttc gggcaatacc tgcgttgagc tgaacccgta ctactcgcag     180
tgcctgccca cagccaggt gactacctcg accagcaaga ccacctccac caccaccagg      240
agcagcacca ccagccacag cagcggtccc accagcacga gcaccaccac caccagcagt     300
cccgtggtca ctaccccgcc gagtacctcc atccccggcg gtgcctcgtc aacggccagc     360
tggtccggca cccgttctc gggcgtgcag atgtgggcca acgactacta cgcctccgag      420
gtctcgtcgc tggccatccc cagcatgacg ggcgccatgg ccaccaaggc ggccgaggtg     480
gccaaggtgc ccagcttcca gtggcttgac cgcaacgtca ccatcgacac gctgttcgcc     540
cacacgctgt cgcagatccg cgcggccaac cagaaaggcg ccaacccgcc ctacgcgggc     600
atcttcgtgg tctacgacct ccggaccgc gactgcgccg ccgccgcgtc caacggcgag      660
ttctccatcg cgaacaacgg ggcggccaac tacaagacgt acatcgacgc gatccggagc     720
ctcgtcatcc agtactcaga catccgcatc atcttcgtca tcgagcccga tcgctggcc      780 aacatggtga ccaacctgaa cgtggccaag tgcgccaacg ccgagtcgac ctacaaggag     840
ttgaccgtct acgcgctgca gcagctgaac ctgcccaacg tggccatgta cctggacgcc     900
ggccacgccg gctggctcgg ctggcccgcc aacatccagc cggccgccaa cctcttcgcc     960
gagatctaca cgagcgccgg caagccggcc gccgtgcgcg gcctcgccac caacgtggcc     1020
aactacaacg gctggagcct ggccacgccg ccctcgtaca cccagggcga cccaactac     1080 gacgagagcc actacgtcca ggccctcgcc ccgctgctca ccgccaacgg cttccccgcc     1140
cacttcatca ccgacaccgg ccgcaacggc aagcagccga ccggacaacg gcaatgggga     1200
gactggtgca cgttatcgg aactggcttc ggcgtgcgcc cgacgacaaa caccggcctc     1260
gacatcgagg acgccttcgt ctgggtcaag cccggcggcg agtgcgacgg cacgagcaac     1320
acgacctctc ccgctacga ctaccactgc ggcctgtcgg acgcgctgca gcctgctccg     1380
gaggccggca cttggttcca ggcctacttc gagcagctcc tgaccaacgc caaccccgcc     1440
tttttaa                                                               1446
```

<210> SEQ ID NO 34
<211> LENGTH: 481
<212> TYPE: PRT
<213> ORGANISM: Thielavia terrestris

<400> SEQUENCE: 34

```
Met Ala Gln Lys Leu Leu Ala Ala Ala Leu Ala Ser Ala Leu
 1               5                  10                  15

Ala Ala Pro Val Val Glu Glu Arg Gln Asn Cys Gly Ser Val Trp Ser
            20                  25                  30

Gln Cys Gly Gly Ile Gly Trp Ser Gly Ala Thr Cys Cys Ala Ser Gly
        35                  40                  45

Asn Thr Cys Val Glu Leu Asn Pro Tyr Tyr Ser Gln Cys Leu Pro Asn
    50                  55                  60

Ser Gln Val Thr Thr Ser Thr Lys Thr Thr Ser Thr Thr Thr Arg
65                  70                  75                  80

Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
        115                 120                 125

Val Gln Met Trp Ala Asn Asp Tyr Tyr Ala Ser Glu Val Ser Ser Leu
    130                 135                 140

Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ser Asn Gly Glu Phe Ser Ile Ala
    210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
        355                 360                 365

Leu Ala Pro Leu Leu Thr Ala Asn Gly Phe Pro Ala His Phe Ile Thr
    370                 375                 380
```

```
Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
            405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
            435                 440                 445

His Cys Gly Leu Ser Asp Ala Leu Gln Pro Ala Pro Glu Ala Gly Thr
            450                 455                 460

Trp Phe Gln Ala Tyr Phe Glu Gln Leu Leu Thr Asn Ala Asn Pro Pro
465                 470                 475                 480

Phe

<210> SEQ ID NO 35
<211> LENGTH: 1593
<212> TYPE: DNA
<213> ORGANISM: Chaetomium thermophilum

<400> SEQUENCE: 35
atgatgtaca agaagttcgc cgctctcgcc gccctcgtgg ctggcgccgc cgcccagcag    60
gcttgctccc tcaccactga gacccacccc agactcactt ggaagcgctg cacctctggc   120
ggcaactgct cgaccgtgaa cggcgccgtc accatcgatg ccaactggcg ctggactcac   180
actgtttccg gctcgaccaa ctgctacacc ggcaacgagt gggatacctc catctgctct   240
gatggcaaga gctgcgccca gacctgctgc gtcgacggcg ctgactactc ttcgacctat   300
ggtatcacca ccagcggtga ctccctgaac ctcaagttcg tcaccaagca ccagcacggc   360
accaatgtcg gctctcgtgt ctacctgatg gagaacgaca ccaagtacca gatgttcgag   420
ctcctcggca acgagttcac cttcgatgtc gatgtctcta acctgggctg cggtctcaac   480
ggcgccctct acttcgtctc catggacgct gatggtggta tgagcaagta ctctggcaac   540
aaggctggcg ccaagtacgg taccggctac tgcgatgctc agtgcccgcg cgaccttaag   600
ttcatcaacg gcgaggccaa cattgagaac tggacccctt cgaccaatga tgccaacgcc   660
ggtttcggcc gctatggcag ctgctgctct gagatggata tctgggatgc caacaacatg   720
gctactgcct tcactcctca cccttgcacc attatcggcc agagccgctg cgagggcaac   780
agctgcggtg gcacctacag ctctgagcgc tatgctggtg tttgcgatcc tgatggctgc   840
gacttcaacg cctaccgcca gggcgacaag accttctacg gcaagggcat gaccgtcgac   900
accaccaaga agatgaccgt cgtcacccag ttccacaaga actcggctgg cgtcctcagc   960
gagatcaagc gcttctacgt tcaggacggc aagatcattg ccaacgccga gtccaagatc  1020
cccggcaacc ccggcaactc catcacccag gagtggtgcg atgcccagaa ggtcgccttc  1080
ggtgacatcg atgacttcaa ccgcaagggc ggtatggctc agatgagcaa ggccctcgag  1140
ggccctatgg tcctggtcat gtccgtctgg gatgaccact acgccaacat gctctggctc  1200
gactcgacct accccattga caaggccggc accccggcg ccgagcgcgg tgcttgcccg  1260
accacctccg gtgtccctgc cgagattgag gcccaggtcc ccaacagcaa cgttatcttc  1320
tccaacatcc gcttcggccc catcggctcg accgtccctg gcctcgacgg cagcaccccc  1380
agcaacccga ccgccaccgt tgctcctccc acttctacca ccaccagcgt gagaagcagc  1440
actactcaga tttccacccc gactagccag cccggcggct gcaccaccca gaagtggggc  1500
```

```
cagtgcggtg gtatcggcta caccggctgc actaactgcg ttgctggcac tacctgcact    1560
gagctcaacc cctggtacag ccagtgcctg taa                                 1593

<210> SEQ ID NO 36
<211> LENGTH: 530
<212> TYPE: PRT
<213> ORGANISM: Chaetomium thermophilum

<400> SEQUENCE: 36
```

Met Met Tyr Lys Lys Phe Ala Ala Leu Ala Ala Leu Val Ala Gly Ala
1               5                   10                  15

Ala Ala Gln Gln Ala Cys Ser Leu Thr Thr Glu Thr His Pro Arg Leu
            20                  25                  30

Thr Trp Lys Arg Cys Thr Ser Gly Gly Asn Cys Ser Thr Val Asn Gly
        35                  40                  45

Ala Val Thr Ile Asp Ala Asn Trp Arg Trp Thr His Thr Val Ser Gly
    50                  55                  60

Ser Thr Asn Cys Tyr Thr Gly Asn Glu Trp Asp Thr Ser Ile Cys Ser
65                  70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln His Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Ile
        195                 200                 205

Glu Asn Trp Thr Pro Ser Thr Asn Asp Ala Asn Ala Gly Phe Gly Arg
    210                 215                 220

Tyr Gly Ser Cys Cys Ser Glu Met Asp Ile Trp Asp Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asn Ser Cys Gly Gly Thr Tyr Ser Ser Glu Arg Tyr Ala
            260                 265                 270

Gly Val Cys Asp Pro Asp Gly Cys Asp Phe Asn Ala Tyr Arg Gln Gly
        275                 280                 285

Asp Lys Thr Phe Tyr Gly Lys Gly Met Thr Val Asp Thr Thr Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335

Glu Ser Lys Ile Pro Gly Asn Pro Gly Asn Ser Ile Thr Gln Glu Trp
            340                 345                 350

Cys Asp Ala Gln Lys Val Ala Phe Gly Asp Ile Asp Asp Phe Asn Arg

```
                355                 360                 365
Lys Gly Gly Met Ala Gln Met Ser Lys Ala Leu Glu Gly Pro Met Val
            370                 375                 380

Leu Val Met Ser Val Trp Asp Asp His Tyr Ala Asn Met Leu Trp Leu
385                 390                 395                 400

Asp Ser Thr Tyr Pro Ile Asp Lys Ala Gly Thr Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
                435                 440                 445

Gly Ser Thr Val Pro Gly Leu Asp Gly Ser Thr Pro Ser Asn Pro Thr
            450                 455                 460

Ala Thr Val Ala Pro Pro Thr Ser Thr Thr Thr Ser Val Arg Ser Ser
465                 470                 475                 480

Thr Thr Gln Ile Ser Thr Pro Thr Ser Gln Pro Gly Gly Cys Thr Thr
                485                 490                 495

Gln Lys Trp Gly Gln Cys Gly Gly Ile Gly Tyr Thr Gly Cys Thr Asn
            500                 505                 510

Cys Val Ala Gly Thr Thr Cys Thr Glu Leu Asn Pro Trp Tyr Ser Gln
                515                 520                 525

Cys Leu
    530

<210> SEQ ID NO 37
<211> LENGTH: 1434
<212> TYPE: DNA
<213> ORGANISM: Chaetomium thermophilum

<400> SEQUENCE: 37
atggctaagc agctgctgct cactgccgct cttgcggcca cttcgctggc tgcccctctc      60
cttgaggagc gccagagctg ctcctccgtc tggggtcaat gcggtggcat caattacaac     120
ggcccgacct gctgccagtc cggcagtgtt tgcacttacc tgaatgactg gtacagccag     180
tgcattcccg gtcaggctca gcccggcacg actagcacca cggctcggac caccagcacc     240
agcaccacca gcacttcgtc ggtccgcccg accacctcga ataccctgt gacgactgct     300 cccccgacga ccaccatccc gggcggcgcc tcgagcacgg ccagctacaa cggcaacccg     360
ttttcgggtg ttcaactttg gccaacacc tactactcgt ccgaggtgca cactttggcc     420
atccccagct tgtctcctga gctggctgcc aaggccgcca aggtcgctga ggttcccagc     480
ttccagtggc tcgaccgcaa tgtgactgtt gacactctct ctccggcac tcttgccgaa     540 atccgcgccg ccaaccagcg cggtgccaac ccgccttatg ccggcatttt cgtggtttat     600
gacttaccag accgtgattg cgcggctgct gcttcgaacg gcgagtggtc tatcgccaac     660
aatggtgcca caactacaa gcgctacatc gaccggatcc gtgagctcct tatccagtac     720
tccgatatcc gcactattct ggtcattgaa cctgattccc tggccaacat ggtcaccaac     780
atgaacgtcc agaagtgctc gaacgctgcc tccacttaca aggagcttac tgtctatgcc     840
ctcaaacagc tcaatcttcc tcacgttgcc atgtacatgg atgctggcca cgctggctgg     900
cttggctggc cgccaacat ccagcctgct gctgagctct tgctcaaat ctaccgcgac     960 gctggcaggc ccgctgctgt ccgcggtctt gcgaccaacg ttgccaacta caatgcttgg    1020
tcgatcgcca gccctccgtc ctacacctct cctaacccga actacgacga aagcactat    1080
```

```
attgaggcct tgctcctct ctccgcaac cagggcttcg acgcaaagtt catcgtcgac    1140
accggccgta acggcaagca gcccactggc cagcttgaat ggggtcactg gtgcaatgtc    1200
aagggaactg gcttcggtgt gcgccctact gctaacactg gcatgaact tgttgatgct    1260 ttcgtgtggg tcaagcccgg tggcgagtcc gacggcacca gtgcggacac cagcgctgct    1320
cgttatgact atcactgcgg cctttccgac gcactgactc cggcgcctga ggctggccaa    1380
tggttccagg cttatttcga acagctgctc atcaatgcca ccctccgct ctga    1434
```

<210> SEQ ID NO 38
<211> LENGTH: 477
<212> TYPE: PRT
<213> ORGANISM: Chaetomium thermophilum

<400> SEQUENCE: 38

```
Met Ala Lys Gln Leu Leu Leu Thr Ala Ala Leu Ala Ala Thr Ser Leu
1               5                   10                  15

Ala Ala Pro Leu Leu Glu Glu Arg Gln Ser Cys Ser Ser Val Trp Gly
            20                  25                  30

Gln Cys Gly Gly Ile Asn Tyr Asn Gly Pro Thr Cys Cys Gln Ser Gly
        35                  40                  45

Ser Val Cys Thr Tyr Leu Asn Asp Trp Tyr Ser Gln Cys Ile Pro Gly
    50                  55                  60

Gln Ala Gln Pro Gly Thr Thr Ser Thr Thr Ala Arg Thr Thr Ser Thr
65                  70                  75                  80

Ser Thr Thr Ser Thr Ser Ser Val Arg Pro Thr Thr Ser Asn Thr Pro
                85                  90                  95

Val Thr Thr Ala Pro Pro Thr Thr Thr Ile Pro Gly Gly Ala Ser Ser
            100                 105                 110

Thr Ala Ser Tyr Asn Gly Asn Pro Phe Ser Gly Val Gln Leu Trp Ala
        115                 120                 125

Asn Thr Tyr Tyr Ser Ser Glu Val His Thr Leu Ala Ile Pro Ser Leu
    130                 135                 140

Ser Pro Glu Leu Ala Ala Lys Ala Ala Lys Val Ala Glu Val Pro Ser
145                 150                 155                 160

Phe Gln Trp Leu Asp Arg Asn Val Thr Val Asp Thr Leu Phe Ser Gly
                165                 170                 175

Thr Leu Ala Glu Ile Arg Ala Ala Asn Gln Arg Gly Ala Asn Pro Pro
            180                 185                 190

Tyr Ala Gly Ile Phe Val Val Tyr Asp Leu Pro Asp Arg Asp Cys Ala
        195                 200                 205

Ala Ala Ala Ser Asn Gly Glu Trp Ser Ile Ala Asn Asn Gly Ala Asn
    210                 215                 220

Asn Tyr Lys Arg Tyr Ile Asp Arg Ile Arg Glu Leu Leu Ile Gln Tyr
225                 230                 235                 240

Ser Asp Ile Arg Thr Ile Leu Val Ile Glu Pro Asp Ser Leu Ala Asn
                245                 250                 255

Met Val Thr Asn Met Asn Val Gln Lys Cys Ser Asn Ala Ala Ser Thr
            260                 265                 270

Tyr Lys Glu Leu Thr Val Tyr Ala Leu Lys Gln Leu Asn Leu Pro His
        275                 280                 285

Val Ala Met Tyr Met Asp Ala Gly His Ala Gly Trp Leu Gly Trp Pro
    290                 295                 300

Ala Asn Ile Gln Pro Ala Ala Glu Leu Phe Ala Gln Ile Tyr Arg Asp
305                 310                 315                 320
```

```
Ala Gly Arg Pro Ala Ala Val Arg Gly Leu Ala Thr Asn Val Ala Asn
                325                 330                 335

Tyr Asn Ala Trp Ser Ile Ala Ser Pro Ser Tyr Thr Ser Pro Asn
            340                 345                 350

Pro Asn Tyr Asp Glu Lys His Tyr Ile Glu Ala Phe Ala Pro Leu Leu
            355                 360                 365

Arg Asn Gln Gly Phe Asp Ala Lys Phe Ile Val Asp Thr Gly Arg Asn
        370                 375                 380

Gly Lys Gln Pro Thr Gly Gln Leu Glu Trp Gly His Trp Cys Asn Val
385                 390                 395                 400

Lys Gly Thr Gly Phe Gly Val Arg Pro Thr Ala Asn Thr Gly His Glu
                405                 410                 415

Leu Val Asp Ala Phe Val Trp Val Lys Pro Gly Gly Glu Ser Asp Gly
                420                 425                 430

Thr Ser Ala Asp Thr Ser Ala Ala Arg Tyr Asp Tyr His Cys Gly Leu
            435                 440                 445

Ser Asp Ala Leu Thr Pro Ala Pro Glu Ala Gly Gln Trp Phe Gln Ala
        450                 455                 460

Tyr Phe Glu Gln Leu Leu Ile Asn Ala Asn Pro Pro Leu
465                 470                 475

<210> SEQ ID NO 39
<211> LENGTH: 2586
<212> TYPE: DNA
<213> ORGANISM: Aspergillus oryzae

<400> SEQUENCE: 39
atgaagcttg gttggatcga ggtggccgca ttggcggctg cctcagtagt cagtgccaag      60
gatgatctcg cgtactcccc tcctttctac ccttccccat gggcagatgg tcagggtgaa     120
tgggcggaag tatacaaacg cgctgtagac atagtttccc agatgacgtt gacagagaaa     180
gtcaacttaa cgactggaac aggatggcaa ctagagaggt gtgttggaca aactggcagt     240
gttcccagac tcaacatccc cagcttgtgt ttgcaggata gtcctcttgg tattcgtttc     300
tcggactaca attcagcttt ccctgcgggt gttaatgtcg ctgccacctg gacaagacg      360
ctcgcctacc ttcgtggtca ggcaatgggt gaggagttca gtgataaggg tattgacgtt     420
cagctgggtc ctgctgctgg ccctctcggt gctcatccgg atggcggtag aaactgggaa     480
ggtttctcac cagatccagc cctcaccggt gtacttttg cggagacgat taagggtatt     540
caagatgctg gtgtcattgc gacagctaag cattatatca tgaacgaaca agagcatttc     600
cgccaacaac ccgaggctgc gggttacgga ttcaacgtaa gcgacagttt gagttccaac     660
gttgatgaca agactatgca tgaattgtac ctctggccct tcgcggatgc agtacgcgct     720
ggagtcggtg ctgtcatgtg ctcttacaac caaatcaaca acagctacgg ttgcgagaat     780
agcgaaactc tgaacaagct tttgaaggcg gagcttggtt ccaaggcttc gtcatgagt     840
gattggaccg ctcatcacag cggcgtaggc gctgctttag caggtctgga tatgtcgatg     900
cccggtgatg ttaccttcga tagtggtacg tctttctggg gtgcaaactt gacggtcggt     960
gtccttaacg tacaatccc ccaatggcgt gttgatgaca tggctgtccg tatcatggcc    1020
gcttattaca aggttggccg cgacaccaaa tacaccctc ccaacttcag ctcgtggacc    1080
agggacgaat atggtttcgc gcataaccat gtttcggaag tgcttacga gagggtcaac    1140
gaattcgtgg acgtgcaacg cgatcatgcc gacctaatcc gtcgcatcgg cgcgcagagc    1200
```

```
actgttctgc tgaagaacaa gggtgccttg cccttgagcc gcaaggaaaa gctggtcgcc    1260
cttctgggag aggatgcggg ttccaactcg tggggcgcta acggctgtga tgaccgtggt    1320
tgcgataacg gtaccttgc catggcctgg ggtagcggta ctgcgaattt cccatacctc     1380
gtgacaccag agcaggcgat tcagaacgaa gttcttcagg gccgtggtaa tgtcttcgcc    1440
gtgaccgaca gttgggcgct cgacaagatc gctgcggctg cccgccaggc cagcgtatct    1500
ctcgtgttcg tcaactccga ctcaggagaa ggctatctta gtgtggatgg aaatgagggc    1560
gatcgtaaca acatcactct gtggaagaac ggcgacaatg tggtcaagac cgcagcgaat    1620
aactgtaaca acaccgttgt catcatccac tccgtcggac cagttttgat cgatgaatgg    1680
tatgaccacc ccaatgtcac tggtattctc tgggctggtc tgccaggcca ggagtctggt    1740
aactccattg ccgatgtgct gtacggtcgt gtcaaccctg cgccaagtc tcctttcact     1800
tggggcaaga cccgggagtc gtatggttct cccttggtca aggatgccaa caatggcaac    1860
ggagcgcccc agtctgattt cacccagggt gttttcatcg attaccgcca tttcgataag    1920
ttcaatgaga cccctatcta cgagtttggc tacggcttga gctacaccac cttcgagctc    1980
tccgacctcc atgttcagcc ctgaacgcg tcccgataca ctcccaccag tggcatgact     2040
gaagctgcaa agaactttgg tgaaattggc gatgcgtcgg agtacgtgta ccggaggggg    2100
ctggaaagga tccatgagtt tatctatccc tggatcaact ctaccgacct gaaggcatcg    2160
tctgacgatt ctaactacgg ctgggaagac tccaagtata ttcccgaagg cgccacggat    2220
gggtctgccc agccccgttt gcccgctagt ggtggtgccg aggaaacccc cggtctgtac    2280
gaggatcttt tccgcgtctc tgtgaaggtc aagaacacgg gcaatgtcgc cggtgatgaa    2340
gttcctcagc tgtacgtttc cctaggcggc ccgaatgagc ccaaggtggt actgcgcaag    2400
tttgagcgta ttcacttggc cccttcgcag gaggccgtgt ggacaacgac ccttacccgt    2460
cgtgaccttg caaactggga cgtttcggct caggactgga ccgtcactcc ttaccccaag    2520
acgatctacg ttggaaactc ctcacggaaa ctgccgctcc aggcctcgct gcctaaggcc    2580
cagtaa                                                               2586
```

<210> SEQ ID NO 40
<211> LENGTH: 861
<212> TYPE: PRT
<213> ORGANISM: Aspergillus oryzae

<400> SEQUENCE: 40

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125
```

```
Met Gly Glu Glu Phe Ser Asp Lys Gly Ile Asp Val Gln Leu Gly Pro
            130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

Asn His Val Ser Glu Gly Ala Tyr Glu Arg Val Asn Glu Phe Val Asp
    370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
                485                 490                 495

Ala Ser Val Ser Leu Val Phe Val Asn Ser Asp Ser Gly Glu Gly Tyr
            500                 505                 510

Leu Ser Val Asp Gly Asn Glu Gly Asp Arg Asn Asn Ile Thr Leu Trp
        515                 520                 525

Lys Asn Gly Asp Asn Val Val Lys Thr Ala Ala Asn Asn Cys Asn Asn
    530                 535                 540
```

```
Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
        595                 600                 605

Gly Ser Pro Leu Val Lys Asp Ala Asn Asn Gly Asn Gly Ala Pro Gln
610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
                660                 665                 670

Tyr Thr Pro Thr Ser Gly Met Thr Glu Ala Ala Lys Asn Phe Gly Glu
            675                 680                 685

Ile Gly Asp Ala Ser Glu Tyr Val Tyr Pro Glu Gly Leu Glu Arg Ile
        690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
                740                 745                 750

Ala Gly Gly Asn Pro Gly Leu Tyr Glu Asp Leu Phe Arg Val Ser Val
            755                 760                 765

Lys Val Lys Asn Thr Gly Asn Val Ala Gly Asp Glu Val Pro Gln Leu
        770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
                820                 825                 830

Trp Thr Val Thr Pro Tyr Pro Lys Thr Ile Tyr Val Gly Asn Ser Ser
            835                 840                 845

Arg Lys Leu Pro Leu Gln Ala Ser Leu Pro Lys Ala Gln
850                 855                 860

<210> SEQ ID NO 41
<211> LENGTH: 3060
<212> TYPE: DNA
<213> ORGANISM: Aspergillus fumigatus

<400> SEQUENCE: 41
atgagattcg gttggctcga ggtggccgct ctgacggccg cttctgtagc caatgcccag    60
gtttgtgatg ctttcccgtc attgtttcgg atatagttga caatagtcat ggaaataatc   120
aggaattggc tttctctcca ccattctacc cttcgccttg ggctgatggc cagggagagt   180
gggcagatgc ccatcgacgc gccgtcgaga tcgtttctca gatgacactg gcggagaagg   240
ttaaccttac aacgggtact gggtgggttg cgacttttt gttgacagtg agctttcttc    300
actgaccatc tacacagatg ggaaatggac cgatgcgtcg gtcaaaccgg cagcgttccc   360
```

```
aggtaagctt gcaattctgc aacaacgtgc aagtgtagtt gctaaaacgc ggtggtgcag    420
acttggtatc aactggggtc tttgtggcca ggattcccct ttgggtatcc gtttctgtga    480
gctatacccg cggagtcttt cagtccttgt attatgtgct gatgattgtc tctgtatagc    540
tgacctcaac tccgccttcc ctgctggtac taatgtcgcc cgacatggg acaagacact     600
cgcctacctt cgtggcaagg ccatgggtga ggaattcaac gacaagggcg tggacatttt    660
gctgggcct gctgctggtc ctctcggcaa atacccggac ggcggcagaa tctgggaagg     720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg atatggtta acatcacg agacgatca gctccaacgt        900
ggatgacaag accatgcacg agttgtacct tggtgagta gttgacactg caaatgagga    960
ccttgattga tttgactgac ctggaatgca ggcccttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg ggcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt cccctaact tcagctcctg gacccgggat    1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttcccctta ccttgtcacc   1740
cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg aagaacggc gaggccgtca ttgacactgt tgtcagccac    2040
tgcaacaaca cgattgtggt tattcacagt gttgggcccg tcttgatcga ccggtggtat   2100
gataaccca acgtcactgc catcatctgg gccggcttgc ccggtcagga gagtggcaac    2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgaggcgtc ttcattgact accgtcactt tgacaagcgc    2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaacccct cctgaaggct ggcggcgctc ctggtggtaa ccctaccctt   2700
```

-continued

```
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 42
<211> LENGTH: 863
<212> TYPE: PRT
<213> ORGANISM: Aspergillus fumigatus

<400> SEQUENCE: 42

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320
```

```
Val Leu Asn Gly Thr Val Pro Ala Trp Arg Val Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
            565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
    595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735
```

```
Pro Glu Gly Ala Arg Asp Gly Ser Pro Gln Pro Leu Leu Lys Ala Gly
                740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
        770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 43
<211> LENGTH: 2800
<212> TYPE: DNA
<213> ORGANISM: Penicillium brasilianum

<400> SEQUENCE: 43
tgaaaatgca gggttctaca atctttctgg ctttcgcctc atgggcgagc caggttgctg      60
ccattgcgca gcccatacag aagcacgagg tttgttttat cttgctcatg acgtgctttt     120
gacttgacta attgttttac atacagcccg gatttctgca cgggcccaa gccatagaat     180 cgttctcaga accgttctac ccgtcgccct ggatgaatcc tcacgccgag ggctgggagg     240
ccgcatatca gaaagctcaa gattttgtct cgcaactcac tatcttggag aaaataaatc     300
tgaccaccgg tgttgggtaa gtctctccga ctgcttctgg gtcacggtgc gacgagccac     360 tgacttttg aagctgggaa atgggccgt gtgtaggaaa cactggatca attcctcgtc     420
tcggattcaa aggattttgt acccaggatt caccacaggg tgttcggttc gcagattatt     480
cctccgcttt cacatctagc caaatggccg ccgcaacatt tgaccgctca attctttatc     540
aacgaggcca agccatggca caggaacaca aggctaaggg tatcacaatt caattgggcc     600
ctgttgccgg ccctctcggt cgcatccccg agggcggccg caactgggaa ggattctccc     660
ctgatcctgt cttgactggt atagccatgg ctgagacaat taagggcatg caggatactg     720
gagtgattgc ttgcgctaaa cattatattg gaaacgagca ggagcacttc cgtcaagtgg     780
gtgaagctgc gggtcacgga tacactattt ccgatactat ttcatctaat attgacgacc     840
gtgctatgca tgagctatac ttgtggccat ttgctgatgc cgttcgcgct ggtgtggggtt     900 ctttcatgtg ctcatactct cagatcaaca actcctacgg atgccaaaac agtcagaccc     960
tcaacaagct cctcaagagc gaattgggct tccaaggctt tgtcatgagc gattggggtg    1020
cccatcactc tggagtgtca tcggcgctag ctggacttga tatgagcatg ccgggtgata    1080
ccgaatttga ttctggcttg agcttctggg gctctaacct caccattgca attctgaacg    1140
gcacggttcc cgaatggcgc ctggatgaca tggcgatgcg aattatggct gcatacttca    1200
aagttggcct tactattgag gatcaaccag atgtcaactt caatgcctgg acccatgaca    1260
cctacggata taaatacgct tatagcaagg aagattacga gcaggtcaac tggcatgtcg    1320
atgttcgcag cgaccacaat aagctcattc gcgagactgc cgcgaagggt acagttctgc    1380
tgaagaacaa ctttcatgct ctccctctga agcagcccag gttcgtggcc gtcgttggtc    1440
```

```
aggatgccgg gccaaacccc aagggcccta acggctgcgc agaccgagga tgcgaccaag    1500
gcactctcgc aatgggatgg ggctcagggt ctaccgaatt cccttacctg gtcactcctg    1560
acactgctat tcagtcaaag gtcctcgaat acggggtcg atacgagagt atttttgata    1620
actatgacga caatgctatc ttgtcgcttg tctcacagcc tgatgcaacc tgtatcgttt    1680
ttgcaaatgc cgattccggt gaaggctaca tcactgtcga caacaactgg ggtgaccgca    1740
acaatctgac cctctggcaa aatgccgatc aagtgattag cactgtcagc tcgcgatgca    1800
acaacacaat cgttgttctc cactctgtcg gaccagtgtt gctaaatggt atatatgagc    1860
acccgaacat cacagctatt gtctgggcag ggatgccagg cgaagaatct ggcaatgctc    1920
tcgtggatat tctttggggc aatgttaacc ctgccggtcg cactccgttc acctgggcca    1980
aaagtcgaga ggactatggc actgatataa tgtacgagcc caacaacggc cagcgtgcgc    2040
ctcagcagga tttcaccgag agcatctacc tcgactaccg ccatttcgac aaagctggta    2100
tcgagccaat ttacgagttt ggattcggcc tctcctatac caccttcgaa tactctgacc    2160
tccgtgttgt gaagaagtat gttcaaccat acagtcccac gaccggcacc ggtgctcaag    2220
caccttccat cggacagcca cctagccaga acctggatac ctacaagttc ctgctacat    2280 acaagtacat caaaaccttc atttatccct acctgaacag cactgtctcc ctccgcgctg    2340
cttccaagga tcccgaatac ggtcgtacag actttatccc accccacgcg cgtgatggct    2400
cccctcaacc tctcaacccc gctggagacc cagtggccag tggtggaaac aacatgctct    2460
acgacgaact ttacgaggtc actgcacaga tcaaaaacac tggcgacgtg gccggcgacg    2520
aagtcgtcca gctttacgta gatctcgggg gtgacaaccc gcctcgtcag ttgagaaact    2580
ttgacaggtt ttatctgctg cccggtcaga gctcaacatt ccgggctaca ttgacgcgcc    2640
gtgatttgag caactgggat attgaggcgc agaactggcg agttacggaa tcgcctaaga    2700
gagtgtatgt tggacggtcg agtcgggatt tgccgctgag ctcacaattg gagtaatgat    2760
catgtctacc aatagatgtt gaatgtctgg tgtggatatt                          2800
```

<210> SEQ ID NO 44
<211> LENGTH: 878
<212> TYPE: PRT
<213> ORGANISM: Penicillium brasilianum

<400> SEQUENCE: 44

```
Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125
```

```
Met Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
        195                 200                 205

Tyr Ile Gly Asn Glu Gln Glu His Phe Arg Gln Val Gly Glu Ala Ala
210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
                260                 265                 270

Tyr Gly Cys Gln Asn Ser Gln Thr Leu Asn Lys Leu Leu Lys Ser Glu
            275                 280                 285

Leu Gly Phe Gln Gly Phe Val Met Ser Asp Trp Gly Ala His His Ser
            290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
                340                 345                 350

Met Arg Ile Met Ala Ala Tyr Phe Lys Val Gly Leu Thr Ile Glu Asp
        355                 360                 365

Gln Pro Asp Val Asn Phe Asn Ala Trp Thr His Asp Thr Tyr Gly Tyr
370                 375                 380

Lys Tyr Ala Tyr Ser Lys Glu Asp Tyr Glu Gln Val Asn Trp His Val
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
            420                 425                 430

Pro Arg Phe Val Ala Val Gly Gln Asp Ala Gly Pro Asn Pro Lys
        435                 440                 445

Gly Pro Asn Gly Cys Ala Asp Arg Gly Cys Asp Gln Gly Thr Leu Ala
    450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asp Asn Ala Ile Leu Ser Leu Val Ser
                500                 505                 510

Gln Pro Asp Ala Thr Cys Ile Val Phe Ala Asn Ala Asp Ser Gly Glu
            515                 520                 525

Gly Tyr Ile Thr Val Asp Asn Asn Trp Gly Asp Arg Asn Asn Leu Thr
            530                 535                 540

Leu Trp Gln Asn Ala Asp Gln Val Ile Ser Thr Val Ser Ser Arg Cys
```

```
              545                 550                 555                 560
Asn Asn Thr Ile Val Val Leu His Ser Val Gly Pro Val Leu Leu Asn
                    565                 570                 575
Gly Ile Tyr Glu His Pro Asn Ile Thr Ala Ile Val Trp Ala Gly Met
                580                 585                 590
Pro Gly Glu Glu Ser Gly Asn Ala Leu Val Asp Ile Leu Trp Gly Asn
            595                 600                 605
Val Asn Pro Ala Gly Arg Thr Pro Phe Thr Trp Ala Lys Ser Arg Glu
610                 615                 620
Asp Tyr Gly Thr Asp Ile Met Tyr Glu Pro Asn Asn Gly Gln Arg Ala
625                 630                 635                 640
Pro Gln Gln Asp Phe Thr Glu Ser Ile Tyr Leu Asp Tyr Arg His Phe
                645                 650                 655
Asp Lys Ala Gly Ile Glu Pro Ile Tyr Glu Phe Gly Phe Gly Leu Ser
                660                 665                 670
Tyr Thr Thr Phe Glu Tyr Ser Asp Leu Arg Val Val Lys Lys Tyr Val
            675                 680                 685
Gln Pro Tyr Ser Pro Thr Thr Gly Thr Gly Ala Gln Ala Pro Ser Ile
        690                 695                 700
Gly Gln Pro Pro Ser Gln Asn Leu Asp Thr Tyr Lys Phe Pro Ala Thr
705                 710                 715                 720
Tyr Lys Tyr Ile Lys Thr Phe Ile Tyr Pro Tyr Leu Asn Ser Thr Val
                725                 730                 735
Ser Leu Arg Ala Ala Ser Lys Asp Pro Glu Tyr Gly Arg Thr Asp Phe
                740                 745                 750
Ile Pro Pro His Ala Arg Asp Gly Ser Pro Gln Pro Leu Asn Pro Ala
            755                 760                 765
Gly Asp Pro Val Ala Ser Gly Gly Asn Asn Met Leu Tyr Asp Glu Leu
        770                 775                 780
Tyr Glu Val Thr Ala Gln Ile Lys Asn Thr Gly Asp Val Ala Gly Asp
785                 790                 795                 800
Glu Val Val Gln Leu Tyr Val Asp Leu Gly Gly Asp Asn Pro Pro Arg
                805                 810                 815
Gln Leu Arg Asn Phe Asp Arg Phe Tyr Leu Leu Pro Gly Gln Ser Ser
                820                 825                 830
Thr Phe Arg Ala Thr Leu Thr Arg Arg Asp Leu Ser Asn Trp Asp Ile
            835                 840                 845
Glu Ala Gln Asn Trp Arg Val Thr Glu Ser Pro Lys Arg Val Tyr Val
        850                 855                 860
Gly Arg Ser Ser Arg Asp Leu Pro Leu Ser Ser Gln Leu Glu
865                 870                 875

<210> SEQ ID NO 45
<211> LENGTH: 2583
<212> TYPE: DNA
<213> ORGANISM: Aspergillus niger

<400> SEQUENCE: 45
atgaggttca ctttgatcga ggcggtggct ctgactgccg tctcgctggc cagcgctgat      60
gaattggcct actccccacc gtattaccca tcccctgggg ccaatggcca gggcgactgg     120
gcgcaggcat accagcgcgc tgttgatatt gtctcgcaaa tgacattgga tgagaaggtc     180
aatctgacca caggaactgg atgggaattg aactatgtg ttggtcagac tggcggtgtt     240
ccccgattgg gagttccggg aatgtgttta caggatagcc ctctgggcgt tcgcgactcc     300
```

-continued

```
gactacaact ctgctttccc tgccggcatg aacgtggctg caacctggga caagaatctg    360
gcataccttc gcggcaaggc tatgggtcag gaatttagtg acaagggtgc cgatatccaa    420
ttgggtccag ctgccggccc tctcggtaga agtcccgacg gtggtcgtaa ctgggagggc    480
ttctccccag accctgccct aagtggtgtg ctctttgccg agaccatcaa gggtatccaa    540
gatgctggtg tggttgcgac ggctaagcac tacattgctt acgagcaaga gcatttccgt    600
caggcgcctg aagcccaagg ttttggattt aatatttccg agagtggaag tgcgaacctc    660
gatgataaga ctatgcacga gctgtacctc tggcccttcg cggatgccat ccgtgcaggt    720
gctggcgctg tgatgtgctc ctacaaccag atcaacaaca gttatggctg ccagaacagc    780
tacactctga acaagctgct caaggccgag ctgggcttcc agggctttgt catgagtgat    840
tgggctgctc accatgctgg tgtgagtggt gctttggcag gattggatat gtctatgcca    900
ggagacgtcg actacgacag tggtacgtct tactggggta caaacttgac cattagcgtg    960
ctcaacggaa cggtgcccca atggcgtgtt gatgacatgg ctgtccgcat catggccgcc   1020
tactacaagg tcggccgtga ccgtctgtgg actcctccca acttcagctc atggaccaga   1080
gatgaatacg gctacaagta ctactacgtg tcggagggac cgtacgagaa ggtcaaccag   1140
tacgtgaatg tgcaacgcaa ccacagcgaa ctgattcgcc gcattggagc ggacagcacg   1200
gtgctcctca gaacgacgg cgctctgcct ttgactggta aggagcgcct ggtcgcgctt   1260
atcggagaag atgcgggctc caacccttat ggtgccaacg gctgcagtga ccgtggatgc   1320
gacaatggaa cattggcgat gggctgggga agtggtactg ccaacttccc atacctggtg   1380
accccccgagc aggccatctc aaacgaggtg cttaagcaca agaatggtgt attcaccgcc   1440
accgataact gggctatcga tcagattgag gcgcttgcta agaccgccag tgtctctctt   1500
gtctttgtca cgccgactc tggtgagggt tacatcaatg tggacggaaa cctgggtgac   1560
cgcaggaacc tgaccctgtg gaggaacggc gataatgtga tcaaggctgc tgctagcaac   1620
tgcaacaaca caatcgttgt cattcactct gtcggaccag tcttggttaa cgagtggtac   1680
gacaacccca tgttaccgc tatcctctgg ggtggtttgc ccggtcagga gtctggcaac   1740
tctcttgccg acgtcctcta tggccgtgtc aaccccggtg ccaagtcgcc ctttacctgg   1800
ggcaagactc gtgaggccta ccaagactac ttggtcaccg agcccaacaa cggcaacgga   1860
gcccctcagg aagactttgt cgagggcgtc ttcattgact accgtggatt tgacaagcgc   1920
aacgagaccc cgatctacga gttcggctat ggtctgagct acaccacttt caactactcg   1980
aaccttgagg tgcaggtgct gagcgcccct gcatacgagc tgcttcgggg tgagaccgag   2040
gcagcgccaa ccttcggaga ggttggaaat gcgtcggatt acctctaccc cagcggattg   2100
cagagaatta ccaagttcat ctaccccgtgg ctcaacggta ccgatctcga ggcatcttcc   2160
ggggatgcta gctacgggca ggactcctcc gactatcttc ccgagggagc caccgatggc   2220
tctgcgcaac cgatcctgcc tgccggtggc ggtcctggcg caacccctcg cctgtacgac   2280
gagctcatcc gcgtgtcagt gaccatcaag aacaccggca aggttgctgg tgatgaagtt   2340
ccccaactgt atgtttccct tggcggtccc aatgagccca agatcgtgct gcgtcaattc   2400
gagcgcatca cgctgcagcc gtcggaggag acgaagtgga gcacgactct gacgcgccgt   2460
gaccttgcaa actggaatgt tgagaagcag gactgggaga ttacgtcgta tcccaagatg   2520
gtgtttgtcg gaagctcctc gcggaagctg ccgctccggg cgtctctgcc tactgttcac   2580
taa                                                                 2583
```

<210> SEQ ID NO 46
<211> LENGTH: 860
<212> TYPE: PRT
<213> ORGANISM: Aspergillus niger

<400> SEQUENCE: 46

Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn Gln Tyr Val Asn Val
    370                 375                 380

-continued

```
Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Val Thr Pro Glu Gln
        450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
            515                 520                 525

Asn Gly Asp Asn Val Ile Lys Ala Ala Ala Ser Asn Cys Asn Asn Thr
        530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
        610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
            675                 680                 685

Gly Asn Ala Ser Asp Tyr Leu Tyr Pro Ser Gly Leu Gln Arg Ile Thr
        690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Asp Tyr Leu Pro Glu Gly
                725                 730                 735

Ala Thr Asp Gly Ser Ala Gln Pro Ile Leu Pro Ala Gly Gly Pro
            740                 745                 750

Gly Gly Asn Pro Arg Leu Tyr Asp Glu Leu Ile Arg Val Ser Val Thr
            755                 760                 765

Ile Lys Asn Thr Gly Lys Val Ala Gly Asp Glu Val Pro Gln Leu Tyr
        770                 775                 780

Val Ser Leu Gly Gly Pro Asn Glu Pro Lys Ile Val Leu Arg Gln Phe
785                 790                 795                 800
```

```
Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860

<210> SEQ ID NO 47
<211> LENGTH: 2583
<212> TYPE: DNA
<213> ORGANISM: Aspergillus aculeatus

<400> SEQUENCE: 47
atgaagctca gttggcttga ggcggctgcc ttgacggctg cttcagtcgt cagcgctgat    60
gaactggcgt tctctcctcc tttctacccc tctccgtggg ccaatggcca gggagagtgg   120
gcggaagcct accagcgtgc agtggccatt gtatcccaga tgactctgga tgagaaggtc   180
aacctgacca ccggaactgg atgggagctg agaagtgcg tcggtcagac tggtggtgtc    240
ccaagactga acatcggtgg catgtgtctt caggacagtc ccttgggaat tcgtgatagt   300
gactacaatt cggctttccc tgctggtgtc aacgttgctg cgacatggga caagaacctt   360
gcttatctac gtggtcaggc tatgggtcaa gagttcagtg acaaggaat tgatgttcaa    420 ttgggaccgg ccgcgggtcc cctcggcagg agccctgatg aggtcgcaa ctgggaaggt    480 ttctctccag acccggctct tactggtgtg ctctttgcgg agacgattaa gggtattcaa   540
gacgctggtg tcgtggcgac agccaagcat tacattctca atgagcaaga gcatttccgc   600
caggtcgcag aggctgcggg ctacggattc aatatctccg cacgatcag ctctaacgtt    660 gatgacaaga ccattcatga aatgtacctc tggcccttcg cggatgccgt tcgcgccggc   720
gttggcgcca tcatgtgttc ctacaaccag atcaacaaca gctacggttg ccagaacagt   780
tacactctga caagcttct gaaggccgag ctcggcttcc agggctttgt gatgtctgac    840
tggggtgctc accacagtgg tgttggctct gcttttggccg gcttggatat gtcaatgcct   900
ggcgatatca ccttcgattc tgccactagt ttctggggta ccaacctgac cattgctgtg   960
ctcaacggta ccgtcccgca gtggcgcgtt gacgacatgg ctgtccgtat catggctgcc  1020
tactacaagg ttggccgcga ccgcctgtac cagccgccta acttcagctc ctggactcgc  1080
gatgaatacg gcttcaagta tttctacccc caggaagggc cctatgagaa ggtcaatcac  1140
tttgtcaatg tgcagcgcaa ccacagcgag gttattcgca agttgggagc agacagtact  1200
gttctactga gaacaacaa tgccctgccg ctgaccggaa aggagcgcaa agttgcgatc  1260
ctgggtgaag atgctggatc caactcgtac ggtgccaatg gctgctctga ccgtggctgt  1320
gacaacggta ctcttgctat ggcttgggt agcggcactg ccgaattccc atatctcgtg  1380 accctgagc aggctattca agccgaggtg ctcaagcata agggcagcgt ctacgccatc  1440
acggacaact gggcgctgag ccaggtggag accctcgcta acaagccag tgtctctctt  1500 gtatttgtca actcggacgc gggagagggc tatatctccg tggacggaaa cgagggcgac  1560
cgcaacaacc tcaccctctg aagaacggc gacaacctca tcaaggctgc tgcaaacaac  1620
tgcaacaaca ccatcgttgt catccactcc gttggacctg ttttggttga cgagtggtat  1680
gaccacccca acgttactgc catcctctgg gcgggcttgc ctggccagga gtctggcaac  1740
tccttggctg acgtgctcta cggccgcgtc aacccgggcg ccaaatctcc attcacctgg  1800
```

```
ggcaagacga gggaggcgta cggggattac cttgtccgtg agctcaacaa cggcaacgga    1860
gctccccaag atgatttctc ggaaggtgtt ttcattgact accgcggatt cgacaagcgc    1920
aatgagaccc cgatctacga gttcggacat ggtctgagct acaccacttt caactactct    1980
ggccttcaca tccaggttct caacgcttcc tccaacgctc aagtagccac tgagactggc    2040
gccgctccca ccttcggaca agtcggcaat gcctctgact acgtgtaccc tgagggattg    2100
accagaatca gcaagttcat ctatccctgg cttaattcca cagacctgaa ggcctcatct    2160
ggcgacccgt actatggagt cgacaccgcg gagcacgtgc ccgagggtgc tactgatggc    2220
tctccgcagc ccgttctgcc tgccggtggt ggctctggtg gtaacccgcg cctctacgat    2280
gagttgatcc gtgtttcggt gacagtcaag aacactggtc gtgttgccgg tgatgctgtg    2340
cctcaattgt atgtttccct tggtggaccc aatgagccca aggttgtgtt gcgcaaattc    2400
gaccgcctca ccctcaagcc ctccgaggag acggtgtgga cgactaccct gacccgccgc    2460
gatctgtcta actgggacgt tgcggctcag gactgggtca tcacttctta cccgaagaag    2520
gtccatgttg gtagctcttc gcgtcagctg ccccttcacg cggcgctccc gaaggtgcaa    2580
tga                                                                  2583
```

<210> SEQ ID NO 48
<211> LENGTH: 860
<212> TYPE: PRT
<213> ORGANISM: Aspergillus aculeatus

<400> SEQUENCE: 48

```
Met Lys Leu Ser Trp Leu Glu Ala Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
        35                  40                  45

Ala Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Ala Gly Tyr
        195                 200                 205

Gly Phe Asn Ile Ser Asp Thr Ile Ser Ser Asn Val Asp Asp Lys Thr
    210                 215                 220
```

```
Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
            245                 250                 255

Cys Gln Asn Ser Tyr Thr Leu Asn Lys Leu Leu Lys Ala Glu Leu Gly
        260                 265                 270

Phe Gln Gly Phe Val Met Ser Asp Trp Gly Ala His His Ser Gly Val
    275                 280                 285

Gly Ser Ala Leu Ala Gly Leu Asp Met Ser Met Pro Gly Asp Ile Thr
290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
            325                 330                 335

Ile Met Ala Ala Tyr Tyr Lys Val Gly Arg Asp Arg Leu Tyr Gln Pro
                340                 345                 350

Pro Asn Phe Ser Ser Trp Thr Arg Asp Glu Tyr Gly Phe Lys Tyr Phe
            355                 360                 365

Tyr Pro Gln Glu Gly Pro Tyr Glu Lys Val Asn His Phe Val Asn Val
370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
            420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
    450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
            485                 490                 495

Ser Val Ser Leu Val Phe Val Asn Ser Asp Ala Gly Glu Gly Tyr Ile
        500                 505                 510

Ser Val Asp Gly Asn Glu Gly Asp Arg Asn Asn Leu Thr Leu Trp Lys
    515                 520                 525

Asn Gly Asp Asn Leu Ile Lys Ala Ala Asn Cys Asn Asn Thr
530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
            565                 570                 575

Glu Ser Gly Asn Ser Leu Ala Asp Val Leu Tyr Gly Arg Val Asn Pro
        580                 585                 590

Gly Ala Lys Ser Pro Phe Thr Trp Gly Lys Thr Arg Glu Ala Tyr Gly
    595                 600                 605

Asp Tyr Leu Val Arg Glu Leu Asn Asn Gly Asn Gly Ala Pro Gln Asp
610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
```

```
                    645                 650                 655
Phe Asn Tyr Ser Gly Leu His Ile Gln Val Leu Asn Ala Ser Ser Asn
                660                 665                 670

Ala Gln Val Ala Thr Glu Thr Gly Ala Ala Pro Thr Phe Gly Gln Val
            675                 680                 685

Gly Asn Ala Ser Asp Tyr Val Tyr Pro Glu Gly Leu Thr Arg Ile Ser
        690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
850                 855                 860

<210> SEQ ID NO 49
<211> LENGTH: 3294
<212> TYPE: DNA
<213> ORGANISM: Aspergillus oryzae

<400> SEQUENCE: 49
atgcgttcct cccccctcct ccgctccgcc gttgtggccg ccctgccggt gttggccctt        60
gccgctgatg gcaggtccac ccgctactgg gactgctgca agccttcgtg cggctgggcc       120
aagaaggctc ccgtgaacca gcctgtcttt tcctgcaacg ccaacttcca gcgtatcacg       180
gacttcgacg ccaagtccgg ctgcgagccg ggcggtgtcg cctactcgtg cgccgaccag       240
accccatggg ctgtgaacga cgacttcgcg ctcggttttg ctgccaccte tattgccggc       300 agcaatgagg cgggctggtg ctgcgcctgc tacgagctca ccttcacatc cggtcctgtt       360
gctggcaaga gatggtcgt ccagtccacc agcactggcg tgatcttgg agcaaccac          420 ttcgatctca acatccccgg cggcggcgtc ggcatcttcg acggatgcac tccccagttc       480
ggtggtctgc ccggccagcg ctacggcggc atctcgtccc gcaacgagtg cgatcggttc       540
cccgacgccc tcaagcccgg ctgctactgg cgcttcgact ggttcaagaa cgccgacaat       600
ccgagcttca gcttccgtca ggtccagtgc ccagccgagc tcgtcgctcg caccggatgc       660
cgccgcaacg acgacggcaa cttccctgcc gtccagatcc ccatgcgttc ctcccccctc       720
ctccgctccg ccgttgtggc cgccctgccg gtgttggccc ttgccaagga tgatctcgcg       780 tactccccte ctttctaccc ttccccatgg gcagatggtc agggtgaatg ggcggaagta       840
tacaaacgcg ctgtagacat agtttcccag atgacgttga cagagaaagt caacttaacg       900
```

```
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaagg tttctcacca   1200
gatccagccc tcaccggtgt acttttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gtcatgtgct cttacaacca aatcaacaac agctacggtt gcgagaatag cgaaactctg   1500
aacaagcttt tgaaggcgga gcttggtttc caaggcttcg tcatgagtga ttggaccgct   1560
catcacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata cacccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acgtcgtgt caaccctggc gccaagtctc ctttcacttg ggcaagacc    2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
gttcagcccc tgaacgcgtc ccgatacact cccaccagtg gcatgactga agctgcaaag   2760
aactttggtg aaattggcga tgcgtcggag tacgtgtatc cggaggggct ggaaaggatc   2820
catgagttta tctatccctg gatcaactct accgacctga aggcatcgtc tgacgattct   2880
aactacggct gggaagactc caagtatatt cccgaaggcg ccacggatgg gtctgcccag   2940
ccccgtttgc ccgctagtgg tggtgccgga ggaaacccccg gtctgtacga ggatctttc    3000
cgcgtctctg tgaaggtcaa gaacacgggc aatgtcgccg gtgatgaagt tcctcagctg   3060
tacgtttccc taggcggccc gaatgagccc aaggtggtac tgcgcaagtt tgagcgtatt   3120
cacttggccc cttcgcagga ggccgtgtgg acaacgaccc ttaccgtcg tgaccttgca    3180
aactgggacg tttcggctca ggactggacc gtcactcctt accccaagac gatctacgtt   3240
ggaaactcct cacggaaact gccgctccag gcctcgctgc ctaaggccca gtaa          3294
```

<210> SEQ ID NO 50
<211> LENGTH: 1097
<212> TYPE: PRT
<213> ORGANISM: Aspergillus oryzae

<400> SEQUENCE: 50

Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro

-continued

```
            370                 375                 380
Leu Gly Ala His Pro Asp Gly Arg Asn Trp Glu Gly Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Lys His Tyr Ile Met Asn Glu
                420                 425                 430

Gln Glu His Phe Arg Gln Gln Pro Glu Ala Ala Gly Tyr Gly Phe Asn
            435                 440                 445

Val Ser Asp Ser Leu Ser Ser Asn Val Asp Asp Lys Thr Met His Glu
450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala His His Ser Gly Val Gly Ala Ala
            515                 520                 525

Leu Ala Gly Leu Asp Met Ser Met Pro Gly Asp Val Thr Phe Asp Ser
530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
                580                 585                 590

Ser Ser Trp Thr Arg Asp Glu Tyr Gly Phe Ala His Asn His Val Ser
            595                 600                 605

Glu Gly Ala Tyr Glu Arg Val Asn Glu Phe Val Asp Val Gln Arg Asp
610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
            675                 680                 685

Gly Thr Ala Asn Phe Pro Tyr Leu Val Thr Pro Glu Gln Ala Ile Gln
690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Ala Arg Gln Ala Ser Val Ser
                725                 730                 735

Leu Val Phe Val Asn Ser Asp Ser Gly Glu Gly Tyr Leu Ser Val Asp
                740                 745                 750

Gly Asn Glu Gly Asp Arg Asn Asn Ile Thr Leu Trp Lys Asn Gly Asp
            755                 760                 765

Asn Val Val Lys Thr Ala Ala Asn Asn Cys Asn Asn Thr Val Val Ile
        770                 775                 780

Ile His Ser Val Gly Pro Val Leu Ile Asp Glu Trp Tyr Asp His Pro
785                 790                 795                 800
```

```
Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
                820                 825                 830

Ser Pro Phe Thr Trp Gly Lys Thr Arg Glu Ser Tyr Gly Ser Pro Leu
                835                 840                 845

Val Lys Asp Ala Asn Asn Gly Asn Gly Ala Pro Gln Ser Asp Phe Thr
                850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
                900                 905                 910

Ser Gly Met Thr Glu Ala Ala Lys Asn Phe Gly Glu Ile Gly Asp Ala
                915                 920                 925

Ser Glu Tyr Val Tyr Pro Glu Gly Leu Glu Arg Ile His Glu Phe Ile
                930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
                965                 970                 975

Gly Ser Ala Gln Pro Arg Leu Pro Ala Ser Gly Gly Ala Gly Gly Asn
                980                 985                 990

Pro Gly Leu Tyr Glu Asp Leu Phe Arg Val Ser Val Lys Val Lys Asn
                995                 1000                1005

Thr Gly Asn Val Ala Gly Asp Glu Val Pro Gln Leu Tyr Val Ser
        1010                1015                1020

Leu Gly Gly Pro Asn Glu Pro Lys Val Val Leu Arg Lys Phe Glu
        1025                1030                1035

Arg Ile His Leu Ala Pro Ser Gln Glu Ala Val Trp Thr Thr Thr
        1040                1045                1050

Leu Thr Arg Arg Asp Leu Ala Asn Trp Asp Val Ser Ala Gln Asp
        1055                1060                1065

Trp Thr Val Thr Pro Tyr Pro Lys Thr Ile Tyr Val Gly Asn Ser
        1070                1075                1080

Ser Arg Lys Leu Pro Leu Gln Ala Ser Leu Pro Lys Ala Gln
        1085                1090                1095

<210> SEQ ID NO 51
<211> LENGTH: 3294
<212> TYPE: DNA
<213> ORGANISM: Aspergillus oryzae

<400> SEQUENCE: 51
atgcgttcct ccccctcct ccgctccgcc gttgtggccg ccctgccggt gttggccctt     60
gccgctgatg caggtccac ccgctactgg gactgctgca agccttcgtg cggctgggcc    120
aagaaggctc ccgtgaacca gcctgtcttt tcctgcaacg ccaacttcca gcgtatcacg    180
gacttcgacg ccaagtccgg ctgcgagccg ggcggtgtcg cctactcgtg cgccgaccag    240 acccccatggg ctgtgaacga cgacttcgcg ctcggttttg ctgccacctc tattgccggc    300
agcaatgagg cgggctggtg ctgcgccctgc tacgagctca ccttcacatc cggtcctgtt    360
gctggcaaga agatggtcgt ccagtccacc agcactggcg gtgatcttgg cagcaaccac    420
```

```
ttcgatctca acatccccgg cggcggcgtc ggcatcttcg acggatgcac tccccagttc      480
ggtggtctgc ccggccagcg ctacggcggc atctcgtccc gcaacgagtg cgatcggttc      540
cccgacgccc tcaagcccgg ctgctactgg cgcttcgact ggttcaagaa cgccgacaat      600
ccgagcttca gcttccgtca ggtccagtgc ccagccgagc tcgtcgctcg caccggatgc      660
cgccgcaacg acgacggcaa cttccctgcc gtccagatcc ccatgcgttc ctcccccctc      720
ctccgctccg ccgttgtggc cgccctgccg gtgttggccc ttgccaagga tgatctcgcg      780
tactcccctc ctttctaccc ttccccatgg gcagatggtc agggtgaatg ggcggaagta      840
tacaaacgcg ctgtagacat agtttcccag atgacgttga cagagaaagt caacttaacg      900
actggaacag gatggcaact agagaggtgt gttggacaaa ctggcagtgt cccagactc      960 aacatcccca gcttgtgttt gcaggatagt cctcttggta ttcgtttctc ggactacaat     1020
tcagctttcc ctgcgggtgt taatgtcgct gccacctggg acaagacgct cgcctacctt     1080
cgtggtcagg caatgggtga ggagttcagt gataagggta ttgacgttca gctgggtcct     1140
gctgctggcc ctctcggtgc tcatccggat ggcggtagaa actgggaaag tttctcacca     1200
gatccagccc tcaccggtgt acttttttgcg gagacgatta agggtattca agatgctggt     1260
gtcattgcga cagctaagca ttatatcatg aacgaacaag agcatttccg ccaacaaccc     1320
gaggctgcgg gttacggatt caacgtaagc gacagtttga gttccaacgt tgatgacaag     1380
actatgcatg aattgtacct ctggcccttc gcggatgcag tacgcgctgg agtcggtgct     1440
gttatgtgct cttacaacca aatcaacaac agctacggtt gcgagaatag cgaaactctg     1500
aacaagcttt tgaaggcgga gcttggtttc caaggcttcg tcatgagtga ttggaccgct     1560
caacacagcg gcgtaggcgc tgctttagca ggtctggata tgtcgatgcc cggtgatgtt     1620
accttcgata gtggtacgtc tttctggggt gcaaacttga cggtcggtgt ccttaacggt     1680
acaatccccc aatggcgtgt tgatgacatg gctgtccgta tcatggccgc ttattacaag     1740
gttggccgcg acaccaaata caccccctccc aacttcagct cgtggaccag ggacgaatat     1800
ggtttcgcgc ataaccatgt ttcggaaggt gcttacgaga gggtcaacga attcgtggac     1860
gtgcaacgcg atcatgccga cctaatccgt cgcatcggcg cgcagagcac tgttctgctg     1920
aagaacaagg gtgccttgcc cttgagccgc aaggaaaagc tggtcgccct tctgggagag     1980
gatgcgggtt ccaactcgtg gggcgctaac ggctgtgatg accgtggttg cgataacggt     2040
acccttgcca tggcctgggg tagcggtact gcgaatttcc catacctcgt gacaccagag     2100
caggcgattc agaacgaagt tcttcagggc cgtggtaatg tcttcgccgt gaccgacagt     2160
tgggcgctcg acaagatcgc tgcggctgcc cgccaggcca gcgtatctct cgtgttcgtc     2220
aactccgact caggagaagg ctatcttagt gtggatggaa atgagggcga tcgtaacaac     2280
atcactctgt ggaagaacgg cgacaatgtg gtcaagaccg cagcgaataa ctgtaacaac     2340
accgttgtca tcatccactc cgtcggacca gttttgatcg atgaatggta tgaccacccc     2400
aatgtcactg gtattctctg ggctggtctg ccaggccagg agtctggtaa ctccattgcc     2460
gatgtgctgt acggtcgtgt caaccctggc gccaagtctc ctttcacttg ggcaagacc      2520 cgggagtcgt atggttctcc cttggtcaag gatgccaaca atggcaacgg agcgccccag     2580
tctgatttca cccagggtgt tttcatcgat taccgccatt tcgataagtt caatgagacc     2640
cctatctacg agtttggcta cggcttgagc tacaccacct tcgagctctc cgacctccat     2700
gttcagcccc tgaacgcgtc ccgatacact cccaccagtg gcatgactga agctgcaaag     2760
```

-continued

```
aactttggtg aaattggcga tgcgtcggag tacgtgtatc cggaggggct ggaaaggatc    2820
catgagttta tctatccctg gatcaactct accgacctga aggcatcgtc tgacgattct    2880
aactacggct gggaagactc caagtatatt cccgaaggcg ccacggatgg gtctgcccag    2940
ccccgtttgc ccgctagtgg tggtgccgga ggaaaccccg gtctgtacga ggatcttttc    3000
cgcgtctctg tgaaggtcaa gaacacgggc aatgtcgccg gtgatgaagt tcctcagctg    3060
tacgtttccc taggcggccc gaatgagccc aaggtggtac tgcgcaagtt tgagcgtatt    3120
cacttggccc cttcgcagga ggccgtgtgg acaacgaccc ttacccgtcg tgaccttgca    3180
aactgggacg tttcggctca ggactggacc gtcactcctt accccaagac gatctacgtt    3240
ggaaactcct cacggaaact gccgctccag gcctcgctgc ctaaggccca gtaa          3294
```

<210> SEQ ID NO 52
<211> LENGTH: 1097
<212> TYPE: PRT
<213> ORGANISM: Aspergillus oryzae

<400> SEQUENCE: 52

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285
```

```
Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
370                 375                 380

Leu Gly Ala His Pro Asp Gly Arg Asn Trp Glu Ser Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala Gln His Ser Gly Val Gly Ala Ala
        515                 520                 525

Leu Ala Gly Leu Asp Met Ser Met Pro Gly Asp Val Thr Phe Asp Ser
530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
690                 695                 700
```

Asn Glu Val Leu Gln Gly Arg Gly Asn Val Phe Ala Val Thr Asp Ser
705                 710                 715                 720

Trp Ala Leu Asp Lys Ile Ala Ala Ala Arg Gln Ala Ser Val Ser
            725                 730                 735

Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
            755                 760                 765

Asn Val Val Lys Thr Ala Ala Asn Cys Asn Asn Thr Val Val Ile
        770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
                820                 825                 830

Ser Pro Phe Thr Trp Gly Lys Thr Arg Glu Ser Tyr Gly Ser Pro Leu
        835                 840                 845

Val Lys Asp Ala Asn Asn Gly Asn Gly Ala Pro Gln Ser Asp Phe Thr
850                 855                 860

Gln Gly Val Phe Ile Asp Tyr Arg His Phe Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
        900                 905                 910

Ser Gly Met Thr Glu Ala Ala Lys Asn Phe Gly Glu Ile Gly Asp Ala
        915                 920                 925

Ser Glu Tyr Val Tyr Pro Glu Gly Leu Glu Arg Ile His Glu Phe Ile
    930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
                965                 970                 975

Gly Ser Ala Gln Pro Arg Leu Pro Ala Ser Gly Gly Ala Gly Gly Asn
            980                 985                 990

Pro Gly Leu Tyr Glu Asp Leu Phe Arg Val Ser Val Lys Val Lys Asn
            995                 1000                1005

Thr Gly Asn Val Ala Gly Asp Glu Val Pro Gln Leu Tyr Val Ser
    1010                1015                1020

Leu Gly Gly Pro Asn Glu Pro Lys Val Val Leu Arg Lys Phe Glu
    1025                1030                1035

Arg Ile His Leu Ala Pro Ser Gln Glu Ala Val Trp Thr Thr Thr
    1040                1045                1050

Leu Thr Arg Arg Asp Leu Ala Asn Trp Asp Val Ser Ala Gln Asp
    1055                1060                1065

Trp Thr Val Thr Pro Tyr Pro Lys Thr Ile Tyr Val Gly Asn Ser
    1070                1075                1080

Ser Arg Lys Leu Pro Leu Gln Ala Ser Leu Pro Lys Ala Gln
    1085                1090                1095

<210> SEQ ID NO 53
<211> LENGTH: 1846
<212> TYPE: DNA

<213> ORGANISM: Thielavia terrestris

<400> SEQUENCE: 53

```
aattgaagga gggagtggcg gagtggccac caagtcaggc ggctgtcaac taaccaagga      60
tgggaacagt tcggctcgcc ttgcccgagg gcagcgttcc ctgatgggga cgaaccatgg     120
gactggggtc agctgctgta taaaagttca atcgatgat ctctcagatg gcgctgctgg      180
ggtgttctgc gcttttccat cctcgcaacc tggtatccca ctagtccagc gttcggcacc     240
atgaagtcgt tcaccattgc cgccttggca gccctatggg cccaggaggc cgccgcccac     300
gcgaccttcc aggacctctg gattgatgga gtcgactacg gctcgcaatg tgtccgcctc     360
ccggcgtcca actcccccgt caccaatgtt gcgtccgacg atatccgatg caatgtcggc     420
acctcgaggc ccaccgtcaa gtgcccggtc aaggccggct ccacggtcac gatcgagatg     480
caccaggttc gcacgcctct ctgcgtaggc ccccagcta ctatatggca ctaacacgac      540
ctccagcaac ctggcgaccg gtcttgcgcc aacgaggcta tcggcggcga ccactacggc     600
cccgtaatgg tgtacatgtc caaggtcgat gacgcggtga cagccgacgg ttcatcgggc     660
tggttcaagg tgttccagga cagctgggcc aagaacccgt cgggttcgac gggcgacgac     720
gactactggg gcaccaagga cctcaactcg tgctgcggca agatgaacgt caagatcccc     780
gaagacatcg agccgggcga ctacctgctc cgcgccgagg ttatcgcgct gcacgtggcc     840
gccagctcgg gcggcgcgca gttctacatg tcctgctacc agctgaccgt gacgggctcc     900
ggcagcgcca ccccctcgac cgtgaatttc ccgggcgcct actcggccag cgacccgggc     960
atcctgatca acatccacgc gcccatgtcg acctacgtcg tcccgggccc gaccgtgtac    1020
gcgggcggct cgaccaagtc ggctggcagc tcctgctccg gctgcgaggc gacctgcacg    1080
gttggttccg gccccagcgc gacactgacg cagcccacct ccaccgcgac cgcgaccctcc   1140
gcccctggcg gcggcggctc cggctgcacg gcggccaagt accagcagtg cggcggcacc    1200
ggctacactg ggtgcaccac ctgcgctgta agttccctcg tgatatgcag cggaacaccg    1260
tctggactgt tttgctaact cgcgtcgtag tccgggtcta cctgcagcgc cgtctcgcct    1320
ccgtactact cgcagtgcct ctaagccggg agcgcttgct cagcgggctg ctgtgaagga    1380
gctccatgtc cccatgccgc catggccgga gtaccgggct gagcgcccaa ttcttgtata    1440
tagttgagtt ttcccaatca tgaatacata tgcatctgca tggactgttg cgtcgtcagt    1500
ctacatcctt tgctccactg aactgtgaga ccccatgtca tccggaccat cgatcggtg    1560
ctcgctctac catctcggtt gatgggtctg ggcttgagag tcactggcac gtcctcggcg    1620
gtaatgaaat gtggaggaaa gtgtgagctg tctgacgcac tcggcgctga tgagacgttg    1680
agcgcggccc acactggtgt tctgtaagcc agcacacaaa agaatactcc aggatggccc    1740
atagcggcaa atatacagta tcagggatgc aaaaagtgca aaagtaaggg gctcaatcgg    1800
ggatcgaacc cgagacctcg cacatgactt atttcaagtc aggggt                    1846
```

<210> SEQ ID NO 54
<211> LENGTH: 326
<212> TYPE: PRT
<213> ORGANISM: Thielavia terrestris

<400> SEQUENCE: 54

```
Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
            20                  25                  30
```

Tyr Gly Ser Gln Cys Val Arg Leu Pro Ala Ser Asn Ser Pro Val Thr
            35                  40                  45

Asn Val Ala Ser Asp Asp Ile Arg Cys Asn Val Gly Thr Ser Arg Pro
 50                  55                  60

Thr Val Lys Cys Pro Val Lys Ala Gly Ser Thr Val Thr Ile Glu Met
 65                  70                  75                  80

His Gln Gln Pro Gly Asp Arg Ser Cys Ala Asn Glu Ala Ile Gly Gly
                 85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
            115                 120                 125

Trp Ala Lys Asn Pro Ser Gly Ser Thr Gly Asp Asp Tyr Trp Gly
            130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
            195                 200                 205

Asn Phe Pro Gly Ala Tyr Ser Ala Ser Asp Pro Gly Ile Leu Ile Asn
            210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Ser Gly
            275                 280                 285

Cys Thr Ala Ala Lys Tyr Gln Gln Cys Gly Gly Thr Gly Tyr Thr Gly
            290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 55
<211> LENGTH: 880
<212> TYPE: DNA
<213> ORGANISM: Thielavia terrestris

<400> SEQUENCE: 55
accccgggat cactgcccct aggaaccagc acacctcggt ccaatcatgc ggttcgacgc      60
cctctccgcc ctcgctcttg cgccgcttgt ggctggccac ggcgccgtga ccagctacat     120
catcggcggc aaaacctatc ccggctacga gggcttctcg cctgcctcga gcccgccgac     180
gatccagtac cagtggcccg actacaaccc gaccctgagc gtgaccgacc cgaagatgcg     240
ctgcaacggc ggcacctcgg cagagctcag cgcgcccgtc caggccggcg agaacgtgac     300
ggccgtctgg aagcagtgga cccaccagca aggccccgtc atggtctgga tgttcaagtg     360
ccccggcgac ttctcgtcgt gccacggcga cggcaagggc tggttcaaga tcgaccagct     420

```
gggcctgtgg ggcaacaacc tcaactcgaa caactggggc accgcgatcg tctacaagac    480
cctccagtgg agcaacccga tccccaagaa cctcgcgccg ggcaactacc tcatccgcca    540
cgagctgctc gccctgcacc aggccaacac gccgcagttc tacgccgagt gcgcccagct    600
ggtcgtctcc ggcagcggct ccgccctgcc cccgtccgac tacctctaca gcatccccgt    660
ctacgcgccc cagaacgacc ccggcatcac cgtgagtggg cttccgttcc gcggcgagct    720
ctgtggaaat cttgctgacg atgggctagg ttgacatcta caacggcggg cttacctcct    780
acaccccgcc cggcggcccc gtctggtctg gcttcgagtt ttaggcgcat tgagtcgggg    840
gctacgaggg gaaggcatct gttcgcatga gcgtgggtac                         880
```

```
<210> SEQ ID NO 56
<211> LENGTH: 239
<212> TYPE: PRT
<213> ORGANISM: Thielavia terrestris

<400> SEQUENCE: 56

Met Arg Phe Asp Ala Leu Ser Ala Leu Ala Leu Ala Pro Leu Val Ala
1               5                   10                  15

Gly His Gly Ala Val Thr Ser Tyr Ile Ile Gly Lys Thr Tyr Pro
            20                  25                  30

Gly Tyr Glu Gly Phe Ser Pro Ala Ser Ser Pro Thr Ile Gln Tyr
        35                  40                  45

Gln Trp Pro Asp Tyr Asn Pro Thr Leu Ser Val Thr Asp Pro Lys Met
    50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Trp Gly Thr Ala Ile Val Tyr Lys
    130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
    210                 215                 220

Ser Tyr Thr Pro Pro Gly Gly Pro Val Trp Ser Gly Phe Glu Phe
225                 230                 235
```

```
<210> SEQ ID NO 57
<211> LENGTH: 1000
<212> TYPE: DNA
<213> ORGANISM: Thielavia terrestris

<400> SEQUENCE: 57
ctcctgttcc tgggccaccg cttgttgcct gcactattgg tagagttggt ctattgctag     60
```

```
agttggccat gcttctcaca tcagtcctcg gctcggctgc cctgcttgct agcggcgctg    120
cggcacacgg cgccgtgacc agctacatca tcgccggcaa gaattacccg ggtgggtag    180 ctgattattg agggcgcatt caaggttcat accggtgtgc atggctgaca accggctggc    240
agataccaag gcttttctcc tgcgaactcg ccgaacgtca tccaatggca atggcatgac    300
tacaaccccg tcttgtcgtg cagcgactcg aagcttcgct gcaacggcgg cacgtcggcc    360
accctgaacg ccacggccgc accgggcgac accatcaccg ccatctgggc cagtggacg    420 cacagccagg gccccatcct ggtgtggatg tacaagtgcc cgggctcctt cagctcctgt    480
gacggctccg gcgctggctg gttcaagatc gacgaggccg gcttccacgg cgacggcgtc    540
aaggtcttcc tcgacaccga gaacccgtcc ggctgggaca tcgccaagct cgtcggcggc    600
aacaagcagt ggagcagcaa ggtccccgag ggcctcgccc ccggcaacta cctcgtccgc    660
cacgagttga tcgccctgca ccaggccaac aacccgcagt tctacccgga gtgcgcccag    720
gtcgtcatca ccggctccgg caccgcgcag ccggatgcct catacaaggc ggctatcccc    780
ggctactgca accagaatga cccgaacatc aaggtgagat ccaggcgtaa tgcagtctac    840
tgctggaaag aaagtggtcc aagctaaacc gcgctccagg tgcccatcaa cgaccactcc    900
atccctcaga cctacaagat tcccggccct cccgtcttca agggcaccgc cagcaagaag    960
gcccgggact tcaccgcctg aagttgttga atcgatggag                         1000
```

<210> SEQ ID NO 58
<211> LENGTH: 258
<212> TYPE: PRT
<213> ORGANISM: Thielavia terrestris

<400> SEQUENCE: 58

```
Met Leu Leu Thr Ser Val Leu Gly Ser Ala Ala Leu Leu Ala Ser Gly
1               5                   10                  15

Ala Ala Ala His Gly Ala Val Thr Ser Tyr Ile Ile Ala Gly Lys Asn
            20                  25                  30

Tyr Pro Gly Tyr Gln Gly Phe Ser Pro Ala Asn Ser Pro Asn Val Ile
        35                  40                  45

Gln Trp Gln Trp His Asp Tyr Asn Pro Val Leu Ser Cys Ser Asp Ser
    50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
        115                 120                 125

Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175

Leu Ile Ala Leu His Gln Ala Asn Asn Pro Gln Phe Tyr Pro Glu Cys
            180                 185                 190

Ala Gln Val Val Ile Thr Gly Ser Gly Thr Ala Gln Pro Asp Ala Ser
        195                 200                 205
```

Tyr Lys Ala Ala Ile Pro Gly Tyr Cys Asn Gln Asn Asp Pro Asn Ile
    210                 215                 220

Lys Val Pro Ile Asn Asp His Ser Ile Pro Gln Thr Tyr Lys Ile Pro
225                 230                 235                 240

Gly Pro Pro Val Phe Lys Gly Thr Ala Ser Lys Lys Ala Arg Asp Phe
                245                 250                 255

Thr Ala

<210> SEQ ID NO 59
<211> LENGTH: 681
<212> TYPE: DNA
<213> ORGANISM: Thielavia terrestris

<400> SEQUENCE: 59
atgctcgcaa acggtgccat cgtcttcctg gccgccgccc tcggcgtcag tggccactac      60
acctggccac gggttaacga cggcgccgac tggcaacagg tccgtaaggc ggacaactgg     120
caggacaacg gctacgtcgg ggatgtcacg tcgccacaga tccgctgttt ccaggcgacc     180
ccgtccccgg ccccatccgt cctcaacacc acggccggct cgaccgtgac ctactgggcc     240
aaccccgacg tctaccaccc cgggcctgtg cagttttaca tggcccgcgt gcccgatggc     300
gaggacatca actcgtggaa cggcgacggc gccgtgtggt tcaaggtgta cgaggaccat     360 cctaccttt gcgctcagct cacatggccc agcacgggca gagctcgtt cgcggttccc      420 atcccccgt gcatcaagtc cggctactac ctcctccggg cggagcaaat cggcctgcac      480
gtcgcccaga gcgtaggcgg agcgcagttc tacatctcat cgcccagct cagcgtcacc      540 ggcggcggca gcaccgagcc gccgaacaag gtggccttcc ccggcgctta cagtgcgacg     600
gacccgggca ttctgatcaa catctactac cctgttccca cgtcctacca gaaccccggc     660
ccggccgtct tcagctgctg a                                              681

<210> SEQ ID NO 60
<211> LENGTH: 226
<212> TYPE: PRT
<213> ORGANISM: Thielavia terrestris

<400> SEQUENCE: 60

Met Leu Ala Asn Gly Ala Ile Val Phe Leu Ala Ala Ala Leu Gly Val
1               5                   10                  15

Ser Gly His Tyr Thr Trp Pro Arg Val Asn Asp Gly Ala Asp Trp Gln
                20                  25                  30

Gln Val Arg Lys Ala Asp Asn Trp Gln Asp Asn Gly Tyr Val Gly Asp
            35                  40                  45

Val Thr Ser Pro Gln Ile Arg Cys Phe Gln Ala Thr Pro Ser Pro Ala
    50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225

<210> SEQ ID NO 61
<211> LENGTH: 960
<212> TYPE: DNA
<213> ORGANISM: Thielavia terrestris

<400> SEQUENCE: 61
atgaagggac ttttcagtgc cgccgccctc tccctggccg tcggccaggc ttcggcccat      60
tacatcttcc agcaactctc catcaacggg aaccagtttc cggtgtacca atatattcgc     120
aagaacacca attataacag tcccgttacc gatctcacgt ccgacgatct tcggtgcaat     180
gtcggcgccc agggtgctgg gacagacacc gtcacggtga aggccggcga ccagttcacc     240
ttcacccttg acacccctgt ttaccaccag gggcccatct ccatctacat gtccaaggcc     300
ccgggcgcgg cgtcagacta cgatggcagc ggcggctggt tcaagatcaa ggactggggc     360
ccgactttca cgccgacgg cacggccacc tgggacatgg ccggctcata cctacaac       420
atcccgacct gcattcccga cggcgactat ctgctccgca tccagtcgct ggccatccac     480
aaccccctggc cggcgggcat cccgcagttc tacatctcct gcgcccagat caccgtgacc     540
ggcggcggca acggcaaccc tggccccgacg gcccctcatcc ccggcgcctt caaggacacc     600
gacccgggct acacggtgaa catctacacg aacttccaca actacacggt tcccggcccg     660
gaggtcttca gctgcaacgg cggcggctcg aaccccgcccc cgccggtgag tagcagcacg     720
cccgcgacca cgacgctggt cacgtcgacg cgcaccacgt cctccacgtc ctccgcctcg     780
acgccggcct cgaccggcgg ctgcaccgtc gccaagtggg gccagtgcgg cggcaacggg     840
tacaccggct gcacgacctg cgcggccggg tccacctgca gcaagcagaa cgactactac     900
tcgcagtgct gtaagggag gccgcaaagc atgaggtgtt tgaagaggag gagaggggtc     960

<210> SEQ ID NO 62
<211> LENGTH: 304
<212> TYPE: PRT
<213> ORGANISM: Thielavia terrestris

<400> SEQUENCE: 62

Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
        35                  40                  45

Val Thr Asp Leu Thr Ser Asp Asp Leu Arg Cys Asn Val Gly Ala Gln
    50                  55                  60

Gly Ala Gly Thr Asp Thr Val Thr Val Lys Ala Gly Asp Gln Phe Thr

```
            65                  70                  75                  80
        Phe Thr Leu Asp Thr Pro Val Tyr His Gln Gly Pro Ile Ser Ile Tyr
                            85                  90                  95

Met Ser Lys Ala Pro Gly Ala Ala Ser Asp Tyr Asp Gly Ser Gly Gly
                        100                 105                 110

Trp Phe Lys Ile Lys Asp Trp Gly Pro Thr Phe Asn Ala Asp Gly Thr
                    115                 120                 125

Ala Thr Trp Asp Met Ala Gly Ser Tyr Thr Tyr Asn Ile Pro Thr Cys
                130                 135                 140

Ile Pro Asp Gly Asp Tyr Leu Leu Arg Ile Gln Ser Leu Ala Ile His
        145                 150                 155                 160

Asn Pro Trp Pro Ala Gly Ile Pro Gln Phe Tyr Ile Ser Cys Ala Gln
                        165                 170                 175

Ile Thr Val Thr Gly Gly Gly Asn Gly Asn Pro Gly Pro Thr Ala Leu
                    180                 185                 190

Ile Pro Gly Ala Phe Lys Asp Thr Asp Pro Gly Tyr Thr Val Asn Ile
                195                 200                 205

Tyr Thr Asn Phe His Asn Tyr Thr Val Pro Gly Pro Glu Val Phe Ser
            210                 215                 220

Cys Asn Gly Gly Gly Ser Asn Pro Pro Pro Val Ser Ser Ser Thr
        225                 230                 235                 240

Pro Ala Thr Thr Thr Leu Val Thr Ser Thr Arg Thr Thr Ser Ser Thr
                        245                 250                 255

Ser Ser Ala Ser Thr Pro Ala Ser Thr Gly Gly Cys Thr Val Ala Lys
                    260                 265                 270

Trp Gly Gln Cys Gly Gly Asn Gly Tyr Thr Gly Cys Thr Thr Cys Ala
                275                 280                 285

Ala Gly Ser Thr Cys Ser Lys Gln Asn Asp Tyr Tyr Ser Gln Cys Leu
            290                 295                 300

<210> SEQ ID NO 63
<211> LENGTH: 954
<212> TYPE: DNA
<213> ORGANISM: Thielavia terrestris

<400> SEQUENCE: 63
atgaagggcc tcagcctcct cgccgctgcg tcggcagcga ctgctcatac catcttcgtg     60
cagctcgagt caggggaac gacctatccg gtatcctacg gcatccggga ccctagctac     120
gacggtccca tcaccgacgt cacctccgac tcactggctt gcaatggtcc ccgaaccccc     180
acgacgccgt ccccgtacat catcaacgtc accgccggca ccacggtcgc ggcgatctgg     240
aggcacaccc tcacatccgg ccccgacgat gtcatggacg ccagccacaa ggggccgacc     300
ctggcctacc tcaagaaggt cgatgatgcc ttgaccgaca cgggtatcgg cggcggctgg     360
ttcaagatcc aggaggccgg ttacgacaat ggcaattggg ctaccagcac ggtgatcacc     420
aacggtggct tccaatatat tgacatcccc gcctgcattc ccaacggcca gtatctgctc     480
cgcgccgaga tgatcgcgct ccacgccgcc agcacgcagg tggtgcccca gctctacatg     540
gagtgcgcgc agatcaacgt ggtgggcggc tccggcagcg ccagcccgca gacgtacagc     600
atcccgggca tctaccaggc aaccgacccg gcctgctga tcaacatcta ctccatgacg     660
ccgtccagcc agtacaccat tccgggtccg ccctgttca cctgcagcgg cagcggcaac     720
aacggcggcg gcagcaaccc gtcgggcggg cagaccacga cggcgaagcc cacgacgacg     780
acggcggcga cgaccacctc ctccgccgct cctaccagca gccagggggg cagcagcggt     840
```

```
tgcaccgttc cccagtggca gcagtgcggt ggcatctcgt tcaccggctg caccacctgc    900
gcggcgggct acacctgcaa gtatctgaac gactattact cgcaatgcca gtaa          954
```

<210> SEQ ID NO 64
<211> LENGTH: 317
<212> TYPE: PRT
<213> ORGANISM: Thielavia terrestris

<400> SEQUENCE: 64

```
Met Lys Gly Leu Ser Leu Leu Ala Ala Ala Ser Ala Ala Thr Ala His
1               5                   10                  15

Thr Ile Phe Val Gln Leu Glu Ser Gly Gly Thr Thr Tyr Pro Val Ser
            20                  25                  30

Tyr Gly Ile Arg Asp Pro Ser Tyr Asp Gly Pro Ile Thr Asp Val Thr
        35                  40                  45

Ser Asp Ser Leu Ala Cys Asn Gly Pro Pro Asn Pro Thr Thr Pro Ser
    50                  55                  60

Pro Tyr Ile Ile Asn Val Thr Ala Gly Thr Thr Val Ala Ala Ile Trp
65                  70                  75                  80

Arg His Thr Leu Thr Ser Gly Pro Asp Asp Val Met Asp Ala Ser His
                85                  90                  95

Lys Gly Pro Thr Leu Ala Tyr Leu Lys Lys Val Asp Asp Ala Leu Thr
            100                 105                 110

Asp Thr Gly Ile Gly Gly Gly Trp Phe Lys Ile Gln Glu Ala Gly Tyr
        115                 120                 125

Asp Asn Gly Asn Trp Ala Thr Ser Thr Val Ile Thr Asn Gly Gly Phe
    130                 135                 140

Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Gly Ala
                165                 170                 175

Gln Leu Tyr Met Glu Cys Ala Gln Ile Asn Val Val Gly Gly Ser Gly
            180                 185                 190

Ser Ala Ser Pro Gln Thr Tyr Ser Ile Pro Gly Ile Tyr Gln Ala Thr
        195                 200                 205

Asp Pro Gly Leu Leu Ile Asn Ile Tyr Ser Met Thr Pro Ser Ser Gln
    210                 215                 220

Tyr Thr Ile Pro Gly Pro Pro Leu Phe Thr Cys Ser Gly Ser Gly Asn
225                 230                 235                 240

Asn Gly Gly Gly Ser Asn Pro Ser Gly Gly Gln Thr Thr Thr Ala Lys
                245                 250                 255

Pro Thr Thr Thr Thr Ala Ala Thr Thr Ser Ser Ala Ala Pro Thr
            260                 265                 270

Ser Ser Gln Gly Gly Ser Ser Gly Cys Thr Val Pro Gln Trp Gln Gln
        275                 280                 285

Cys Gly Gly Ile Ser Phe Thr Gly Cys Thr Cys Ala Ala Gly Tyr
    290                 295                 300

Thr Cys Lys Tyr Leu Asn Asp Tyr Tyr Ser Gln Cys Gln
305                 310                 315
```

<210> SEQ ID NO 65
<211> LENGTH: 799
<212> TYPE: DNA
<213> ORGANISM: Thermoascus aurantiacus

<400> SEQUENCE: 65

```
atgtccttttt ccaagataat tgctactgcc ggcgttcttg cctctgcttc tctagtggct    60
ggccatggct tcgttcagaa catcgtgatt gatggtaaaa agtatgtcat tgcaagacgc   120
acataagcgg caacagctga caatcgacag ttatggcggg tatctagtga accagtatcc   180
atacatgtcc aatcctccag aggtcatcgc ctggtctact acggcaactg atcttggatt   240
tgtggacggt actggatacc aaaccccaga tatcatctgc cataggggcg ccaagcctgg   300
agccctgact gctccagtct ctccaggagg aactgttgag cttcaatgga ctccatggcc   360
tgattctcac catggcccag ttatcaacta ccttgctccg tgcaatggtg attgttccac   420
tgtggataag acccaattag aattcttcaa aattgccgag agcggtctca tcaatgatga   480
caatcctcct gggatctggg cttcagacaa tctgatagca gccaacaaca gctggactgt   540
caccattcca accacaattg cacctggaaa ctatgttctg aggcatgaga ttattgctct   600
tcactcagct cagaaccagg atggtgccca gaactatccc cagtgcatca atctgcaggt   660
cactggaggt ggttctgata cccctgctgg aactcttgga acggcactct accacgatac   720
cgatcctgga attctgatca acatctatca gaaactttcc agctatatca tccctggtcc   780
tcctctgtat actggttaa                                                 799
```

<210> SEQ ID NO 66
<211> LENGTH: 250
<212> TYPE: PRT
<213> ORGANISM: Thermoascus aurantiacus

<400> SEQUENCE: 66

```
Met Ser Phe Ser Lys Ile Ile Ala Thr Ala Gly Val Leu Ala Ser
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220
```

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 67
<211> LENGTH: 1172
<212> TYPE: DNA
<213> ORGANISM: Trichoderma reesei

<400> SEQUENCE: 67

```
ggatctaagc cccatcgata tgaagtcctg cgccattctt gcagcccttg gctgtcttgc      60
cgggagcgtt ctcggccatg gacaagtcca aaacttcacg atcaatggac aatacaatca     120
gggtttcatt ctcgattact actatcagaa gcagaatact ggtcacttcc caacgttgc     180
tggctggtac gccgaggacc tagacctggg cttcatctcc cctgaccaat acaccacgcc     240
cgacattgtc tgtcacaaga acgcggcccc aggtgccatt tctgccactg cagcggccgg     300
cagcaacatc gtcttccaat ggggccctgg cgtctggcct caccctacg gtcccatcgt     360
tacctacgtg gctgagtgca gcggatcgtg cacgaccgtg aacaagaaca acctgcgctg     420
ggtcaagatt caggaggccg gcatcaacta taacacccaa gtctgggcgc agcaggatct     480
gatcaaccag gcaacaagt ggactgtgaa gatcccgtcg agcctcaggc ccggaaacta     540
tgtcttccgc catgaacttc ttgctgccca tggtgcctct agtgcgaacg gcatgcagaa     600
ctatcctcag tgcgtgaaca tcgccgtcac aggctcgggc acgaaagcgc tccctgccgg     660
aactcctgca actcagctct acaagcccac tgaccctggc atcttgttca acccttacac     720
aacaatcacg agctacacca tccctggccc agccctgtgg caaggctaga tccagggta     780
cggtgttggc gttcgtgaag tcggagctgt tgacaaggat atctgatgat gaacggagag     840
gactgatggg cgtgactgag tgtatatatt tttgatgacc aaattgtata cgaaatccga     900
acgcatggtg atcattgttt atccctgtag tatattgtct ccaggctgct aagagcccac     960
cgggtgtatt acggcaacaa agtcaggaat ttgggtggca atgaacgcag gtctccatga    1020
atgtatatgt gaagaggcat cggctggcat gggcattacc agatatagac cctgtgaaac    1080
atatagtact tgaacgtgct actggaacgg atcataagca agtcatcaac atgtgaaaaa    1140
acactacatg taaaaaaaaa aaaaaaaaaa aa                                  1172
```

<210> SEQ ID NO 68
<211> LENGTH: 249
<212> TYPE: PRT
<213> ORGANISM: Trichoderma reesei

<400> SEQUENCE: 68

Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
                20                  25                  30

Asn Gln Gly Phe Ile Leu Asp Tyr Tyr Tyr Gln Lys Gln Asn Thr Gly
            35                  40                  45

His Phe Pro Asn Val Ala Gly Trp Tyr Ala Glu Asp Leu Asp Leu Gly
        50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Ala Gly Ser Asn

|  |  |  |  | 85 |  |  |  | 90 |  |  |  | 95 |  |  |
|---|---|---|---|---|---|---|---|---|---|---|---|---|---|---|

Ile Val Phe Gln Trp Gly Pro Gly Val Trp Pro His Pro Tyr Gly Pro
                    100                    105                  110

Ile Val Thr Tyr Val Val Glu Cys Ser Gly Ser Cys Thr Thr Val Asn
                 115                   120                  125

Lys Asn Asn Leu Arg Trp Val Lys Ile Gln Glu Ala Gly Ile Asn Tyr
130                   135                   140

Asn Thr Gln Val Trp Ala Gln Gln Asp Leu Ile Asn Gln Gly Asn Lys
145                   150                   155                  160

Trp Thr Val Lys Ile Pro Ser Ser Leu Arg Pro Gly Asn Tyr Val Phe
                 165                   170                  175

Arg His Glu Leu Leu Ala Ala His Gly Ala Ser Ser Ala Asn Gly Met
                 180                   185                  190

Gln Asn Tyr Pro Gln Cys Val Asn Ile Ala Val Thr Gly Ser Gly Thr
                 195                   200                  205

Lys Ala Leu Pro Ala Gly Thr Pro Ala Thr Gln Leu Tyr Lys Pro Thr
                 210                   215                  220

Asp Pro Gly Ile Leu Phe Asn Pro Tyr Thr Thr Ile Thr Ser Tyr Thr
225                   230                   235                  240

Ile Pro Gly Pro Ala Leu Trp Gln Gly
                 245

<210> SEQ ID NO 69
<211> LENGTH: 1327
<212> TYPE: DNA
<213> ORGANISM: Aspergillus aculeatus

<400> SEQUENCE: 69

| | | | | | |
|---|---|---|---|---|---|
| aaaatggtcg | gactgctttc | aatcaccgcg | gcgcttgccg | cgactgtgtt | gccaaacatt | 60 |
| gtctctgccg | ttggtctgga | tcaggctgca | gttgccaaag | gacttcaata | cctttggcaca | 120 |
| gctacggata | tccccgagct | cacggatatt | ccatacgtta | ctcagctgaa | caacaccgcg | 180 |
| gactttggtc | aaattacccc | tggaaactcg | atgaagtggg | atgccacaga | accatctcag | 240 |
| ggcaccttca | cgttcacgaa | aggcgatgtc | attgcagatc | tggctgaggg | taatggccaa | 300 |
| tatctccgat | gtcatactct | ggtttggtat | aatcagctac | ctagctgggt | gactagcgga | 360 |
| acttggacta | tgctactct | caccgccgca | ttgaagaacc | acatcacgaa | tgtggtgtcg | 420 |
| cactacaaag | ggaaatgtct | tcattgggac | gtggtcaatg | aggcgttgaa | tgacgacgga | 480 |
| acctaccgca | ccaacatctt | ctacaccacc | atcggcgaag | cctacatccc | cattgccttt | 540 |
| gccgcagcgg | ctgcagccga | cccggacgcg | aagctgttct | acaatgacta | caacctcgaa | 600 |
| tacgcggcg | ccaaagccgc | cagcgcccgc | gccattgtcc | agctggtcaa | gaatgcaggt | 660 |
| gccaagatcg | acggggtagg | gttgcaggcc | catttcagcg | tcggcaccgt | gccgagtacg | 720 |
| agctcgctcg | tctcggtgct | gcaatctttc | actgcgctcg | gggtcgaggt | cgcctacacg | 780 |
| gaggccgacg | tgcgcattct | cctgcccacc | accgccacta | ccctggccca | acagtcgagc | 840 |
| gatttccagg | ccctggtgca | atcctgtgtg | cagacaacgg | gctgcgtcgg | cttcactatc | 900 |
| tgggattgga | cagataagta | cagctggggt | cccagcacgt | tctcgggcta | tgggcggcg | 960 |
| ctaccctggg | atgagaacct | ggttaagaag | cccgcgtaca | atggcttgtt | ggccggcatg | 1020 |
| gggggttacag | ttaccactac | gactaccacc | accactgcta | ctgccactgg | taagactacg | 1080 |
| actaccacaa | cgggtgccac | gagcacgggg | actacggctg | cgcattgggg | gcagtgtgga | 1140 |
| gggctcaact | ggagtggacc | gacggcgtgt | gccactgggt | acacctgcac | ttatgtcaat | 1200 |

```
gactattact cgcagtgtct gtgaagtata gcccaaccta aacctgccgg cgtgcttgcc    1260
attcagtcag tgagatttat atatcacaat actcaaaatt cattgctcga cctctgaaaa    1320
aaaaaaa                                                              1327
```

<210> SEQ ID NO 70
<211> LENGTH: 406
<212> TYPE: PRT
<213> ORGANISM: Aspergillus aculeatus

<400> SEQUENCE: 70

```
Met Val Gly Leu Leu Ser Ile Thr Ala Ala Leu Ala Ala Thr Val Leu
1               5                   10                  15

Pro Asn Ile Val Ser Ala Val Gly Leu Asp Gln Ala Ala Val Ala Lys
            20                  25                  30

Gly Leu Gln Tyr Phe Gly Thr Ala Thr Asp Asn Pro Glu Leu Thr Asp
        35                  40                  45

Ile Pro Tyr Val Thr Gln Leu Asn Asn Thr Ala Asp Phe Gly Gln Ile
    50                  55                  60

Thr Pro Gly Asn Ser Met Lys Trp Asp Ala Thr Glu Pro Ser Gln Gly
65                  70                  75                  80

Thr Phe Thr Phe Thr Lys Gly Asp Val Ile Ala Asp Leu Ala Glu Gly
                85                  90                  95

Asn Gly Gln Tyr Leu Arg Cys His Thr Leu Val Trp Tyr Asn Gln Leu
            100                 105                 110

Pro Ser Trp Val Thr Ser Gly Thr Trp Thr Asn Ala Thr Leu Thr Ala
        115                 120                 125

Ala Leu Lys Asn His Ile Thr Asn Val Val Ser His Tyr Lys Gly Lys
    130                 135                 140

Cys Leu His Trp Asp Val Val Asn Glu Ala Leu Asn Asp Asp Gly Thr
145                 150                 155                 160

Tyr Arg Thr Asn Ile Phe Tyr Thr Thr Ile Gly Glu Ala Tyr Ile Pro
                165                 170                 175

Ile Ala Phe Ala Ala Ala Ala Ala Asp Pro Asp Ala Lys Leu Phe
            180                 185                 190

Tyr Asn Asp Tyr Asn Leu Glu Tyr Gly Gly Ala Lys Ala Ser Ala
        195                 200                 205

Arg Ala Ile Val Gln Leu Val Lys Asn Ala Gly Ala Lys Ile Asp Gly
    210                 215                 220

Val Gly Leu Gln Ala His Phe Ser Val Gly Thr Val Pro Ser Thr Ser
225                 230                 235                 240

Ser Leu Val Ser Val Leu Gln Ser Phe Thr Ala Leu Gly Val Glu Val
                245                 250                 255

Ala Tyr Thr Glu Ala Asp Val Arg Ile Leu Pro Thr Thr Ala Thr
            260                 265                 270

Thr Leu Ala Gln Gln Ser Ser Asp Phe Gln Ala Leu Val Gln Ser Cys
        275                 280                 285

Val Gln Thr Thr Gly Cys Val Gly Phe Thr Ile Trp Asp Trp Thr Asp
    290                 295                 300

Lys Tyr Ser Trp Val Pro Ser Thr Phe Ser Gly Tyr Gly Ala Ala Leu
305                 310                 315                 320

Pro Trp Asp Glu Asn Leu Val Lys Lys Pro Ala Tyr Asn Gly Leu Leu
                325                 330                 335

Ala Gly Met Gly Val Thr Val Thr Thr Thr Thr Thr Thr Thr Ala
```

```
                340            345            350
Thr Ala Thr Gly Lys Thr Thr Thr Thr Thr Gly Ala Thr Ser Thr
            355                360                365

Gly Thr Thr Ala Ala His Trp Gly Gln Cys Gly Gly Leu Asn Trp Ser
        370                375                380

Gly Pro Thr Ala Cys Ala Thr Gly Tyr Thr Cys Thr Tyr Val Asn Asp
385                390                395                400

Tyr Tyr Ser Gln Cys Leu
            405

<210> SEQ ID NO 71
<211> LENGTH: 1110
<212> TYPE: DNA
<213> ORGANISM: Thielavia terrestris

<400> SEQUENCE: 71
atgcatctcg cctccgcgtt gctcttcctc gcctcgctgc ccctcgggct ggcgggcaag      60
gacaagggca agccgtgcaa gaagggcctc aacacgctcg ccaagcaggc cggcctcaag     120
tacttcggct cggccaccga ctcgccgggc ttccgcgagc gcgccggcta cgaggccgtg     180
tacccgcagt acgaccagat catgtggaag tcgggcgagt ccacatgac  gacgcccacc     240 aacggcatga agtgggtctt caccgagccg gagcgcggcg tgttcaactt caccgagggc     300
gagatcgtgg cgtcgctcgc caagcagaac ggcttcatgc tgcgctgcca cgcgctcgtc     360
tggcacagcc agctccccga ctgggtcacg gcgaccaact ggaccgccgc tgaactgcgc     420
cagatcatcg tcaaccacat cacccacgtg gtcggccatt ggaagggcca gtgctatgcc     480
tgggacgtcg ttaacgaggc gctcaacgag gacggcacct accgcgactc catcttctac     540
caggtgctcg cgaggagta catcaagctg gcctttgaga ctgcctccaa gattgacccg     600
catgccaagc tgtactacaa cgactacaac ctcgagtatc ccggccccaa ggtcaccggc     660
gcccagaaca tcgtcaagat gctcaagacc gctggcatcc gcatcgacgg cgtcggcctg     720
cagtcgcacc tcgtcgccga gccacccg acgctcgacc agcacatcga cgccatccgg     780
tccttctcca gcctcggcgt cgaggtcgcc ctgaccgagc tcgacgtccg cctgacgctg     840
cccgccaacg cgacgaacct ggccgagcag aacgacgcct acaagaacat cgtcggcgcc     900
tgcgtccagg tccgcggctg catcggcgtc accatctggg acttctacga ccccttcagc     960
tgggtccccg ccaccttccc cggccagggc gcgccgctgc tgtggttcga gaacttcacc    1020
acccacccgg cgtaccacgg cgtcgccgag gccctgacga acaagaccac ccgcggccgg    1080
gcccggcgcg cccagctgcg gagcgcctaa                                      1110

<210> SEQ ID NO 72
<211> LENGTH: 369
<212> TYPE: PRT
<213> ORGANISM: Thielavia terrestris

<400> SEQUENCE: 72

Met His Leu Ala Ser Ala Leu Leu Phe Leu Ala Ser Leu Pro Leu Gly
1               5                   10                  15

Leu Ala Gly Lys Asp Lys Gly Lys Pro Cys Lys Lys Gly Leu Asn Thr
            20                  25                  30

Leu Ala Lys Gln Ala Gly Leu Lys Tyr Phe Gly Ser Ala Thr Asp Ser
        35                  40                  45

Pro Gly Phe Arg Glu Arg Ala Gly Tyr Glu Ala Val Tyr Pro Gln Tyr
    50                  55                  60
```

```
Asp Gln Ile Met Trp Lys Ser Gly Glu Phe His Met Thr Thr Pro Thr
 65                  70                  75                  80

Asn Gly Met Lys Trp Val Phe Thr Glu Pro Glu Arg Gly Val Phe Asn
                 85                  90                  95

Phe Thr Glu Gly Glu Ile Val Ala Ser Leu Ala Lys Gln Asn Gly Phe
            100                 105                 110

Met Leu Arg Cys His Ala Leu Val Trp His Ser Gln Leu Pro Asp Trp
        115                 120                 125

Val Thr Ala Thr Asn Trp Thr Ala Ala Glu Leu Arg Gln Ile Ile Val
    130                 135                 140

Asn His Ile Thr His Val Val Gly His Trp Lys Gly Gln Cys Tyr Ala
145                 150                 155                 160

Trp Asp Val Val Asn Glu Ala Leu Asn Glu Asp Gly Thr Tyr Arg Asp
                165                 170                 175

Ser Ile Phe Tyr Gln Val Leu Gly Glu Glu Tyr Ile Lys Leu Ala Phe
            180                 185                 190

Glu Thr Ala Ser Lys Ile Asp Pro His Ala Lys Leu Tyr Tyr Asn Asp
        195                 200                 205

Tyr Asn Leu Glu Tyr Pro Gly Pro Lys Val Thr Gly Ala Gln Asn Ile
210                 215                 220

Val Lys Met Leu Lys Thr Ala Gly Ile Arg Ile Asp Gly Val Gly Leu
225                 230                 235                 240

Gln Ser His Leu Val Ala Glu Ser His Pro Thr Leu Asp Gln His Ile
                245                 250                 255

Asp Ala Ile Arg Ser Phe Ser Ser Leu Gly Val Glu Val Ala Leu Thr
            260                 265                 270

Glu Leu Asp Val Arg Leu Thr Leu Pro Ala Asn Ala Thr Asn Leu Ala
        275                 280                 285

Glu Gln Asn Asp Ala Tyr Lys Asn Ile Val Gly Ala Cys Val Gln Val
    290                 295                 300

Arg Gly Cys Ile Gly Val Thr Ile Trp Asp Phe Tyr Asp Pro Phe Ser
305                 310                 315                 320

Trp Val Pro Ala Thr Phe Pro Gly Gln Gly Ala Pro Leu Leu Trp Phe
                325                 330                 335

Glu Asn Phe Thr Thr His Pro Ala Tyr His Gly Val Ala Glu Ala Leu
            340                 345                 350

Thr Asn Lys Thr Thr Arg Gly Arg Ala Arg Ala Gln Leu Arg Ser
        355                 360                 365

Ala
```

<210> SEQ ID NO 73
<211> LENGTH: 1245
<212> TYPE: DNA
<213> ORGANISM: Thielavia terrestris

<400> SEQUENCE: 73

```
atgcgctccc aggctgtgtg ggccgcgata ctcgcgccgg ccaccgtgtc ggccacgctc    60
aacgacctcg ccgtccgggc cgggctcaag tacttcggca cctgcctcag cgagagttac   120
atcaacagcg atagccagta tgcggccctc atcaatgaca agaccgagtt cggcgggctc   180
gtgcctgaga cggcatgaa gtgggacgcc accgagccca gccagggcca gttcagcttc   240
agccagggcg acatcacggc gaacacggcc aagaagaacg ccaggtcct cgctgccac    300 accctggtct ggtacagcca gcttccagga tgggtgacgt cgggctcctg gaccaggagc   360
```

-continued

```
acgctgcagt cggtcatgca gacgcacatc acgaacgtca tgggccacta caagggccag    420
tgctatgcgt gggacgtggt gaacgaggcc atcgccgacg acggcacgtg gcgcaccagc    480
gtgttctaca acaccttctc gaccgactac atcccgcttg ccttcaacat cgccaagacg    540
gccgacccca cgccaagct gtactacaac gactacaacc tcgagtacaa cggcgccaag    600
acggacacgg ccgtgcagct cgtgcagctc gtgcagtcgg ccggcgcgcc catcgacggc    660
gtcggcttcc agggccacct gatcgtcggc agcacgcccg ccgcagcag cctggcgacc    720 gcgctcaagc gcttcaccgc cctcggcctg gaggtggcct acacggagct cgacatccgg    780
cactccagcc tgccgccgtc cacctcggcg ctcgcgacgc agggcaacga cttcgccaac    840
gtggtcggct cgtgcctcga cgtcgccggc tgcatcggcg tgaccgtctg gggcgtgacc    900
gacaagtact cgtggatccc gcagaccttc ccgggcgccg cgacgcccct gctctacgac    960
gacaactaca acaagaagcc cgcctggacc tcggtctcgt ccgtcctcgc cgccaaggcc    1020
accagcccgc cgcctcgtc gtccaccacc ctcaccaccg tcatcaccac ggccccaacc    1080
tccaccccga cgagcaccac cgcgcccacc accacgtcgt cctcgaacgg cgcccagcag    1140
acccactggg gccagtgcgg tggcattggc tggaccggcg ctacgcagtg ccagagcccg    1200
tacacctgcc agaagctgaa cgactggtac tatcagtgcc tgtaa                    1245
```

<210> SEQ ID NO 74
<211> LENGTH: 414
<212> TYPE: PRT
<213> ORGANISM: Thielavia terrestris

<400> SEQUENCE: 74

```
Met Arg Ser Gln Ala Val Trp Ala Ala Ile Leu Ala Pro Ala Thr Val
1               5                   10                  15

Ser Ala Thr Leu Asn Asp Leu Ala Val Arg Ala Gly Leu Lys Tyr Phe
                20                  25                  30

Gly Thr Cys Leu Ser Glu Ser Tyr Ile Asn Ser Asp Ser Gln Tyr Ala
            35                  40                  45

Ala Leu Ile Asn Asp Lys Thr Glu Phe Gly Gly Leu Val Pro Glu Asn
        50                  55                  60

Gly Met Lys Trp Asp Ala Thr Glu Pro Ser Gln Gly Gln Phe Ser Phe
65                  70                  75                  80

Ser Gln Gly Asp Ile Thr Ala Asn Thr Ala Lys Lys Asn Gly Gln Val
                85                  90                  95

Leu Arg Cys His Thr Leu Val Trp Tyr Ser Gln Leu Pro Gly Trp Val
            100                 105                 110

Thr Ser Gly Ser Trp Thr Arg Ser Thr Leu Gln Ser Val Met Gln Thr
        115                 120                 125

His Ile Thr Asn Val Met Gly His Tyr Lys Gly Gln Cys Tyr Ala Trp
    130                 135                 140

Asp Val Val Asn Glu Ala Ile Ala Asp Asp Gly Thr Trp Arg Thr Ser
145                 150                 155                 160

Val Phe Tyr Asn Thr Phe Ser Thr Asp Tyr Ile Pro Leu Ala Phe Asn
                165                 170                 175

Ile Ala Lys Thr Ala Asp Pro Asn Ala Lys Leu Tyr Tyr Asn Asp Tyr
            180                 185                 190

Asn Leu Glu Tyr Asn Gly Ala Lys Thr Asp Thr Ala Val Gln Leu Val
        195                 200                 205

Gln Leu Val Gln Ser Ala Gly Ala Pro Ile Asp Gly Val Gly Phe Gln
```

```
                    210                 215                 220
Gly His Leu Ile Val Gly Ser Thr Pro Gly Arg Ser Ser Leu Ala Thr
225                 230                 235                 240

Ala Leu Lys Arg Phe Thr Ala Leu Gly Leu Glu Val Ala Tyr Thr Glu
                245                 250                 255

Leu Asp Ile Arg His Ser Ser Leu Pro Pro Ser Thr Ser Ala Leu Ala
            260                 265                 270

Thr Gln Gly Asn Asp Phe Ala Asn Val Val Gly Ser Cys Leu Asp Val
        275                 280                 285

Ala Gly Cys Ile Gly Val Thr Val Trp Gly Val Thr Asp Lys Tyr Ser
    290                 295                 300

Trp Ile Pro Gln Thr Phe Pro Gly Ala Gly Asp Ala Leu Leu Tyr Asp
305                 310                 315                 320

Asp Asn Tyr Asn Lys Lys Pro Ala Trp Thr Ser Val Ser Val Ser Val Leu
                325                 330                 335

Ala Ala Lys Ala Thr Ser Pro Pro Ala Ser Ser Thr Thr Leu Thr
            340                 345                 350

Thr Val Ile Thr Thr Ala Pro Thr Ser Thr Pro Thr Ser Thr Thr Ala
        355                 360                 365

Pro Thr Thr Thr Ser Ser Ser Asn Gly Ala Gln Gln Thr His Trp Gly
    370                 375                 380

Gln Cys Gly Gly Ile Gly Trp Thr Gly Ala Thr Gln Cys Gln Ser Pro
385                 390                 395                 400

Tyr Thr Cys Gln Lys Leu Asn Asp Trp Tyr Tyr Gln Cys Leu
                405                 410
```

<210> SEQ ID NO 75
<211> LENGTH: 1145
<212> TYPE: DNA
<213> ORGANISM: Aspergillus fumigatus

<400> SEQUENCE: 75

```
atgcgtttct cccttgccgc caccgctctt ctcgctggcc tggccacggc agcgccttcg      60
agcaacaaga caacgtcaa  tcttgataag  cttgctcggc gtaatggcat gctttggttc    120
ggcactgcag ccgatatccc tggtacctca gaaacaaccg acaagcctta tctgagcatc     180
ctgcgcaagc agttcggcga aatgacaccc gcaaacgcat tgaaggtgag ccagagtgat     240
agtacacctc atctcgtgtc ggcgctgacc agacgatgtt attcacatag ttcatgtata     300
ccgagcccga gcagaatgtc ttcaacttca ctcaagggga ctacttcatg gacttggccg     360
atcactatgg tcacgccgtg cgctgccata acctcgtctg ggccagccaa gtgtccgact     420
gggtcaccct caggaactgg accgccacag aactcaaaga agtgatgaag aaccacatat     480
tcaagaccgt ccaacatttt ggcaagcgct gctacgcgtg ggacgtcgtc aatgaagcta     540
ttaatgggga cggaaccttt tcctccagtg tgtggtacga cacaattggc gaggaatact     600
tctaccttgc attccagtat gcccaggaag ccctggcgca gattcacgcc aaccaggtca     660
agctttacta taacgactat ggcattgaga ccccggcccc aaggcagat  gctgttctga     720
agctagtcgc cgagttgcgg aagcggggca ttcgcattga cggagtcggt ctcgagtccc     780
acttcatcgt cggcgagact ccttcgctgg ctgaccagct cgccaccaag aaggcttata     840
tcgaggccgg acttgaggtc gccatcaccg aacttgacgt ccgcttttct caggccccgt     900
tctacaccgc cgaggcccaa aagcagcagg ctgccgacta ctatgctagc gtcgccagtt     960
gcaagcatgc cggaccgcgc tgtgttggtg ttgtagtctg ggatttcgat gacgcctact    1020
```

```
cgtggattcc gggtaccttc gagggacagg gtggcgcctg tctatataat gagacactcg    1080
aggtgaagcc ggccttctat gctgctgccg aggcgttgga gaacaagccc tgcactgtat    1140
gctag                                                                1145
```

<210> SEQ ID NO 76
<211> LENGTH: 364
<212> TYPE: PRT
<213> ORGANISM: Aspergillus fumigatus

<400> SEQUENCE: 76

```
Met Arg Phe Ser Leu Ala Ala Thr Ala Leu Leu Ala Gly Leu Ala Thr
1               5                   10                  15

Ala Ala Pro Ser Ser Asn Lys Asn Val Asn Leu Asp Lys Leu Ala
            20                  25                  30

Arg Arg Asn Gly Met Leu Trp Phe Gly Thr Ala Ala Asp Ile Pro Gly
        35                  40                  45

Thr Ser Glu Thr Thr Asp Lys Pro Tyr Leu Ser Ile Leu Arg Lys Gln
    50                  55                  60

Phe Gly Glu Met Thr Pro Ala Asn Ala Leu Lys Val Ser Gln Ser Asp
65                  70                  75                  80

Phe Met Tyr Thr Glu Pro Glu Gln Asn Val Phe Asn Phe Thr Gln Gly
                85                  90                  95

Asp Tyr Phe Met Asp Leu Ala Asp His Tyr Gly His Ala Val Arg Cys
            100                 105                 110

His Asn Leu Val Trp Ala Ser Gln Val Ser Asp Trp Val Thr Ser Arg
        115                 120                 125

Asn Trp Thr Ala Thr Glu Leu Lys Glu Val Met Lys Asn His Ile Phe
    130                 135                 140

Lys Thr Val Gln His Phe Gly Lys Arg Cys Tyr Ala Trp Asp Val Val
145                 150                 155                 160

Asn Glu Ala Ile Asn Gly Asp Gly Thr Phe Ser Ser Val Trp Tyr
                165                 170                 175

Asp Thr Ile Gly Glu Glu Tyr Phe Tyr Leu Ala Phe Gln Tyr Ala Gln
            180                 185                 190

Glu Ala Leu Ala Gln Ile His Ala Asn Gln Val Lys Leu Tyr Tyr Asn
        195                 200                 205

Asp Tyr Gly Ile Glu Asn Pro Gly Pro Lys Ala Asp Ala Val Leu Lys
    210                 215                 220

Leu Val Ala Glu Leu Arg Lys Arg Gly Ile Arg Ile Asp Gly Val Gly
225                 230                 235                 240

Leu Glu Ser His Phe Ile Val Gly Glu Thr Pro Ser Leu Ala Asp Gln
                245                 250                 255

Leu Ala Thr Lys Lys Ala Tyr Ile Glu Ala Gly Leu Glu Val Ala Ile
            260                 265                 270

Thr Glu Leu Asp Val Arg Phe Ser Gln Ala Pro Phe Tyr Thr Ala Glu
        275                 280                 285

Ala Gln Lys Gln Gln Ala Ala Asp Tyr Tyr Ala Ser Val Ala Ser Cys
    290                 295                 300

Lys His Ala Gly Pro Arg Cys Val Gly Val Val Trp Asp Phe Asp
305                 310                 315                 320

Asp Ala Tyr Ser Trp Ile Pro Gly Thr Phe Glu Gly Gln Gly Gly Ala
                325                 330                 335

Cys Leu Tyr Asn Glu Thr Leu Glu Val Lys Pro Ala Phe Tyr Ala Ala
```

```
            340                 345                 350
Ala Glu Ala Leu Glu Asn Lys Pro Cys Thr Val Cys
            355                 360
```

<210> SEQ ID NO 77
<211> LENGTH: 1400
<212> TYPE: DNA
<213> ORGANISM: Aspergillus fumigatus

<400> SEQUENCE: 77

```
atggtcgtcc tcagcaagct cgtcagcagc attctctttg tctccctggt ttcggcgggc    60
gtgatcgacg aacgccaggc agccggcatc aaccaggcgt ttacctccca tggcaagaag   120
tactttggca ccgccagtga ccaagctctg ctccagaagt cgcagaatga ggccattgtg   180
cgcaaagact tggccagct gacgccggag aatagcatga agtgggatgc gactgagcgt   240
aggtctctcg gccactgtgg ctgacgttaa cttgttgaca tgactgtctg tgtagcatcg   300
caaggaagat tcaacttcgc tggtgctgat ttcctggtat gcaatctgct catctcggtc   360
gagctcctgc tgaaggacaa taaataggtc aactatgcaa acagaatgg caagaaggtc   420
cgcggacaca ccttaggtat tcatgcgccc tcacggcatt tcgaggatac agccaagctg   480
acagtgtagt ctggcactcc caactcccgt cctgggtgtc ggctatcagc gacaaaaaca   540
ccctgacctc ggtgctgaag aaccacatca ccaccgtcat gacccggtac aagggccaga   600
tctacgcctg gtattttgc cctctatccc acacaatgcc agccccagct aatagctgca   660
aaggacgtcg tcaacgagat cttcaacgag gacggctccc tccgcgacag cgtcttctcc   720
cgcgtgctgg cgaggacttt gtgcggattg ccttcgaga cggcgcgctc tgtggatccc   780
tcggcgaagc tgtacatcaa cgattacaag taagcttgtg gttttgtcga gagatgtact   840
ccgtcctgga tctgaccatc acagtctcga ctcggctagc tatggcaaaa cccaggggat   900
ggtgagatat gtcaagaagt ggctggctgc gggcattcct atcgatggaa tcggtgagca   960
caggtcgcgg agctgtgtgt gatgattgta cgctgactct tcctgaaggc actcaaaccc  1020
accttggtgc gggtgcttcg tccagcgtca aaggataagt ctccttggtt ttcttgccta  1080
cgtaacgctg accccccgtg tacagcattg actgctcttg cgtcttccgg cgtctctgag  1140
gtcgccatta ccgagctgga tatcgcgggt gcgagctccc aggactacgt caatgtatgt  1200
ctcctgattg ccagtggcag ggtcatcgat actaatagaa acaggtcgtc aaggcatgcc  1260
tggatgtccc caagtgtgtg ggaatcaccg tctgggggt gtcggacagg gactcgtggc  1320
gctccggctc gtcccgctg ctgttcgaca gcaactacca gcccaaggcg gcgtataatg  1380
ccatcattgc tgctctctga                                              1400
```

<210> SEQ ID NO 78
<211> LENGTH: 323
<212> TYPE: PRT
<213> ORGANISM: Aspergillus fumigatus

<400> SEQUENCE: 78

```
Met Val Val Leu Ser Lys Leu Val Ser Ile Leu Phe Val Ser Leu
1               5                   10                  15

Val Ser Ala Gly Val Ile Asp Glu Arg Gln Ala Ala Gly Ile Asn Gln
            20                  25                  30

Ala Phe Thr Ser His Gly Lys Lys Tyr Phe Gly Thr Ala Ser Asp Gln
        35                  40                  45

Ala Leu Leu Gln Lys Ser Gln Asn Glu Ala Ile Val Arg Lys Asp Phe
```

```
            50                  55                  60
Gly Gln Leu Thr Pro Glu Asn Ser Met Lys Trp Asp Ala Thr Glu Ala
 65                  70                  75                  80

Ser Gln Gly Arg Phe Asn Phe Ala Gly Ala Asp Phe Leu Val Asn Tyr
                 85                  90                  95

Ala Lys Gln Asn Gly Lys Lys Val Arg Gly His Thr Leu Trp His Ser
            100                 105                 110

Gln Leu Pro Ser Trp Val Ser Ala Ile Ser Asp Lys Asn Thr Leu Thr
        115                 120                 125

Ser Val Leu Lys Asn His Ile Thr Thr Val Met Thr Arg Tyr Lys Gly
130                 135                 140

Gln Ile Tyr Ala Trp Asp Val Val Asn Glu Ile Phe Asn Glu Asp Gly
145                 150                 155                 160

Ser Leu Arg Asp Ser Val Phe Ser Arg Val Leu Gly Glu Asp Phe Val
                165                 170                 175

Arg Ile Ala Phe Glu Thr Ala Arg Ser Val Asp Pro Ser Ala Lys Leu
            180                 185                 190

Tyr Ile Asn Asp Tyr Lys Leu Asp Ser Ala Ser Tyr Gly Lys Thr Gln
        195                 200                 205

Gly Met Val Arg Tyr Val Lys Lys Trp Leu Ala Ala Gly Ile Pro Ile
210                 215                 220

Asp Gly Ile Gly Gln Thr His Leu Gly Ala Gly Ala Ser Ser Ser Val
225                 230                 235                 240

Lys Gly Ala Leu Thr Ala Leu Ala Ser Ser Gly Val Ser Glu Val Ala
                245                 250                 255

Ile Thr Glu Leu Asp Ile Ala Gly Ala Ser Ser Gln Asp Tyr Val Asn
            260                 265                 270

Val Val Lys Ala Cys Leu Asp Val Pro Lys Cys Val Gly Ile Thr Val
        275                 280                 285

Trp Gly Val Ser Asp Arg Asp Ser Trp Arg Ser Gly Ser Ser Pro Leu
290                 295                 300

Leu Phe Asp Ser Asn Tyr Gln Pro Lys Ala Ala Tyr Asn Ala Ile Ile
305                 310                 315                 320

Ala Ala Leu

<210> SEQ ID NO 79
<211> LENGTH: 1415
<212> TYPE: DNA
<213> ORGANISM: Aspergillus fumigatus

<400> SEQUENCE: 79
atggtccatc tatcttcatt ggcagcagcc ctggctgctc tgcctctgta tgtttaccca    60
ctcacgagag gaggaacagc tttgacattg ctatagtgta tatggagctg gcctgaacac   120
agcagccaaa gccaaaggac taaagtactt tggttccgcc acggacaatc agagctcac   180 ggactctgcg tatgtcgcgc aactgagcaa caccgatgat tttggtcaaa tcacacccgg   240
aaactccatg aaggtttgct acgtctgcc tccctggagc attgcctcaa agctaattg   300 gttgttttgt ttggatagtg ggatgccacc gagccttctc agaattcttt ttcgttcgca   360
aatggagacg ccgtggtcaa tctggcgaac aagaatggcc agctgatgcg atgccatact   420
ctggtctggc acagtcagct accgaactgg ggtatgtaaa cgtcttgtct attctcaaat   480
actctctaac agttgacagt ctctagcggg tcatggacca atgcgaccct tttgcggcc   540 atgaagaatc atatcaccaa tgtggttact cactacaagg ggaagtgcta cgcctgggat   600
```

```
gttgtcaatg aaggtttgtt gctccatcta tcctcaatag ttcttttgaa actgacaagc    660
ctgtcaatct agccctgaac gaggacggta ctttccgtaa ctctgtcttc taccagatca    720
tcggcccagc atacattcct attgcgttcg ccacggctgc tgccgcagat cccgacgtga    780
aactctacta caacgactac aacattgaat actcaggcgc caaagcgact gctgcgcaga    840
atatcgtcaa gatgatcaag gcctacggcg cgaagatcga cggcgtcggc ctccaggcac    900
actttatcgt cggcagcact ccgagtcaat cggatctgac gaccgtcttg aagggctaca    960
ctgctctcgg cgttgaggtg gcctataccg aacttgacat ccgcatgcag ctgccctcga   1020
ccgccgcaaa gctggcccag cagtccactg acttccaagg cgtggccgca gcatgcgtta   1080
gcaccactgg ctgcgtgggt gtcactatct gggactggac cgacaagtac tcctgggtcc   1140
ccagcgtgtt ccaaggctac ggcgccccat tgccttggga tgagaactat gtgaagaagc   1200
cagcgtacga tggcctgatg gcgggtcttg agcaagcgg ctccggcacc acaacgacca   1260
ctactactac ttctactacg acaggaggta cggaccctac tggagtcgct cagaaatggg   1320
gacagtgtgg cggtattggc tggaccgggc caacaacttg tgtcagtggt accacttgcc   1380
aaaagctgaa tgactggtac tcacagtgcc tgtaa                              1415

<210> SEQ ID NO 80
<211> LENGTH: 397
<212> TYPE: PRT
<213> ORGANISM: Aspergillus fumigatus

<400> SEQUENCE: 80

Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220
```

```
Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
            245                 250                 255

Glu Leu Asp Ile Arg Met Gln Leu Pro Ser Thr Ala Ala Lys Leu Ala
        260                 265                 270

Gln Gln Ser Thr Asp Phe Gln Gly Val Ala Ala Cys Val Ser Thr
    275                 280                 285

Thr Gly Cys Val Gly Val Thr Ile Trp Asp Trp Thr Asp Lys Tyr Ser
290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
            325                 330                 335

Gly Ala Ser Gly Ser Gly Thr Thr Thr Thr Thr Thr Thr Ser Thr
        340                 345                 350

Thr Thr Gly Gly Thr Asp Pro Thr Gly Val Ala Gln Lys Trp Gly Gln
    355                 360                 365

Cys Gly Gly Ile Gly Trp Thr Gly Pro Thr Thr Cys Val Ser Gly Thr
370                 375                 380

Thr Cys Gln Lys Leu Asn Asp Trp Tyr Ser Gln Cys Leu
385                 390                 395
```

<210> SEQ ID NO 81
<211> LENGTH: 1380
<212> TYPE: DNA
<213> ORGANISM: Trichoderma reesei

<400> SEQUENCE: 81

```
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccggggggtg cgtggcccag gacacctcgg tggtccttga ctggaactac     180
cgctggatgc acgacgcaaa ctacaactcg tgcaccgtca acggcggcgt caacaccacg     240
ctctgccctg acgaggcgac ctgtggcaag aactgcttca tcgagggcgt cgactacgcc     300
gcctcgggcg tcacgacctc gggcagcagc ctcaccatga accagtacat gccagcagc     360 tctggcggct acagcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
tataacacgg ccggtgccaa ctacgggagc ggctactgcg atgctcagtg ccccgtccag     600
acatggagga acggcaccct caacactagc caccagggct ctgctgcaa cgagatggat     660 atcctggagg gcaactcgag ggcgaatgcc ttgaccccctc actcttgcac ggccacggcc     720
tgcgactctg ccggttgcgg cttcaacccc tatggcagcg gctacaaaag ctactacggc     780
cccggagata ccgttgacac ctccaagacc ttcaccatca tcacccagtt caacacggac     840
aacggctcgc cctcgggcaa ccttgtgagc atcacccgca gtaccagca aaacggcgtc     900 gacatcccca gcgcccagcc cggcggcgac accatctcgt cctgcccgtc cgcctcagcc     960
tacggcggcc tcgccaccat gggcaaggcc ctgagcagcg gcatggtgct cgtgttcagc    1020
atttggaacg acaacagcca gtacatgaac tggctcgaca gcggcaacgc cggcccctgc    1080
agcagcaccg agggcaaccc atccaacatc ctggccaaca accccaacac gcacgtcgtc    1140
```

-continued

```
ttctccaaca tccgctgggg agacattggg tctactacga actcgactgc gcccccgccc    1200
ccgcctgcgt ccagcacgac gttttcgact cacggaggag gctcgacgac ttcgagcagc    1260
ccgagctgca cgcagactca ctgggggcag tgcggtggca ttgggtacag cgggtgcaag    1320
acgtgcacgt cgggcactac gtgccagtat agcaacgact actactcgca atgccttag    1380
```

<210> SEQ ID NO 82
<211> LENGTH: 459
<212> TYPE: PRT
<213> ORGANISM: Trichoderma reesei

<400> SEQUENCE: 82

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
            115                 120                 125

Pro Arg Leu Tyr Leu Leu Asp Ser Asp Gly Glu Tyr Val Met Leu Lys
        130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335
```

| | | | | | | | | | | | |
|---|---|---|---|---|---|---|---|---|---|---|---|
|Leu|Val|Phe|Ser|Ile|Trp|Asn|Asp|Asn|Ser|Gln|Tyr|Met|Asn|Trp|Leu|
| | | |340| | | |345| | | |350|

Asp Ser Gly Asn Ala Gly Pro Cys Ser Ser Thr Glu Gly Asn Pro Ser
                355                 360                 365

Asn Ile Leu Ala Asn Asn Pro Asn Thr His Val Val Phe Ser Asn Ile
        370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Arg Arg Ser Ser Thr
            405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
        450                 455

```
<210> SEQ ID NO 83
<211> LENGTH: 1849
<212> TYPE: DNA
<213> ORGANISM: Trichoderma reesei

<400> SEQUENCE: 83
tgccatttct gacctggata ggttttccta tggtcattcc tataagagac acgctctttc      60
gtcggcccgt agatatcaga ttggtattca gtcgcacaga cgaaggtgag ttgatcctcc     120
aacatgagtt ctatgagccc ccccttgcc cccccccgtt caccttgacc tgcaatgaga     180
atcccacctt ttacaagagc atcaagaagt attaatggcg ctgaatagcc tctgctcgat     240
aatatctccc cgtcatcgac aatgaacaag tccgtggctc cattgctgct tgcagcgtcc     300
atactatatg gcggcgccgt cgcacagcag actgtctggg ccagtgtgg aggtattggt     360
tggagcggac ctacgaattg tgctcctggc tcagcttgtt cgaccctcaa tccttattat     420
gcgcaatgta ttccgggagc cactactatc accacttcga cccggccacc atccggtcca     480
accaccacca ccagggctac ctcaacaagc tcatcaactc cacccacgag ctctggggtc     540
cgatttgccg gcgttaacat cgcggggttt gactttggct gtaccacaga gtgagtaccc     600
ttgtttcctg gtgttgctgg ctggttgggc gggtatacag cgaagcggac gcaagaacac     660
cgccggtccg ccaccatcaa gatgtgggtg gtaagcggcg gtgtttttgta caactacctg    720
acagctcact caggaaatga gaattaatgg aagtcttgtt acagtggcac ttgcgttacc     780
tcgaaggttt atcctccgtt gaagaacttc accggctcaa caactaccc cgatggcatc      840
ggccagatgc agcacttcgt caacgaggac gggatgacta ttttccgctt acctgtcgga     900
tggcagtacc tcgtcaacaa caatttgggc ggcaatcttg attccacgag catttccaag     960
tatgatcagc ttgttcaggg gtgcctgtct ctgggcgcat actgcatcgt cgacatccac    1020
aattatgctc gatggaacgg tgggatcatt ggtcagggcg ccctactaa tgctcaattc    1080
acgagccttt ggtcgcagtt ggcatcaaag tacgcatctc agtcgagggt gtggttcggc    1140
atcatgaatg agccccacga cgtgaacatc aacacctggg ctgccacggt ccaagaggtt    1200
gtaaccgcaa tccgcaacgc tggtgctacg tcgcaattca tctctttgcc tggaaatgat    1260
tggcaatctg ctggggcttt catatccgat ggcagtgcag ccgccctgtc tcaagtcacg    1320
aacccggatg ggtcaacaac gaatctgatt tttgacgtgc acaaatactt ggactcagac    1380
aactccggta ctcacgccga atgtactaca aataacattg acggcgcctt ttctccgctt    1440
```

-continued

```
gccacttggc tccgacagaa caatcgccag gctatcctga cagaaaccgg tggtggcaac    1500
gttcagtcct gcatacaaga catgtgccag caaatccaat atctcaacca gaactcagat    1560
gtctatcttg gctatgttgg ttggggtgcc ggatcatttg atagcacgta tgtcctgacg    1620
gaaacaccga ctggcagtgg taactcatgg acggacacat ccttggtcag ctcgtgtctc    1680
gcaagaaagt agcactctga gctgaatgca gaagcctcgc caacgtttgt atctcgctat    1740
caaacatagt agctactcta tgaggctgtc tgttctcgat ttcagcttta tatagtttca    1800
tcaaacagta catattccct ctgtggccac gcaaaaaaaa aaaaaaaa                 1849
```

<210> SEQ ID NO 84
<211> LENGTH: 418
<212> TYPE: PRT
<213> ORGANISM: Trichoderma reesei

<400> SEQUENCE: 84

```
Met Asn Lys Ser Val Ala Pro Leu Leu Ala Ser Ile Leu Tyr
 1               5                  10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300
```

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
            325                 330                 335

Thr Trp Leu Arg Gln Asn Asn Arg Gln Ala Ile Leu Thr Glu Thr Gly
        340                 345                 350

Gly Gly Asn Val Gln Ser Cys Ile Gln Asp Met Cys Gln Gln Ile Gln
            355                 360                 365

Tyr Leu Asn Gln Asn Ser Asp Val Tyr Leu Gly Tyr Val Gly Trp Gly
        370                 375                 380

Ala Gly Ser Phe Asp Ser Thr Tyr Val Leu Thr Glu Pro Thr Gly
385                 390                 395                 400

Ser Gly Asn Ser Trp Thr Asp Thr Ser Leu Val Ser Ser Cys Leu Ala
            405                 410                 415

Arg Lys

<210> SEQ ID NO 85
<211> LENGTH: 826
<212> TYPE: DNA
<213> ORGANISM: Trichoderma reesei

<400> SEQUENCE: 85
atgaagttcc ttcaagtcct ccctgccctc ataccggccg ccctggccca aaccagctgt      60
gaccagtggg caaccttcac tggcaacggc tacacagtca gcaacaacct tggggagca     120 tcagccggct ctggatttgg ctgcgtgacg gcggtatcgc tcagcggcgg ggcctcctgg     180
cacgcagact ggcagtggtc cggcggccag aacaacgtca agtcgtacca gaactctcag     240
attgccattc cccagaagag gaccgtcaac agcatcagca gcatgcccac cactgccagc     300
tggagctaca gcgggagcaa catccgcgct aatgttgcgt atgacttgtt caccgcagcc     360
aacccgaatc atgtcacgta ctcggggaga tacgaactca tgatctggta agccataaga     420
agtgaccctc cttgatagtt tcgactaaca acatgtcttg aggcttggca aatacggcga     480
tattgggccg attgggtcct cacagggaac agtcaacgtc ggtggccaga gctggacgct     540
ctactatggc tacaacggag ccatgcaagt ctattccttt gtggcccaga ccaacactac     600 caactcagc ggagatgtca agaacttctt caattatctc cgagacaata aaggatacaa     660
cgctgcaggc caatatgttc ttagtaagtc accctcactg tgactgggct gagtttgttg     720
caacgtttgc taacaaaacc ttcgtatagg ctaccaattt ggtaccgagc ccttcacggg     780
cagtggaact ctgaacgtcg catcctggac cgcatctatc aactaa                   826

<210> SEQ ID NO 86
<211> LENGTH: 234
<212> TYPE: PRT
<213> ORGANISM: Trichoderma reesei

<400> SEQUENCE: 86

Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

```
Gln Trp Ser Gly Gly Gln Asn Val Lys Ser Tyr Gln Asn Ser Gln
 65                  70                  75                  80

Ile Ala Ile Pro Gln Lys Arg Thr Val Asn Ser Ile Ser Ser Met Pro
             85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230

<210> SEQ ID NO 87
<211> LENGTH: 1035
<212> TYPE: DNA
<213> ORGANISM: Trichoderma reesei

<400> SEQUENCE: 87
atgatccaga agctttccaa cctccttgtc accgcactgg cggtggctac tggcgttgtc      60
ggacatggac atattaatga cattgtcatc aacggggtgt ggtatcaggc ctatgatcct     120
acaacgtttc catacgagtc aaaccccccc atagtagtgg gctggacggc tgccgacctt     180
gacaacggct tcgtttcacc cgacgcatac caaaaccctg acatcatctg ccacaagaat     240
gctacgaatg ccaaggggca cgcgtctgtc aaggccggag acactattct cttccagtgg     300
gtgccagttc catggccgca ccctggtccc attgtcgact acctggccaa ctgcaatggt     360
gactgcgaga ccgttgacaa gacgacgctt gagttcttca gatcgatgg cgttggtctc      420 ctcagcggcg gggatccggg cacctgggcc tcagacgtgc tgatctccaa caacaacacc     480
tgggtcgtca agatccccga caatcttgcg ccaggcaatt acgtgctccg ccacgagatc     540
atcgcgttac acagcgccgg gcaggcaaac ggcgctcaga actaccccca gtgcttcaac     600
attgccgtct caggctcggg ttctctgcag cccagcggcg ttctagggac cgacctctat     660
cacgcgacgg accctggtgt tctcatcaac atctacacca gcccgctcaa ctacatcatc     720
cctggaccta ccgtggtatc aggcctgcca acgagtgttg cccaggggag ctccgccgcg     780
acggccaccg ccagcgccac tgttcctgga ggcggtagcg gcccgaccag cagaaccacg     840
acaacggcga ggacgacgca ggcctcaagc aggcccagct ctacgcctcc cgcaaccacg     900
tcggcacctg ctggcggccc aacccagact ctgtacggcc agtgtggtgg cagcggttac     960
agcgggccta ctcgatgcgc gccgccagcc acttgctcta ccttgaaccc ctactacgcc    1020
cagtgcctta actag                                                     1035
```

<210> SEQ ID NO 88
<211> LENGTH: 344
<212> TYPE: PRT
<213> ORGANISM: Trichoderma reesei

<400> SEQUENCE: 88

Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
            20                  25                  30

Val Trp Tyr Gln Ala Tyr Asp Pro Thr Thr Phe Pro Tyr Glu Ser Asn
        35                  40                  45

Pro Pro Ile Val Val Gly Trp Thr Ala Ala Asp Leu Asp Asn Gly Phe
50                  55                  60

Val Ser Pro Asp Ala Tyr Gln Asn Pro Asp Ile Ile Cys His Lys Asn
65                  70                  75                  80

Ala Thr Asn Ala Lys Gly His Ala Ser Val Lys Ala Gly Asp Thr Ile
                85                  90                  95

Leu Phe Gln Trp Val Pro Val Pro Trp Pro His Pro Gly Pro Ile Val
            100                 105                 110

Asp Tyr Leu Ala Asn Cys Asn Gly Asp Cys Glu Thr Val Asp Lys Thr
        115                 120                 125

Thr Leu Glu Phe Phe Lys Ile Asp Gly Val Gly Leu Leu Ser Gly Gly
130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
            180                 185                 190

Gln Asn Tyr Pro Gln Cys Phe Asn Ile Ala Val Ser Gly Ser Gly Ser
        195                 200                 205

Leu Gln Pro Ser Gly Val Leu Gly Thr Asp Leu Tyr His Ala Thr Asp
210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Val Pro Gly Gly Gly
            260                 265                 270

Ser Gly Pro Thr Ser Arg Thr Thr Thr Ala Arg Thr Thr Gln Ala
        275                 280                 285

Ser Ser Arg Pro Ser Ser Thr Pro Pro Ala Thr Thr Ser Ala Pro Ala
290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
                325                 330                 335

Pro Tyr Tyr Ala Gln Cys Leu Asn
            340

<210> SEQ ID NO 89
<211> LENGTH: 729
<212> TYPE: DNA
<213> ORGANISM: Trichoderma reesei -continued

<400> SEQUENCE: 89

```
atgaaggcaa ctctggttct cggctccctc attgtaggcg ccgtttccgc gtacaaggcc        60
accaccacgc gctactacga tgggcaggag ggtgcttgcg gatgcggctc gagctccggc       120
gcattcccgt ggcagctcgg catcggcaac ggagtctaca cggctgccgg ctcccaggct       180
ctcttcgaca cggccggagc ttcatggtgc ggcgccggct gcggtaaatg ctaccagctc       240
acctcgacgg gccaggcgcc ctgctccagc tgcggcacgg gcggtgctgc tggcagagc        300
atcatcgtca tggtgaccaa cctgtgcccg aacaatggga acgcgcagtg gtgcccggtg       360
gtcggcggca ccaaccaata cggctacagc taccatttcg acatcatggc gcagaacgag       420
atctttggag acaatgtcgt cgtcgacttt gagcccattg cttgccccgg gcaggctgcc       480
tctgactggg gacgtgcct ctgcgtggga cagcaagaga cggatcccac gcccgtcctc       540
ggcaacgaca cgggctcaac tcctcccggg agctcgccgc cagcgacatc gtcgagtccg       600
ccgtctggcg gcggccagca gacgctctat ggccagtgtg gaggtgccgg ctggacggga       660
cctacgacgt gccaggcccc agggacctgc aaggttcaga accagtggta ctcccagtgt       720
cttccttga                                                                729
```

<210> SEQ ID NO 90
<211> LENGTH: 242
<212> TYPE: PRT
<213> ORGANISM: Trichoderma reesei

<400> SEQUENCE: 90

```
Met Lys Ala Thr Leu Val Leu Gly Ser Leu Ile Val Gly Ala Val Ser
1               5                  10                  15
Ala Tyr Lys Ala Thr Thr Thr Arg Tyr Tyr Asp Gly Gln Glu Gly Ala
            20                  25                  30
Cys Gly Cys Gly Ser Ser Gly Ala Phe Pro Trp Gln Leu Gly Ile
        35                  40                  45
Gly Asn Gly Val Tyr Thr Ala Ala Gly Ser Gln Ala Leu Phe Asp Thr
    50                  55                  60
Ala Gly Ala Ser Trp Cys Gly Ala Gly Cys Gly Lys Cys Tyr Gln Leu
65                  70                  75                  80
Thr Ser Thr Gly Gln Ala Pro Cys Ser Ser Cys Gly Thr Gly Gly Ala
                85                  90                  95
Ala Gly Gln Ser Ile Ile Val Met Val Thr Asn Leu Cys Pro Asn Asn
            100                 105                 110
Gly Asn Ala Gln Trp Cys Pro Val Val Gly Gly Thr Asn Gln Tyr Gly
        115                 120                 125
Tyr Ser Tyr His Phe Asp Ile Met Ala Gln Asn Glu Ile Phe Gly Asp
    130                 135                 140
Asn Val Val Asp Phe Glu Pro Ile Ala Cys Pro Gly Gln Ala Ala
145                 150                 155                 160
Ser Asp Trp Gly Thr Cys Leu Cys Val Gly Gln Glu Thr Asp Pro
                165                 170                 175
Thr Pro Val Leu Gly Asn Asp Thr Gly Ser Thr Pro Pro Gly Ser Ser
            180                 185                 190
Pro Pro Ala Thr Ser Ser Pro Ser Gly Gly Gln Gln Thr
        195                 200                 205
Leu Tyr Gly Gln Cys Gly Gly Ala Gly Trp Thr Gly Pro Thr Thr Cys
    210                 215                 220
Gln Ala Pro Gly Thr Cys Lys Val Gln Asn Gln Trp Tyr Ser Gln Cys
```

Leu Pro

<210> SEQ ID NO 91
<211> LENGTH: 30
<212> TYPE: DNA
<213> ORGANISM: Myceliophthora thermophila

<400> SEQUENCE: 91
attggcagcc cggatctggg acagagtctg                                    30

<210> SEQ ID NO 92
<211> LENGTH: 30
<212> TYPE: DNA
<213> ORGANISM: Myceliophthora thermophila

<400> SEQUENCE: 92
ccggtcatgc taggaatggc gagattgtgg                                    30

<210> SEQ ID NO 93
<211> LENGTH: 24
<212> TYPE: DNA
<213> ORGANISM: Myceliophthora thermophila

<400> SEQUENCE: 93
gctgtaaact gcgaatgggt tcag                                          24

<210> SEQ ID NO 94
<211> LENGTH: 20
<212> TYPE: DNA
<213> ORGANISM: Myceliophthora thermophila

<400> SEQUENCE: 94
gggtcccaca tgctgcgcct                                               20

<210> SEQ ID NO 95
<211> LENGTH: 20
<212> TYPE: DNA
<213> ORGANISM: Myceliophthora thermophila

<400> SEQUENCE: 95
aaaattcacg agacgccggg                                               20

<210> SEQ ID NO 96
<211> LENGTH: 36
<212> TYPE: DNA
<213> ORGANISM: Myceliophthora thermophila

<400> SEQUENCE: 96
actggattta ccatggccaa gaagcttttc atcacc                             36

<210> SEQ ID NO 97
<211> LENGTH: 38
<212> TYPE: DNA
<213> ORGANISM: Myceliophthora thermophila

<400> SEQUENCE: 97
tcacctctag ttaattaatt agaagggcgg gttggcgt                           38

<210> SEQ ID NO 98
<211> LENGTH: 1387
<212> TYPE: DNA
<213> ORGANISM: Penicillium sp.

<400> SEQUENCE: 98

```
atggttcgcc tcagtccagt cctgctggca tcgatcgcag gctctggcct gcctctgtac    60
gcacaagcag ccggcctcaa caccgccgcc aaagccatcg gcctgaaata cttcggcacg   120
gcgaccgaca cccccgaact gagcgacacc gcgtacgaga cggaactgaa caacacgcag   180
gatttcgggc agttgacacc tgcgaattcg atgaaggtga gtctgacagc tccccccct   240
cctggggtga gtgagtgagt tcgacgctaa tggttttgc agtgggacgc aaccgagccc   300
cagcaaaaca ctttcacgtt cagcggcggc gatcagatcg ctaacctggc caaggcgaat   360
ggccagatgt tgaggtgcca taatcttgtt tggtataatc agttgccgtc gtggggtatg   420
tatagtacct gcgtacttgt ttgtaatgat tgtcttggct gatttgtgaa gtcaccggtg   480
gatcctggac caacgagacg ctgcttgctg ccatgaagaa tcacatcacc aacgtcgtta   540
cccattacaa gggccagtgc tatgcatggg atgtcgtgaa tgagggtacg tccatataat   600
tgctgttact atcgagagga atcagctaat gacgacagcc ctcaacgacg acggcaccta   660
ccgcagcaac gtcttctacc agtatatcgg ggaggcgtac atccccatcg ccttcgcgac   720
ggccgccgcc gccgacccg acgccaagct gtactacaac gactacaaca tcgagtaccc   780
cggcgccaag gccacggcgg cgcagaacat cgtcaagctg gtgcagtcgt acggggcgcg   840
catcgacggc gtcggcctgc agtcgcactt catcgtgggc cagacgccca gcacgagcgc   900
ccagcagcag aacatggccg ccttcaccgc gctgggcgtc gaggtcgcca tcaccgagct   960
cgacatccgc atgcagctgc ccgagacgtc cgcgcagctg acgcagcagg cgaccgacta  1020
ccagagcacg gtccaggcct gcgtcaacac cgacagctgc gtcggcatta ccctctggga  1080
ctggaccgac aagtactcgt gggtgcccag caccttctca ggctggggcg acgcctgtcc  1140
ctgggacgac aactaccaga gaaacccgc gtacaacggc atcctcactg ctctgggagg  1200
cacgccctcc tccagtacca gctacaccct cacgccgacg acgacctcaa gcggcggcag  1260
tggcagcccg actgacgtgg cccagcattg ggagcagtgc ggtggcctgg ctggactgg  1320
gccgacggtt tgcgccagtg gcttcacttg cactgtcatc aacgagtatt actcgcagtg  1380
tctgtaa                                                            1387
```

<210> SEQ ID NO 99
<211> LENGTH: 403
<212> TYPE: PRT
<213> ORGANISM: Penicillium sp.

<400> SEQUENCE: 99

```
Met Val Arg Leu Ser Pro Val Leu Leu Ala Ser Ile Ala Gly Ser Gly
1               5                   10                  15

Leu Pro Leu Tyr Ala Gln Ala Ala Gly Leu Asn Thr Ala Ala Lys Ala
            20                  25                  30

Ile Gly Leu Lys Tyr Phe Gly Thr Ala Thr Asp Asn Pro Glu Leu Ser
        35                  40                  45

Asp Thr Ala Tyr Glu Thr Glu Leu Asn Asn Thr Gln Asp Phe Gly Gln
    50                  55                  60

Leu Thr Pro Ala Asn Ser Met Lys Trp Asp Ala Thr Glu Pro Gln Gln
65                  70                  75                  80

Asn Thr Phe Thr Phe Ser Gly Gly Asp Gln Ile Ala Asn Leu Ala Lys
                85                  90                  95

Ala Asn Gly Gln Met Leu Arg Cys His Asn Leu Val Trp Tyr Asn Gln
            100                 105                 110
```

```
Leu Pro Ser Trp Val Thr Gly Gly Ser Trp Thr Asn Glu Thr Leu Leu
        115                 120                 125

Ala Ala Met Lys Asn His Ile Thr Asn Val Val Thr His Tyr Lys Gly
    130                 135                 140

Gln Cys Tyr Ala Trp Asp Val Val Asn Glu Ala Leu Asn Asp Asp Gly
145                 150                 155                 160

Thr Tyr Arg Ser Asn Val Phe Tyr Gln Tyr Ile Gly Glu Ala Tyr Ile
                165                 170                 175

Pro Ile Ala Phe Ala Thr Ala Ala Ala Asp Pro Asp Ala Lys Leu
                180                 185                 190

Tyr Tyr Asn Asp Tyr Asn Ile Glu Tyr Pro Gly Ala Lys Ala Thr Ala
        195                 200                 205

Ala Gln Asn Ile Val Lys Leu Val Gln Ser Tyr Gly Ala Arg Ile Asp
    210                 215                 220

Gly Val Gly Leu Gln Ser His Phe Ile Val Gly Gln Thr Pro Ser Thr
225                 230                 235                 240

Ser Ala Gln Gln Gln Asn Met Ala Ala Phe Thr Ala Leu Gly Val Glu
                245                 250                 255

Val Ala Ile Thr Glu Leu Asp Ile Arg Met Gln Leu Pro Glu Thr Ser
        260                 265                 270

Ala Gln Leu Thr Gln Gln Ala Thr Asp Tyr Gln Ser Thr Val Gln Ala
    275                 280                 285

Cys Val Asn Thr Asp Ser Cys Val Gly Ile Thr Leu Trp Asp Trp Thr
290                 295                 300

Asp Lys Tyr Ser Trp Val Pro Ser Thr Phe Ser Gly Trp Gly Asp Ala
305                 310                 315                 320

Cys Pro Trp Asp Asp Asn Tyr Gln Lys Lys Pro Ala Tyr Asn Gly Ile
                325                 330                 335

Leu Thr Ala Leu Gly Gly Thr Pro Ser Ser Thr Ser Tyr Thr Leu
        340                 345                 350

Thr Pro Thr Thr Thr Ser Ser Gly Gly Ser Gly Ser Pro Thr Asp Val
    355                 360                 365

Ala Gln His Trp Glu Gln Cys Gly Gly Leu Gly Trp Thr Gly Pro Thr
    370                 375                 380

Val Cys Ala Ser Gly Phe Thr Cys Thr Val Ile Asn Glu Tyr Tyr Ser
385                 390                 395                 400

Gln Cys Leu

<210> SEQ ID NO 100
<211> LENGTH: 25
<212> TYPE: DNA
<213> ORGANISM: Unknown
<220> FEATURE:
<223> OTHER INFORMATION: Penicillium
<220> FEATURE:
<221> NAME/KEY: misc_feature
<222> LOCATION: (14)..(14)
<223> OTHER INFORMATION: Y=C OR T
<220> FEATURE:
<221> NAME/KEY: misc_feature
<222> LOCATION: (16)..(16)
<223> OTHER INFORMATION: N=A,C,G, OR T
<220> FEATURE:
<221> NAME/KEY: misc_feature
<222> LOCATION: (17)..(17)
<223> OTHER INFORMATION: M=A OR C
<220> FEATURE:
<221> NAME/KEY: misc_feature
<222> LOCATION: (19)..(19)
```

```
<223> OTHER INFORMATION: N=A,C,G, OR T
<220> FEATURE:
<221> NAME/KEY: misc_feature
<222> LOCATION: (22)..(22)
<223> OTHER INFORMATION: Y=C OR T
<220> FEATURE:
<221> NAME/KEY: misc_feature
<222> LOCATION: (25)..(25)
<223> OTHER INFORMATION: Y=C OR T

<400> SEQUENCE: 100
caacggccag atgytnmgnt gycay                                     25

<210> SEQ ID NO 101
<211> LENGTH: 23
<212> TYPE: DNA
<213> ORGANISM: Unknown
<220> FEATURE:
<223> OTHER INFORMATION: Penicillium
<220> FEATURE:
<221> NAME/KEY: misc_feature
<222> LOCATION: (9)..(9)
<223> OTHER INFORMATION: S=C OR G
<220> FEATURE:
<221> NAME/KEY: misc_feature
<222> LOCATION: (12)..(12)
<223> OTHER INFORMATION: Y=C OR T
<220> FEATURE:
<221> NAME/KEY: misc_feature
<222> LOCATION: (15)..(15)
<223> OTHER INFORMATION: N=A,C,G, OR T
<220> FEATURE:
<221> NAME/KEY: misc_feature
<222> LOCATION: (18)..(18)
<223> OTHER INFORMATION: S=C OR G
<220> FEATURE:
<221> NAME/KEY: misc_feature
<222> LOCATION: (20)..(20)
<223> OTHER INFORMATION: R=A OR G
<220> FEATURE:
<221> NAME/KEY: misc_feature
<222> LOCATION: (21)..(21)
<223> OTHER INFORMATION: Y=C OR T

<400> SEQUENCE: 101
gcgccgtasg aytgnacsar ytt                                       23

<210> SEQ ID NO 102
<211> LENGTH: 29
<212> TYPE: DNA
<213> ORGANISM: Unknown
<220> FEATURE:
<223> OTHER INFORMATION: Penicillium

<400> SEQUENCE: 102
gcccttgtaa tgggtaacga cgttggtga                                 29

<210> SEQ ID NO 103
<211> LENGTH: 28
<212> TYPE: DNA
<213> ORGANISM: Unknown
<220> FEATURE:
<223> OTHER INFORMATION: Penicillium

<400> SEQUENCE: 103
gcaagcagcg tctcgttggt ccaggatc                                  28

<210> SEQ ID NO 104
<211> LENGTH: 29
<212> TYPE: DNA
<213> ORGANISM: Unknown
```

```
<220> FEATURE:
<223> OTHER INFORMATION: Penicillium

<400> SEQUENCE: 104
ggcacctacc gcagcaacgt cttctacca                                29

<210> SEQ ID NO 105
<211> LENGTH: 26
<212> TYPE: DNA
<213> ORGANISM: Unknown
<220> FEATURE:
<223> OTHER INFORMATION: Penicillium

<400> SEQUENCE: 105
acggcggcgc agaacatcgt caagct                                   26

<210> SEQ ID NO 106
<211> LENGTH: 37
<212> TYPE: DNA
<213> ORGANISM: Unknown
<220> FEATURE:
<223> OTHER INFORMATION: Penicillium

<400> SEQUENCE: 106
acacaactgg ccatggttcg cctcagtcca gtcctgc                       37

<210> SEQ ID NO 107
<211> LENGTH: 41
<212> TYPE: DNA
<213> ORGANISM: Unknown
<220> FEATURE:
<223> OTHER INFORMATION: Penicillium

<400> SEQUENCE: 107
cagtcacctc tagttattac agacactgcg agtaatactc g                  41

<210> SEQ ID NO 108
<211> LENGTH: 25
<212> TYPE: DNA
<213> ORGANISM: Unknown
<220> FEATURE:
<223> OTHER INFORMATION: Penicillium

<400> SEQUENCE: 108
actcaattta cctctatcca cactt                                    25

<210> SEQ ID NO 109
<211> LENGTH: 25
<212> TYPE: DNA
<213> ORGANISM: Unknown
<220> FEATURE:
<223> OTHER INFORMATION: Penicillium

<400> SEQUENCE: 109
ctatagcgaa atggattgat tgtct                                    25

<210> SEQ ID NO 110
<211> LENGTH: 19
<212> TYPE: DNA
<213> ORGANISM: Unknown
<220> FEATURE:
<223> OTHER INFORMATION: Penicillium

<400> SEQUENCE: 110
atgttgaggt gccataatc                                           19
```

<210> SEQ ID NO 111
<211> LENGTH: 19
<212> TYPE: DNA
<213> ORGANISM: Unknown
<220> FEATURE:
<223> OTHER INFORMATION: Penicillium

<400> SEQUENCE: 111
tctggtagtc ggtcgcctg                                                  19

<210> SEQ ID NO 112
<211> LENGTH: 977
<212> TYPE: DNA
<213> ORGANISM: Thielavia terrestris

<400> SEQUENCE: 112
atgaagctgt catcccagct cgccgccctc acgctggccg cggcctccgt gtcaggccac      60
tacatcttcg agcagattgc ccatggcggc accaagttcc caccttacga gtacatccga     120
agaaacacga actataacag ccctgtcacc agtctctcgt cgaacgacct gcgatgcaac     180
gtaggcggcg agacggctgg caacacgacc gtcctcgacg tgaaggcggg cgactccttc     240
accttctact cggacgtggc cgtgtaccac caggggccca tctcactgtg cgtgccccgg     300
gccaactttg atcagtccca agcggactgt ccgctcgcct ggataaccac aattgactga     360
cagcccgcac agctacatgt ccaaggctcc cggctccgtc gtggactacg acggctccgg     420
cgactggttc aagatccacg actggggccc gaccttcagc aacggccagg cctcgtggcc     480
gctgcggggt gcgtcccttc cctttccctc cccttcctc cccttcctc cccccctttc     540 cccccttttc tgtctggtcg cacgccctgc tgacgtcccc gtagacaact accagtacaa     600
catcccgacg tgcatcccga acggcgagta cctgctgcgc atccagtcgc tggcgatcca     660
caacccgggc gccacgccgc agttctacat cagctgcgcg caggtccggg tctcgggcgg     720
cggcagcgcc tccccctccc caacggccaa gatccccggc gcgttcaagg cgaccgatcc     780
cgggtatacc gcgaatgtga gtgccctatg ttccttgcgc tccttgttcc ttgctccttg     840
ctcggcgtgc ttgaacgcta cgggctgtgg agggagggat ggatggatga ataggatgct     900
gactgatggt gggacaccag atttacaata acttccactc gtatacggtg ccgggtccgg     960
cggtctttca gtgctag                                                   977

<210> SEQ ID NO 113
<211> LENGTH: 223
<212> TYPE: PRT
<213> ORGANISM: Thielavia terrestris

<400> SEQUENCE: 113

Met Lys Leu Ser Ser Gln Leu Ala Ala Leu Thr Leu Ala Ala Ala Ser
1               5                  10                  15

Val Ser Gly His Tyr Ile Phe Glu Gln Ile Ala His Gly Gly Thr Lys
                20                  25                  30

Phe Pro Pro Tyr Glu Tyr Ile Arg Arg Asn Thr Asn Tyr Asn Ser Pro
            35                  40                  45

Val Thr Ser Leu Ser Ser Asn Asp Leu Arg Cys Asn Val Gly Gly Glu
        50                  55                  60

Thr Ala Gly Asn Thr Thr Val Leu Asp Val Lys Ala Gly Asp Ser Phe
65                  70                  75                  80

Thr Phe Tyr Ser Asp Val Ala Val Tyr His Gln Gly Pro Ile Ser Leu
                85                  90                  95

```
Tyr Met Ser Lys Ala Pro Gly Ser Val Val Asp Tyr Asp Gly Ser Gly
            100                 105                 110

Asp Trp Phe Lys Ile His Asp Trp Gly Pro Thr Phe Ser Asn Gly Gln
        115                 120                 125

Ala Ser Trp Pro Leu Arg Asp Asn Tyr Gln Tyr Asn Ile Pro Thr Cys
130                 135                 140

Ile Pro Asn Gly Glu Tyr Leu Leu Arg Ile Gln Ser Leu Ala Ile His
145                 150                 155                 160

Asn Pro Gly Ala Thr Pro Gln Phe Tyr Ile Ser Cys Ala Gln Val Arg
                165                 170                 175

Val Ser Gly Gly Gly Ser Ala Ser Pro Ser Pro Thr Ala Lys Ile Pro
            180                 185                 190

Gly Ala Phe Lys Ala Thr Asp Pro Gly Tyr Thr Ala Asn Ile Tyr Asn
        195                 200                 205

Asn Phe His Ser Tyr Thr Val Pro Gly Pro Ala Val Phe Gln Cys
    210                 215                 220
```

<210> SEQ ID NO 114
<211> LENGTH: 924
<212> TYPE: DNA
<213> ORGANISM: Myceliophthora thermophila

<400> SEQUENCE: 114

```
atgaagttca cctcgtccct cgctgtcctg gccgctgccg gcgcccaggc tcactgttag      60
tcgaccctcg aacccaacac ccccctcccc ccttttctcc tccatctcct cggcctcact     120
tagtagccgc tgacaacgac tagataccct tcctagggcc ggcactggtg gctcgctctc     180
tggcgagtgg gaggtggtcc gcatgaccga gaaccattac tcgcacggcc cggtcaccga     240
tgtcaccagc cccgagatga cctgctatca gtccggcgtg cagggtgcgc cccagaccgt     300
ccaggtcaag gcgggctccc aattcacctt cagcgtggat ccctcgatcg ccaccccgg     360
ccctctccag ttctacatgg ctaaggtgcc gtcgggccag acggccgcca cctttgacgg     420
cacgggagcc gtgtggttca agatcctacca agacggcccg aacggcctcg caccgacag     480
cattacctgg cccagcgccg gttcgtgact tcctccccac tcgcttttttt tttttttatt    540
tttatttttt tttctttcgg aactcaagaa tctttctctc tctctcccgt ctttggcctt     600
gaacaacact aaaactcttc cttactgtat taattaggca aaaccgaggt ctcggtcacc     660
atccccagct gcatcgatga tggcgagtac ctgctccggg tcgagcacat cgcgctccac     720
agcgccagca gcgtgggcgg cgctcagttc tacattgcct gcgcccagct ctccgtcacc     780
ggcggctccg gcaccctcaa cacgggctcg ctcgtctccc tgcccggcgc ctacaaggcc     840
accgaccccg gcatcctctt ccagctctac tggcccatcc cgaccgagta catcaacccc     900
ggcccggccc ccgtctcttg ctaa                                           924
```

<210> SEQ ID NO 115
<211> LENGTH: 232
<212> TYPE: PRT
<213> ORGANISM: Myceliophthora thermophila

<400> SEQUENCE: 115

```
Met Lys Phe Thr Ser Ser Leu Ala Val Leu Ala Ala Gly Ala Gln
1               5                  10                  15

Ala His Tyr Thr Phe Pro Arg Ala Gly Thr Gly Gly Ser Leu Ser Gly
            20                  25                  30
```

```
Glu Trp Glu Val Val Arg Met Thr Glu Asn His Tyr Ser His Gly Pro
         35                  40                  45
Val Thr Asp Val Thr Ser Pro Glu Met Thr Cys Tyr Gln Ser Gly Val
 50                  55                  60
Gln Gly Ala Pro Gln Thr Val Gln Val Lys Ala Gly Ser Gln Phe Thr
 65                  70                  75                  80
Phe Ser Val Asp Pro Ser Ile Gly His Pro Gly Pro Leu Gln Phe Tyr
                 85                  90                  95
Met Ala Lys Val Pro Ser Gly Gln Thr Ala Ala Thr Phe Asp Gly Thr
                100                 105                 110
Gly Ala Val Trp Phe Lys Ile Tyr Gln Asp Gly Pro Asn Gly Leu Gly
            115                 120                 125
Thr Asp Ser Ile Thr Trp Pro Ser Ala Gly Lys Thr Glu Val Ser Val
130                 135                 140
Thr Ile Pro Ser Cys Ile Asp Asp Gly Glu Tyr Leu Leu Arg Val Glu
145                 150                 155                 160
His Ile Ala Leu His Ser Ala Ser Ser Val Gly Gly Ala Gln Phe Tyr
                165                 170                 175
Ile Ala Cys Ala Gln Leu Ser Val Thr Gly Gly Ser Gly Thr Leu Asn
                180                 185                 190
Thr Gly Ser Leu Val Ser Leu Pro Gly Ala Tyr Lys Ala Thr Asp Pro
            195                 200                 205
Gly Ile Leu Phe Gln Leu Tyr Trp Pro Ile Pro Thr Glu Tyr Ile Asn
210                 215                 220
Pro Gly Pro Ala Pro Val Ser Cys
225                 230

<210> SEQ ID NO 116
<211> LENGTH: 854
<212> TYPE: DNA
<213> ORGANISM: Myceliophthora thermophila

<400> SEQUENCE: 116
atgaaggccc tctctctcct tgcggctgcc tcggcagtct ctgcgcatac catcttcgtc      60
cagctcgaag cagacggcac gaggtacccg gtctcgtacg ggatccggga cccaagctac     120
gacggcccca tcaccgacgt cacatccaac gacgttgctt gcaacggcgg gccgaacccg     180
acgacccccct ccagcgacgt catcaccgtc accgcgggca ccacggtcaa ggccatctgg     240
aggcacaccc tccaatccgg cccggacgat gtcatggacg ccagccacaa gggcccgacc     300
ctggcctacc tcaagaaggt cggcgatgcc accaaggact cgggcgtcgg cggtggctgg     360
ttcaagattc aggaggacgg ctacaacaac ggccagtggg gcaccagcac cgttatctcc     420
aacggcggcg agcactacat gtgagccatt cctccgagag aagaccaaga ctcttgacga     480
tctcgctgac ccgtgcaaca agtgacatcc cggcctgcat ccccgagggt cagtacctcc     540
tccgcgccga tgatcgcc ctccacgcgc ccgggtcccc cggcggtgcc cagctctacg     600
taagcctctg cccttccccc cttcctcttg atcgaatcgg actgcccacc cccctttttcg     660
actccgacta acaccgttgc cagatggaat gtgcccagat caacatcgtc ggcggctccg     720
gctcggtgcc cagctcgacc gtcagcttcc cggcgcgta cagccccaac gacccgggtc     780
tcctcatcaa catctattcc atgtcgccct cgagctcgta caccatcccg ggcccgcccg     840
tcttcaagtg ctag                                                      854

<210> SEQ ID NO 117
```

<211> LENGTH: 235
<212> TYPE: PRT
<213> ORGANISM: Myceliophthora thermophila

<400> SEQUENCE: 117

```
Met Lys Ala Leu Ser Leu Leu Ala Ala Ala Ser Ala Val Ser Ala His
1               5                   10                  15

Thr Ile Phe Val Gln Leu Glu Ala Asp Gly Thr Arg Tyr Pro Val Ser
            20                  25                  30

Tyr Gly Ile Arg Asp Pro Ser Tyr Asp Gly Pro Ile Thr Asp Val Thr
        35                  40                  45

Ser Asn Asp Val Ala Cys Asn Gly Pro Asn Pro Thr Thr Pro Ser
50                  55                  60

Ser Asp Val Ile Thr Val Thr Ala Gly Thr Thr Val Lys Ala Ile Trp
65                  70                  75                  80

Arg His Thr Leu Gln Ser Gly Pro Asp Asp Val Met Asp Ala Ser His
                85                  90                  95

Lys Gly Pro Thr Leu Ala Tyr Leu Lys Lys Val Gly Asp Ala Thr Lys
            100                 105                 110

Asp Ser Gly Val Gly Gly Gly Trp Phe Lys Ile Gln Glu Asp Gly Tyr
        115                 120                 125

Asn Asn Gly Gln Trp Gly Thr Ser Thr Val Ile Ser Asn Gly Gly Glu
    130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Asn Ile Val Gly Gly Ser Gly
            180                 185                 190

Ser Val Pro Ser Ser Thr Val Ser Phe Pro Gly Ala Tyr Ser Pro Asn
        195                 200                 205

Asp Pro Gly Leu Leu Ile Asn Ile Tyr Ser Met Ser Pro Ser Ser Ser
    210                 215                 220

Tyr Thr Ile Pro Gly Pro Pro Val Phe Lys Cys
225                 230                 235
```

<210> SEQ ID NO 118
<211> LENGTH: 862
<212> TYPE: DNA
<213> ORGANISM: Aspergillus fumigatus

<400> SEQUENCE: 118

```
atgactttgt ccaagatcac ttccattgct ggccttctgg cctcagcgtc tctcgtggct    60
ggccacggct tgtttctgg cattgttgct gatgggaaat agtatgtgct gaaccacac    120 aaatgacagc tgcaacagct aacttctatt ccagttacgg agggtacctt gttaaccaat   180 accctacat gagcaaccct cccgacacca ttgcctggtc caccaccgcc accgacctcg    240
gctttgtgga cggcaccggc taccagtctc cggatattat ctgccacaga gacgcaaaga   300
atggcaagtt gaccgcaacc gttgcagccg gttcacagat cgaattccag tggacgacgt    360
ggccagagtc tcaccatgga ccggtacgac gccgaagaga agagaacata ttgtgaccag   420
ataggctaac atagcatagt tgattactta cctcgctcca tgcaacggcg actgtgccac   480
cgtggacaag accaccctga gtttgtcaa gatcgccgct caaggcttga tcgacggctc   540
caacccacct ggtgtttggg ctgatgatga aatgatcgcc aacaacaaca cggccacagt   600
```

-continued

```
gaccattcct gcctcctatg cccccggaaa ctacgtcctt cgccacgaga tcatcgccct    660
tcactctgcg ggtaacctga acggcgcgca gaactacccc cagtgtttca acatccaaat    720
caccggtggc ggcagtgctc agggatctgg caccgctggc acgtccctgt acaagaatac    780
tgatcctggc atcaagtttg acatctactc ggatctgagc ggtggatacc ctattcctgg    840
tcctgcactg ttcaacgctt aa                                              862
```

<210> SEQ ID NO 119
<211> LENGTH: 250
<212> TYPE: PRT
<213> ORGANISM: Aspergillus fumigatus

<400> SEQUENCE: 119

```
Met Thr Leu Ser Lys Ile Thr Ser Ile Ala Gly Leu Leu Ala Ser Ala
1               5                   10                  15

Ser Leu Val Ala Gly His Gly Phe Val Ser Gly Ile Val Ala Asp Gly
                20                  25                  30

Lys Tyr Tyr Gly Gly Tyr Leu Val Asn Gln Tyr Pro Tyr Met Ser Asn
            35                  40                  45

Pro Pro Asp Thr Ile Ala Trp Ser Thr Thr Ala Thr Asp Leu Gly Phe
        50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95

Glu Phe Gln Trp Thr Thr Trp Pro Glu Ser His His Gly Pro Leu Ile
            100                 105                 110

Thr Tyr Leu Ala Pro Cys Asn Gly Asp Cys Ala Thr Val Asp Lys Thr
        115                 120                 125

Thr Leu Lys Phe Val Lys Ile Ala Ala Gln Gly Leu Ile Asp Gly Ser
    130                 135                 140

Asn Pro Pro Gly Val Trp Ala Asp Asp Glu Met Ile Ala Asn Asn Asn
145                 150                 155                 160

Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
    210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250
```

METHODS AND COMPOSITIONS FOR DEGRADING CELLULOSIC MATERIAL

CROSS-REFERENCE TO RELATED APPLICATIONS

This application is a divisional application of U.S. application Ser. No. 16/052,082, filed Aug. 1, 2018, which is a divisional application of U.S. application Ser. No. 15/591,935, filed May 10, 2017, now U.S. Pat. No. 10,059,972, which is a divisional application of U.S. application Ser. No. 14/849,204, filed Sep. 9, 2015, now U.S. Pat. No. 9,677,102, which is a divisional application of U.S. application Ser. No. 14/248,039, filed Apr. 8, 2014, now U.S. Pat. No. 9,145,569, which is a divisional application of U.S. application Ser. No. 14/010,199, filed Aug. 26, 2013, now U.S. Pat. No. 8,703,464, which is a divisional application of U.S. application Ser. No. 12/612,401, filed Nov. 4, 2009, now U.S. Pat. No. 8,518,684, which claims the benefit of U.S. Provisional Application No. 61/115,829, filed Nov. 18, 2008, and U.S. Provisional Application No. 61/174,221, filed Apr. 30, 2009, which applications are incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

Field of the Invention

The present invention relates to enzyme compositions and methods of degrading or converting cellulosic material with the enzyme compositions.

Description of the Related Art

Cellulose is a polymer of the simple sugar glucose linked by beta-1,4 bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

There is a need in the art to improve cellulolytic protein compositions through supplementation with additional enzymes to increase efficiency and to provide cost-effective enzyme solutions for degradation of lignocellulose.

WO 2004/056981 discloses a partial cellobiohydrolase from *Myceliophthera thermophila*. WO 2008/008070 discloses a cellobiohydrolase from *Chrysosporium lucknowense*. WO 94/021785 discloses a Family 10 xylanase from *Aspergillus aculeatus*. Ustinov et al., 2008, *Enzyme and Microbial Technology* 43: 56-65, disclose a Family 10 xylanase from *Myceliophthera thermophila*.

The present invention relates to improved enzyme compositions for degrading or converting cellulosic material.

SUMMARY OF THE INVENTION

The present invention relates to enzyme compositions comprising a polypeptide having cellobiohydrolase II activity, a polypeptide having xylanase activity, and one or more (several) cellulolytic proteins selected from the group consisting of an endoglucanase, a cellobiohydrolase, and a beta-glucosidase, wherein one or both of the polypeptide having cellobiohydrolase II activity and the polypeptide having xylanase activity are foreign to the one or more (several) cellulolytic proteins.

The present invention also relates to methods for degrading or converting a cellulosic material, comprising: treating the cellulosic material with an enzyme composition comprising a polypeptide having cellobiohydrolase II activity, a polypeptide having xylanase activity, and one or more (several) cellulolytic proteins selected from the group consisting of an endoglucanase, a cellobiohydrolase, and a beta-glucosidase, wherein one or both of the polypeptide having cellobiohydrolase II activity and the polypeptide having xylanase activity are foreign to the one or more (several) cellulolytic proteins.

The present invention also relates to methods for producing a fermentation product, comprising:

(a) saccharifying a cellulosic material with an enzyme composition comprising a polypeptide having cellobiohydrolase II activity, a polypeptide having xylanase activity, and one or more (several) cellulolytic proteins selected from the group consisting of an endoglucanase, a cellobiohydrolase, and a beta-glucosidase, wherein one or both of the polypeptide having cellobiohydrolase II activity and the polypeptide having xylanase activity are foreign to the one or more (several) cellulolytic proteins;

(b) fermenting the saccharified cellulosic material with one or more (several) fermenting microorganisms; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition comprising a polypeptide having cellobiohydrolase II activity, a polypeptide having xylanase activity, and one or more (several) cellulolytic proteins selected from the group consisting of an endoglucanase, a cellobiohydrolase, and a beta-glucosidase, wherein one or both of the polypeptide having cellobiohydrolase II activity and the polypeptide having xylanase activity are foreign to the one or more (several) cellulolytic proteins.

In one aspect, the polypeptide having cellobiohydrolase II activity is a CELE polypeptide. In another aspect, the polypeptide having xylanase activity is a GH10 polypeptide.

DEFINITIONS

Figure 1:
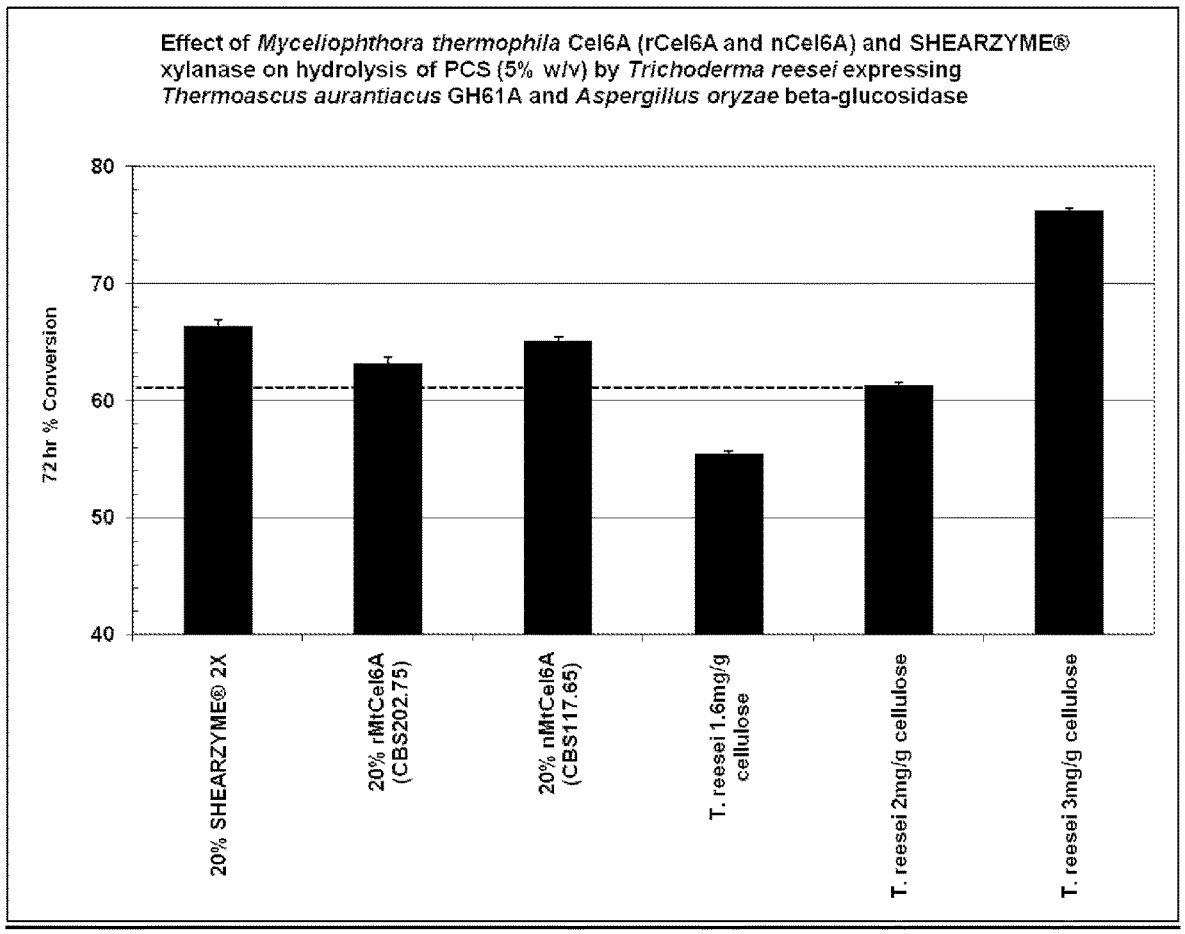
FIG. 1 shows the effect of *Myceliophthora thermophila* CBS 117.65 Family 6 cellobiohydrolases II, *Myceliophthora thermophila* CBS 202.75 Family 6 cellobiohydrolases II, or *Aspergillus aculeatus* Family 10 xylanase (on a 72 hour hydrolysis of PCS (5% w/v) at 50° C. by a fermentation broth of *Trichoderma reesei* expressing *Thermoascus aurantiacus* GH61A polypeptide having cellulolytic enhancing activity and an *Aspergillus oryzae* beta-glucosidase fusion protein. Each enzyme was added as a 20% replacement (by protein) of the *Trichoderma reesei* cellulolytic protein composition. The dotted line shows the percent conversion by 2 mg of a *Trichoderma reesei* cellulolytic protein composition per g of cellulose. Enhancement of hydrolysis was demonstrated with mixtures that reach percent conversion above the dotted line at an equivalent protein loading. Error bars from triplicate measurements are shown.

Cellobiohydrolase II activity: The term "cellobiohydrolase II activity" is defined herein as a 1,4-D-glucan cellobiohydrolase (E.C. 3.2.1.91) activity that catalyzes the hydrolysis of 1,4-beta-D-glucosidic linkages in cellulose, cellotetriose, or any beta-1,4-linked glucose containing polymer, releasing cellobiose from the non-reducing end of the chain. For purposes of the present invention, cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative.

Cellulolytic activity: The term "cellulolytic activity" is defined herein as a biological activity that hydrolyzes a cellulosic material. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic activity is determined by measuring the increase in hydrolysis of a cellulosic material by cellulolytic enzyme(s) under the following conditions: 1-20 mg of cellulolytic protein/g of cellulose in PCS for 3-7 days at 50-65° C. compared to a control hydrolysis without addition of cellulolytic protein. Typical conditions are 1 ml reactions, washed or unwashed PCS, 5% insoluble solids, 50 mM sodium acetate pH 5, 1 mM $MnSO_4$, 50-65° C., 72 hours, sugar analysis by AMINEX® HPX-87H column (Bio-Rad Laboratories, Inc., Hercules, Calif., USA).

Endoglucanase: The term "endoglucanase" is defined herein as an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined based on a reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) hydrolysis according to the procedure of Ghose, 1987, *Pure and Appl. Chem.* 59: 257-268.

Beta-glucosidase: The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase activity is defined as 1.0 µmole of p-nitrophenol produced per minute at 40° C., pH 5 from 1 mM p-nitrophenyl-beta-D-glucopyranoside as substrate in 100 mM sodium citrate containing 0.01% TWEEN® 20.

Cellulolytic enhancing activity: The term "cellulolytic enhancing activity" is defined herein as a biological activity that enhances the hydrolysis of a cellulosic material by polypeptides having cellulolytic activity. For purposes of the present invention, cellulolytic enhancing activity is determined by measuring the increase in reducing sugars or in the increase of the total of cellobiose and glucose from the hydrolysis of a cellulosic material by cellulolytic protein under the following conditions: 1-50 mg of total protein/g of cellulose in PCS, wherein total protein is comprised of 50-99.5% w/w cellulolytic protein and 0.5-50% w/w protein of cellulolytic enhancing activity for 1-7 day at 50-65° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsvrd, Denmark) in the presence of 3% of total protein weight *Aspergillus oryzae* beta-glucosidase (recombinantly produced in *Aspergillus oryzae* according to WO 02/095014) or 3% of total protein weight *Aspergillus fumigatus* beta-glucosidase (recombinantly produced in *Aspergillus oryzae* as described in WO 2002/095014) of cellulase protein loading is used as the source of the cellulolytic activity.

The polypeptides having cellulolytic enhancing activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the mature polypeptide of a GH61 polypeptide.

The polypeptides having cellulolytic enhancing activity enhance the hydrolysis of a cellulosic material catalyzed by proteins having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Xylan degrading activity: The terms "xylan degrading activity" or "xylanolytic activity" are defined herein as a biological activity that hydrolyzes xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by Schizophyllum commune, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase activity: The term "xylanase activity" is defined herein as a 1,4-beta-D-xylan-xylohydrolase activity (E.C. 3.2.1.8) that catalyzes the endo-hydrolysis of 1,4-beta-D-xylosidic linkages in xylans. For purposes of the present invention, xylanase activity is determined using birchwood xylan as substrate. One unit of xylanase activity is defined as 1.0 µmole of reducing sugar (measured in glucose equivalents as described by Lever, 1972, A new reaction for colorimetric determination of carbohydrates, *Anal. Biochem* 47: 273-279) produced per minute during the initial period of hydrolysis at 50° C., pH 5 from 2 g of birchwood xylan per liter as substrate in 50 mM sodium acetate containing 0.01% TWEEN® 20.

Beta-xylosidase activity: The term "beta-xylosidase activity" is defined herein as a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase activity is defined as 1.0 μmole of p-nitrophenol produced per minute at 40° C., pH 5 from 1 mM p-nitrophenyl-beta-D-xyloside as substrate in 100 mM sodium citrate containing 0.01% TWEEN® 20.

Acetylxylan esterase activity: The term "acetylxylan esterase activity" is defined herein as a carboxylesterase activity (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase activity is defined as the amount of enzyme capable of releasing 1 μmole of p-nitrophenolate anion per minute at pH 5, 25° C.

Feruloyl esterase activity: The term "feruloyl esterase activity" is defined herein as a 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase activity equals the amount of enzyme capable of releasing 1 μmole of p-nitrophenolate anion per minute at pH 5, 25° C.

Alpha-glucuronidase activity: The term "alpha-glucuronidase activity" is defined herein as an alpha-D-glucosiduronate glucuronohydrolase activity (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase activity equals the amount of enzyme capable of releasing 1 μmole of glucuronic or 4-O-methylglucuronic acid per minute at pH 5, 40° C.

Alpha-L-arabinofuranosidase activity: The term "alpha-L-arabinofuranosidase activity" is defined herein as an alpha-L-arabinofuranoside arabinofuranohydrolase activity (EC 3.2.1.55) that catalyzes the hydrolysis of terminal non-reducing alpha-L-arabinofuranoside residues in alpha-L-arabinosides. The enzyme activity acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Family 6 or 10 or 61, or GH6, GH10, or GH61, or CEL6: The terms "Family 6", "Family 10", "Family 61", "GH6", "GH10", "GH61", or "CEL6" are defined herein as a polypeptide falling into the glycoside hydrolase Families 6, 10, and 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. According to such a classification, SEQ ID NOs: 26, 30, 32, 34, and 38 or the mature polypeptides thereof belong to Family 6 and are predicted to be a cellobiohydrolase II.

Cellulosic material: The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp.105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp.23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" is defined herein as a cellulosic material derived from corn stover by treatment with heat and dilute sulfuric acid.

Xylan-containing material: The term "xylan-containing material" is defined herein as any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having enzyme activity that is in its final form following translation and any post-translational modifications, such as N-terminal processing, C-terminal truncation, glycosylation, phosphorylation, etc.

Mature polypeptide coding sequence: The term "mature polypeptide coding sequence" is defined herein as a nucleotide sequence that encodes a mature polypeptide having enzyme activity.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Polypeptide fragment: The term "polypeptide fragment" is defined herein as a polypeptide having one or more (several) amino acids deleted from the amino and/or carboxyl terminus of a mature polypeptide; or a homologous sequence thereof; wherein the fragment has enzyme activity.

Subsequence: The term "subsequence" is defined herein as a nucleotide sequence having one or more (several) nucleotides deleted from the 5' and/or 3' end of a mature polypeptide coding sequence; or a homologous sequence thereof; wherein the subsequence encodes a polypeptide fragment having enzyme activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

DETAILED DESCRIPTION OF THE INVENTION

The present invention relates to enzyme compositions comprising a polypeptide having cellobiohydrolase II activity, a polypeptide having xylanase activity, and one or more (several) cellulolytic proteins selected from the group consisting of an endoglucanase, a cellobiohydrolase, and a beta-glucosidase, wherein one or both of the polypeptide having cellobiohydrolase II activity and the polypeptide having xylanase activity are foreign to the one or more (several) cellulolytic proteins.

The present invention also relates to methods for degrading or converting a cellulosic material, comprising: treating the cellulosic material with an enzyme composition comprising a polypeptide having cellobiohydrolase II activity, a polypeptide having xylanase activity, and one or more (several) cellulolytic proteins selected from the group consisting of an endoglucanase, a cellobiohydrolase, and a beta-glucosidase, wherein one or both of the polypeptide having cellobiohydrolase II activity and the polypeptide having xylanase activity are foreign to the one or more (several) cellulolytic proteins.

In one aspect, the method above further comprises recovering the degraded or converted cellulosic material. Soluble products of degradation or conversion of the cellulosic material can be separated from the insoluble cellulosic material using technology well known in the art such as, for example, centrifugation, filtration, and gravity settling.

The present invention also relates to methods for producing a fermentation product, comprising: (a) saccharifying a cellulosic material with an enzyme composition comprising a polypeptide having cellobiohydrolase II activity, a polypeptide having xylanase activity, and one or more (several) cellulolytic proteins selected from the group consisting of an endoglucanase, a cellobiohydrolase, and a beta-glucosidase, wherein one or both of the polypeptide having cellobiohydrolase II activity and the polypeptide having xylanase activity are foreign to the one or more (several) cellulolytic proteins; (b) fermenting the saccharified cellulosic material with one or more (several) fermenting microorganisms; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition comprising a polypeptide having cellobiohydrolase II activity, a polypeptide having xylanase activity, and one or more (several) cellulolytic proteins selected from the group consisting of an endoglucanase, a cellobiohydrolase, and a beta-glucosidase, wherein one or both of the polypeptide having cellobiohydrolase II activity and the polypeptide having xylanase activity are foreign to the one or more (several) cellulolytic proteins. In a preferred aspect, the fermenting of the cellulosic material produces a fermentation product. In another preferred aspect, the method further comprises recovering the fermentation product from the fermentation.

The presence of the polypeptide having cellobiohydrolase II activity and the polypeptide having xylanase activity increases the hydrolysis of a cellulosic material by the enzyme composition compared to their absence or the additive effect of each alone. The increase is preferably at least 1.02-fold, more preferably at least 1.05-fold, more preferably at least 1.1-fold, more preferably at least 1.2-fold, more preferably at least 1.4-fold, more preferably at least 1.6-fold, more preferably at least 1.8-fold, more preferably at least 2-fold, even more preferably at least 5-fold, and most preferably at least 10-fold in the presence of the polypeptide having cellobiohydrolase II activity and the polypeptide having xylanase activity compared to their absence or the additive effect of each alone.

In one aspect, the polypeptide having cellobiohydrolase II activity is foreign to the one or more (several) cellulolytic proteins. In another aspect, the polypeptide having xylanase activity is foreign to the one or more (several) cellulolytic proteins. In another aspect, the polypeptide having cellobiohydrolase II activity and the polypeptide having xylanase activity are foreign to the one or more (several) cellulolytic proteins.

Enzyme Compositions

In the methods of the present invention, the enzyme composition comprises a polypeptide having cellobiohydrolase II activity, a polypeptide having xylanase activity, and one or more (several) cellulolytic proteins selected from the group consisting of an endoglucanase, a cellobiohydrolase, and a beta-glucosidase.

For cellulose degradation, at least three categories of enzymes are important for converting cellulose into fermentable sugars: endoglucanases (EC 3.2.1.4) that hydrolyze the cellulose chains at random; cellobiohydrolases (EC 3.2.1.91) that cleave cellobiosyl units from the cellulose chain ends, and beta-glucosidases (EC 3.2.1.21) that convert cellobiose and soluble cellodextrins into glucose.

The cellulolytic protein, e.g., endoglucanase, cellobiohydrolase, and/or beta-glucosidase, may be a bacterial cellulolytic protein. For example, the cellulolytic protein may be a gram positive bacterial cellulolytic protein such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* cellulolytic protein, or a Gram negative bacterial cellulolytic protein such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* cellulolytic protein.

In a preferred aspect, the cellulolytic protein is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* cellulolytic protein.

In another preferred aspect, the cellulolytic protein is a *Streptococcus equisimilis*, *Streptococcus pyogenes*, *Streptococcus uberis*, or *Streptococcus equi* subsp. *Zooepidemicus* cellulolytic protein.

In another preferred aspect, the cellulolytic protein is a *Streptomyces achromogenes*, *Streptomyces avermitilis*, *Streptomyces coelicolor*, *Streptomyces griseus*, or *Streptomyces lividans* cellulolytic protein.

The cellulolytic protein, e.g., endoglucanase, cellobiohydrolase, and/or beta-glucosidase, may also be a fungal cellulolytic protein, and more preferably a yeast cellulolytic protein such as a *Candida*, *Kluyveromyces*, *Pichia*, *Saccharomyces*, *Schizosaccharomyces*, or *Yarrowia* cellulolytic protein; or more preferably a filamentous fungal cellulolytic protein such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* cellulolytic protein.

In a preferred aspect, the cellulolytic protein is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cellulolytic protein.

In another preferred aspect, the cellulolytic protein is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*,

*Trichoderma koningii, Trichoderma longibrachiatum, Trichoderma reesei, Trichoderma viride,* or *Trichophaea saccata* cellulolytic protein.

The cellulolytic proteins may have activity, i.e., hydrolyze cellulose, either in the acid, neutral, or alkaline pH range. Chemically modified or protein engineered mutants of cellulolytic proteins may also be used.

One or more components of the enzyme composition may be wild-type proteins, recombinant proteins, or a combination of wild-type proteins and recombinant proteins. For example, one or more components may be native proteins of a cell, which is used as a host cell to express recombinantly one or more (several) other components of the enzyme composition. One or more components of the enzyme composition may be produced as monocomponents, which are then combined to form the enzyme composition. The enzyme composition may be a combination of multicomponent and monocomponent protein preparations.

Examples of bacterial endoglucanases that can be used in the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, Gene 45: 253-263; *Trichoderma reesei* Cel7B endoglucanase I; GENBANK™ accession no. M15665; SEQ ID NO: 82); *Trichoderma reesei* endoglucanase II (Saloheimo, et al., 1988, Gene 63:11-22; *Trichoderma reesei* Cel5A endoglucanase II; GENBANK™ accession no. M19373; SEQ ID NO: 84); *Trichoderma reesei* endoglucanase III (Okada et al., 1988, Appl. Environ. Microbiol. 64: 555-563; GENBANK™ accession no. AB003694; SEQ ID NO: 86); *Trichoderma reesei* endoglucanase IV (Saloheimo et al., 1997, Eur. J. Biochem. 249: 584-591; GENBANK™ accession no. Y11113; SEQ ID NO: 88); *Trichoderma reesei* endoglucanase V (Saloheimo et al., 1994, Molecular Microbiology 13: 219-228; GENBANK™ accession no. Z33381; SEQ ID NO: 90); *Aspergillus aculeatus* endoglucanase (Ooi et al., 1990, Nucleic Acids Research 18: 5884); *Aspergillus kawachii* endoglucanase (Sakamoto et al., 1995, Current Genetics 27: 435-439); *Erwinia carotovara* endoglucanase (Saarilahti et al., 1990, Gene 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V (SEQ ID NO: 2); *Myceliophthora thermophila* CBS 117.65 endoglucanase (SEQ ID NO: 4); basidiomycete CBS 495.95 endoglucanase (SEQ ID NO: 6); basidiomycete CBS 494.95 endoglucanase (SEQ ID NO: 8); *Thielavia terrestris* NRRL 8126 CEL6B endoglucanase (SEQ ID NO: 10); *Thielavia terrestris* NRRL 8126 CEL6C endoglucanase (SEQ ID NO: 12); *Thielavia terrestris* NRRL 8126 CEL7C endoglucanase (SEQ ID NO: 14); *Thielavia terrestris* NRRL 8126 CEL7E endoglucanase (SEQ ID NO: 16); *Thielavia terrestris* NRRL 8126 CEL7F endoglucanase (SEQ ID NO: 18); *Cladorrhinum foecundissimum* ATCC 62373 CEL7A endoglucanase (SEQ ID NO: 20); and *Trichoderma reesei* strain No. VTT-D-80133 endoglucanase (SEQ ID NO: 22; GENBANK™ accession no. M15665). The endoglucanases of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 82, SEQ ID NO: 84, SEQ ID NO: 86, SEQ ID NO: 88, and SEQ ID NO: 90 described above are encoded by the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 81, SEQ ID NO: 83, SEQ ID NO: 85, SEQ ID NO: 87, and SEQ ID NO: 89, respectively.

Examples of cellobiohydrolases useful in the present invention include, but are not limited to, *Trichoderma reese* cellobiohydrolase I (SEQ ID NO: 24); *Trichoderma reesei* cellobiohydrolase II (SEQ ID NO: 26); *Humicola insolens* cellobiohydrolase I (SEQ ID NO: 28), *Myceliophthora thermophila* cellobiohydrolase II (SEQ ID NO: 30 and SEQ ID NO: 32), *Thielavia terrestris* cellobiohydrolase II (CEL6A) (SEQ ID NO: 34), *Chaetomium thermophilum* cellobiohydrolase I (SEQ ID NO: 36), and *Chaetomium thermophilum* cellobiohydrolase II (SEQ ID NO: 38). The cellobiohydrolases of SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38 described above are encoded by the mature polypeptide coding sequence of SEQ ID NO: 23, SEQ ID NO: 25, SEQ ID NO: 27, SEQ ID NO: 29, SEQ ID NO: 31, SEQ ID NO: 33, SEQ ID NO: 35, and SEQ ID NO: 37, respectively.

Examples of beta-glucosidases useful in the present invention include, but are not limited to, *Aspergillus oryzae* beta-glucosidase (SEQ ID NO: 40); *Aspergillus fumigatus* beta-glucosidase (SEQ ID NO: 42); *Penicillium brasilianum* IBT 20888 beta-glucosidase (SEQ ID NO: 44); *Aspergillus niger* beta-glucosidase (SEQ ID NO: 46); and *Aspergillus aculeatus* beta-glucosidase (SEQ ID NO: 48). The beta-glucosidases of SEQ ID NO: 40, SEQ ID NO: 42, SEQ ID NO: 44, SEQ ID NO: 46, and SEQ ID NO: 48 described above are encoded by the mature polypeptide coding sequence of SEQ ID NO: 39, SEQ ID NO: 41, SEQ ID NO: 43, SEQ ID NO: 45, and SEQ ID NO: 47, respectively.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The *Aspergillus niger* polypeptide having beta-glucosidase activity can be obtained according to Dan et al., 2000, J. Biol. Chem. 275: 4973-4980. The *Aspergillus aculeatus* polypeptide having beta-glucosidase activity can be obtained according to Kawaguchi et al., 1996, Gene 173: 287-288.

Other endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, Biochem. J. 280: 309-316, and Henrissat B., and Bairoch A., 1996, Updating the sequence-based classification of glycosyl hydrolases, Biochem. J. 316: 695-696.

In one aspect, the one or more (several) cellulolytic proteins comprise endoglucanase. In another aspect, the one or more (several) cellulolytic proteins comprise endoglucanase I. In another aspect, the one or more (several) cellulolytic proteins comprise endoglucanase II. In another aspect, the one or more (several) cellulolytic proteins comprise endoglucanase III. In another aspect, the one or more (several) cellulolytic proteins comprise endoglucanase IV. In another aspect, the one or more (several) cellulolytic proteins comprise endoglucanase V. In another aspect, the one or more (several) cellulolytic proteins comprise cellobiohydrolase. In another aspect, the one or more (several) cellulolytic proteins comprise cellobiohydrolase I. In another aspect, the one or more (several) cellulolytic proteins comprise beta-glucosidase. In another aspect, the one or more (several) cellulolytic proteins comprise a beta-glucosidase fusion protein. In another aspect, the one or more (several) cellulolytic proteins comprise endoglucanase and beta-glucosidase. In another aspect, the one or more (several) cellulolytic proteins comprise endoglucanase and cellobiohydrolase I. In another aspect, the one or more (several) cellulolytic proteins comprise endoglucanase, cellobiohydrolase I, and beta-glucosidase.

In another aspect, the beta-glucosidase is *Aspergillus oryzae* beta-glucosidase (SEQ ID NO: 40). In another aspect, the beta-glucosidase is *Aspergillus fumigatus* beta-glucosidase (SEQ ID NO: 42). In another aspect, the beta-glucosidase is *Penicillium brasilianum* IBT 20888 beta-glucosidase (SEQ ID NO: 44). In another aspect, the beta-glucosidase is *Aspergillus niger* beta-glucosidase (SEQ ID NO: 46). In another aspect, the beta-glucosidase is and *Aspergillus aculeatus* beta-glucosidase. In another aspect, the beta-glucosidase is the *Aspergillus oryzae* beta-glucosidase variant fusion protein of SEQ ID NO: 50 or the *Aspergillus oryzae* beta-glucosidase fusion protein of SEQ ID NO: 52. In another aspect, the *Aspergillus oryzae* beta-glucosidase variant fusion protein is encoded by the polynucleotide of SEQ ID NO: 49 or the *Aspergillus oryzae* beta-glucosidase fusion protein is encoded by the polynucleotide of SEQ ID NO: 51.

In another aspect, the one or more (several) cellulolytic proteins comprise a commercial cellulolytic protein preparation. Commercial cellulolytic protein preparations suitable for use in the present invention include, for example, CELLIC™ Ctec (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150 L (Dyadic International, Inc.). The cellulase enzymes are added in amounts effective from about 0.001 to about 5.0 wt % of solids, more preferably from about 0.025 to about 4.0 wt % of solids, and most preferably from about 0.005 to about 2.0 wt % of solids. The cellulase enzymes are added in amounts effective from about 0.001 to about 5.0 wt % of solids, more preferably from about 0.025 to about 4.0 wt % of solids, and most preferably from about 0.005 to about 2.0 wt % of solids.

In another aspect, the one or more (several) cellulolytic proteins comprise a beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B). In another aspect, the one or more (several) cellulolytic proteins comprise an *Aspergillus oryzae* beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B). In another aspect, the one or more (several) cellulolytic proteins comprise an *Aspergillus niger* beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B). In another aspect, the one or more (several) cellulolytic proteins comprise an *Aspergillus fumigatus* beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B). In another aspect, the one or more (several) cellulolytic proteins comprise a *Penicillium brasilianum* beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B). In another aspect, the one or more (several) cellulolytic proteins comprise an *Aspergillus oryzae* beta-glucosidase variant BG fusion protein (for example, SEQ ID NO: 50), a *Trichoderma reesei* cellobiohydrolase I (CEL7A), a *Trichoderma reesei* cellobiohydrolase II (CEL6A), and a *Trichoderma reesei* endoglucanase I (CEL7B). In another aspect, the one or more (several) cellulolytic proteins comprise an *Aspergillus oryzae* beta-glucosidase fusion protein (for example, SEQ ID NO: 52), a *Trichoderma reesei* cellobiohydrolase I (CEL7A), a *Trichoderma reesei* cellobiohydrolase II (CEL6A), and a *Trichoderma reesei* endoglucanase I (CEL7B).

In another aspect, the one or more (several) cellulolytic proteins above further comprise one or more (several) enzymes selected from the group consisting of a *Trichoderma reesei* endoglucanase II (CELSA), a *Trichoderma reesei* endoglucanase V (CEL45A), and a *Trichoderma reesei* endoglucanase III (CEL12A).

The enzyme composition may further comprise a polypeptide(s) having cellulolytic enhancing activity. In another aspect, the one or more (several) cellulolytic proteins above further comprise a polypeptide(s) having cellulolytic enhancing activity comprising the following motifs:

[ILMV]-P-X(4,5)-G-X-Y-[ILMV]-X-R-X-[EQ]-X(4)-[HNQ] and [FW]-[TF]-K-[AIV], wherein X is any amino acid, X(4,5) is any amino acid at 4 or 5 contiguous positions, and X(4) is any amino acid at 4 contiguous positions.

The isolated polypeptide comprising the above-noted motifs may further comprise:
H-X(1,2)-G-P-X(3)-[YW]-[AILMV],
[EQ]-X-Y-X(2)-C-X-[EHQN]-[FILV]-X-[ILV], or
H-X(1,2)-G-P-X(3)-[YW]-[AILMV] and [EQ]-X-Y-X(2)-C-X-[EHQN]-[FILV]-X-[ILV], wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In one aspect, the isolated polypeptide having cellulolytic enhancing activity further comprises H-X(1,2)-G-P-X(3)-[YVV]-[AILMV]. In another aspect, the isolated polypeptide having cellulolytic enhancing activity further comprises [EQ]-X-Y-X(2)-C-X-[EHQN]-[FILV]-X-[ILV]. In another aspect, the isolated polypeptide having cellulolytic enhancing activity further comprises H-X(1,2)-G-P-X(3)-[YVV]-[AILMV] and [EQ]-X-Y-X(2)-C-X-[EHQN]-[FILV]-X-[ILV].

Examples of isolated polypeptides having cellulolytic enhancing activity include *Thielavia terrestris* polypeptides having cellulolytic enhancing activity (the mature polypeptide of SEQ ID NO: 54, SEQ ID NO: 56, SEQ ID NO: 58, SEQ ID NO: 60, SEQ ID NO: 62, SEQ ID NO: 64, or SEQ ID NO: 113); *Thermoascus aurantiacus* (the mature polypeptide of SEQ ID NO: 66); *Trichoderma reesei* (the mature polypeptide of SEQ ID NO: 68); *Myceliophthora thermo-*

*phila* (SEQ ID NO: 115 or SEQ ID NO: 117); or *Aspergillus fumigatus* (SEQ ID NO: 119). The polypeptides having cellulolytic enhancing activity of SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 113, SEQ ID NO: 113, SEQ ID NO: 115, SEQ ID NO: 117, and SEQ ID NO: 119 described above are encoded by the mature polypeptide coding sequence of SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 112, SEQ ID NO: 114, SEQ ID NO: 116, and SEQ ID NO: 118, respectively.

In one aspect, the one or more (several) cellulolytic proteins further comprise a *Thielavia terrestris* polypeptide having cellulolytic enhancing activity (the mature polypeptide of SEQ ID NO: 54). In another aspect, the one or more (several) cellulolytic proteins further comprise a *Thielavia terrestris* polypeptide having cellulolytic enhancing activity (the mature polypeptide of SEQ ID NO: 56). In another aspect, the one or more (several) cellulolytic proteins further comprise a *Thielavia terrestris* polypeptide having cellulolytic enhancing activity (the mature polypeptide of SEQ ID NO: 58). In another aspect, the one or more (several) cellulolytic proteins further comprise a *Thielavia terrestris* polypeptide having cellulolytic enhancing activity (the mature polypeptide of SEQ ID NO: 60). In another aspect, the one or more (several) cellulolytic proteins further comprise a *Thielavia terrestris* polypeptide having cellulolytic enhancing activity (the mature polypeptide of SEQ ID NO: 62). In another aspect, the one or more (several) cellulolytic proteins further comprise a *Thielavia terrestris* polypeptide having cellulolytic enhancing activity (the mature polypeptide of SEQ ID NO: 64). In another aspect, the one or more (several) cellulolytic proteins further comprise a *Thermoascus aurantiacus* polypeptide having cellulolytic enhancing activity (the mature polypeptide of SEQ ID NO: 66). In another aspect, the one or more (several) cellulolytic proteins further comprise a *Trichoderma reesei* polypeptide having cellulolytic enhancing activity (the mature polypeptide of SEQ ID NO: 68). In another aspect, the one or more (several) cellulolytic proteins further comprise a *Thielavia terrestris* polypeptide having cellulolytic enhancing activity (the mature polypeptide of SEQ ID NO: 113). In another aspect, the one or more (several) cellulolytic proteins further comprise a *Myceliophthora thermophila* polypeptide having cellulolytic enhancing activity (the mature polypeptide of SEQ ID NO: 115). In another aspect, the one or more (several) cellulolytic proteins further comprise a *Myceliophthora thermophila* polypeptide having cellulolytic enhancing activity (the mature polypeptide of SEQ ID NO: 117). In another aspect, the one or more (several) cellulolytic proteins further comprise an *Aspergillus fumigatus* polypeptide having cellulolytic enhancing activity (the mature polypeptide of SEQ ID NO: 119).

Other cellulolytic enzymes that may be used in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 4,435,307, 5,457,046, 5,648,263, 5,686,593, 5,691,178, 5,763,254, and 5,776,757.

In another aspect, the enzyme composition may further comprise one or more xylan-degrading enzymes. In another aspect, the one or more xylan-degrading enzymes are selected from the group consisting of a xylanase, an acetyxylan esterase, a feruloyl esterase, an arabinofuranosidase, a xylosidase, and a glucuronidase. In a preferred aspect, the xylosidase is a beta-xylosidase. In a more preferred aspect, the beta-xylosidase is a *Trichoderma reesei* beta-xylosidase.

Examples of commercial xylan degrading enzyme preparations suitable for use in the present invention include, for example, SHEARZYME™ (Novozymes A/S), CELLIC™ Htec (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8X212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number Q0UHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alcc12), *Trichoderma reesei* alpha-glucuronidase (Uniprot accession number Q99024), *Talaromyces emersonii* alpha-glucuronidase (UniProt accession number Q8X211), *Aspergillus niger* alpha-glucuronidase (Uniprot accession number Q96WX9), *Aspergillus terreus* alpha-glucuronidase (SwissProt accession number Q0CJP9), and

*Aspergillus fumigatus* alpha-glucuronidase (SwissProt accession number Q4WW45).

An enzyme composition of the present invention may be used as a supplement to another enzyme composition, where the enzyme composition of the present invention is simply added to the other enzyme composition or is added as a replacement of a portion of the other enzyme composition. Replacement of a portion of another enzyme composition, e.g., a commercial preparation, is preferably at least 1%, more preferably at least 2%, more preferably at least 5%, more preferably at least 10%, more preferably at least 15%, more preferably at least 20%, more preferably at least 25%, and most preferably at least 50% replacement of the other enzyme composition.

The enzymes and proteins used in the present invention may be fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

The enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Polypeptides Having Cellobiohydrolase II Activity and Polynucleotides Thereof

In the methods of the present invention, the polypeptide having cellobiohydrolase II activity may be obtained from microorganisms of any genus. In a preferred aspect, the polypeptide obtained from a given source is secreted extracellularly.

A polypeptide having cellobiohydrolase II activity may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* polypeptide having cellobiohydrolase II activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having cellobiohydrolase II activity.

In a preferred aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having cellobiohydrolase II activity.

In another preferred aspect, the polypeptide is a *Streptococcus equisimilis*, *Streptococcus pyogenes*, *Streptococcus uberis*, or *Streptococcus equi* subsp. *Zooepidemicus* polypeptide having cellobiohydrolase II activity.

In another preferred aspect, the polypeptide is a *Streptomyces achromogenes*, *Streptomyces avermitilis*, *Streptomyces coelicolor*, *Streptomyces griseus*, or *Streptomyces lividans* polypeptide having cellobiohydrolase II activity.

The polypeptide having cellobiohydrolase II activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having cellobiohydrolase II activity; or more preferably a filamentous fungal polypeptide such as aan *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Me/anocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudop/ectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having cellobiohydrolase II activity.

In a preferred aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having cellobiohydrolase II activity.

In another preferred aspect, the polypeptide is an *Acremonium cellulolyticus*, *Aspergillus acu/eatus*, *Aspergillus*

*awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having cellobiohydrolase II activity.

In one aspect, the polypeptide having cellobiohydrolase II activity is a CEL6 polypeptide.

In another aspect, the CEL6 polypeptide having cellobiohydrolase II activity is obtained from *Myceliophthora thermophila* CBS 202.75.

In one aspect, the CEL6 polypeptide having cellobiohydrolase II activity comprises an amino acid sequence having a degree of identity to the mature polypeptide of SEQ ID NO: 30 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have cellobiohydrolase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 30.

In another aspect, the CEL6 polypeptide having cellobiohydrolase II activity comprises the amino acid sequence of SEQ ID NO: 30 or an allelic variant thereof; or a fragment thereof that has cellobiohydrolase activity. In a preferred aspect, the polypeptide comprises the amino acid sequence of SEQ ID NO: 30. In another preferred aspect, the polypeptide comprises the mature polypeptide of SEQ ID NO: 30. In another preferred aspect, the polypeptide comprises amino acids 18 to 482 of SEQ ID NO: 30, or an allelic variant thereof; or a fragment thereof that has cellobiohydrolase activity. In another preferred aspect, the polypeptide comprises amino acids 18 to 482 of SEQ ID NO: 30. In another preferred aspect, the polypeptide consists of the amino acid sequence of SEQ ID NO: 30 or an allelic variant thereof; or a fragment thereof that has cellobiohydrolase activity. In another preferred aspect, the polypeptide consists of the amino acid sequence of SEQ ID NO: 30. In another preferred aspect, the polypeptide consists of the mature polypeptide of SEQ ID NO: 30. In another preferred aspect, the polypeptide consists of amino acids 18 to 482 of SEQ ID NO: 30 or an allelic variant thereof; or a fragment thereof that has cellobiohydrolase activity. In another preferred aspect, the polypeptide consists of amino acids 18 to 482 of SEQ ID NO: 30.

In another aspect, the CEL6 polypeptide having cellobiohydrolase II activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 29, (ii) the cDNA sequence contained in the mature polypeptide coding sequence of SEQ ID NO: 29, or (iii) a complementary strand of (i) or (ii). In a preferred aspect, the mature polypeptide coding sequence is nucleotides 52 to 1809 of SEQ ID NO: 29.

In another aspect, the CEL6 polypeptide having cellobiohydrolase II activity is encoded by a polynucleotide comprising or consisting of a nucleotide sequence that has a degree of identity to the mature polypeptide coding sequence of SEQ ID NO: 29 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a active polypeptide having cellobiohydrolase II activity.

In another aspect, the CEL6 polypeptide having cellobiohydrolase II activity is encoded by a polynucleotide comprising or consisting of the nucleotide sequence of SEQ ID NO: 29. In another more preferred aspect, the nucleotide sequence comprises or consists of the sequence contained in plasmid pSMai182 which is contained in *E. coli* NRRL B-50059. In another preferred aspect, the nucleotide sequence comprises or consists of the mature polypeptide coding region of SEQ ID NO: 29. In another preferred aspect, the nucleotide sequence comprises or consists of nucleotides 52 to 1809 of SEQ ID NO: 29. In another more preferred aspect, the nucleotide sequence comprises or consists of the mature polypeptide coding region contained in plasmid pSMai182 which is contained in *E. coli* NRRL B-50059. The present invention also encompasses nucleotide sequences which encode a polypeptide comprising or consisting of the amino acid sequence of SEQ ID NO: 30 or the mature polypeptide thereof, which differ from SEQ ID NO: 29 or the mature polypeptide coding sequence thereof by virtue of the degeneracy of the genetic code. The present invention also relates to subsequences of SEQ ID NO: 29 which encode fragments of SEQ ID NO: 30 that have cellobiohydrolase activity.

In another preferred aspect, the CEL6 polypeptide having cellobiohydrolase II activity is obtained from *Myceliophthora thermophila* CBS 117.65.

In one aspect, the CEL6 polypeptide having cellobiohydrolase II activity comprises an amino acid sequence having a degree of identity to the mature polypeptide of SEQ ID NO: 32 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have cellobiohydrolase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 32.

In another aspect, the CEL6 polypeptide having cellobiohydrolase II activity comprises the amino acid sequence of SEQ ID NO: 32 or an allelic variant thereof; or a fragment thereof that has cellobiohydrolase activity. In a preferred aspect, the polypeptide comprises the amino acid sequence of SEQ ID NO: 32. In another preferred aspect, the polypeptide comprises the mature polypeptide of SEQ ID NO: 32. In another preferred aspect, the polypeptide comprises amino acids 19 to 471 of SEQ ID NO: 32, or an allelic variant thereof; or a fragment thereof that has cellobiohydrolase activity. In another preferred aspect, the polypeptide comprises amino acids 19 to 471 of SEQ ID NO: 32. In another preferred aspect, the polypeptide consists of the amino acid sequence of SEQ ID NO: 32 or an allelic variant thereof; or a fragment thereof that has cellobiohydrolase activity. In another preferred aspect, the polypeptide consists of the amino acid sequence of SEQ ID NO: 32. In another preferred aspect, the polypeptide consists of the mature polypeptide of SEQ ID NO: 32. In another preferred aspect, the polypeptide consists of amino acids 19 to 471 of SEQ ID NO: 32 or an allelic variant thereof; or a fragment thereof that has cellobiohydrolase activity. In another preferred aspect, the polypeptide consists of amino acids 19 to 471 of SEQ ID NO: 32.

In another aspect, the CEL6 polypeptide having cellobiohydrolase II activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 31, (ii) the cDNA sequence contained in the mature polypeptide coding sequence of SEQ ID NO: 31, or (iii) a complementary strand of (i) or (ii). In a preferred aspect, the mature polypeptide coding sequence is nucleotides 107 to 1465 of SEQ ID NO: 31.

In another aspect, the CEL6 polypeptide having cellobiohydrolase II activity is encoded by a polynucleotide comprising or consisting of a nucleotide sequence that has a degree of identity to the mature polypeptide coding sequence of SEQ ID NO: 31 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the CEL6 polypeptide having cellobiohydrolase II activity is encoded by a polynucleotide comprising or consisting of the nucleotide sequence of SEQ ID NO: 31. In another preferred aspect, the nucleotide sequence comprises or consists of the mature polypeptide coding region of SEQ ID NO: 31. In another preferred aspect, the nucleotide sequence comprises or consists of nucleotides 107 to 1465 of SEQ ID NO: 31. The present invention also encompasses nucleotide sequences which encode a polypeptide comprising or consisting of the amino acid sequence of SEQ ID NO: 32 or the mature polypeptide thereof, which differ from SEQ ID NO: 31 or the mature polypeptide coding sequence thereof by virtue of the degeneracy of the genetic code. The present invention also relates to subsequences of SEQ ID NO: 31 which encode fragments of SEQ ID NO: 32 that have cellobiohydrolase activity.

In another preferred aspect, the CEL6 polypeptide having cellobiohydrolase II activity is obtained from *Thielavia terrestris* NRRL 8126.

In one aspect, the CEL6 polypeptide having cellobiohydrolase II activity comprises an amino acid sequence having a degree of identity to the mature polypeptide of SEQ ID NO: 34 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have cellobiohydrolase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 34.

In another aspect, the CEL6 polypeptide having cellobiohydrolase II activity comprises the amino acid sequence of SEQ ID NO: 34 or an allelic variant thereof; or a fragment thereof that has cellobiohydrolase activity. In a preferred aspect, the polypeptide comprises the amino acid sequence of SEQ ID NO: 34. In another preferred aspect, the polypeptide comprises the mature polypeptide of SEQ ID NO: 34. In another preferred aspect, the polypeptide comprises amino acids 18 to 481 of SEQ ID NO: 34, or an allelic variant thereof; or a fragment thereof that has cellobiohydrolase activity. In another preferred aspect, the polypeptide comprises amino acids 18 to 481 of SEQ ID NO: 34. In another preferred aspect, the polypeptide consists of the amino acid sequence of SEQ ID NO: 34 or an allelic variant thereof; or a fragment thereof that has cellobiohydrolase activity. In another preferred aspect, the polypeptide consists of the amino acid sequence of SEQ ID NO: 34. In another preferred aspect, the polypeptide consists of the mature polypeptide of SEQ ID NO: 34. In another preferred aspect, the polypeptide consists of amino acids 18 to 481 of SEQ ID NO: 34 or an allelic variant thereof; or a fragment thereof that has cellobiohydrolase activity. In another preferred aspect, the polypeptide consists of amino acids 18 to 481 of SEQ ID NO: 34.

In another aspect, the CEL6 polypeptide having cellobiohydrolase II activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 33, (ii) the genomic DNA sequence comprising the mature polypeptide coding sequence of SEQ ID NO: 33, or (iii) a complementary strand of (i) or (ii) (J. Sambrook, E. F. Fritsch, and T. Maniatis, 1989, *Molecular Cloning, A Laboratory Manual*, 2d edition, Cold Spring Harbor, New York). In a preferred aspect, the mature polypeptide coding sequence is nucleotides 52 to 1443 of SEQ ID NO: 33.

In another aspect, the CEL6 polypeptide having cellobiohydrolase II activity is encoded by a polynucleotide comprising or consisting of a nucleotide sequence that has a degree of identity to the mature polypeptide coding sequence of SEQ ID NO: 33 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the CEL6 polypeptide having cellobiohydrolase II activity is encoded by a polynucleotide comprising or consisting of the nucleotide sequence of SEQ ID NO: 33. In another preferred aspect, the nucleotide sequence comprises or consists of the mature polypeptide coding region of SEQ ID NO: 33. In another preferred aspect, the nucleotide sequence comprises or consists of nucleotides 52 to 1443 of SEQ ID NO: 33. The present invention also encompasses nucleotide sequences which encode a polypeptide comprising or consisting of the amino acid sequence of SEQ ID NO: 34 or the mature polypeptide thereof, which differ from SEQ ID NO: 33 or the mature polypeptide coding sequence thereof by virtue of the degeneracy of the genetic code. The present invention also relates to subsequences of SEQ ID NO: 33 which encode fragments of SEQ ID NO: 34 that have cellobiohydrolase activity.

In another preferred aspect, the CEL6 polypeptide having cellobiohydrolase II activity is obtained from *Trichoderma reesei*.

In one aspect, the CEL6 polypeptide having cellobiohydrolase II activity comprises an amino acid sequence having a degree of identity to the mature polypeptide of SEQ ID NO: 26 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have cellobiohydrolase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 26.

In another aspect, the CEL6 polypeptide having cellobiohydrolase II activity comprises the amino acid sequence of SEQ ID NO: 26 or an allelic variant thereof; or a fragment thereof that has cellobiohydrolase activity. In a preferred aspect, the polypeptide comprises the amino acid sequence of SEQ ID NO: 26. In another preferred aspect, the polypeptide comprises the mature polypeptide of SEQ ID NO: 26. In another preferred aspect, the polypeptide comprises amino acids 25 to 471 of SEQ ID NO: 26, or an allelic variant thereof; or a fragment thereof that has cellobiohydrolase activity. In another preferred aspect, the polypeptide comprises amino acids 25 to 471 of SEQ ID NO: 26. In another preferred aspect, the polypeptide consists of the amino acid sequence of SEQ ID NO: 26 or an allelic variant thereof; or a fragment thereof that has cellobiohydrolase activity. In another preferred aspect, the polypeptide consists of the amino acid sequence of SEQ ID NO: 26. In another preferred aspect, the polypeptide consists of the mature polypeptide of SEQ ID NO: 26. In another preferred aspect, the polypeptide consists of amino acids 25 to 471 of SEQ ID NO: 26 or an allelic variant thereof; or a fragment thereof that has cellobiohydrolase activity. In another preferred aspect, the polypeptide consists of amino acids 25 to 471 of SEQ ID NO: 26.

In another aspect, the CEL6 polypeptide having cellobiohydrolase II activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 25, (ii) the genomic DNA sequence comprising the mature polypeptide coding sequence of SEQ ID NO: 25, or (iii) a complementary strand of (i) or (ii). In a preferred aspect, the mature polypeptide coding sequence is nucleotides 125 to 1465 of SEQ ID NO: 25.

In another aspect, the CEL6 polypeptide having cellobiohydrolase II activity is encoded by a polynucleotide comprising or consisting of a nucleotide sequence that has a degree of identity to the mature polypeptide coding sequence of SEQ ID NO: 25 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the CEL6 polypeptide having cellobiohydrolase II activity is encoded by a polynucleotide comprising or consisting of the nucleotide sequence of SEQ ID NO: 25. In another preferred aspect, the nucleotide sequence comprises or consists of the mature polypeptide coding region of SEQ ID NO: 25. In another preferred aspect, the nucleotide sequence comprises or consists of nucleotides 125 to 1465 of SEQ ID NO: 25. The present invention also encompasses nucleotide sequences which encode a polypeptide comprising or consisting of the amino acid sequence of SEQ ID NO: 26 or the mature polypeptide thereof, which differ from SEQ ID NO: 25 or the mature polypeptide coding sequence thereof by virtue of the degeneracy of the genetic code. The present invention also relates to subsequences of SEQ ID NO: 25 which encode fragments of SEQ ID NO: 26 that have cellobiohydrolase activity.

In another preferred aspect, the CEL6 polypeptide having cellobiohydrolase II activity is obtained from *Chaetomium thermophilum*.

In one aspect, the CEL6 polypeptide having cellobiohydrolase II activity comprises an amino acid sequence having a degree of identity to the mature polypeptide of SEQ ID NO: 38 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 38.

In another aspect, the CEL6 polypeptide having cellobiohydrolase II activity comprises the amino acid sequence of SEQ ID NO: 38 or an allelic variant thereof; or a fragment thereof that has cellobiohydrolase II activity. In a preferred aspect, the polypeptide comprises the amino acid sequence of SEQ ID NO: 38. In another preferred aspect, the polypeptide comprises the mature polypeptide of SEQ ID NO:

38. In another preferred aspect, the polypeptide comprises amino acids 18 to 477 of SEQ ID NO: 38, or an allelic variant thereof; or a fragment thereof that has cellobiohydrolase II activity. In another preferred aspect, the polypeptide comprises amino acids 18 to 477 of SEQ ID NO: 38. In another preferred aspect, the polypeptide consists of the amino acid sequence of SEQ ID NO: 38 or an allelic variant thereof; or a fragment thereof that has cellobiohydrolase II activity. In another preferred aspect, the polypeptide consists of the amino acid sequence of SEQ ID NO: 38. In another preferred aspect, the polypeptide consists of the mature polypeptide of SEQ ID NO: 38. In another preferred aspect, the polypeptide consists of amino acids 18 to 477 of SEQ ID NO: 38 or an allelic variant thereof; or a fragment thereof that has cellobiohydrolase II activity. In another preferred aspect, the polypeptide consists of amino acids 18 to 477 of SEQ ID NO: 38.

In another aspect, the CEL6 polypeptide having cellobiohydrolase II activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 37, (ii) the genomic DNA sequence comprising the mature polypeptide coding sequence of SEQ ID NO: 37, or (iii) a complementary strand of (i) or (ii). In a preferred aspect, the mature polypeptide coding sequence is nucleotides 15 to 1731 of SEQ ID NO: 37.

In another aspect, the CEL6 polypeptide having cellobiohydrolase II activity is encoded by a polynucleotide comprising or consisting of a nucleotide sequence that has a degree of identity to the mature polypeptide coding sequence of SEQ ID NO: 37 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the CELE polypeptide having cellobiohydrolase II activity is encoded by a polynucleotide comprising or consisting of the nucleotide sequence of SEQ ID NO: 37. In another preferred aspect, the nucleotide sequence comprises or consists of the mature polypeptide coding region of SEQ ID NO: 37. In another preferred aspect, the nucleotide sequence comprises or consists of nucleotides 15 to 1731 of SEQ ID NO: 37. The present invention also encompasses nucleotide sequences which encode a polypeptide comprising or consisting of the amino acid sequence of SEQ ID NO: 38 or the mature polypeptide thereof, which differ from SEQ ID NO: 37 or the mature polypeptide coding sequence thereof by virtue of the degeneracy of the genetic code. The present invention also relates to subsequences of SEQ ID NO: 37 which encode fragments of SEQ ID NO: 38 that have cellobiohydrolase II activity.

For purposes of the present invention, hybridization indicates that the nucleotide sequence hybridizes to a labeled nucleic acid probe corresponding to the mature polypeptide coding sequence or its full-length complementary strand; under very low to very high stringency conditions. Molecules to which the nucleic acid probe hybridizes under these conditions can be detected using, for example, X-ray film. For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Myceliophthora*, or another or related organism and thus, for example, may be an allelic or species variant of the polypeptide encoding region of the nucleotide sequence.

Polypeptides Having Xylanase Activity and Polynucleotides Thereof

In the methods of the present invention, the enzyme composition comprises a polypeptide having xylanase activity. The polypeptide having xylanase activity may be obtained from microorganisms of any genus. In a preferred aspect, the polypeptide obtained from a given source is secreted extracellularly.

A polypeptide having xylanase activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having xylanase activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having xylanase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having xylanase activity.

In another preferred aspect, the polypeptide is a *Streptococcus equisimilis, Streptococcus pyogenes, Streptococcus uberis,* or *Streptococcus equi* subsp. *Zooepidemicus* polypeptide having xylanase activity.

In another preferred aspect, the polypeptide is a *Streptomyces achromogenes, Streptomyces avermitilis, Streptomyces coelicolor, Streptomyces griseus,* or *Streptomyces lividans* polypeptide having xylanase activity.

The polypeptide having xylanase activity may also be a fungal polypeptide, and more preferably a yeast polypeptide such as a *Candida, Kluyveromyces, Pichia, Saccharomyces,*

*Schizosaccharomyces*, or *Yarrowia* polypeptide having xylanase activity; or more preferably a filamentous fungal polypeptide such as aan *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having xylanase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having xylanase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia austra/einsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having xylanase activity.

In a preferred aspect, the polypeptide having xylanase activity is a GH10 polypeptide. In another preferred aspect, the polypeptide having xylanase activity is a GH11 polypeptide.

In another preferred aspect, the GH10 polypeptide having xylanase activity is obtained from *Aspergillus aculeatus*.

In one aspect, the GH10 polypeptide having xylanase activity comprises an amino acid sequence having a degree of identity to the mature polypeptide of SEQ ID NO: 70 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 70.

In another aspect, the GH10 polypeptide having xylanase activity comprises the amino acid sequence of SEQ ID NO: 70 or an allelic variant thereof; or a fragment thereof that has xylanase activity. In a preferred aspect, the polypeptide comprises the amino acid sequence of SEQ ID NO: 70. In another preferred aspect, the polypeptide comprises the mature polypeptide of SEQ ID NO: 70. In another preferred aspect, the polypeptide comprises amino acids 23 to 406 of SEQ ID NO: 70, or an allelic variant thereof; or a fragment thereof that has xylanase activity. In another preferred aspect, the polypeptide comprises amino acids 23 to 406 of SEQ ID NO: 70. In another preferred aspect, the polypeptide consists of the amino acid sequence of SEQ ID NO: 70 or an allelic variant thereof; or a fragment thereof that has xylanase activity. In another preferred aspect, the polypeptide consists of the amino acid sequence of SEQ ID NO: 70. In another preferred aspect, the polypeptide consists of the mature polypeptide of SEQ ID NO: 70. In another preferred aspect, the polypeptide consists of amino acids 23 to 406 of SEQ ID NO: 70 or an allelic variant thereof; or a fragment thereof that has xylanase activity. In another preferred aspect, the polypeptide consists of amino acids 23 to 406 of SEQ ID NO: 70.

In another aspect, the GH10 polypeptide having xylanase activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 69, (ii) the genomic DNA sequence comprising the mature polypeptide coding sequence of SEQ ID NO: 69, or (iii) a complementary strand of (i) or (ii). In a preferred aspect, the mature polypeptide coding sequence is nucleotides 69 to 1314 of SEQ ID NO: 69.

In another aspect, the GH10 polypeptide having xylanase activity is encoded by a polynucleotide comprising or consisting of a nucleotide sequence that has a degree of identity to the mature polypeptide coding sequence of SEQ ID NO: 69 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the GH10 polypeptide having xylanase activity is encoded by a polynucleotide comprising or consisting of the nucleotide sequence of SEQ ID NO: 69. In another preferred aspect, the nucleotide sequence comprises or consists of the mature polypeptide coding region of SEQ ID NO: 69. In another preferred aspect, the nucleotide sequence comprises or consists of nucleotides 69 to 1314 of SEQ ID NO: 69. The present invention also encompasses nucleotide sequences which encode the polypeptide comprising or consisting of the amino acid sequence of SEQ ID NO: 70 or the mature polypeptide thereof, which differ from SEQ ID NO: 69 or the mature polypeptide coding sequence thereof by virtue of the degeneracy of the genetic code. The present invention also relates to subsequences of SEQ ID NO: 69 which encode fragments of SEQ ID NO: 70 that have xylanase activity.

In another preferred aspect, the GH10 polypeptide having xylanase activity is obtained from *Thielavia terrestris* NRRL 8126.

In one aspect, the GH10 polypeptide having xylanase activity comprises an amino acid sequence having a degree of identity to the mature polypeptide of SEQ ID NO: 72 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 72.

In another aspect, the GH10 polypeptide having xylanase activity comprises the amino acid sequence of SEQ ID NO: 72 or an allelic variant thereof; or a fragment thereof that has xylanase activity. In a preferred aspect, the polypeptide comprises the amino acid sequence of SEQ ID NO: 72. In another preferred aspect, the polypeptide comprises the mature polypeptide of SEQ ID NO: 72. In another preferred aspect, the polypeptide comprises amino acids 20 to 369 of SEQ ID NO: 72, or an allelic variant thereof; or a fragment thereof that has xylanase activity. In another preferred aspect, the polypeptide comprises amino acids 20 to 369 of SEQ ID NO: 72. In another preferred aspect, the polypeptide consists of the amino acid sequence of SEQ ID NO: 72 or an allelic variant thereof; or a fragment thereof that has xylanase activity. In another preferred aspect, the polypeptide consists of the amino acid sequence of SEQ ID NO: 72. In another preferred aspect, the polypeptide consists of the mature polypeptide of SEQ ID NO: 72. In another preferred aspect, the polypeptide consists of amino acids 20 to 369 of SEQ ID NO: 72 or an allelic variant thereof; or a fragment thereof that has xylanase activity. In another preferred aspect, the polypeptide consists of amino acids 20 to 369 of SEQ ID NO: 72.

In another aspect, the GH10 polypeptide having xylanase activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 71, (ii) the genomic DNA sequence comprising the mature polypeptide coding sequence of SEQ ID NO: 71, or (iii) a complementary strand of (i) or (ii). In a preferred aspect, the mature polypeptide coding sequence is nucleotides 58 to 1107 of SEQ ID NO: 71.

In another aspect, the GH10 polypeptide having xylanase activity is encoded by a polynucleotide comprising or consisting of a nucleotide sequence that has a degree of identity to the mature polypeptide coding sequence of SEQ ID NO: 71 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the GH10 polypeptide having xylanase activity is encoded by a polynucleotide comprising or consisting of the nucleotide sequence of SEQ ID NO: 71. In another preferred aspect, the nucleotide sequence comprises or consists of the mature polypeptide coding region of SEQ ID NO: 71. In another preferred aspect, the nucleotide sequence comprises or consists of nucleotides 58 to 1107 of SEQ ID NO: 71. The present invention also encompasses nucleotide sequences which encode a polypeptide comprising or consisting of the amino acid sequence of SEQ ID NO: 72 or the mature polypeptide thereof, which differ from SEQ ID NO: 71 or the mature polypeptide coding sequence thereof by virtue of the degeneracy of the genetic code. The present invention also relates to subsequences of SEQ ID NO: 71 which encode fragments of SEQ ID NO: 72 that have xylanase activity.

In another aspect, the GH10 polypeptide having xylanase activity comprises an amino acid sequence having a degree of identity to the mature polypeptide of SEQ ID NO: 74 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 74.

In another aspect, the GH10 polypeptide having xylanase activity comprises the amino acid sequence of SEQ ID NO: 74 or an allelic variant thereof; or a fragment thereof that has xylanase activity. In a preferred aspect, the polypeptide comprises the amino acid sequence of SEQ ID NO: 74. In another preferred aspect, the polypeptide comprises the mature polypeptide of SEQ ID NO: 74. In another preferred aspect, the polypeptide comprises amino acids 19 to 414 of SEQ ID NO: 74, or an allelic variant thereof; or a fragment thereof that has xylanase activity. In another preferred aspect, the polypeptide comprises amino acids 19 to 414 of SEQ ID NO: 74. In another preferred aspect, the polypeptide consists of the amino acid sequence of SEQ ID NO: 74 or an allelic variant thereof; or a fragment thereof that has xylanase activity. In another preferred aspect, the polypeptide consists of the amino acid sequence of SEQ ID NO: 74. In another preferred aspect, the polypeptide consists of the mature polypeptide of SEQ ID NO: 74. In another preferred aspect, the polypeptide consists of amino acids 19 to 414 of SEQ ID NO: 74 or an allelic variant thereof; or a fragment thereof that has xylanase activity. In another preferred aspect, the polypeptide consists of amino acids 19 to 414 of SEQ ID NO: 74.

In another aspect, the GH10 polypeptide having xylanase activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 73, (ii) the genomic DNA sequence comprising the mature polypeptide coding sequence of SEQ ID NO: 73, or (iii) a complementary strand of (i) or (ii). In a preferred aspect, the mature polypeptide coding sequence is nucleotides 55 to 1242 of SEQ ID NO: 73.

In another aspect, the GH10 polypeptide having xylanase activity is encoded by a polynucleotide comprising or consisting of a nucleotide sequence that has a degree of identity to the mature polypeptide coding sequence of SEQ ID NO: 73 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the GH10 polypeptide having xylanase activity is encoded by a polynucleotide comprising or consisting of the nucleotide sequence of SEQ ID NO: 73. In another preferred aspect, the nucleotide sequence comprises or consists of the mature polypeptide coding region of SEQ ID NO: 73. In another preferred aspect, the nucleotide sequence comprises or consists of nucleotides 55 to 1242 of SEQ ID NO: 73. The present invention also encompasses nucleotide sequences which encode a polypeptide comprising or consisting of the amino acid sequence of SEQ ID NO: 74 or the mature polypeptide thereof, which differ from SEQ ID NO: 73 or the mature polypeptide coding sequence thereof by virtue of the degeneracy of the genetic code. The present invention also relates to subsequences of SEQ ID NO: 73 which encode fragments of SEQ ID NO: 74 that have xylanase activity.

In another preferred aspect, the GH10 polypeptide having xylanase activity is obtained from *Aspergillus fumigatus*.

In another aspect, the GH10 polypeptide having xylanase activity comprises an amino acid sequence having a degree of identity to the mature polypeptide of SEQ ID NO: 76 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 76.

In another aspect, the GH10 polypeptide having xylanase activity comprises the amino acid sequence of SEQ ID NO: 76 or an allelic variant thereof; or a fragment thereof that has xylanase activity. In a preferred aspect, the polypeptide comprises the amino acid sequence of SEQ ID NO: 76. In another preferred aspect, the polypeptide comprises the mature polypeptide of SEQ ID NO: 76. In another preferred aspect, the polypeptide comprises amino acids 18 to 364 of SEQ ID NO: 76, or an allelic variant thereof; or a fragment thereof that has xylanase activity. In another preferred aspect, the polypeptide comprises amino acids 18 to 364 of SEQ ID NO: 76. In another preferred aspect, the polypeptide consists of the amino acid sequence of SEQ ID NO: 76 or an allelic variant thereof; or a fragment thereof that has xylanase activity. In another preferred aspect, the polypeptide consists of the amino acid sequence of SEQ ID NO: 76.

In another preferred aspect, the polypeptide consists of the mature polypeptide of SEQ ID NO: 76. In another preferred aspect, the polypeptide consists of amino acids 18 to 364 of SEQ ID NO: 76 or an allelic variant thereof; or a fragment thereof that has xylanase activity. In another preferred aspect, the polypeptide consists of amino acids 18 to 364 of SEQ ID NO: 76.

In another aspect, the GH10 polypeptide having xylanase activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 75, (ii) the genomic DNA sequence comprising the mature polypeptide coding sequence of SEQ ID NO: 75, or (iii) a complementary strand of (i) or (ii). In a preferred aspect, the mature polypeptide coding sequence is nucleotides 52 to 1145 of SEQ ID NO: 75.

In another aspect, the GH10 polypeptide having xylanase activity is encoded by a polynucleotide comprising or consisting of a nucleotide sequence that has a degree of identity to the mature polypeptide coding sequence of SEQ ID NO: 75 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the GH10 polypeptide having xylanase activity is encoded by a polynucleotide comprising or consisting of the nucleotide sequence of SEQ ID NO: 75. In another preferred aspect, the nucleotide sequence comprises or consists of the mature polypeptide coding region of SEQ ID NO: 75. In another preferred aspect, the nucleotide sequence comprises or consists of nucleotides 52 to 1145 of SEQ ID NO: 75. The present invention also encompasses nucleotide sequences which encode a polypeptide comprising or consisting of the amino acid sequence of SEQ ID NO: 76 or the mature polypeptide thereof, which differ from SEQ ID NO: 75 or the mature polypeptide coding sequence thereof by virtue of the degeneracy of the genetic code. The present invention also relates to subsequences of SEQ ID NO: 75 which encode fragments of SEQ ID NO: 76 that have xylanase activity.

In another aspect, the GH10 polypeptide having xylanase activity comprises an amino acid sequence having a degree of identity to the mature polypeptide of SEQ ID NO: 78 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 78.

In another aspect, the GH10 polypeptide having xylanase activity comprises the amino acid sequence of SEQ ID NO: 78 or an allelic variant thereof; or a fragment thereof that has xylanase activity. In a preferred aspect, the polypeptide comprises the amino acid sequence of SEQ ID NO: 78. In another preferred aspect, the polypeptide comprises the mature polypeptide of SEQ ID NO: 78. In another preferred aspect, the polypeptide comprises amino acids 20 to 323 of SEQ ID NO: 78, or an allelic variant thereof; or a fragment thereof that has xylanase activity. In another preferred aspect, the polypeptide comprises amino acids 20 to 323 of SEQ ID NO: 78. In another preferred aspect, the polypeptide consists of the amino acid sequence of SEQ ID NO: 78 or an allelic variant thereof; or a fragment thereof that has xylanase activity. In another preferred aspect, the polypeptide consists of the amino acid sequence of SEQ ID NO: 78. In another preferred aspect, the polypeptide consists of the mature polypeptide of SEQ ID NO: 78. In another preferred aspect, the polypeptide consists of amino acids 20 to 323 of SEQ ID NO: 78 or an allelic variant thereof; or a fragment thereof that has xylanase activity. In another preferred aspect, the polypeptide consists of amino acids 20 to 323 of SEQ ID NO: 78.

In another aspect, the GH10 polypeptide having xylanase activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 77, (ii) the genomic DNA sequence comprising the mature polypeptide coding sequence of SEQ ID NO: 77, or (iii) a complementary strand of (i) or (ii). In a preferred aspect, the mature polypeptide coding sequence is nucleotides 58 to 1400 of SEQ ID NO: 77.

In another aspect, the GH10 polypeptide having xylanase activity is encoded by a polynucleotide comprising or consisting of a nucleotide sequence that has a degree of identity to the mature polypeptide coding sequence of SEQ ID NO: 77 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the GH10 polypeptide having xylanase activity is encoded by a polynucleotide comprising or consisting of the nucleotide sequence of SEQ ID NO: 77. In another preferred aspect, the nucleotide sequence comprises or consists of the mature polypeptide coding region of SEQ ID NO: 77. In another preferred aspect, the nucleotide sequence comprises or consists of nucleotides 58 to 1400 of SEQ ID NO: 77. The present invention also encompasses nucleotide sequences which encode a polypeptide comprising or consisting of the amino acid sequence of SEQ ID NO: 78 or the mature polypeptide thereof, which differ from SEQ ID NO: 77 or the mature polypeptide coding sequence thereof by virtue of the degeneracy of the genetic code. The present invention also relates to subsequences of SEQ ID NO: 77 which encode fragments of SEQ ID NO: 78 that have xylanase activity.

In another aspect, the GH10 polypeptide having xylanase activity comprises an amino acid sequence having a degree of identity to the mature polypeptide of SEQ ID NO: 80 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 80.

In another aspect, the GH10 polypeptide having xylanase activity comprises the amino acid sequence of SEQ ID NO: 80 or an allelic variant thereof; or a fragment thereof that has xylanase activity. In a preferred aspect, the polypeptide comprises the amino acid sequence of SEQ ID NO: 80. In another preferred aspect, the polypeptide comprises the mature polypeptide of SEQ ID NO: 80. In another preferred aspect, the polypeptide comprises amino acids 20 to 397 of SEQ ID NO: 80, or an allelic variant thereof; or a fragment thereof that has xylanase activity. In another preferred aspect, the polypeptide comprises amino acids 20 to 397 of SEQ ID NO: 80. In another preferred aspect, the polypeptide consists of the amino acid sequence of SEQ ID NO: 80 or an allelic variant thereof; or a fragment thereof that has xylanase activity. In another preferred aspect, the polypeptide consists of the amino acid sequence of SEQ ID NO: 80. In another preferred aspect, the polypeptide consists of the mature polypeptide of SEQ ID NO: 80. In another preferred aspect, the polypeptide consists of amino acids 20 to 397 of SEQ ID NO: 80 or an allelic variant thereof; or a fragment thereof that has xylanase activity. In another preferred aspect, the polypeptide consists of amino acids 20 to 397 of SEQ ID NO: 80.

In another aspect, the GH10 polypeptide having xylanase activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 79, (ii) the genomic DNA sequence comprising the mature polypeptide coding sequence of SEQ ID NO: 79, or (iii) a complementary strand of (i) or (ii). In a preferred aspect, the mature polypeptide coding sequence is nucleotides 107 to 1415 of SEQ ID NO: 79.

In another aspect, the GH10 polypeptide having xylanase activity is encoded by a polynucleotide comprising or consisting of a nucleotide sequence that has a degree of identity to the mature polypeptide coding sequence of SEQ ID NO: 79 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the GH10 polypeptide having xylanase activity is encoded by a polynucleotide comprising or consisting of the nucleotide sequence of SEQ ID NO: 79. In another preferred aspect, the nucleotide sequence comprises or consists of the mature polypeptide coding region of SEQ ID NO: 79. In another preferred aspect, the nucleotide sequence comprises or consists of nucleotides 107 to 1415 of SEQ ID NO: 79. The present invention also encompasses nucleotide sequences which encode a polypeptide comprising or consisting of the amino acid sequence of SEQ ID NO:

80 or the mature polypeptide thereof, which differ from SEQ ID NO: 79 or the mature polypeptide coding sequence thereof by virtue of the degeneracy of the genetic code. The present invention also relates to subsequences of SEQ ID NO: 79 which encode fragments of SEQ ID NO: 80 that have xylanase activity.

In another preferred aspect, the GH10 polypeptide having xylanase activity is obtained from *Penicillium* sp.

In another aspect, the GH10 polypeptide having xylanase activity comprises an amino acid sequence having a degree of identity to the mature polypeptide of SEQ ID NO: 99 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another preferred aspect, the homologous polypeptides comprise amino acid sequences which differ preferably by ten amino acids, more preferably by five amino acids, more preferably by four amino acids, even more preferably by three amino acids, most preferably by two amino acids, and even most preferably by one amino acid from the mature polypeptide of SEQ ID NO: 99.

In another aspect, the GH10 polypeptide having xylanase activity comprises the amino acid sequence of SEQ ID NO: 99 or an allelic variant thereof; or a fragment thereof that has xylanase activity. In a preferred aspect, the polypeptide comprises the amino acid sequence of SEQ ID NO: 99. In another preferred aspect, the polypeptide comprises the mature polypeptide of SEQ ID NO: 99. In another preferred aspect, the polypeptide comprises amino acids 24 to 403 of SEQ ID NO: 99, or an allelic variant thereof; or a fragment thereof that has xylanase activity. In another preferred aspect, the polypeptide comprises amino acids 24 to 403 of SEQ ID NO: 99. In another preferred aspect, the polypeptide consists of the amino acid sequence of SEQ ID NO: 99 or an allelic variant thereof; or a fragment thereof that has xylanase activity. In another preferred aspect, the polypeptide consists of the amino acid sequence of SEQ ID NO: 99. In another preferred aspect, the polypeptide consists of the mature polypeptide of SEQ ID NO: 99. In another preferred aspect, the polypeptide consists of amino acids 24 to 403 of SEQ ID NO: 99 or an allelic variant thereof; or a fragment thereof that has xylanase activity. In another preferred aspect, the polypeptide consists of amino acids 24 to 403 of SEQ ID NO: 99.

In another aspect, the GH10 polypeptide having xylanase activity is encoded by a polynucleotide that hybridizes under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 98, (ii) the cDNA sequence contained in the mature polypeptide coding sequence of SEQ ID NO: 98, or (iii) a complementary strand of (i) or (ii). In a preferred aspect, the mature polypeptide coding sequence is nucleotides 70 to 1385 of SEQ ID NO: 98.

In another aspect, the GH10 polypeptide having xylanase activity is encoded by a polynucleotide comprising or consisting of a nucleotide sequence that has a degree of identity to the mature polypeptide coding sequence of SEQ ID NO: 98 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

In another aspect, the GH10 polypeptide having xylanase activity is encoded by a polynucleotide comprising or consisting of the nucleotide sequence of SEQ ID NO: 98. In another preferred aspect, the nucleotide sequence comprises or consists of the mature polypeptide coding region of SEQ ID NO: 98. In another preferred aspect, the nucleotide sequence comprises or consists of nucleotides 70 to 1385 of SEQ ID NO: 98. The present invention also encompasses nucleotide sequences which encode the polypeptide comprising or consisting of the amino acid sequence of SEQ ID NO: 99 or the mature polypeptide thereof, which differ from SEQ ID NO: 98 or the mature polypeptide coding sequence thereof by virtue of the degeneracy of the genetic code. The present invention also relates to subsequences of SEQ ID NO: 98 which encode fragments of SEQ ID NO: 99 that have xylanase activity.

Nucleic Acid Constructs

An isolated polynucleotide encoding a cellulolytic protein, a polypeptide having cellulolytic enhancing activity, a polypeptide having xylanase activity, or a polypeptide having cellobiohydrolase II activity may be manipulated in a variety of ways to provide for expression of the polypeptide by constructing a nucleic acid construct comprising an isolated polynucleotide encoding the polypeptide operably linked to one or more (several) control sequences that direct the expression of the coding sequence in a suitable host cell under conditions compatible with the control sequences. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding such a polypeptide. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding region that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The various nucleic acids and control sequences described herein may be joined together to produce a recombinant expression vector comprising a polynucleotide encoding a cellulolytic protein, a polypeptide having cellulolytic enhancing activity, a polypeptide having xylanase activity, or a polypeptide having cellobiohydrolase II activity, a promoter, and transcriptional and translational stop signals. The expression vectors may include one or more (several) convenient restriction sites to allow for insertion or substitution of the polynucleotide sequence encoding the polypeptide at such sites. Alternatively, a polynucleotide encoding such a polypeptide may be expressed by inserting the polynucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hpt (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAM111 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide encoding such a polypeptide may be inserted into the host cell to increase production of the polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

Recombinant host cells comprising a polynucleotide encoding a cellulolytic protein, a polypeptide having cellulolytic enhancing activity, a polypeptide having xylanase activity, or a polypeptide having cellobiohydrolase II activity can be advantageously used in the recombinant production of the polypeptide. A vector comprising such a polynucleotide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

The bacterial host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (*Endomycetales*), basidiosporogenous yeast, and yeast belonging to the Fungi Imperfecti (*Blastomycetes*). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

Methods for producing a cellulolytic protein, a polypeptide having cellulolytic enhancing activity, a polypeptide having xylanase activity, or a polypeptide having cellobiohydrolase II activity, comprise (a) cultivating a cell, which in its wild-type form is capable of producing the polypeptide, under conditions conducive for production of the polypeptide; and (b) recovering the polypeptide.

Alternatively, methods for producing cellulolytic protein, a polypeptide having cellulolytic enhancing activity, a polypeptide having xylanase activity, a polypeptide having cellobiohydrolase II activity, or combinations thereof, comprise (a) cultivating a recombinant host cell under conditions conducive for production of the polypeptide; and (b) recovering the polypeptide.

In the production methods, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides are detected using the methods described herein.

The resulting broth may be used as is or the polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Methods for Processing Cellulosic Material

The compositions and methods of the present invention can be used to hydrolyze (saccharify) a cellulosic material, e.g., lignocellulose, to fermentable sugars and convert the fermentable sugars to many useful substances, e.g., chemicals and fuels. The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and fermentation (HHCF); and direct microbial conversion (DMC). SHF uses separate process steps to first enzymatically hydrolyze cellulosic material to fermentable sugars, e.g., glucose, cellobiose, cellotriose, and pentose sugars, and then ferment the fermentable sugars to ethanol. In SSF, the enzymatic hydrolysis of cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flavio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment. In practicing the methods of the present invention, any pretreatment process known in the art can be used to disrupt plant cell wall components of cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, Bioresource Technology 855: 1-33; Galbe and Zacchi, 2002, Appl. Microbiol. Biotechnol. 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, Appl. Biochem. Biotechnol. 129-132: 496-508; Varga et al., 2004, Appl. Biochem. Biotechnol. 113-116: 509-523; Sassner et al., 2006, Enzyme Microb. Technol. 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, Bioresource Technol. 91: 179-188; Lee et al., 1999, Adv. Biochem. Eng. Biotechnol. 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, Bioresource Technol. 96: 1959-1966; Mosier et al., 2005, Bioresource Technol. 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, Bioresource Technol. 64: 139-151; Palonen et al., 2004, Appl. Biochem. Biotechnol. 117: 1-17; Varga et al., 2004, Biotechnol. Bioeng. 88: 567-574; Martin et al., 2006, J. Chem. Technol. Biotechnol. 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, Appl. Biochem. Biotechnol. 98: 23-35; Chundawat et al., 2007, Biotechnol. Bioeng. 96: 219-231; Alizadeh et al., 2005, Appl. Biochem. Biotechnol. 121: 1133-1141; Teymouri et al., 2005, Bioresource Technol. 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, Biotechnol. Bioeng. 90: 473-481; Pan et al., 2006, Biotechnol. Bioeng. 94: 851-861; Kurabi et al., 2005, Appl. Biochem. Biotechnol. 121: 219-230). Sulphuric acid is usually added as a catalyst. In organosolv pretreatment, the majority of hemicellulose is removed.

Other examples of suitable pretreatment methods are described by Schell et al., 2003, Appl. Biochem. and Biotechnol. Vol. 105-108, p. 69-85, and Mosier et al., 2005, Bioresource Technology 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: Cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the pretreated cellulosic material is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically using an enzyme composition in the presence of a polypeptide having cellobiohydrolase II activity and a polypeptide having xylanase activity. The composition can further comprise one or more hemicellulolytic enzymes. The enzymes of the compositions can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The enzyme composition preferably comprises a polypeptide having cellobiohydrolase II activity, a polypeptide having xylanase activity, and one or more (several) cellulolytic proteins selected from the group consisting of an endoglucanase, a cellobiohydrolase, and a beta-glucosidase.

The optimum amounts of the enzymes and polypeptides having cellulolytic enhancing activity depend on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In one aspect, an effective amount of cellulolytic protein(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another aspect, an effective amount of polypeptide(s) having cellulolytic enhancing activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another aspect, an effective amount of polypeptide(s) having cellulolytic enhancing activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

In another aspect, an effective amount of polypeptide(s) having cellobiohydrolase II activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another aspect, an effective amount of polypeptide(s) having cellobiohydrolase II activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

In another aspect, an effective amount of polypeptide(s) having xylanase activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.025 to about 1.25 mg, more preferably at about 0.05 to about 1.25 mg, more preferably at about 0.05 to about 1.25 mg, even more preferably at about 0.05 to about 1.0 mg, and most preferably at about 0.05 to about 0.75 mg per g of cellulosic material.

In another aspect, an effective amount of polypeptide(s) having xylanase activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

Fermentation. The fermentable sugars obtained from the pretreated and hydrolyzed cellulosic material can be fermented by one or more fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. MicrobioL Biotechnol.* 69: 627-642.

Examples of fermenting microorganisms that can ferment C6 sugars include bacterial and fungal organisms, such as yeast. Preferred yeast includes strains of the *Saccharomyces* spp., preferably *Saccharomyces cerevisiae*.

Examples of fermenting organisms that can ferment C5 sugars include bacterial and fungal organisms, such as yeast. Preferred C5 fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic*Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces sp*.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Micro-* biol. Biotechnol. 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Materials

Chemicals used as buffers and substrates were commercial products of at least reagent grade.

Media

PDA plates were composed of 39 g of potato dextrose agar and deionized water to 1 liter.

Minimal medium plates were composed per liter of 6 g of $NaNO_3$, 0.52 g of KCl, 1.52 g of $KH_2PO_4$, 1 ml of COVE trace elements solution, 20 g of Noble agar, 20 ml of 50% glucose, 2.5 ml of $MgSO_4.7H_2O$, 20 ml of a 0.02% biotin solution, and deionized water to 1 liter.

COVE trace elements solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

MDU2BP medium was composed of 45 g of maltose, 1 g of $MgSO_4.7H_2O$, 1 g of NaCl, 2 g of $K_2SO_4$, 12 g of $KH_2PO_4$, 7 g of yeast extract, 2 g of urea, 0.5 ml of AMG trace metals solution; pH 5.0, and deionized water to 1 liter.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, 3 g of citric acid, and deionized water to 1 liter.

YEG medium was composed of 20 g of dextrose, 5 g of yeast extract, and deionized water to 1 liter.

LB medium was composed of 10 g of tryptone, 5 g of yeast extract, 5 g of sodium chloride, and deionized water to 1 liter.

YP medium was composed of 10 g of yeast extract, 20 g of Bacto peptone, and deionized water to 1 liter.

Example 1

*Myceliophthora thermophila* CBS 202.75 Genomic DNA Extraction

*Myceliophthora thermophila* CBS 202.75 was grown in 100 ml of YEG medium in a baffled shake flask at 45° C. for 2 days with shaking at 200 rpm. Mycelia were harvested by filtration using MIRACLOTH® (Calbiochem, La Jolla, Calif., USA), washed twice in deionized water, and frozen under liquid nitrogen. Frozen mycelia were ground by mortar and pestle to a fine powder, and total DNA was isolated using a DNEASY® Plant Maxi Kit (QIAGEN Inc., Valencia, Calif., USA).

Example 2

Isolation of a Full-Length Family 6 Cellobiohydrolase Gene (cel6a) from *Myceliophthora thermophila* CBS 202.75

A full-length Family 6 cellobiohydrolase gene (cel6a) was isolated from *Myceliophthora thermophila* CBS 202.75 using a GENOMEWALKER™ Universal Kit (Clontech Laboratories, Inc., Mountain View, Calif., USA) according to the manufacturer's instructions. Briefly, total genomic DNA from *Myceliophthora thermophila* CBS 202.75 was digested separately with four different restriction enzymes (Dra I, Eco RV, Pvu II, and Stu I) that leave blunt ends. Each batch of digested genomic DNA was then ligated separately to the GENOMEWALKER™ Adaptor (Clontech Laboratories, Inc., Mountain View, Calif., USA) to create four libraries. These libraries were then employed as templates in PCR reactions using two gene-specific primers shown below, one for primary PCR and one for secondary PCR. The primers were designed based on a partial Family 6 cellobiohydrolase gene (cel6a) sequence from *Myceliophthora thermophila* (WO 2004/056981).

```
Primer MtCel6a-R4:
                                    (SEQ ID NO: 91)
5'-ATTGGCAGCCCGGATCTGGGACAGAGTCTG-3'

Pimer MtCel6a-R5:
                                    (SEQ ID NO: 92)
5'-CCGGTCATGCTAGGAATGGCGAGATTGTGG-3'
```

The primary amplifications were composed of 1 µl (approximately 6 ng) of each library as template, 0.4 mM each of dATP, dTTP, dGTP, and dCTP, 10 pmol of Adaptor Primer 1 (Clontech Laboratories, Inc., Mountain View, Calif., USA), 10 pmol of primer MtCel6a-R4, 1× ADVANTAGE® GC-Melt LA Buffer (Clontech Laboratories, Inc., Mountain View, Calif., USA), and 1.25 units of ADVANTAGE® GC Genomic Polymerase Mix (Clontech Laboratories, Inc., Mountain View, Calif., USA) in a final volume of 25 µl. The amplifications were performed using an EPPENDORF® MASTERCYCLER® 5333 (Eppendorf Scientific, Inc., Westbury, N.Y., USA) programmed for pre-denaturing at 94° C. for 1 minute; 7 cycles each at a denaturing temperature of 94° C. for 30 seconds; annealing and elongation at 72° C. for 5 minutes; and 32 cycles each at 67° C. for 5 minutes.

The secondary ampliifications were composed of 1 µl of each primary PCR product as template, 0.4 mM each of dATP, dTTP, dGTP, and dCTP, 10 pmol of Adaptor Primer 2 (Clontech Laboratories, Inc., Mountain View, Calif., USA), 10 pmol of primer MtCel6a-R5, 1× ADVANTAGE® GC-Melt LA Buffer, and 1.25 units of ADVANTAGE® GC Genomic Polymerase Mix in a final volume of 25 µl. The amplifications were performed using an EPPENDORF® MASTERCYCLER® 5333 programmed for pre-denaturing at 94° C. for 1 minute; 5 cycles each at a denaturing temperature of 94° C. for 30 seconds; annealing and elongation at 72° C. for 5 minutes; and 20 cycles at 67° C. for 5 minutes.

The reaction products were isolated by 1.0% agarose gel electrophoresis using 40 mM Tris base-20 mM sodium acetate-1 mM disodium EDTA (TAE) buffer where a 3.5 kb product band from the Eco RV library was excised from the gel, purified using a QIAQUICK® Gel Extraction Kit (QIAGEN, Valencia, Calif., USA) according to the manufacturer's instructions, and sequenced.

Example 3

Characterization of the *Myceliophthora thermophila* CBS 202.75 Genomic Sequence Encoding a Family 6 Cellobiohydrolase II DNA sequencing of the 3.5 kb PCR fragment was performed with a Perkin-Elmer Applied Biosystems Model 377 XL Automated DNA Sequencer (Perkin-Elmer/Applied Biosystems, Inc., Foster City, Calif., USA) using dye-terminator chemistry (Giesecke et al., 1992, *Journal of Virology Methods* 38: 47-60) and primer walking strategy. The following gene specific primers were used for sequencing:

```
MtCel6a-F2:
                                    (SEQ ID NO: 93)
5'-GCTGTAAACTGCGAATGGGTTCAG-3'

MtCel6a-F3:
                                    (SEQ ID NO: 94)
5'-GGGTCCCACATGCTGCGCCT-3'

MtCel6a-R8:
                                    (SEQ ID NO: 95)
5'-AAAATTCACGAGACGCCGGG-3'
```

Nucleotide sequence data were scrutinized for quality and all sequences were compared to each other with assistance of PHRED/PHRAP software (University of Washington, Seattle, Wash., USA). The 3.5 kb sequence was compared and aligned with a partial Family 6 cellobiohydrolase gene (cel6a) sequence from *Myceliophthora thermophila* (WO 2004/056981).

A gene model for the *Myceliophthora thermophila* sequence was constructed based on similarity of the encoded protein to homologous glycoside hydrolase Family 6 proteins from *Thielavia terrestris, Chaetomium thermophilum, Humicola insolens* and *Trichoderma reesei*. The nucleotide sequence and deduced amino acid sequence are shown in SEQ ID NO: 29 and SEQ ID NO: 30, respectively. The genomic fragment encodes a polypeptide of 482 amino acids, interrupted by 3 introns of 96, 87, and 180 bp. The % G+C content of the gene and the mature coding sequence are 61.6% and 64%, respectively. Using the SignalP software program (Nielsen et al., 1997, *Protein Engineering* 10: 1-6), a signal peptide of 17 residues was predicted. The predicted mature protein contains 465 amino acids with a molecular mass of 49.3 kDa.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Myceliophthora thermophila* gene encoding the CEL6A mature polypeptide having cellobiohydrolase activity shared 78.6% and 77.6% identity (excluding gaps) to the deduced amino acid sequences of two glycoside hydrolase Family 6 proteins from *Chaetomium thermophilum* and *Humicola insolens*, respectively (GeneSeqP accession numbers ADP84824 and AAW44853, respectively).

Example 4

Cloning of the *Myceliophthora thermophila* CBS 202.75 Cellobiohydrolase Gene (cel6a) and Construction of an *Aspergillus oryzae* Expression Vector Two synthetic oligonucleotide primers shown below were designed to PCR amplify the *Myceliophthora thermophila* cellobiohydrolase gene from the genomic DNA prepared in Example 1. An IN-FUSION™ Cloning Kit (BD Biosciences, Palo Alto, Calif., USA) was used to clone the fragment directly into the expression vector pAlLo2 (WO 2004/099228), without the need for restriction digestion and ligation.

```
MtCel6a-F4:
                                        (SEQ ID NO: 96)
5'-ACTGGATTTACCATGGCCAAGAAGCTTTTCATCACC-3'

MtCel6a-R9:
                                        (SEQ ID NO: 97)
5'-TCACCTCTAGTTAATTAATTAGAAGGGCGGGTTGGCGT-3'
```

Bold letters represent coding sequence. The remaining sequence is homologous to insertion sites of pAlLo2.

Fifty picomoles of each of the primers above were used in a PCR reaction composed of 100 ng of *Myceliophthora thermophila* genomic DNA, 1× ADVANTAGE® GC-Melt LA Buffer, 0.4 mM each of dATP, dTTP, dGTP, and dCTP, and 1.25 units of ADVANTAGE® GC Genomic Polymerase Mix in a final volume of 25 µl. The amplification was performed using an EPPENDORF® MASTERCYCLER® 5333 programmed for 1 cycle at 94° C. for 1 minutes; and 30 cycles each at 94° C. for 30 seconds, 62° C. for 30 seconds, and 72° C. for 2 minutes. The heat block then went to a 4° C. soak cycle.

The reaction products were isolated by 1.0% agarose gel electrophoresis using TAE buffer where a 1842 bp product band was excised from the gel, and purified using a QIAQUICK® Gel Extraction Kit according to the manufacturer's instructions.

Plasmid pAlLo2 (WO 2004/099228) was digested with Nco I and Pac I, isolated by 1.0% agarose gel electrophoresis using TAE buffer, and purified using a QIAQUICK® Gel Extraction Kit according to the manufacturer's instructions.

The gene fragment and the digested vector were ligated together using an IN-FUSION™ Cloning Kit (BD Biosciences, Palo Alto, Calif., USA) resulting in pSMai180 in which transcription of the cellobiohydrolase gene was under the control of a hybrid of promoters from the genes for *Aspergillus niger* neutral alpha-amylase and *Aspergillus nidulans* triose phosphate isomerase (NA2-tpi promoter). The ligation reaction (50 µl) was composed of 1× IN-FUSION™ Buffer (BD Biosciences, Palo Alto, Calif., USA), 1× BSA (BD Biosciences, Palo Alto, Calif., USA), 1 µl of IN-FUSION™ enzyme (diluted 1:10) (BD Biosciences, Palo Alto, Calif., USA), 100 ng of pAlLo2 digested with Nco I and Pac I, and 50 ng of the *Myceliophthora thermophila* cel6a purified PCR product. The reaction was incubated at room temperature for 30 minutes. One µl of the reaction was used to transform *E. coli* XL10 SOLOPACK® Gold Supercompetent cells (Stratagene, La Jolla, Calif., USA). An *E. coli* transformant containing pSMai180 was detected by restriction digestion and plasmid DNA was prepared using a BIOROBOT® 9600 (QIAGEN Inc., Valencia, Calif., USA). The *Myceliophthora thermophila* cel6a insert in pSMai180 was confirmed by DNA sequencing.

The same 1842 bp PCR fragment was cloned into pCR®2. 1-TOPO® vector (Invitrogen, Carlsbad, Calif., USA) using a TOPO® TA CLONING® Kit (Invitrogen, Carlsbad, Calif., USA) to generate pSMai182. The *Myceliophthora thermophila* cel6a insert in pSMai182 was confirmed by DNA sequencing. *E. coli* pSMai182 was deposited with the Agricultural Research Service Patent Culture Collection, Northern Regional Research Center, Peoria, Ill., USA, on Sep. 6, 2007 and assigned accession number NRRL B-50059.

Example 5

Expression of the *Myceliophthora thermophila* CBS 202.75 Family 6 Cellobiohydrolase cel6a Gene in *Aspergillus oryzae* JaL355

*Aspergillus oryzae* JaL355 (WO 2002/40694) protoplasts were prepared according to the method of Christensen et al., 1988, *Bio/Technology* 6: 1419-1422. Three µg of pSMai180 were used to transform *Aspergillus oryzae* JaL355.

The transformation of *Aspergillus oryzae* JaL355 with pSMai180 yielded about 50 transformants. Twenty transformants were isolated to individual Minimal medium plates.

Confluent Minimal Medium plates of the 20 transformants were washed with 5 ml of 0.01% TWEEN® 20 and inoculated separately into 25 ml of MDU2BP medium in 125 ml glass shake flasks and incubated at 34° C. with shaking at 250 rpm. After 5 days incubation, 5 µl of supernatant from each culture were analyzed by SDS-PAGE using a 8-16% CRITERION™ SDS-PAGE gel (Bio-Rad Laboratories, Inc. Hercules, Calif., USA) and a CRITERION® Cell (Bio Rad Laboratories, Inc., Hercules, Calif., USA), according to the manufacturer's instructions. The resulting gel was stained with BIO-SAFE™ Coomassie Stain (Bio-Rad Laboratories, Inc., Hercules, Calif., USA). SDS-PAGE profiles of the cultures showed that the majority of the transformants had a major band of approximately 70 kDa.

A confluent plate of one transformant, designated transformant 14, was washed with 10 ml of 0.01% TWEEN® 20 and inoculated into two 2 liter Fernbach flasks each containing 500 ml of MDU2BP medium to generate broth for characterization of the enzyme. The culture broths were harvested on day 5 and filtered using a 0.22 µm EXPRESS™ Plus Membrane (Millipore, Bedford, Mass., USA).

Example 6

Purification of Recombinant *Myceliophthora thermophila* CBS 202.75 Family 6 Cellobiohydrolase II Expressed in *Aspergillus oryzae*

The filtered culture broth described in Example 5 was concentrated 20-fold to 50 ml using an ultrafiltration device (Millipore, Bedford, Mass., USA) equipped with a 10 kDa polyethersulfone membrane at 70 psi, 4° C. The concentrated broth was desalted into 20 mM Tris-HCl pH 8 buffer using a HIPREP™ 26/10 desalting column (GE Healthcare, Piscataway, N.J., USA). The desalted broth was mixed with an appropriate volume of 20 mM Tris-HCl pH 7.5 containing 3.4 M ammonium sulfate for a final concentration of 1.2 M ammonium sulfate. The sample was loaded onto a PHENYL SUPEROSE☐ column (HR 16/10, GE Healthcare, Piscataway, N.J., USA) equilibrated with 360 mM ammonium sulfate in 20 mM Tris-HCl pH 7.5. Contaminants were eluted with a step gradient of 120 mM ammonium sulfate followed by elution of *Myceliophthora thermophila* Cel6A cellobiohydrolase with 20 mM Tris-HCl pH 7.5. Fractions were analyzed using 8-16% CRITERION™ SDS-PAGE gels and stained with GELCODE® Blue Stain Reagent (Thermo Fisher Scientific, Waltham, Mass., USA). *Myceliophthora thermophila* Cel6A cellobiohydrolase was >90% pure as judged by SDS-PAGE. Protein concentration was determined using a BCA Protein Assay Kit (Thermo Fisher Scientific, Waltham, Mass., USA) in which bovine serum albumin was used as a protein standard.

Example 7

Growth of Wild-Type *Myceliophthora thermophila* Srain CBS 117.65

One hundred ml of shake flask medium in a 500 ml shake flask was inoculated with two plugs from a solid plate culture of *Myceliophthora thermophila* strain CBS 117.65 and incubated at 45° C. on an orbital shaker at 200 rpm for 48 hours. The shake flask medium was composed of 15 g of glucose, 4 g of $K_2HPO_4$, 1 g of NaCl, 0.2 g of $MgSO_4.7H_2O$, 2 g of MES free acid, 1 g of Bacto Peptone, 5 g of yeast extract, 2.5 g of citric acid, 0.2 g of $CaCl_2.2H_2O$, 5 g of $NH_4NO_3$, 1 ml of trace elements solution, and deionized water to 1 liter. The trace elements solution was composed of 1.2 g of $FeSO_4.7H_2O$, 10 g of $ZnSO_4.7H_2O$, 0.7 g of $MnSO_4.H_2O$, 0.4 g of $CuSO_4.5H_2O$, 0.4 g of $Na_2B_4O_7.10H_2O$, 0.8 g of $Na_2MoO_2.2H_2O$, and deionized water to 1 liter. Fifty ml of the shake flask broth was used to inoculate a 2 liter fermentation vessel.

A total of 1.8 liters of the fermentation batch medium was added to a two liter glass jacketed fermentor (Applikon Biotechnology, Schiedam, Netherlands). The fermentation batch medium was composed per liter of 5 g of yeast extract, 176 g of powdered cellulose, 2 g of glucose, 1 g of NaCl, 1 g of Bacto Peptone, 4 g of $K_2HPO_4$, 0.2 g of $CaCl_2.2H_2O$, 0.2 g of $MgSO_4.7H_2O$, 2.5 g of citric acid, 5 g of $NH_4NO_3$, 1.8 ml of anti-foam, 1 ml of trace elements solution (above), and deionized water to 1 liter. Fermentation feed medium was composed of water and antifoam. The fermentation feed medium was dosed at a rate of 4 g/l/hr for a period of 72 hours. The fermentation vessel was maintained at a temperature of 45° C. and pH was controlled using an Applikon 1030 control system (Applikon Biotechnology, Schiedam, Netherlands) to a set-point of 5.6+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000× g to remove the biomass.

Example 8

Purification of Native Cel6A Cellobiohydrolase II from Wild-Type *Myceliophthora thermophila* CBS 117.65 Whole Broth The harvested broth obtained in Example 7 was centrifuged in 500 ml bottles at 13,000×g for 20 minutes at 4° C. and then sterile filtered using a 0.22 µm polyethersulfone membrane (Millipore, Bedford, Mass., USA). The filtered broth was concentrated and buffer exchanged with 20 mM Tris-HCl pH 8.5 using a tangential flow concentrator (Pall Filtron, North Borough, Mass., USA) equipped with a 10 kDa polyethersulfone membrane at approximately 20 psi. To decrease the amount of pigment, the concentrate was applied to a 60 ml Q SEPHAROSE™ Big Bead column (GE Healthcare, Piscataway, N.J., USA) equilibrated with 20 mM Tris-HCl pH 8.5, and step eluted with equilibration buffer containing 600 mM NaCl. Flow-through and eluate fractions were analyzed using 8-16% CRITERION™ SDS-PAGE gels stained with GELCODE® Blue Stain Reagent. The flow-through fraction contained *Myceliophthora thermophila* Cel6A cellobiohydrolase as judged by the presence of a band corresponding to the apparent molecular weight of the protein by SDS-PAGE (Cel6A cellobiohydrolase: approximately 70 kDa).

The flow-through fraction was concentrated using an Amicon ultrafiltration device (Millipore, Bedford, Mass., USA) equipped with a 10 kDa polyethersulfone membrane at 40 psi, 4° C. and mixed with an equal volume of 20 mM Tris-HCl pH 7.5 containing 3.4 M ammonium sulfate for a final concentration of 1.7 M ammonium sulfate. The sample was filtered (0.2 µM syringe filter, polyethersulfone membrane, Whatman, Maidstone, United Kingdom) to remove particulate matter prior to loading onto a PHENYL SUPEROSE™ column (HR 16/10, GE Healthcare, Piscataway, N.J., USA) equilibrated with 1.7 M ammonium sulfate in 20 mM Tris-HCl pH 7.5. Bound proteins were eluted with a 12 column volume decreasing salt gradient of 1.7 M ammonium sulfate to 0 M ammonium sulfate in 20 mM Tris-HCl pH 7.5. Fractions were analyzed by 8-16% SDS-PAGE gel electrophoresis as described above, which revealed that the Cel6A cellobiohydrolase eluted at the very end of the gradient (approximately 20 mM ammonium sulfate).

Fractions containing Cel6A cellobiohydrolase II were pooled and diluted 10-fold in 20 mM Tris-HCl pH 9.0 (to lower the salt and raise the pH) and then applied to a 1 ml RESOURCE™ Q column (GE Healthcare, Piscataway, N.J., USA) equilibrated with 20 mM Tris-HCl pH 9.0. Bound proteins were eluted with a 20 column volume salt gradient from 0 mM to 550 mM NaCl in 20 mM Tris-HCl pH 9.0. *M. thermophila* Cel6A cellobiohydrolase II eluted as a single peak early in the gradient (~25 mM NaCl). The cellobiohydrolase II was >90% pure as judged by SDS-PAGE. Protein concentrations were determined using a BCA Protein Assay Kit in which bovine serum albumin was used as a protein standard.

Example 9

Preparation of *Aspergillus aculeatus* Family 10 Xylanase

*Aspergillus aculeatus* Family 10 xylanase (SHEARZYME® 2X; Novozymes A/S, Bagsvaerd, Denmark) was desalted into 20 mM Tris-HCl pH 8.0-150 mM NaCl prior to use. Three ml of SHEARZYME® 2× was loaded onto an ECONO-PAC® 10 DG desalting column (Bio-Rad Laboratories, Inc. Hercules, Calif., USA) equilibrated with 20 mM Tris-HCl pH 8.0-150 mM NaCl. Protein was eluted by the addition of 4 ml of equilibration buffer. Protein concentrations were determined using a BCA Protein Assay Kit in which bovine serum albumin was used as a protein standard.

Example 10

Effect of *Myceliophthora thermophila* CBS 117.65 Family 6 Cellobiohydrolase II, *Myceliophthora thermophila* CBS 202.75 Family 6 Cellobiohydrolase II, or *Aspergillus aculeatus* Family 10 Xylanase on PCS Hydrolysis by a *Trichoderma reesei* Cellulolytic Protein Composition Corn stover was pretreated at the U.S. Department of Energy National Renewable Energy Laboratory (NREL) using dilute sulfuric acid. The following conditions were used for the pretreatment: 1.4 wt. % sulfuric acid at 165° C. and 107 psi for 8 minutes. According to NREL, the water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003. The PCS was washed with a large volume of DDI water on a glass filter.

*Myceliophthora thermophila* CBS 202.75 CEL6 cellobiohydrolase II (recombinant), *Myceliophthora thermophila* CBS 117.65 CEL6 cellobiohydrolase II (native), or *Aspergillus aculeatus* xylanase were evaluated for their ability to enhance the hydrolysis of washed PCS by a *Trichoderma reesei* cellulolytic protein composition (*Trichoderma reesei* broth expressing *Thermoascus aurantiacus* GH61A polypeptide having cellulolytic enhancing activity and *Aspergillus oryzae* beta-glucosidase fusion protein) obtained according to WO 2008/151079.

The hydrolysis of PCS was conducted using 2.2 ml deep-well plates (Axygen, Union City, Calif., USA) in a total reaction volume of 1.0 ml. The hydrolysis was performed with 50 mg of PCS per ml of 50 mM sodium acetate pH 5.0 buffer containing 1 mM manganese sulfate and a fixed protein loading of 2 mg of the *Trichoderma reesei* cellulolytic protein composition per gram of cellulose or a 20% replacement (by protein) of the *T. reesei* cellulolytic protein composition with each enzyme (3.2 mg of the *Trichoderma reesei* cellulolytic protein composition per g of cellulose and 0.8 mg of each enzyme per g of cellulose). Hydrolysis assays were performed in triplicate for 72 hours at 50° C. Following hydrolysis, samples were filtered using a 0.45 μm Multiscreen 96-well filter plate (Millipore, Bedford, Mass., USA) and filtrates analyzed for sugar content as described below.

When not used immediately, filtered sugary aliquots were frozen at −20° C. Sugar concentrations of samples diluted in 0.005 M $H_2SO_4$ were measured after elution by 0.005 M $H_2SO_4$ with 0.05% w/w benzoic acid at a flow rate of 0.6 ml per minute from a 4.6×250 mm AMINEX® HPX-87H column (Bio-Rad Laboratories, Inc. Hercules, Calif., USA) at 65° C. with quantitation by integration of the glucose and cellobiose signals by refractive index detection (CHEMSTATION®, AGILENT® 1100 HPLC, Agilent Technologies, Santa Clara, Calif., USA) calibrated by pure sugar samples. The resultant equivalents were used to calculate the percentage of cellulose conversion for each reaction.

The degree of cellulose conversion was calculated using the following equation: % conversion=[glucose concentration+1.053×(cellobiose concentration)]/[(glucose concentration+1.053×(cellobiose concentration) in a limit digest]. The 1.053 factor for cellobiose takes into account the increase in mass when cellobiose is converted to glucose. Sixty mg of the *T. reesei* cellulolytic protein preparation per g of cellulose was used for the limit digest.

The results shown in FIG. 1 demonstrated that a 20% replacement (by protein) of the *T. reesei* cellulolytic protein composition (loaded at 2 mg per g of cellulose) with the *M. thermophila* CBS 202.75 recombinant Cel6A cellobiohydrolase II or the native *M. thermophila* CBS 117.65 Cel6A cellobiohydrolase II improved the 72 hour hydrolysis yield by 3.1% and 6.2%, respectively. Alternatively, the percent conversion with a 20% replacement of a *T. reesei* cellulolytic protein composition (loaded at 2 mg per g of cellulose) with the *M. thermophila* CBS 202.75 recombinant Cel6A cellobiohydrolase II was equivalent to a loading of 2.15 mg of the *T. reesei* cellulolytic protein composition per g of cellulose (a 1.08-fold improvement). With the *M. thermophila* native CBS 117.65 Cel6A cellobiohydrolase II the percent conversion with a 20% replacement was equivalent to a loading of 2.25 mg of the *T. reesei* cellulolytic protein composition per g of cellulose (a 1.13-fold improvement). A 20% replacement of the *T. reesei* cellulolytic protein composition (loaded at 2 mg per g of cellulose) with the *A. aculeatus* xylanase improved the hydrolysis yield by 8.2%. The percent conversion with a 20% replacement of a *T. reesei* cellulolytic protein composition (loaded at 2 mg per g of cellulose) with the *A. aculeatus* xylanase was equivalent to a loading of 2.33 mg of the *T. reesei* cellulolytic protein composition per g of cellulose (a 1.17-fold improvement).

Example 11

Effect of *Myceliophthora thermophila* Cel6A Cellobiohydrolase IIs and *Aspergillus aculeatus* Xylanase on the Hydrolysis of PCS Example 10 demonstrated that *Myceliophthora thermophila* CBS 202.75 CEL6 cellobiohydrolase II (recombinant), *Myceliophthora thermophila* CBS 117.65 CEL6 cellobiohydrolase II (native), or *Aspergillus aculeatus* xylanase enhanced the hydrolysis of washed PCS by the *Trichoderma reesei* cellulolytic protein composition (WO 2008/151079).

A PCS hydrolysis assay was performed as described in Example 10 with a 20% replacement of the *T. reesei* cellulolytic protein composition (2 mg per g of cellulose total loading) with a 50:50 mixture of the *M. thermophila* CBS 202.75 CEL6 cellobiohydrolase II (recombinant) or the *M. thermophila* CBS 117.65 CEL6 cellobiohydrolase II (native) and the *A. aculeatus* xylanase (1.6 mg of the *T. reesei* cellulolytic protein composition per g cellulose; 0.2 mg of the *M. thermophila* CBS 202.75 cellobiohydrolase II or the *M. thermophila* CBS 117.65 cellobiohydrolase II per g cellulose; and 0.2 mg of the *A. aculeatus* xylanase per g cellulose).

Figure 2:
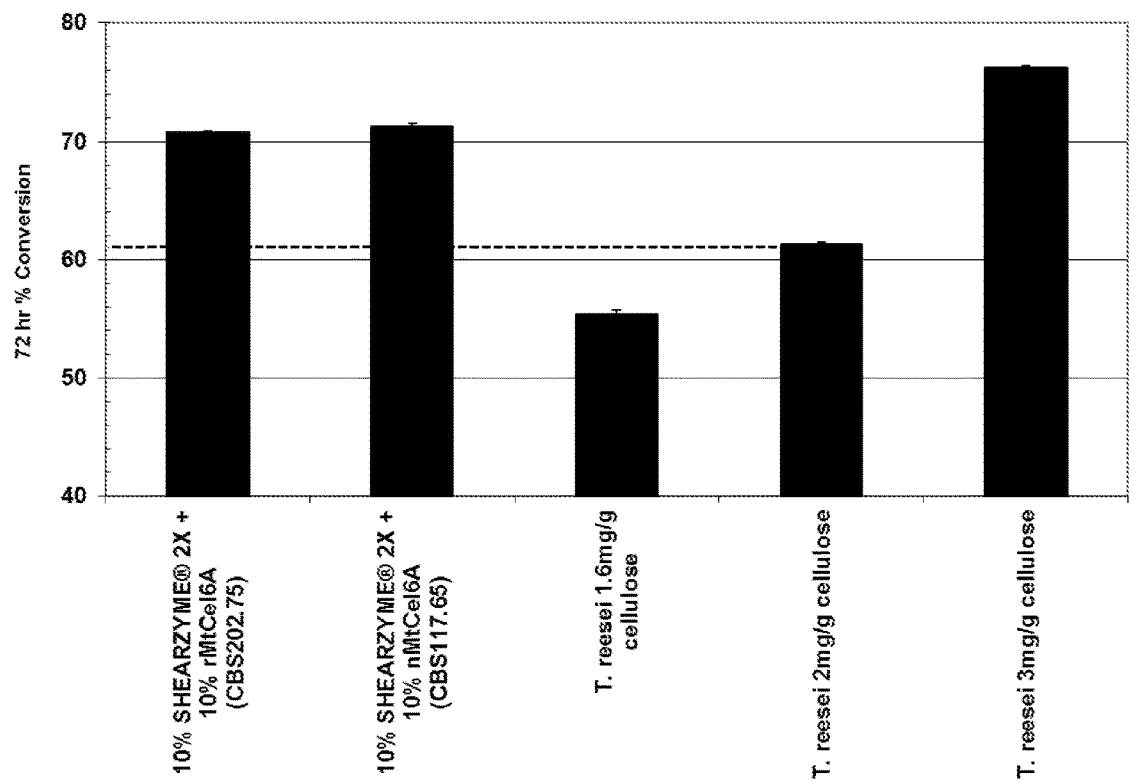
FIG. 2 shows the synergistic enhancement of a 72 hour hydrolysis of PCS (5% w/v) at 50° C. by a fermentation broth of *Trichoderma reesei* expressing *Thermoascus aurantiacus* GH61A polypeptide having cellulolytic enhancing activity and *Aspergillus oryzae* beta-glucosidase fusion protein in the presence of combinations of *Myceliophthora thermophila* CBS 202.75 CEL6 cellobiohydrolase II (recombinant) or *Myceliophthora thermophila* CBS 117.65 CEL6 cellobiohydrolase II (native) and *Aspergillus aculeatus* Family 10 xylanase. The mixtures were added as 20% replacements (by protein) of the *Trichoderma reesei* cellulolytic protein composition with a 50:50 mixture of the *Myceliophthora thermophila* Cel6A cellobiohydrolase II and the *Aspergillus aculeatus* Family 10 xylanase. The dotted line shows the percent conversion by 2 mg of the *Trichoderma reesei* cellulolytic protein composition per g of cellulose. Enhancement of hydrolysis was demonstrated with mixtures that reach percent conversion above the dotted line at an equivalent protein loading. Error bars from triplicate measurements are shown.

As shown in FIG. 2 a mixture of *Myceliophthora thermophila* CBS 202.75 CEL6 cellobiohydrolase II (recombinant) or *Myceliophthora thermophila* CBS 117.65 CEL6 cellobiohydrolase II (native) and *Aspergillus aculeatus* xylanase demonstrated a 15.3% and 16.1% improvement of the 72 hour hydrolysis yield, respectively. These results corresponded to a percent conversion equivalent of 2.63 mg/g cellulose and 2.65 mg/g cellulose, respectively, of the *Trichoderma reesei* cellulolytic protein composition (a 1.32 and 1.33 fold improvement).

A significant enhancement in percent conversion of PCS by a cellulase mixture comprising a 10% replacement with the *M. thermophila* CBS 202.75 CEL6 cellobiohydrolase II (recombinant) or *M. thermophila* CBS 117.65 CEL6 cellobiohydrolase II (native) plus a 10% replacement with the *A. aculeatus* xylanase (*M. thermophila* CBS 202.75 recombinant CEL6 cellobiohydrolase II+*A. aculeatus* xylanase: 15.3%; *M. thermophila* CBS 117.65 native CEL6 cellobiohydrolase II+*A. aculeatus* xylanase: 16.1%) relative to a 20% replacement with each protein individually (*M. thermophila* CBS 202.75 CEL6 cellobiohydrolase II (recombinant): 3.1%; *M. thermophila* CBS 117.65 CEL6 cellobiohydrolase II (native): 6.2%; or *A. aculeatus* xylanase: 8.2%) demonstrated that the *M. thermophila* Cel6A (both recombinant from *M. thermophila* CBS 202.75 strain and native from *M. thermophila* CBS 11.65 strain) and the *A. aculeatus* xylanase displayed synergism in the enhancement of the *T. reesei* cellulolytic protein composition.

Example 12

Isolation of *Penicillium* sp.

*Penicillium* sp. NN51602 was isolated from a compost sample of rice straw and cattle dung located in a rural village in Yunnan China on July 2007. The strain was isolated on PDA plates incubated at 45° C.

Example 13

Growth of Wild-Type *Penicillium* sp.

One hundred ml of shake flask medium in a 500 ml shake flask was inoculated with two plugs from a solid plate culture of *Penicillium* sp. NN51602 and incubated at 45° C. on an orbital shaker at 200 rpm for 48 hours. The shake flask medium was composed of 15 g of glucose, 4 g of $K_2HPO_4$, 1 g of NaCl, 0.2 g of $MgSO_4.7H_2O$, 2 g of MES free acid, 1 g of Bacto Peptone, 5 g of yeast extract, 2.5 g of citric acid, 0.2 g of $CaCl_2.2H_2O$, 5 g of $NH_4NO_3$ 1 ml of trace elements solution, and deionized water to 1 liter. The trace elements solution was composed of 1.2 g of $FeSO_4.7H_2O$, 10 g of $ZnSO_4.7H_2O$, 0.7 g of $MnSO_4.H_2O$, 0.4 g of $CuSO_4.5H_2O$, 0.4 g of $Na_2B_4O_7.10H_2O$, 0.8 g of $Na_2MoO_2.2H_2O$, and deionized water to 1 liter. Fifty ml of the 48 hour shake flask broth was used to inoculate a 2 liter fermentation vessel.

A total of 1.8 liters of fermentation batch medium was added to a two liter glass jacketed fermentor (Applikon Biotechnology, Schiedam, Netherlands). The fermentation batch medium was composed per liter of 5 g of yeast extract, 176 g powdered cellulose, 2 g of glucose, 1 g of NaCl, 1 g of Bacto Peptone, 4 g of $K_2HPO_4$, 0.2 g of $CaCl_2.2H_2O$, 0.2 g of $MgSO_4.7H_2O$, 2.5 g of citric acid, 5 g of $NH_4NO_3$, 1.8 ml of anti-foam, and 1 ml of trace elements solution. Fermentation feed medium was dosed at a rate of 4 g/l/hr for a period of 72 hours. The fermentation feed medium was composed of water and antifoam. The fermentation vessel was maintained at a temperature of 45° C. and pH was controlled using an Applikon 1030 control system (Applikon Biotechnology, Schiedam, Netherlands) to a set-point of 5.6+/−0.1. Air was added to the vessel at a rate of 1 vvm and the broth was agitated by a Rushton impeller rotating at 1100 to 1300 rpm. At the end of the fermentation, whole broth was harvested from the vessel and centrifuged at 3000×g to remove the biomass.

Example 14

Purification of a Xylanase from Wild-Type *Penicillium* sp. Whole Broth

The harvested broth obtained in Example 13 was centrifuged in 500 ml bottles at 13,000×g for 20 minutes at 4° C. and then sterile filtered using a 0.22 μm polyethersulfone membrane (Millipore, Bedford, Mass., USA). The filtered broth was concentrated and buffer exchanged with 20 mM Tris-HCl pH 8.5 using a tangential flow concentrator (Pall Filtron, North Borough, Mass., USA) equipped with a 10 kDa polyethersulfone membrane at approximately 20 psi. To decrease the amount of pigment, the concentrate was applied to a 60 ml Q SEPHAROSE™ Big Bead column equilibrated with 20 mM Tris-HCl pH 8.5, and step eluted with equilibration buffer containing 600 mM NaCl. Flow-through and eluate fractions were examined on 8-16% CRITERION™ SDS-PAGE gels stained with GELCODE® Blue Stain Reagent. The eluate fraction contained a protein band of approximately 50 kDa by SDS-PAGE.

The eluate fraction was concentrated using an ultrafiltration device (Millipore, Bedford, Mass., USA) equipped with a 10 kDa polyethersulfone membrane at 40 psi, 4° C. and desalted into 20 mM Tris-HCl pH 8.5 using a HIPREP™ 26/10 desalting column. The desalted material was loaded onto a MONO Q™ HR 16/10 column (GE Healthcare, Piscataway, N.J., USA) equilibrated with 20 mM Tris-HCl pH 8.5. Bound proteins were eluted with a salt gradient of 0 M NaCl to 600 mM NaCl in 20 mM Tris-HCl pH 8.5 (20 column volumes). Fractions were examined by SDS-PAGE as described above, which revealed that the *Penicillium* sp. xylanase eluted at approximately 120 mM NaCl.

Fractions containing the xylanase were pooled and mixed with an equal volume of 20 mM Tris-HCl pH 7.5 containing 3.4 M ammonium sulfate for a final concentration of 1.7 M ammonium sulfate. The sample was filtered (0.2 μM syringe filter, polyethersulfone membrane, Whatman, Maidstone, United Kingdom) to remove particulate matter prior to loading onto a PHENYL SUPEROSE™ column (HR 16/10, GE Healthcare, Piscataway, N.J., USA) equilibrated with 1.7 M ammonium sulfate in 20 mM Tris-HCl pH 7.5. Bound proteins were eluted with a decreasing salt gradient of 1.7 M ammonium sulfate to 0 M ammonium sulfate in 20 mM Tris-HCl pH 7.5 (15 column volumes). Fractions were analyzed by SDS-PAGE as described above, which revealed the *Penicillium* sp xylanase eluted at the very end of the gradient (approximately 50 mM ammonium sulfate). The *Penicillium* sp. xylanase was >90% pure as judged by SDS-PAGE. Protein concentrations were determined using a BCA Protein Assay Kit in which bovine serum albumin was used as a protein standard.

Example 15

Protein Identification of *Penicillium* sp. GH10B Xylanase

In-gel digestion of polypeptides for peptide sequencing. A MULTIPROBE® II Liquid Handling Robot (PerkinElmer Life and Analytical Sciences, Boston, Mass., USA) was used to perform in-gel digestions. The 50 kDa protein gel band (Example 14) was reduced with 50 μl of 10 mM dithiothreitol (DTT) in 100 mM ammonium bicarbonate pH 8.0 for 30 minutes. Following reduction, the gel piece was alkylated with 50 μl of 55 mM iodoacetamide in 100 mM ammonium bicarbonate pH 8.0 for 20 minutes. The dried gel piece was allowed to swell in 25 μl of a trypsin digestion solution containing 6 ng of sequencing grade trypsin (Promega, Madison, Wis., USA) per μl of 50 mM ammonium bicarbonate pH 8 for 30 minutes at room temperature, followed by an 8 hour digestion at 40° C. Each of the reaction steps described above was followed by numerous washes and pre-washes with the appropriate solutions following the manufacturer's standard protocol. Fifty μl of acetonitrile was used to de-hydrate the gel piece between reactions and the gel piece was air dried between steps. Peptides were extracted twice with 1% formic acid/2% acetonitrile in HPLC grade water for 30 minutes. Peptide extraction solutions were transferred to a 96 well skirted PCR type plate (ABGene, Rochester, N.Y., USA) that had been cooled to 10-15° C. and covered with a 96-well plate lid (PerkinElmer Life and Analytical Sciences, Boston, Mass., USA) to prevent evaporation. Plates were further stored at 4° C. until mass spectrometry analysis could be performed.

Protein Identification. For de novo peptide sequencing by tandem mass spectrometry, a Q-TOF MICRO™ (Waters Micromass MS Technologies, Milford, Mass., USA), a hybrid orthogonal quadrupole time-of-flight mass spectrometer, was used for LC/MS/MS analysis. The Q-TOF MICRO™ is fully microprocessor controlled using MASSLYNX™ software version 4.1 (Waters Micromass MS Technologies, Milford, Mass., USA). The Q-TOF MICRO™ was fitted with a NANOACQUITY UPLC® (Waters Corp, Milford, Mass., USA) for concentrating and desalting samples. Samples were loaded onto a trapping column (180 µm ID×20 mm, 5 µm SYMMETRY® C18, Waters Corp, Milford, Mass., USA) fitted in the injection loop and washed with 0.1% formic acid in water at 15 µl per minute for 1 minute using a binary solvent manager pump. Peptides were separated on a 100 µm ID×100 mm, C18, 1.7 µm, BEH130™ C18 nanoflow fused capillary column (Waters Corp, Milford, Mass., USA) at a flow rate of 400 nl per minute. A step elution gradient of 1% to 85% acetonitrile in 0.1% formic acid was applied over a 30 minute interval. The column eluent was monitored at 214 nm and introduced into the Q-TOF MICRO™ through an electrospray ion source fitted with a nanospray interface.

Data was acquired in survey scan mode from a mass range of m/z 400 to 1990 with switching criteria for MS to MS/MS to include an ion intensity of greater than 10.0 counts per second and charge states of +2, +3, and +4. Analysis spectra of up to 6 co-eluting species with a scan time of 1.9 seconds and inter-scan time of 0.1 seconds could be obtained. A cone voltage of 45 volts was typically used and the collision energy was programmed to vary according to the mass and charge state of the eluting peptide and in the range of 10-60 volts. The acquired spectra were combined, smoothed, and centered in an automated fashion and a peak list generated. The peak list was searched against selected databases using PROTEINLYNX GLOBAL SERVER™ 2.3 software (Waters Micromass MS Technologies, Milford, Mass., USA) and PEAKS Studio version 4.5 (SP1) (Bioinformatic Solutions Inc., Waterloo, Ontario, Canada). Results from the PROTEINLYNX GLOBAL SERVER™ and PEAKS Studio searches were evaluated and un-identified proteins were analyzed further by evaluating the MS/MS spectrums of each ion of interest and de novo sequence was determined by identifying the y and b ion series and matching mass differences to the appropriate amino acid.

Peptide sequences were obtained from several multiply charged ions for the in-gel digested 50 kDa polypeptide gel band. A doubly charged tryptic peptide ion of 403.231 m/z sequence was determined to be Ala-Asn-Gly-Gln-Met(ox)-[Ile/Leu]-Arg (amino acids 97 to 103 of SEQ ID NO: 99). Another doubly charged tryptic peptide ion of 442.592 m/z sequence was determined to be Asn-His-[Ile/Leu]-Thr-Asn-Val-Val-Thr-His-Tyr-Lys (amino acids 133 to 142 of SEQ ID NO: 99). Another doubly charged tryptic peptide ion of 447.1993 m/z sequence was determined to be [Ile/Leu]-Val-Gln-Ser-Tyr-Gly-Ala-Arg (amino acids 215 to 222 of SEQ ID NO: 99). Another doubly charged tryptic peptide ion of 458.262 m/z sequence was determined to be Ala-Thr-Ala-Ala-Gln-Asn-[Ile/Leu]-Val-Lys (amino acids 206 to 214 of SEQ ID NO: 99). Another doubly charged tryptic peptide ion of 663.380 m/z a partial sequence was determined to be Ser-Gly-Gly-Asp-[Ile/Leu]-Ala-Asn-[Ile/Leu]-Ala-Lys (amino acids 86 to 96 of SEQ ID NO: 99). Met(ox) is oxidized methionine. [Ile/Leu] and [Gln/Lys] cannot be distinguished because they have equivalent masses.

Example 16

Penicillium sp. Genomic DNA Extraction

Penicillium sp. was grown on PDA plates at 37° C. to confluence. Three 4 mm² squares were cut from the PDA plates, inoculated into 25 ml of YP medium containing 2% glucose in a baffled 125 ml shake flask, and incubated at 37° C. for 2 days with shaking at 200 rpm. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit.

Example 17

Isolation of a Partial Fragment of a Xylanase Gene from Penicillium sp.

Using the Consensus-Degenerate Hybrid Oligonucleotide Primer Program (CODEHOP; Rose et al., 1998, Nucleic Acids Research 26: 1628-1635), degenerate primers, shown below, were designed to regions of homology with related xylanase sequences based on the identified peptide fragments described in Example 15.

```
Primer Penuldeg220F:
                                       (SEQ ID NO: 100)
5'-CAACGGCCAGATGYTNMGNTGYCAY-3'

Protein translation for degenerate primer
Penuldeg220F:
NGQMXXCH

Primer Penul345R128fold:
                                       (SEQ ID NO: 101)
5'-GCGCCGTASGAYTGNACSARYTT-3'

Protein translation for degenerate primer
Penul345R128fold:
KXVQSYG
```

To obtain the initial DNA fragment of the Penicillium sp. xylanase gene, gradient PCR was performed at 6 different annealing temperatures ranging from 45° C. to 65° C. Amplification reactions (25 µl) were composed of 100 ng of Penicillium sp. genomic DNA as template, 0.4 mM each of dATP, dTTP, dGTP, and dCTP, 50 pmol each of primer Penuldeg220F and primer Penu1345R128fold, 1× ADVANTAGE® GC-Melt LA Buffer, and 1.25 units of ADVANTAGE® GC Genomic Polymerase Mix. The amplifications were performed using an EPPENDORF® MASTERCYCLER® 5333 programmed for pre-denaturing at 95° C. for 1 minute; 30 cycles each at a denaturing temperature of 95° C. for 30 seconds; annealing temperature of 55° C.+/−10° C. for 30 seconds (6 gradient options) and elongation at 70° C. for 1 minute; and final elongation at 70° C. for 5 minutes.

The reaction products were isolated by 1.0% agarose gel electrophoresis in TBE (10.8 g of Tris base, 5.5 g of boric acid and 4 ml of 0.5 M EDTA pH 8.0 per liter) buffer. A PCR product band of approximately 375 bp from an annealing temperature of 55.8° C. was excised from the gel, purified using a QIAQUICK® Gel Extraction Kit according to the manufacturer's instructions, and sequenced with a Perkin-Elmer Applied Biosystems Model 377 XL Automated DNA Sequencer using dye-terminator chemistry (Giesecke et al., 1992, supra) and primer walking. A partial sequence was obtained, which encoded a peptide comprising several of the peptide fragments identified in Example 15.

Example 18

Identification of a Full-Length *Penicillium* sp. Xylanase Gene

A full-length xylanase gene was identified from *Penicillium* sp. using a GENOMEWALKER™ Universal Kit according to the manufacturer's instructions. Briefly, total genomic DNA from *Penicillium* sp. was digested separately with four different restriction enzymes (Dra I, Eco RV, Pvu II, and Stu I) that leave blunt ends. Each batch of digested genomic DNA was then ligated separately to the GENOMEWALKER™ Adaptor to create four libraries. These four libraries were then employed as templates in PCR reactions using four gene-specific primers shown below, two for a primary and secondary PCR amplifying upstream of the fragment through the 5' end encoding the N-terminus of the xylanase and two for a primary and secondary PCR amplifying downstream of the fragment through the 3' end encoding the C-terminus of the xylanase. The following primers were designed based on the partial xylanase gene sequence from *Penicillium* sp. obtained as described in Example 17.

```
N-terminus:
Primer PenulGSP1R (primary):
                             (SEQ ID NO: 102)
5'-GCCCTTGTAATGGGTAACGACGTTGGTGA-3'

Primer PenulGSP2R (secondary):
                             (SEQ ID NO: 103)
5'-GCAAGCAGCGTCTCGTTGGTCCAGGATC-3'

C-terminus:
Primer PenulGSP1F (primary):
                             (SEQ ID NO: 104)
5'-GGCACCTACCGCAGCAACGTCTTCTACCA-3'

Primer PenulGSP2F (secondary):
                             (SEQ ID NO: 105)
5'-ACGGCGGCGCAGAACATCGTCAAGCT-3'
```

The primary amplifications were composed of 1 µl (approximately 6 ng) of each library as template, 0.4 mM each of dATP, dTTP, dGTP, and dCTP, 10 pmol of Adaptor Primer 1, 50 pmol of primer PenulGSP1R or PenulGSP1F, 1× ADVANTAGE® GC-Melt LA Buffer, and 1.25 units of ADVANTAGE® GC Genomic Polymerase Mix in a final volume of 25 µl. The amplifications were performed using an EPPENDORF® MASTERCYCLER® 5333 programmed for pre-denaturing at 95° C. for 1 minute; 7 cycles each at a denaturing temperature of 95° C. for 25 seconds; annealing and elongation at 72° C. for 5 minutes; 32 cycles each at a denaturing temperature of 95° C. for 25 seconds; annealing and elongation at 67° C. for 5 minutes; and final elongation at 67° C. for 7 minutes.

The secondary amplifications were composed of 1 µl of each primary PCR product as template, 0.4 mM each of dATP, dTTP, dGTP, and dCTP, 10 pmol of Adaptor Primer 2, 50 pmol of primer PenulGSP2R or PenulGSP2F, 1× ADVANTAGE® GC-Melt LA Buffer, and 1.25 units of ADVANTAGE® GC Genomic Polymerase Mix in a final volume of 25 µl. The amplifications were performed using an EPPENDORF® MASTERCYCLER® 5333 programmed for pre-denaturing at 95° C. for 1 minute; 5 cycles each at a denaturing temperature of 95° C. for 25 seconds; annealing and elongation at 72° C. for 5 minutes; 20 cycles each at a denaturing temperature of 95° C. for 25 seconds; annealing and elongation at 67° C. for 5 minutes; and final elongation at 67° C. for 7 minutes.

The reaction products were isolated by 1.0% agarose gel electrophoresis using TBE buffer. From the 5' end PCR amplification, 4 product bands were analyzed: a 450 bp product band from the Dra I library, a 1.6 kb product band from the Eco RV library, a 1.7 kb product band from the Pvu II library, and a 550 bp band from the Stu I library. The 4 product bands were excised from the gel, purified using a QIAQUICK® Gel Extraction Kit according to the manufacturer's instructions, and sequenced. From the 3' end PCR amplification, 3 product bands were analyzed: a 450 bp product band from the Dra I library, and 600 bp and 800 bp product bands from the Eco RV library. The 3 product bands were excised from the gel, purified using a QIAQUICK® Gel Extraction Kit according to the manufacturer's instructions, and sequenced.

DNA sequencing of the PCR fragments was performed with a Perkin-Elmer Applied Biosystems Model 377 XL Automated DNA Sequencer using dye-terminator chemistry (Giesecke et al., 1992, supra) and primer walking strategy using Adaptor Primer 2, primer PenulGSP2R, and primer PenulGSP2F for sequencing.

Nucleotide sequence data were scrutinized for quality and all sequences were compared to each other with assistance of PHRED/PHRAP software (University of Washington, Seattle, Wash., USA). The PCR fragment sequence results were compared and aligned with the partial xylanase gene sequence from *Penicillium* sp. obtained as described in Example 17. A gene model was constructed based on the gene fragments obtained here and in Example 17 allowing determination of the 5' and 3' ends of the gene with other homologous xylanases.

Example 19

Cloning of the *Penicillium* sp. Xylanase Gene and Construction of an *Aspergillus niger* Expression Vector Two synthetic oligonucleotide primers shown below were designed to PCR amplify the *Penicillium* sp. xylanase gene from the genomic DNA prepared in Example 16. An IN-FUSION™ Cloning Kit was used to clone the fragment directly into the expression vector pBM120a (WO 2006/078256).

```
PenulxylNCO1F:
                             (SEQ ID NO: 106)
5'-ACACAACTGGCCATGGTTCGCCTCAGTCCAGTCCTGC-3'

PenulxylPACIR:
                             (SEQ ID NO: 107)
5'-CAGTCACCTCTAGTTATTACAGACACTGCGAGTAATACTCG-3'
```

Bold letters represent coding sequence. The remaining sequence is homologous to the insertion sites of pBM120a.

Fifty picomoles of each of the primers above were used in a PCR reaction composed of 105 ng of *Penicillium* sp. genomic DNA, 1× EXPAND® Buffer 2 (Roche Diagnostics Corporation, Indianapolis, Ind., USA), 0.4 mM each of dATP, dTTP, dGTP, and dCTP, and 1 unit of EXPAND® DNA Polymerase (Roche Diagnostics Corporation, Indianapolis, Ind., USA) in a final volume of 50 µl. The amplification was performed using an EPPENDORF® MASTERCYCLER® 5333 programmed for 1 cycle at 95° C. for 1 minute; 30 cycles each at 95° C. for 30 seconds, 63.5° C. for 30 seconds, and 72° C. for 90 seconds; and a final elongation at 72° C. for 7 minutes. The heat block then went to a 4° C. soak cycle.

The reaction products were isolated by 1.0% agarose gel electrophoresis in TBE buffer where an approximately 1.4 kb product band was excised from the gel, and purified using a QIAQUICK® Gel Extraction Kit according to the manufacturer's instructions.

Plasmid pBM120a was digested with Nco I and Pac I, isolated by 1.0% agarose gel electrophoresis in TBE buffer, and purified using a QIAQUICK® Gel Extraction Kit according to the manufacturer's instructions.

The gene fragment and the digested vector were ligated together using an IN-FUSION™ Cloning Kit resulting in pMMar31 in which transcription of the xylanase gene was under the control of a hybrid of promoters from the genes for *Aspergillus niger* neutral alpha-amylase and *Aspergillus oryzae* triose phosphate isomerase (NA2-tpi promoter). The ligation reaction (20 µl) was composed of 1× IN-FUSION™ Buffer, 1× BSA (BD Biosciences, Palo Alto, Calif., USA), 1 µl of IN-FUSION™ enzyme (diluted 1:10), 132 ng of pBM120a digested with Nco I and Pac I, and 104 ng of the purified *Penicillium* sp. PCR product. The reaction was incubated at room temperature for 30 minutes. Two µl of the reaction were used to transform *E. coli* XL10 SOLOPACK® Gold Ultracompetent cells (Stratagene, La Jolla, Calif., USA) according to the manufacturer's instructions. Transformants were picked into LB medium supplemented with 100 µg of ampicillin per ml and grown overnight at 37° C. Plasmid DNA was prepared from each of the cultures using a BIOROBOT® 9600 and submitted to DNA sequencing with a Perkin-Elmer Applied Biosystems Model 377 XL Automated DNA Sequencer using dye-terminator chemistry (Giesecke et al., 1992, supra) and primer walking strategy using the primers below for sequencing. One *E. coli* transformant was identified containing the *Penicillium* sp. xylanase gene. The plasmid containing the xylanase gene was designated pMMar31.

```
996271 Na2tpi promoter fwd:
                                    (SEQ ID NO: 108)
5'-ACTCAATTTACCTCTATCCACACTT-3'

996270 AMG rev:
                                    (SEQ ID NO: 109)
5'-CTATAGCGAAATGGATTGATTGTCT-3'

Penulxyl367F:
                                    (SEQ ID NO: 110)
5'-ATGTTGAGGTGCCATAATC-3'

Penulxyl1025R:
                                    (SEQ ID NO: 111)
5'-TCTGGTAGTCGGTCGCCTG-3'
```

The same 1.4 kb PCR fragment was cloned into pCR®2.1-TOPO® using a TOPO® TA CLONING Kit to generate pMMar26. The *Penicillium* sp. xylanase insert in pMMar26 was confirmed by DNA sequencing. *E. coli* pMMar26 was deposited with the Agricultural Research Service Patent Culture Collection, Northern Regional Research Center, Peoria, Ill., USA, on Mar. 13, 2009, and assigned accession number NRRL B-50266.

Example 20

Characterization of the *Penicillium* sp. Genomic Sequence Encoding a Family GH10 Xylanase Nucleotide sequence data were scrutinized for quality and all sequences were compared to each other with assistance of PHRED/PHRAP software (University of Washington, Seattle, Wash., USA).

The nucleotide sequence and deduced amino acid sequence are shown in SEQ ID NO: 98 and SEQ ID NO: 99, respectively. The genomic fragment encodes a polypeptide of 403 amino acids, interrupted by 3 predicted introns of 65, 55, and 52 base pairs. The % G+C content of the full-length coding sequence and the mature coding sequence are 60.2% and 60.0%, respectively. Using the SignalP software program (Nielsen et al., 1997, supra), a signal peptide of 23 residues was predicted. The predicted mature protein contains 380 amino acids with a predicted molecular mass of 41.1 kDa. Amino acids 25 to 340 are indicative of a Family 10 glycosyl hydrolase. Based on the deduced amino acid sequence, the xylanase appears to fall into the xylanase Family GH10 according to Coutinho and Henrissat, 1999, supra.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the mature polypeptide of the *Penicillium* sp. Family GH10 xylanase gene shared 93% identity (excluding gaps) to the deduced amino acid sequence of a *Talaromyces emersonii* xylanase gene (GeneSeq accession number AAB84358).

Example 21

Effect of *Myceliophthora thermophila* CBS 117.65 Family 6 Cellobiohydrolase II, *Myceliophthora thermophila* CBS 202.75 Family 6 Cellobiohydrolase II, or *Penicillium* sp. Family 10 Xylanase on PCS Hydrolysis

*Myceliophthora thermophila* CBS 202.75 CEL6 cellobiohydrolase II (recombinant), *Myceliophthora thermophila* CBS 117.65 CEL6 cellobiohydrolase II (native), or *Penicillium* sp. Family 10 xylanase were evaluated for their ability to enhance the hydrolysis of washed PCS by a *Trichoderma reesei* cellulolytic protein composition (*Trichoderma reesei* broth expressing *Thermoascus aurantiacus* GH61A polypeptide having cellulolytic enhancing activity and *Aspergillus oryzae* beta-glucosidase fusion protein) obtained according to WO 2008/151079.

The hydrolysis of PCS was conducted using 2.2 ml deep-well plates in a total reaction volume of 1.0 ml. The hydrolysis was performed with 50 mg of PCS per ml of 50 mM sodium acetate pH 5.0 buffer containing 1 mM manganese sulfate and a fixed protein loading of 2 mg of the *T. reesei* cellulolytic protein composition per gram of cellulose or a 20% replacement (by protein) of the *T. reesei* cellulolytic protein composition with each enzyme (1.6 mg of the *T. reesei* cellulolytic protein composition per g of cellulose and 0.4 mg of each enzyme per g of cellulose). Hydrolysis assays were performed in triplicate for 72 hours at 50° C. Following hydrolysis, samples were filtered with a 0.45 μm Multiscreen 96-well filter plate and filtrates analyzed for sugar content according to Example 10.

Figure 3:
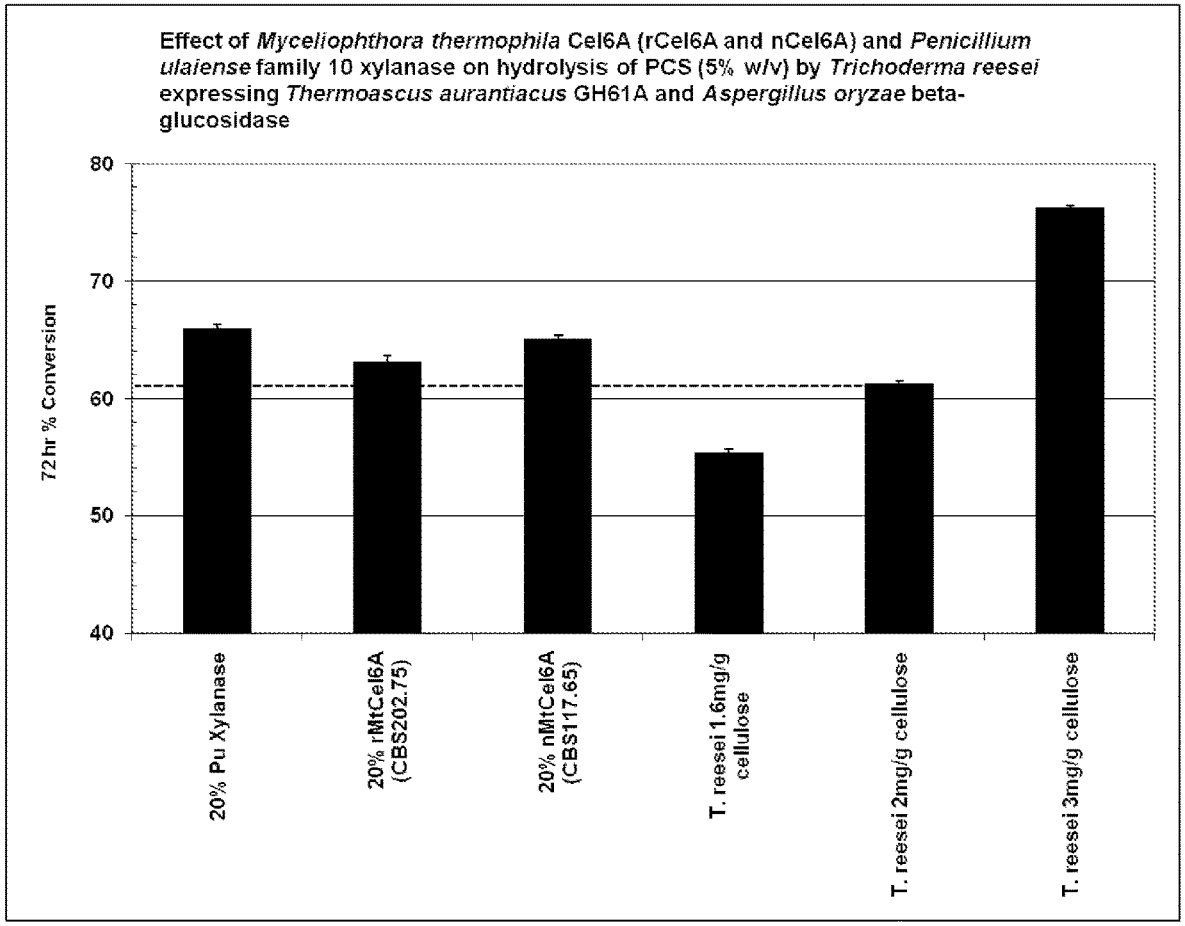
FIG. 3 shows the effect of *Myceliophthora thermophila* CBS 117.65 Family 6 cellobiohydrolase II, *Myceliophthora thermophila* CBS 202.75 Family 6 cellobiohydrolase II, or *Penicillium* sp. Family 10 xylanase on a 72 hour hydrolysis of PCS (5% w/v) at 50° C. by a fermentation broth of *Trichoderma reesei* expressing *Thermoascus aurantiacus* GH61A polypeptide having cellulolytic enhancing activity and *Aspergillus oryzae* beta-glucosidase fusion protein (cellulolytic protein composition). Each enzyme was added as a 20% replacement (by protein) of the *Trichoderma reesei* cellulolytic protein composition. The dotted line shows the percent conversion by 2 mg of the *Trichoderma reesei* cellulolytic protein composition per g cellulose loading. Enhancement of hydrolysis was demonstrated with mixtures that reach percent conversion above the dotted line at an equivalent protein loading. Error bars from triplicate measurements are shown.

The results shown in FIG. 3 demonstrated that a 20% replacement (by protein) of the *T. reesei* cellulolytic protein composition (loaded at 2 mg per g of cellulose) with the *M. thermophila* CBS 202.75 recombinant Cel6A cellobiohydrolase II or native *M. thermophila* CBS 117.65 Cel6A cellobiohydrolase II improved the 72 hour hydrolysis yield by 3.1% and 6.2%, respectively. Alternatively, the percent conversion with a 20% replacement of the *T. reesei* cellulolytic protein composition (loaded at 2 mg per g of cellulose) with the *M. thermophila* CBS 202.75 recombinant Cel6A cellobiohydrolase II was equivalent to a loading of 2.15 mg of the *T. reesei* cellulolytic protein composition per g of cellulose (a 1.08-fold improvement). With the *M. thermophila* native CBS 117.65 Cel6A cellobiohydrolase II the percent conversion with a 20% replacement was equivalent to a loading of 2.25 mg of the *T. reesei* cellulolytic protein composition per g of cellulose (a 1.13-fold improvement). A 20% replacement of the *T. reesei* cellulolytic protein composition (loaded at 2 mg per g of cellulose) with the *Penicillium* sp. Family 10 xylanase improved the hydrolysis yield by 7.7%. The percent conversion with a 20% replacement of the *T. reesei* cellulolytic protein composition (loaded at 2 mg per g of cellulose) with the *Penicillium* sp. xylanase was equivalent to a loading of 2.32 mg of the *T. reesei* cellulolytic protein composition per g of cellulose (a 1.16-fold improvement).

Example 22

Effect of *Myceliophthora thermophila* CBS 202.75 Cel6A Cellobiohydrolase II or *Myceliophthora thermophila* CBS 117.65 Cel6A Cellobiohydrolase II and *Penicillium* sp. Family 10 Xylanase on the Hydrolysis of PCS by a *Trichoderma reesei* Cellulase Mixture A PCS hydrolysis assay was performed as described in Example 21 with a 20% replacement of the *T. reesei* cellulolytic protein composition described in Example 21 (2 mg per g of cellulose total loading) with a 50:50 mixture of the *M. thermophila* CBS 202.75 CEL6 cellobiohydrolase II (recombinant) or the *M. thermophila* CBS 117.65 CEL6 cellobiohydrolase II (native) and the *Penicillium* sp. Family 10 xylanase (1.6 mg of the *T. reesei* cellulolytic protein composition per g cellulose; 0.2 mg of the *M. thermophila* CBS 202.75 cellobiohydrolase II or the *M. thermophila* CBS 117.65 cellobiohydrolase II per g cellulose; and 0.2 mg of the *Penicillium* sp. xylanase per g cellulose).

Figure 4:
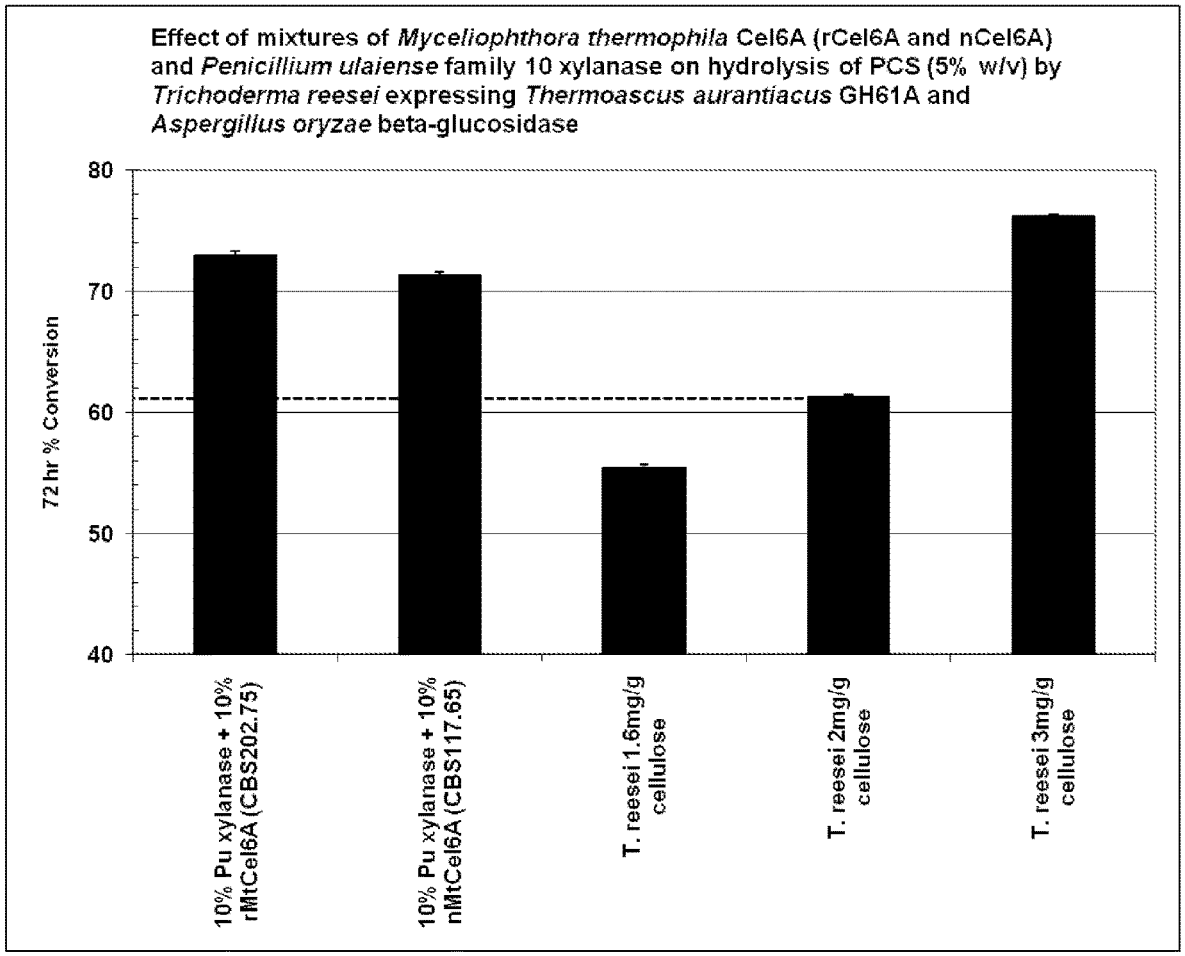
FIG. 4 shows the synergistic enhancement of a 72 hour hydrolysis of PCS (5% w/v) at 50° C. by a fermentation broth of *Trichoderma reesei* expressing *Thermoascus aurantiacus* GH61A polypeptide having cellulolytic enhancing activity and *Aspergillus oryzae* beta-glucosidase fusion protein (cellulolytic protein composition) in the presence of combinations of *Myceliophthora thermophila* CBS 117.65 Family 6 cellobiohydrolase II or *Myceliophthora thermophila* CBS 202.75 Family 6 cellobiohydrolase II and *Penicillium* sp. Family 10 xylanase. The mixtures were added as 20% replacements (by protein) of the *Trichoderma reesei* cellulolytic protein composition with a 50:50 mixture of the *Myceliophthora thermophila* Cel6A cellobiohydrolase II and *Penicillium* sp. xylanase. The dotted line shows the percent conversion by 2 mg of the *Trichoderma reesei* cellulolytic protein composition per g cellulose loading. Enhancement of hydrolysis was demonstrated with mixtures that reach percent conversion above the dotted line at an equivalent protein loading. Error bars from triplicate measurements are shown.

As shown in FIG. 4 a mixture of *Myceliophthora thermophila* CBS 202.75 CEL6 cellobiohydrolase II (recombinant) or *Myceliophthora thermophila* CBS 117.65 CEL6 cellobiohydrolase II (native) and *Penicillium* sp. xylanase demonstrated a 19.2% and 16.6% improvement of the 72 hour hydrolysis yield, respectively. These results corresponded to a percent conversion equivalent of 2.78 mg/g cellulose and 2.68 mg/g cellulose, respectively, of the *Trichoderma reesei* cellulolytic protein composition (a 1.39 and 1.34 fold improvement, respectively).

A significant enhancement in percent conversion of PCS by the *Trichoderma reesei* cellulolytic protein composition comprising a 10% replacement with the *M. thermophila* CBS 202.75 CEL6 cellobiohydrolase II (recombinant) or *M. thermophila* CBS 117.65 CEL6 cellobiohydrolase II (native) plus a 10% replacement with the *Penicillium* sp. xylanase (*M. thermophila* CBS 202.75 recombinant CEL6 cellobiohydrolase II+*Penicillium* sp. xylanase: 19.2%; *M. thermophila* CBS 117.65 native CEL6 cellobiohydrolase II+*Penicillium* sp. xylanase: 16.6%) relative to a 20% replacement with each protein individually (*M. thermophila* CBS 202.75 CEL6 cellobiohydrolase II (recombinant): 3.1%; *M. thermophila* CBS 117.65 CEL6 cellobiohydrolase II (native): 6.2%; *Penicillium* sp. xylanase: 8.2%), demonstrated that the *M. thermophila* Cel6A cellobiohydrolase II (both recombinant from *M. thermophila* CBS 202.75 strain and native from *M. thermophila* CBS 11.65 strain) and *Penicillium* sp. xylanase displayed synergism in the enhancement of the *T. reesei* cellulolytic protein composition.

Example 23

Preparation of *Trichoderma reesei* RutC30 Cel6A Cellobiohydrolase II

The *Trichoderma reesei* RutC30 Cel6A cellobiohydrolase II gene (SEQ ID NO: 25 [DNA sequence] and SEQ ID NO: 26 [deduced amino acid sequence]) was isolated from *Trichoderma reesei* RutC30 as described in WO 2005/056772.

The *Trichoderma reesei* Cel6A cellobiohydrolase II gene was expressed in *Fusarium venenatum* using pEJG61 as an expression vector according to the procedures described in U.S. Published Application No. 20060156437. Fermentation was performed as described in U.S. Published Application No. 20060156437.

Filtered broth was desalted and buffer-exchanged into 20 mM sodium acetate-150 mM NaCl pH 5.0 using a HIPREP® 26/10 Desalting Column according to the manufacturer's instructions. Protein concentration was determined using a Microplate BCA™ Protein Assay Kit in which bovine serum albumin was used as a protein standard.

Example 24

Preparation of *Thielavia terrestris* NRRL 8126 Cel6A Cellobiohydrolase II (CBHII)

*Thielavia terrestris* NRRL 8126 Cel6A cellobiohydrolase II (SEQ ID NO: 33 [DNA sequence] and SEQ ID NO: 34 [deduced amino acid sequence]) was recombinantly prepared according to WO 2006/074435 using *Trichoderma reesei* as a host.

Culture filtrate was desalted and buffer exchanged in 20 mM Tris-150 mM sodium chloride pH 8.5 using an ECONO-PAC® 10-DG desalting column according to the manufacturer's instructions. Protein concentration was determined using a Microplate BCA™ Protein Assay Kit in which bovine serum albumin was used as a protein standard.

Example 25

Effect of *Trichoderma reesei* Cel6A Cellobiohydrolase II or *Thielavia terrestris* Cel6A Cellobiohydrolase II and *Aspergillus aculeatus* Xylanase on the Hydrolysis of PCS by a *Trichoderma reesei* Cellulase Mixture To test synergy between other Cel6A cellobiohydrolase II proteins and *Aspergillus aculeatus* xylanase, a PCS hydrolysis assay was performed (as described in Example 10) with a 10% addition to the *T. reesei* cellulolytic protein composition (2 mg per g of cellulose total loading) of either *T. reesei* CEL6 cellobiohydrolase II or *T. terrestris* CEL6 cellobiohydrolase II alone, or in combination with the *A. aculeatus* xylanase (2 mg of the *T. reesei* cellulolytic protein composition per g cellulose, 0.2 mg of the *T. reesei* CEL6 cellobiohydrolase II or *T. terrestris* CEL6 cellobiohydrolase II per g cellulose; or 2 mg of the *T. reesei* cellulolytic protein composition per g cellulose, 0.2 mg of the *T. reesei* CEL6 cellobiohydrolase II, 0.2 mg of the *A. aculeatus* xylanase per g cellulose; or 2 mg of the *T. reesei* cellulolytic protein composition per g cellulose, 0.2 mg of the *T. terrestris* CEL6 cellobiohydrolase II per g cellulose, 0.2 mg of the *A. aculeatus* xylanase per g cellulose).

Figure 5:
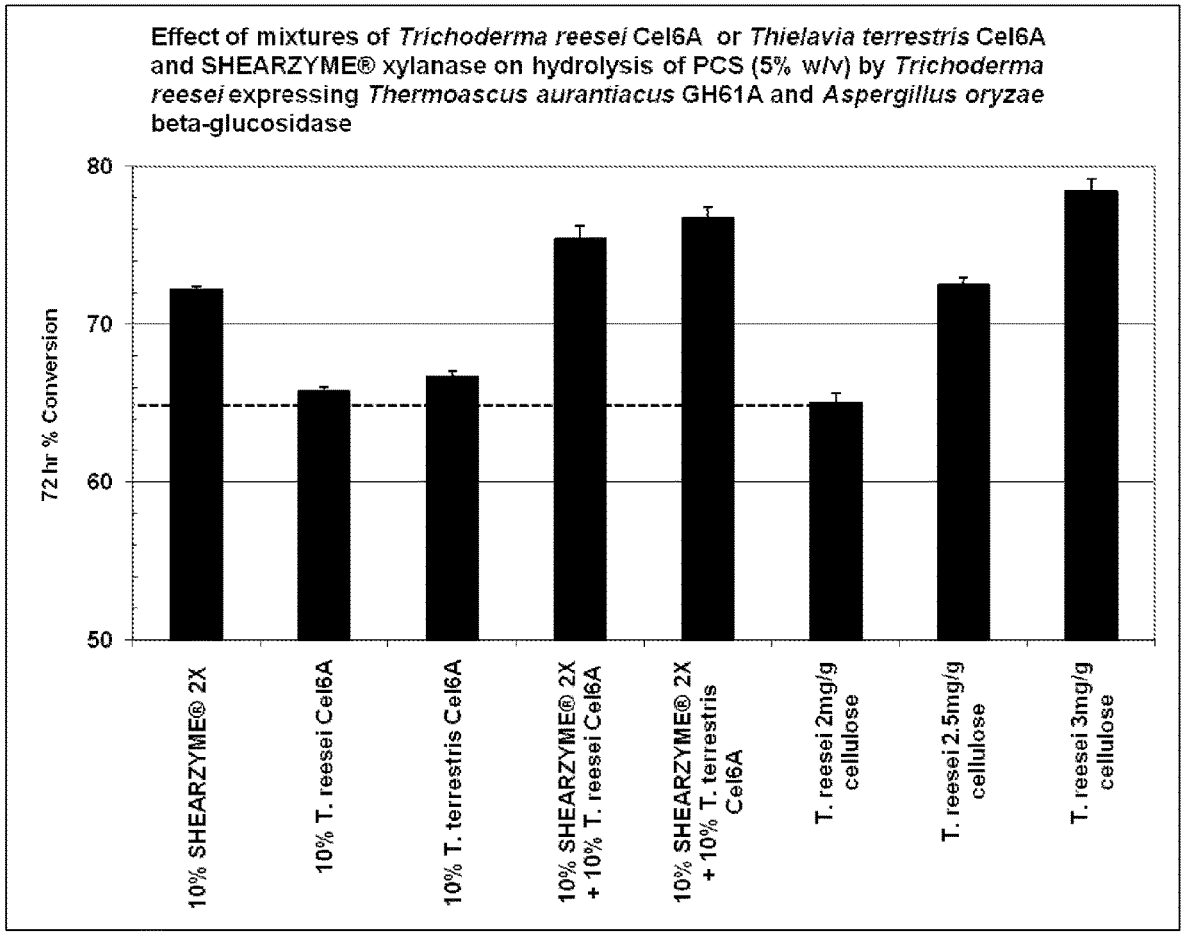
FIG. 5 shows the synergistic enhancement of a 72 hour hydrolysis of PCS (5% w/v) at 50° C. by a fermentation broth of *Trichoderma reesei* expressing *Thermoascus aurantiacus* GH61A polypeptide having cellulolytic enhancing activity and *Aspergillus oryzae* beta-glucosidase fusion protein (cellulolytic protein composition) in the presence of combinations of *Trichoderma reesei* Cel6A cellobiohydrolase II or *Thielavia terrestris* Cel6A cellobiohydrolase II and *Aspergillus aculeatus* Family 10 xylanase. The mixtures were added as 10% additions (by protein) of the *Trichoderma reesei* cellulolytic enzyme preparation with *Trichoderma reesei* Cel6A cellobiohydrolase II, *Thielavia terrestris* Cel6A cellobiohydrolase II and *Aspergillus aculeatus* xylanase separately, or as mixtures of *Trichoderma reesei* Cel6A cellobiohydrolase II or *Thielavia terrestris* Cel6A cellobiohydrolase II and *Aspergillus aculeatus* xylanase. The dotted line shows the percent conversion by 2 mg of the *Trichoderma reesei* cellulolytic protein composition per g cellulose loading. Error bars from triplicate measurements are shown.

As shown in FIG. 5, addition of *T. reesei* CEL6 cellobiohydrolase II, *T. terrestris* CEL6 cellobiohydrolase II, or *A. aculeatus* xylanase demonstrated a 1.2%, 2.5%, or 11.0% improvement of the 72 hour hydrolysis yield, respectively. Addition of *T. reesei* CEL6 cellobiohydrolase II and *A. aculeatus* xylanase or *T. terrestris* CEL6 cellobiohydrolase II and *A. aculeatus* xylanase resulted in a 16% and 18% improvement of the 72 hour hydrolysis yield, respectively. The addition of both *T. reesei* CEL6 cellobiohydrolase II and *A. aculeatus* xylanase or *T. terrestris* CEL6 cellobiohydrolase II and *A. aculeatus* xylanase resulted in a greater enhancement to conversion than would be expected if the enhancements were additive [*T. reesei* CEL6 cellobiohydrolase II and *A. aculeatus* xylanase 16% vs. 12.2% (1.2%+ 11.0%); *T. terrestris* CEL6 cellobiohydrolase II and *A. aculeatus* xylanase 18% vs 13.5% (2.5%+11.0%)], indicating a synergistic enhancement to the PCS hydrolysis activity of the *T. reesei* cellulolytic protein composition.

Deposit of Biological Material

The following biological materials have been deposited under the terms of the Budapest Treaty with the Agricultural Research Service Patent Culture Collection (NRRL), Northern Regional Research Center, 1815 University Street, Peoria, Ill., 61604, USA, and given the following accession numbers:

| Deposit | Accession Number | Date of Deposit |
| --- | --- | --- |
| *E. coli* pSMai182 | NRRL B-50059 | Sep. 6, 2007 |
| *E. coli* (pMMar26) | NRRL B-50266 | Mar. 13, 2009 |

The strains have been deposited under conditions that assure that access to the cultures will be available during the pendency of this patent application to one determined by foreign patent laws to be entitled thereto. The deposits represent substantially pure cultures of the deposited strains. The deposits are vailable as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An enzyme composition comprising a CEL6 polypeptide having cellobiohydrolase II activity, a GH10 polypeptide having xylanase activity, and one or more cellulolytic enzymes selected from the group consisting of an endoglucanase, a cellobiohydrolase, and a beta-glucosidase, wherein one or both of the CEL6 polypeptide having cellobiohydrolase II activity and the GH10 polypeptide having xylanase activity are foreign to the one or more cellulolytic enzymes;
   wherein the CEL6 polypeptide having cellobiohydrolase II activity is selected from the group consisting of:

(a) a polypeptide having cellobiohydrolase II activity comprising an amino acid sequence having a sequence identity of at least 90% to amino acids 18 to 482 of SEQ ID NO: 30;
   (b) a polypeptide having cellobiohydrolase II activity encoded by a polynucleotide that hybridizes under very high stringency conditions with nucleotides 52 to 1809 of SEQ ID NO: 29, or the full-length complement thereof, wherein the very high stringency conditions are defined as prehybridization and hybridization at 42° C. in 5×SSPE, 0.3% SDS, 200 μg/ml sheared and denatured salmon sperm DNA, and 50% formamide for 12 to 24 hours and washing three times each for 15 minutes using 2×SSC, 0.2% SDS at 70° C.;
(c) a polypeptide having cellobiohydrolase II activity encoded by a polynucleotide comprising a nucleotide sequence having a sequence identity of at least 90% to nucleotides 52 to 1809 of SEQ ID NO: 29; and
(d) a polypeptide having cellobiohydrolase II activity comprising amino acids 18 to 482 of SEQ ID NO: 30; and
wherein the GH10 polypeptide having xylanase activity is selected from the group consisting of:
(a) a polypeptide having xylanase activity comprising an amino acid sequence having a sequence identity of at least 90% to amino acids 20 to 369 of SEQ ID NO: 72;
(b) a polypeptide having xylanase activity encoded by a polynucleotide that hybridizes under very high stringency conditions with nucleotides 58 to 1107 of SEQ ID NO: 71, or the full-length complement thereof, wherein the very high stringency conditions are defined as prehybridization and hybridization at 42° C. in 5×SSPE, 0.3% SDS, 200 μg/ml sheared and denatured salmon sperm DNA, and 50% formamide for 12 to 24 hours and washing three times each for 15 minutes using 2×SSC, 0.2% SDS at 70° C.;
(c) a polypeptide having xylanase activity encoded by a polynucleotide comprising a nucleotide sequence having a sequence identity of at least 90% to nucleotides 58 to 1107 of SEQ ID NO: 71; and
(d) a polypeptide having xylanase activity comprising amino acids 20 to 369 of SEQ ID NO: 72;
wherein the one or more cellulolytic enzymes comprise a beta-glucosidase, a *Trichoderma reesei* cellobiohydrolase I (CEL7A), a *Trichoderma reesei* cellobiohydrolase II (CEL6A), and a *Trichoderma reesei* endoglucanase I (CEL7B).

2. The enzyme composition of claim 1, wherein the one or more cellulolytic enzymes further comprise one or more enzymes selected from the group consisting of a *Trichoderma reesei* endoglucanase II (CEL5A), a *Trichoderma reesei* endoglucanase V (CEL45A), and a *Trichoderma reesei* endoglucanase III (CEL12A).

3. The enzyme composition of claim 1, which further comprises a GH61 polypeptide having cellulolytic enhancing activity.

4. The enzyme composition of claim 1, wherein one or more of the cellulolytic enzymes, the CEL6 polypeptide having cellobiohydrolase II activity, and/or the GH10 polypeptide having xylanase activity are in the form of a fermentation broth with or without cells.

5. The enzyme composition of claim 1, wherein the CEL6 polypeptide having cellobiohydrolase II activity has at least 95% sequence identity to amino acids 18 to 482 of SEQ ID NO: 30.

6. The enzyme composition of claim 1, wherein the CEL6 polypeptide having cellobiohydrolase II activity has at least 97% sequence identity to amino acids 18 to 482 of SEQ ID NO: 30.

7. The enzyme composition of claim 1, wherein the CEL6 polypeptide having cellobiohydrolase II activity comprises amino acids 18 to 482 of SEQ ID NO: 30.

8. The enzyme composition of claim 1, wherein the CEL6 polypeptide having cellobiohydrolase II activity consists of amino acids 18 to 482 of SEQ ID NO: 30.

9. The enzyme composition of claim 1, wherein the CEL6 polypeptide having cellobiohydrolase II activity is encoded by a polynucleotide having at least 95% sequence identity to nucleotides 52 to 1809 of SEQ ID NO: 29.

10. The enzyme composition of claim 1, wherein the CEL6 polypeptide having cellobiohydrolase II activity is encoded by a polynucleotide having at least 97% sequence identity to nucleotides 52 to 1809 of SEQ ID NO: 29.

11. The enzyme composition of claim 1, wherein the GH10 polypeptide having xylanase activity has at least 95% sequence identity to amino acids 20 to 369 of SEQ ID NO: 72.

12. The enzyme composition of claim 1, wherein the GH10 polypeptide having xylanase activity has at least 97% sequence identity to amino acids 20 to 369 of SEQ ID NO: 72.

13. The enzyme composition of claim 1, wherein the GH10 polypeptide having xylanase activity comprises amino acids 20 to 369 of SEQ ID NO: 72.

14. The enzyme composition of claim 1, wherein the GH10 polypeptide having xylanase activity consists of amino acids 20 to 369 of SEQ ID NO: 72.

15. The enzyme composition of claim 1, wherein the GH10 polypeptide having xylanase activity is encoded by a polynucleotide having at least 95% sequence identity to nucleotides 58 to 1107 of SEQ ID NO: 71.

16. The enzyme composition of claim 1, wherein the GH10 polypeptide having xylanase activity is encoded by a polynucleotide having at least 97% sequence identity to nucleotides 58 to 1107 of SEQ ID NO: 71.

17. A method for degrading a cellulosic material, comprising: contacting the cellulosic material with the enzyme composition of claim 1.

18. A method for producing a fermentation product, comprising: (a) saccharifying a cellulosic material with the enzyme composition of claim 1; (b) fermenting the saccharified cellulosic material with one or more fermenting microorganisms; and (c) recovering the fermentation product from the fermentation.

19. A method of fermenting a saccharified cellulosic material, comprising: fermenting the saccharified cellulosic material with one or more fermenting microorganisms to produce a fermentation product, and optionally recovering the fermentation product, wherein the cellulosic material is saccharified with the enzyme composition of claim 1.

20. The enzyme composition of claim 1, wherein the CELE polypeptide having cellobiohydrolase II activity is encoded by a polynucleotide comprising nucleotides 52 to 1809 of SEQ ID NO: 29.

21. The enzyme composition of claim 1, wherein the GH10 polypeptide having xylanase activity is encoded by a polynucleotide comprising nucleotides 58 to 1107 of SEQ ID NO: 71.

* * * * *